(12) United States Patent  (10) Patent No.: US 7,115,607 B2
Fotsch et al.  (45) Date of Patent: Oct. 3, 2006

(54) SUBSTITUTED PIPERAZINYL AMIDES AND METHODS OF USE

(75) Inventors: Christopher H. Fotsch, Thousand Oaks, CA (US); Premilla Arasasingham, Thousand Oaks, CA (US); Yunxin Bo, Thousand Oaks, CA (US); Ning Chen, Thousand Oaks, CA (US); Martin H. Goldberg, Woodland Hills, CA (US); Nianhe Han, Thousand Oaks, CA (US); Feng-Yin Hsieh, Thousand Oaks, CA (US); Michael G. Kelly, Thousand Oaks, CA (US); Qingyian Liu, Camarillo, CA (US); Mark H. Norman, Thousand Oaks, CA (US); Duncan M. Smith, Thousand Oaks, CA (US); Markian Stec, Fillmore, CA (US); Nuria Tamayo, Newbury Park, CA (US); Ning Xi, Thousand Oaks, CA (US); Shimin Xu, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 377 days.

(21) Appl. No.: 10/202,823

(22) Filed: Jul. 24, 2002

(65) Prior Publication Data

US 2003/0220324 A1 Nov. 27, 2003

Related U.S. Application Data

(60) Provisional application No. 60/307,831, filed on Jul. 25, 2001.

(51) Int. Cl.
A61K 31/496 (2006.01)
C07D 401/12 (2006.01)
C07D 403/12 (2006.01)

(52) U.S. Cl. ............... 514/252.13; 514/253.05; 514/253.06; 514/253.13; 514/254.09; 544/359; 544/363; 544/365; 544/373; 544/376; 544/379

(58) Field of Classification Search ............... 544/363, 544/359, 365, 373, 376, 379; 514/253.05, 514/253.06, 252.13, 253.13, 254.09
See application file for complete search history.

(56) References Cited

U.S. PATENT DOCUMENTS

| 5,244,895 A | 9/1993 | Hidaka et al. |
| 5,340,809 A * | 8/1994 | Gaudry et al. ......... 514/254.05 |
| 5,518,735 A | 5/1996 | Sturzebecher et al. |

(Continued)

FOREIGN PATENT DOCUMENTS

| EP | 0 513 691 | 7/1996 |
| EP | 1 086 947 | 3/2001 |
| WO | WO 94/05693 | 3/1994 |
| WO | WO 95/34311 | 12/1995 |
| WO | WO 97/03060 | 1/1997 |
| WO | WO 97/19908 | 6/1997 |
| WO | WO 97/19919 | 6/1997 |
| WO | WO 97/40031 | 10/1997 |
| WO | WO 97/49673 | 12/1997 |
| WO | WO 98/11128 | 3/1998 |
| WO | 99/11657 * | 3/1999 |
| WO | WO 96/64002 | 12/1999 |
| WO | WO 00/25786 | 5/2000 |
| WO | WO 00/35874 | 6/2000 |
| WO | WO 00/35875 | 6/2000 |
| WO | 01/34586 A2 * | 11/2000 |
| WO | WO 00/74679 | 12/2000 |
| WO | WO 00/78317 | 12/2000 |
| WO | WO 01/10842 | 2/2001 |
| WO | WO 02/059095 A1 | 8/2002 |
| WO | WO 02/059107 A1 | 8/2002 |
| WO | WO 02/059108 | 8/2002 |
| WO | WO 02/059117 | 8/2002 |
| WO | WO 02/062766 A2 | 8/2002 |
| WO | WO 02/067869 A2 | 9/2002 |
| WO | WO 02/068387 A2 | 9/2002 |
| WO | WO 02/068388 A2 | 9/2002 |
| WO | WO 02/069905 A2 | 9/2002 |
| WO | WO 02/070511 | 9/2002 |
| WO | WO 02/079146 A2 | 10/2002 |
| WO | WO 03/031410 A1 | 4/2003 |
| WO | WO 03/061660 A1 | 7/2003 |
| WO | WO 03/063781 A2 | 8/2003 |

OTHER PUBLICATIONS

Andersson et al. Expert Opin. Ther.Patents, vol. 11, p. 1583–1592 (2001).*

(Continued)

Primary Examiner—Golam M. M. Shameem
Assistant Examiner—Ebenezer Sackey
(74) Attorney, Agent, or Firm—Joseph W. Bulock

(57) ABSTRACT

Selected substituted piperazine compounds of Formula I

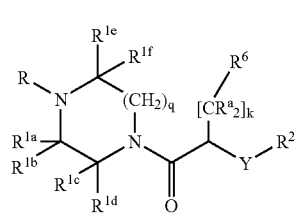

are effective for prophylaxis and treatment of diseases, such as obesity and the like. The invention encompasses novel compounds, analogs, prodrugs and pharmaceutically acceptable salts thereof, pharmaceutical compositions and methods for prophylaxis and treatment of diseases and other maladies or conditions involving activation of the melanocortin receptor. The subject invention also relates to processes for making such compounds as well as to intermediates useful in such processes.

14 Claims, No Drawings

U.S. PATENT DOCUMENTS

| | | | |
|---|---|---|---|
| 5,576,290 | A | 11/1996 | Hadley |
| 5,681,954 | A | 10/1997 | Yamamoto et al. |
| 5,721,251 | A | 2/1998 | Chen et al. |
| 6,051,555 | A | 4/2000 | Hadley |
| 6,054,556 | A | 4/2000 | Huby et al. |
| 6,057,290 | A | 5/2000 | Fukiage et al. |
| 6,767,915 | B1 | 7/2004 | Bakshi et al. |
| 2002/0091090 | A1 | 7/2002 | Cole et al. |
| 2004/0006067 | A1 | 1/2004 | Fotsch et al. |

OTHER PUBLICATIONS

Bohm et al., "Three Dimensional Quantitative Structure—Activity Relationship Analyses Using Comparative Molecular Field Analysis and comparative Molecular Similarity Indices Analysis to Elucidate Selectivity Differences of Inhibitors Binding to Trypsin, Thrombin, and Factor Xa" (1999) J. Med. Chem. 42: 458–477.

Hadley et al., "Melanocortin Receptors: Identification and Characterization by Melanotropic Peptide Agonists and Antagonists" (1996) Pigment Cell Research 9: 213–234.

Haskell–Luevano et al., "Discovery of Prototype Peptidomimetic Agonists at the Human Melanocortin Receptors MC1R and MC4R" (1997) J. Med. Chem., 40: 2133–2139.

Jacobsen et al., "Synthesis of a Series of Stromelysin–Selective Thiadiazole Urea Matrix Metalloproteinase Inhibitors" (1999) J. Med. Chem., 42: 1525–1536.

Sakamoto et al., "Chymotrypsin Inhibition by Dipeptide Esters, Phenylpiperidide and Phenylpiperazides" (1989) Peptide Chemistry 375–378.

Sakamoto et al., "Dipeptide Side Chain–Side chain Hydrophobic Interactions as Conformational Core for Chymotrypsin Inhibition" (1991) Bull. Chem. Soc. Jpn., 64: 2519–2523.

Schioth et al., (1998) "Discovery of Novel Melanocortin$_4$ Receptor Selective MSH Analogues" British Journal of Pharmacology 124: 75–82.

Sturzebecher et al., "Structure–Activity Relationships of Inhibitors Derived From 3–Amidinophenylalanine" (1995) J. Enzyme Inhibition, 9:87–99.

Sturzebecher et al., "Synthesis and Structure—Activity Relationships of Potent Thrombin Inhibitors: Piperazides of 3–Amidinophenylalanine" (1997) J. Med. Chem. 40: 3091–3099.

Wagner et al., "Synthese antiproteolytisch wirksame N–arylsulfonylierter Amidinophenylalaninamide" (1981) Pharmazie 36: 597–603.

Wikberg, Jarl E.S., "Melanocortin receptors: perspectives for novel drugs" (1999) European Journal of Pharmacology 375: 295–310.

Barakat et al., "Synthesis and Biological Activities of Phenyl Piperazine–Based Peptidomimetic Growth Hormone Secretagogues" (1998) Bioorganic & Medicinal Chemistry Letters 8: 1431–1436.

* cited by examiner

SUBSTITUTED PIPERAZINYL AMIDES AND METHODS OF USE

This application claims the benefit of U.S. Provisional Application No. 60/307,831 filed Jul. 25, 2001, which is hereby incorporated by reference.

FIELD OF THE INVENTION

The present invention relates generally to the fields of medicinal chemistry and, more specifically, to novel compounds and their use as anti-obesity agents.

BACKGROUND OF THE INVENTION

Obesity, defined as an excess of body fat relative to lean body mass, contributes to and complicates other diseases. For example, obesity substantially increases the risk of morbidity from hypertension, dyslipidemia, type 2 diabetes, coronary artery disease, stroke, gallbladder disease, osteoarthritis, sleep apnea and respiratory problems, as well as cancers of the endometrium, breast, prostate and colon. As a major cause of preventable death in the United States today, obesity poses a major public health challenge.

Overweight is defined today as a body mass index (BMI) of 25–29.9 kg/m$^2$, and obesity is defined as a BMI$\geq$30 kg/m$^2$. Over 60% of the adult population of the United States and Australia are either overweight (BMI of 25–29.9 kg/m$^2$) or obese (BMI>30 kg/m$^2$). More than 20% of adults fall into this latter category.

The cause of obesity is quite complex and not merely the result of voluntary overeating. Rather, the differential body composition observed between obese and normal subjects results from differences in both metabolism and neurologic/metabolic interactions.

The purpose of weight loss and weight maintenance is to reduce health risks. If weight is regained, health risks increase. A majority of patients who lose weight regain it, so the challenge to the patient and the practitioner is to maintain weight loss. Because of the tendency to regain weight after weight loss, the use of long-term medication to aid in the treatment of obesity may be indicated for carefully selected patients.

The drugs used to promote weight loss are traditionally anorexiants or appetite suppressants. Three classes of anorexiant drugs have been developed, all of which affect neurotransmitters in the brain. They may be designated as follows: (1) those that affect catecholamines, such as dopamine and norepinephrine; (2) those that affect serotonin; and (3) those that affect more than one neurotransmitter. These drugs work by increasing the secretion of dopamine, norepinephrine, or serotonin into the synaptic neural cleft, by inhibiting the reuptake of these neurotransmitters into the neuron, or by a combination of both mechanisms. Sibutramine inhibits the reuptake of norepinephrine and serotonin. Orlistat is not an appetite suppressant and has a different mechanism of action; it blocks about one-third of fat absorption.

Weight loss drugs approved by the FDA for long-term use may be useful as an adjunct to diet and physical activity for patients with a BMI>27 who also have concomitant obesity-related risk factors or diseases. Our thinking about drug therapy has undergone radical changes over the past few years.

Of recent interest as a target has been the melanocortin receptor family. The term melanocortin ("MC") defines a family of peptide hormones that regulate diverse physiological functions through transmembrane G-protein coupled receptors. Melanocortins include melanocyte-stimulating hormones (MSH) such as α-MSH, β-MSH and γ-MSH, as well as adrenocorticotropic hormone (ACTH). The melanocortin (MC) receptors ("MCRs") are a group of cell surface proteins that mediate a variety of physiological effects, including adrenal gland function, production of cortisol and aldosterone, control of melanocyte growth and pigment production, thermoregulation, immunomodulation and analgesia. In the past several years, five distinct melanocortin receptor subtypes have been identified. The five MC receptors, termed MCR1, MCR2, MCR3, MCR4 and MCR5, all couple in a stimulatory fashion to cAMP. MCR1, MCR3, MCR4 and MCR5 constitute subtypes of MSH receptors. The MCRs stimulate adenyl cyclase to generate cAMP.

The MC1 receptor is present on melanocytes and melanoma and is involved in skin pigmentation. The MCR2 receptor is the ACTH receptor and is present predominantly in the adrenal gland. MCR2 plays a role in adrenal steroidogenesis. The mRNA for the MCR3 receptor has been found in the brain, as well as in placental and gut tissues. The MCR4 receptor has been found primarily in the brain. The MCR5 receptor is expressed in the brain, as well as in several peripheral tissues and has been implicated in exocrine gland function.

The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as other events related to parturition.

Recently, MC receptor MCR4 has been shown to function in the regulation of body weight and food intake. Early studies on mice that expressed agouti ectopically, which is a MCR4 antagonist, produced obese animals. Subsequent work has shown that MCR3 and MCR4 antagonists stimulated food intake and that MCR4 knockout mice are obese. Synthetic MC4 agonist peptides that mimic melanocortins and bind to MCR4 injected into the brain, cause suppression of feeding in normal and mutant obese mice. Targeted disruption of MCR4 causes mice to develop a maturity onset of obesity associated with hyperphagia, hyperinsulinemia and hyperglycemia (Huszar et al., supra). Stimulation of the MC4 receptor by an endogenous ligand, α-MSH, produces a satiety signal and may be the downstream mediator of the leptin signalling pathway. These results indicate that the brain MC receptor MCR-4 functions in regulating food intake and body weight and is a promising target in the treatment of obesity. It is believed that by providing potent MC-4 receptor agonists, appetite may be suppressed and weight loss benefits may be achieved. See J. Wikberg, Eur. J. Pharm., 375, 295–310 (1999).

Melanotan II (MTII) is an α-MSH peptide superagonist for MCR4. (M. Hadley et al., Discovery and Development of Novel Melanogenic Drugs, Integration of Pharmaceutical Discovery and Development: Case Studies, Borchardt et al., ed., Plenum Press, New York 1998). Other cyclic and linear α-MSH peptides also have been studied. See, for example, C. Haskell-Luevano et al., J. Med. Chem., 40, 2133–39 (1997); H. Schiöth et al., Brit. J. Pharmacol, 124, 75–82

(1998); H. Schiöth et al., Eur. J. Pharmacol., 349, 359–66 (1998); M. Hadley et al., Pigment Cell Res., 9, 213–34 (1996); M. Bednarek et al., Peptides, 20, 401–09 (1999); and U.S. Pat. Nos. 6,054,556, 6,051,555 and 5,576,290.

WO98/11128, published 19 Mar. 1998, describes phenylalanine derivatives. WO00/78317, published 28 Dec. 2000, describes piperidine derivatives as integrin receptor antagonists. EP1086947, published 29 Aug. 2000, describes piperidine compounds as agonists and antagonists for the SST receptor. WO00/35874, published 22 Jun. 2000, describes arylpiperidine compounds as intermediates for the preparation of 5HT1A agonists and antagonists. WO00/35875, published 22 Jun. 2000, describes arylpiperidine compounds as intermediates for the preparation of 5HT1A agonists and antagonists. WO00/25786, published 11 May 2000, describes substituted piperidines as potassium channel inhibitors. U.S. Pat. No. 5,518,735, issued May 21, 1996, describes phenylalanine derivatives which prevent coagulation or thrombosis. WO97/19908, published 5 Jun. 1997, describes phenylalanine derivatives as fungicides. WO97/49673, published 31 Dec. 1997, describes phenylalanine derivatives as thrombin inhibitors.

WO95/34311, published 21 Dec. 1995, describes substituted piperazine compounds as growth hormone releasing agents. U.S. Pat. No. 5,681,954, issued 28 Oct. 1997, describes substituted piperazines as inhibitors of calmodulin. WO97/03060, published 30 Jan. 1997, describes piperazine derivatives as cysteine protease inhibitors. U.S. Pat. No. 6,057,290, issued May 2, 2000, describes piperazine derivatives as cysteine protease inhibitors. WO97/19919, published 5 Jun. 1997, describes sulfonamides as having antithrombin activity. U.S. Pat. No. 5,244,895, issued Sep. 14, 1993, describes piperazine derivatives as antiulcer agents. EP 513691, published 31 Jul. 1996, describes piperazine derivatives as antiulcer agents. U.S. Pat. No. 5,244,895, issued Sep. 14, 1993, describes sulfonamides having smooth muscle relaxation activity. WO94/05693, published 17 Mar. 1994, describes piperazinyl-phenylalanine derivatives as tachyquinine antagonists. J. Sturzebecher et al. J. Enzyme Inhib., 9, 87–99 (1995), describes piperazinyl-phenylalanine derivatives as thrombin inhibitors. M. Böhm et al. J. Med. Chem., 42, 458–77 (1999), describes piperazinyl-phenylalanine derivatives as thrombin inhibitors. J. Sturzebecher et al., J. Med. Chem., 40, 3091–99 (1997), describes piperazinyl-phenylalanine derivatives as thrombin inhibitors. H. Sakamoto, et al. Pept. Chem., 27, 375–8 (1989) describes piperazinyl-phenylalanine derivatives as chymotrypsin inhibitors. H. Sakamoto, et al., Bull. Chem. Soc. Jpn., 64, 2519–23 (1991) describes piperazinyl-phenylalanine derivatives as chymotrypsin inhibitors. G. Wagner, et al., Pharmazie, 36, 597–603 (1981), describes piperazinyl-phenylalanine derivatives as serine protease inhibitors. E. J. Jacobsen et al. J. Med. Chem., 42, 1525–36 (1999) describes thiazolyl ureas as stromelysin inhibitors. WO97/40031, published 30 Oct. 19978, describes thiazolyl ureas as metalloprotease inhibitors.

WO01/10842, published 15 Feb. 2001, describes melanocortin receptor binding compounds. WO99/64002, published 16 Dec. 1999, describes spiropiperidines as melanocortin receptor agonists. WO00/74679, published 14 Dec. 2000, describes piperidine compounds as melanocortin receptor agonists.

However, compounds of the current invention have not been described as inhibitors of MCRs such as for the treatment of obesity.

DESCRIPTION OF THE INVENTION

A class of compounds useful in treating obesity is defined by Formula I

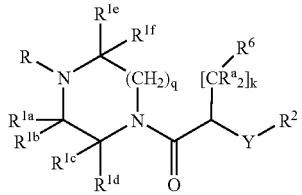

I wherein Y is —NH—, —CH$_2$—, or —O—;
  preferably —NH— or —CH$_2$—;
    more preferably —NH—;
wherein R is selected from
  a) alkyl,
  b) —(CH$_2$)$_n$-cycloalkyl,
  c) —(CH$_2$)$_n$-aryl, and
  d) —(CH$_2$)$_n$-heterocyclyl;
    wherein the cycloalkyl and aryl groups are optionally substituted with 1 to 3 groups selected from R$^4$; the heterocyclyl group is optionally substituted with 1 to 3 groups selected from R$^4$ and oxo; and the alkyl group is optionally substituted with 1 to 3 groups selected from R$^5$;
  preferably selected from
  a) —(CH$_2$)$_n$—C$_{3-8}$-cycloalkyl,
  b) -aryl,
  c) unsubstituted benzyl, and
  d) —(CH$_2$)$_n$-4–10-membered heterocyclyl;
    wherein the cycloalkyl and aryl groups are optionally substituted with 1 to 3 groups selected from R$^4$; and the heterocyclyl group is optionally substituted with 1 to 3 groups selected from R$^4$ and oxo;
    more preferably wherein R is phenyl; wherein R is optionally substituted with 1 or 2 groups selected from R$^4$;
    even more preferably

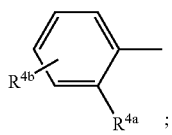

of particular importance

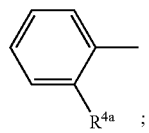

wherein R$^{1a}$, R$^{1b}$, R$^{1c}$, R$^{1d}$, R$^{1e}$, and R$^{1f}$ are independently selected from R$^4$; or wherein R$^{1a}$ and R$^{1b}$, or R$^{1d}$ and R$^{1c}$ form oxo; or wherein R$^{1e}$ and R$^{1c}$ form an alkylenyl or alkenylenyl bridge; or wherein R$^{1a}$, R$^{1b}$, R$^{1c}$, and R$^{1d}$ together with the piperazine ring forms an optionally substituted 1,2,3,4-tetrahydro-quinoxalinyl ring;
  preferably R$^{1a}$, R$^{1b}$, R$^{1c}$, R$^{1d}$, R$^{1e}$, and R$^{1f}$ are independently selected from R$^4$; or wherein R$^{1a}$ and R$^{1b}$ or R$^{1d}$ and R$^{1c}$ form oxo; or wherein R$^{1e}$ and R$^{1c}$ form an $C_{1-4}$-alkylenyl or $C_{2-4}$-alkenylenyl bridge;
or wherein $R^{1a}$, $R^{1b}$, $R^{1c}$, and $R^{1d}$ together with the piperazine ring forms an optionally substituted 1,2,3,4-tetrahydro-quinoxalinyl ring;
  more preferably $R^{1a}$, $R^{1b}$, $R^{1c}$, $R^{1d}$, $R^{1e}$, and $R^{1f}$ are independently selected from $R^4$; or wherein $R^{1a}$ and $R^{1b}$ or $R^{1d}$ and $R^{1c}$ form oxo;
    even more preferably $R^{1a}$, $R^{1b}$, $R^{1c}$, $R^{1d}$, $R^{1e}$, and $R^{1f}$ are H;
wherein $R^2$ is selected from
  a) alkyl,
  b) —$(CH_2)_n$-cycloalkyl,
  c) —$(CH_2)_n$-aryl,
  d) —$(CH_2)_n$-heterocyclyl, e)
  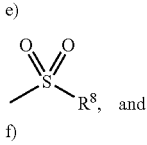

f)
  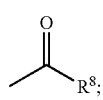

wherein the cycloalkyl and aryl groups are optionally substituted with 1 to 3 groups selected from $R^4$; the heterocyclyl group is optionally substituted with 1 to 3 groups selected from $R^4$ and oxo; and the alkyl group is optionally substituted with 1 to 3 groups selected from $R^5$;
  preferably selected from
    a) —$(CH_2)_n$—$C_3$-cycloalkyl,
    b) —$(CH_2)_n$-aryl,
    c) —$(CH_2)_n$-4–10-membered heterocyclyl, d)
    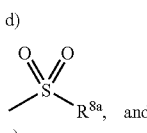

e)
    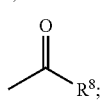

wherein the cycloalkyl and aryl groups are optionally substituted with 1 to 3 groups selected from $R^4$; and the heterocyclyl group is optionally substituted with 1 to 3 groups selected from $R^4$ and oxo;
    more preferably selected from
      a) —$(CH_2)_n$—$C_{3-6}$-cycloalkyl,
      b) —$(CH_2)_n$-phenyl,
      c) —$(CH_2)_n$-5–10-membered heterocyclyl, and d)
      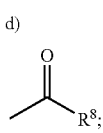

wherein the cycloalkyl and aryl groups are optionally substituted with 1 to 3 groups selected from $R^4$; and the heterocyclyl group is optionally substituted with 1 to 3 groups selected from $R^4$ and oxo;

even more preferably selected from
      a) —$(CH_2)_n$—$C_{3-6}$-cycloalkyl,
      b) —$(CH_2)_n$-phenyl, and
      c) —$(CH_2)_n$-6–10-membered heterocyclyl;
      wherein the cycloalkyl and aryl groups are optionally substituted with 1 to 2 groups selected from $R^{4b}$; and the heterocyclyl group is optionally substituted with 1 to 2 groups selected from $R^{4b}$ and oxo;
    of particular importance $R^2$ is selected from

indolyl $(CH_2)_n$—, phenyl$(CH_2)_n$—, benzoxazolyl$(CH_2)_n$—, oxazolo[4,5-b]pyridyl$(CH_2)_n$—, oxazolo[5,4-b]pyridyl$(CH_2)_n$—, benzoxazolyl$(CH_2)_n$—, 1,2,3,4-tetrahydro-isoquinolyl$(CH_2)_n$—, pyridyl$(CH_2)_n$— and 2,3-dihydro-benzo[1,4]dioxanyl$(CH_2)_n$—,
        wherein $R^2$ is optionally substituted with 1 to 2 groups selected from $R^{4b}$;
wherein $R^3$ is independently selected from H, halo, amino, haloalkyl, alkyl, phenyl, haloalkoxy and alkoxy; or $R^3$ is an alkenylene bridge;
  preferably H, halo, amino, $C_{1-6}$-haloalkyl, $C_{1-6}$-alkyl, phenyl, $C_{1-6}$-haloalkoxy and $C_{1-6}$-alkoxy; or $R^3$ is an $C_{2-4}$-alkenylene bridge;
    more preferably H, chloro, bromo, iodo, phenyl, fluoro, amino, $C_{1-2}$-alkyl, $C_{1-2}$-haloalkyl, $C_{1-2}$-haloalkoxy and $C_{1-2}$-alkoxy;
      even more preferably H, chloro, bromo, iodo, fluoro, amino, methyl, trifluoromethyl, trifluoromethoxy and methoxy;
        of particular interest are H, chloro, bromo, amino, methyl, trifluoromethyl and methoxy;
wherein $R^4$ is selected from H, alkyl, —$(CH_2)_n$-cycloalkyl, —$(CH_2)_n$-aryl, —$(CH_2)_n$-heterocyclyl, halo, —$(CH_2)_n$—$OR^9$, —$NR^9SO_2R^7$, —$[C(R^7)_2]_pNR^9SO_2R^7$, —$[C(R^7)_2]_pNR^9C(O)R^7$, —$N(R^9)_2$, —$C(O)NR^9R^9$, —$NR^9C(O)R^7$, —$NR^aCO_2R^7$, cyano, —$COOR^9$, —$[C(R^7)_2]_n$—$C$=$OR^7$, —$(CH_2)_n$—$C$=$SR^7$, —$(CH_2)_n$—$C$=$(NR^9)R^7$, —$NR^9C$=$(NR^7)N(R^9)_2$, —$[C(R^7)_2]_pN(R^9)_2$, nitro, —$SO_2N(R^9)_2$, —$S(O)_mR^7$, —$[C(R^7)_2]_nSO_2CF_3$, hydroxyalkyl, haloalkyl and haloalkoxy;
  preferably H, $C_{1-6}$-alkyl, —$(CH_2)_n$—$C_{3-6}$-cycloalkyl, —$(CH_2)_n$-aryl, —$(CH_2)_n$-4–10-membered heterocyclyl, halo, —$(CH_2)_n$—$OR^9$, —$NR^9SO_2R^7$, —$N(R^9)_2$, —$C(O)NR^9R^9$, —$NR^9C(O)R^7$, —$NR^9CO_2R^7$, nitro, cyano, —$[C(R^7)_2]_n$—$C(O)R^7$, —$C(O)OR^9$, —$(CH_2)_n$—$C(S)R^7$, —$(CH_2)_n$—$C$=$(NR^9)R^7$, —$NR^9C$=$(NR^7)N(R^7)_2$, —$[C(R^7)_2]_pNR^9SO_2R^7$, —$[C(R^7)_2]_pNR^9C(O)R^7$, —$[C(R^7)_2]_pN(R^9)_2$, —$SO_2N(R^9)_2$, —$S(O)_mR^7$, —$[C(R^7)_2]_nSO_2CF_3$, $C_{1-6}$-hydroxyalkyl, $C_{1-6}$-haloalkyl and $C_{1-6}$-haloalkoxy;
    more preferably H, $C_{1-2}$-alkyl, —$(CH_2)_n$—$C_{5-6}$-cycloalkyl, —$(CH_2)_n$-aryl, —$(CH_2)_n$-4–10-membered heterocyclyl, fluoro, chloro, —$(CH_2)_n$—$OR^{9a}$, —$NR^{9a}SO_2R^7$, —$NR^{9a}R^{9b}$, —$C(O)NR^{9a}R^{9b}$, —$NR^{9a}C(O)R^7$, —$NR^{9a}CO_2R^7$, cyano, nitro, —$C(R^7)_2)_n$—$C(O)R^7$, —$C(O)OR^{9a}$, —$(CH_2)_n$—$C(S)R^7$, —$(CH_2)_n$—$C$=$(NR^{9a})R^7$, —$NR^{9a}C$=$(NR^{9a})N(R^7)_2$, —$[C(R^7)_2]_pNR^{9a}R^{9b}$, —$[C(R^7)_2]_pNR^{9a}SO_2R^7$, —$[C(R^7)_2]_pNR^{9a}C(O)R^7$, —$SO_2NR^{9a}R^{9b}$, —$S(O)_mR^7$, —$C(R^7)_2SO_2CF_3$, $C_{1-2}$-hydroxyalkyl $C_{1-2}$-haloalkyl and $C_{1-2}$-haloalkoxy;

wherein $R^{4a}$ is selected from —$(CH_2)_n$—$OR^{9a}$, 4–6 membered heterocyclyl, —$NR^{9a}SO_2R^{7a}$, —$C_{1-3}$-alkyl-$NR^{9a}SO_2R^{7a}$, —$NR^{9a}R^{9b}$, —$C(O)NR^{9a}R^{9b}$, —$NR^{9a}CO_2R^{7b}$, —$NR^{9a}C(O)R^{7b}$, —$C_{1-3}$-alkyl-$NR^{9a}C(O)R^{7b}$, —$C_{1-3}$-alkyl-$C(O)R^{7a}$, nitro, —$C(O)OR^{9a}$, —$(CH_2)_n$—$C(S)R^{7a}$, —$C_{1-3}$-alkyl-$NR^{9a}R^{9b}$, —$SO_2NR^{9a}R^{9b}$, —$S(O)_mR^{7a}$ and —$C_{1-3}$-alkyl-$SO_2CF_3$;

preferably —$NR^{9a}SO_2R^{7a}$, —$NR^{9a}R^{9b}$, —$C(O)NR^{9a}R^{9b}$, —$C_{1-2}$-alkyl-$NR^{9a}SO_2R^{7a}$, —$C_{1-3}$-alkyl-$NR^{9a}C(O)R^{7b}$, —$NR^{9a}CO_2R^{7b}$, —$NR^{9a}C(O)R^{7b}$ and —$C_{1-3}$-alkyl-$NR^{9a}R^{9b}$;

wherein $R^{4b}$ is selected from H, $C_{1-2}$-alkyl, —$(CH_2)_n$—$C_{5-6}$-cycloalkyl, —$(CH_2)_n$-phenyl, —$(CH_2)_n$-4–10-membered heterocyclyl, fluoro, chloro, —$OR^{9a}$, —$(CH_2)_n$—$OR^{9a}$, —$NR^{9a}SO_2R^{7a}$, —$NR^{9a}R^{9b}$, —$C(O)NR^{9a}R^{9b}$, —$NR^{9a}C(O)R^{7b}$, —$(CH_2)_n$—$C(O)R^{7a}$, nitro, —$C(O)OR^{9a}$, —$(CH_2)_n$—$C(S)R^{7a}$, —$[C(R^{7a})_2]_pNR^{9a}R^{9b}$, —$SO_2NR^{9a}R^{9b}$, —$S(O)_mR^{7a}$, —$C(R^{7a})_2SO_2CF_3$, cyano, $C_{1-2}$-haloalkyl and $C_{1-2}$-haloalkoxy;

wherein $R^5$ is selected from halo, —$OR^9$, $NHSO_2R^7$, —$N(R^9)_2$, cyano, —$COR^7$, —$[C(R^7)_2]_nN(R^9)_2$, nitro, —$SO_2N(R^9)_2$, —$S(O)_mR^7$, haloalkyl, and haloalkoxy;

preferably halo, —$OR^9$, —$NHSO_2R^7$, —$N(R^9)_2$, cyano, —$COR^7$, —$[C(R^7)_2]_nN(R^9)_2$, nitro, —$SO_2N(R^9)_2$, —$S(O)_mR^7$, $C_{1-6}$-haloalkyl and $C_{1-6}$-haloalkoxy;

more preferably halo, —$OR^{9a}$, —$NR^{9a}R^{9b}$, —$C[(R^7)_2]_nNR^{9a}R^{9b}$ and —$SO_2NR^{9a}R^{9b}$;

even more preferably chloro, fluoro, hydroxyl, —$NR^{7a}R^{7b}$ and —$SO_2N(R^{7a})_2$;

wherein $R^6$ is selected from aryl and heteroaryl, wherein $R^6$ is optionally substituted with one or more $R^3$;

preferably phenyl and 6-membered heteroaryl, wherein $R^6$ is optionally substituted with one or more $R^3$;

more preferably phenyl optionally substituted with one or two $R^3$;

wherein $R^7$ is selected from H, alkyl, —$(CH_2)_n$-cycloalkyl, —$(CH_2)_n$-heterocyclyl, —$(CH_2)_n$-aryl, aminoalkyl, alkylamino, alkenyl, alkylcarbonylaminoalkyl, alkylthioalkyl, alkylaminoalkyl, alkoxyalkyl and alkoxy;

preferably H, $C_{1-6}$-alkyl, —$(CH_2)_n$—$C_{3-6}$-cycloalkyl, —$(CH_2)_n$-4–10-membered heterocyclyl, —$(CH_2)_n$-aryl, amino-$C_{1-6}$-alkyl, $C_{1-6}$-alkylamino, $C_{2-6}$-alkenyl, $C_{1-6}$-alkylthio-$C_{1-6}$-alkyl, $C_{1-6}$-alkylcarbonylamino-$C_{1-6}$-alkyl, $C_{1-6}$-alkylamino-$C_{1-6}$-alkyl, $C_{1-6}$-alkoxy-$C_{1-6}$-alkyl and $C_{1-6}$-alkoxy;

more preferably H, $C_{1-4}$-alkyl, —$(CH_2)_n$—$C_{3-6}$-cycloalkyl, —$(CH_2)_n$-4–10-membered heterocyclyl, —$(CH_2)_n$-phenyl, amino-$C_{1-4}$-alkyl, $C_{1-4}$-alkylamino, $C_{2-4}$-alkenyl, $C_{1-4}$-alkylthio-$C_{1-4}$-alkyl, $C_{1-4}$-alkylcarbonylamino-$C_{1-4}$-alkyl, $C_{1-4}$-alkylamino-$C_{1-4}$-alkyl, $C_{1-4}$-alkoxy-$C_{1-4}$-alkyl and $C_{1-4}$-alkoxy;

wherein $R^{7a}$ is selected from H, $C_{1-3}$-alkyl, —$(CH_2)_n$—$C_{5-6}$-cycloalkyl, —$(CH_2)_n$-4–10-membered heterocyclyl and —$(CH_2)_n$-phenyl;

wherein $R^{7b}$ is selected from amino-$C_{1-3}$-alkyl, $C_{1-3}$-alkoxy, $C_{1-3}$-alkylamino, $C_{2-3}$-alkenyl, $C_{1-3}$-alkylthio-$C_{1-3}$-alkyl, $C_{1-3}$-alkylamino-$C_{1-3}$-alkyl, $C_{1-3}$-alkoxy-$C_{1-3}$-alkyl, H, $C_{1-3}$-alkyl, —$(CH_2)_n$—$C_{5-6}$-cycloalkyl, —$(CH_2)_n$-4–10-membered heterocyclyl and —$(CH_2)_n$-phenyl;

wherein $R^8$ is selected from
a) heterocyclyl,
b) aminoalkyl,
c) aminoalkylamino,
d) alkylaminoalkylamino,
e) alkylaminoalkyl,
f) arylaminoalkyl,
g) arylalkylaminoalkyl,
h) heterocyclylalkylaminoalkyl,
i) aryl,
j) alkyl,
k) aralkyl,
l) heterocyclylalkyl,
m) cycloalkylalkyl,
n) —$OR^9$
o) aminoalkoxy,
p) N-(heterocyclylalkyl)amino,
q) aralkyl where the alkyl portion is substituted with amino, hydroxy or alkylamino, and
r) heterocyclylalkylenyl where the alkylenyl portion is substituted with amino, hydroxy or alkylamino; wherein the cycloalkyl and aryl groups are optionally substituted with 1 to 3 groups selected from $R^4$; the heterocyclyl group is optionally substituted with 1 to 3 groups selected from $R^4$ and oxo; and the alkyl group is optionally substituted with 1 to 3 groups selected from $R^5$;

preferably selected from
a) 4–10-membered heterocyclyl,
b) amino-$C_{1-6}$-alkyl,
c) amino-$C_{1-6}$-alkylamino,
d) $C_{1-6}$-alkylamino-$C_{1-6}$-alkylamino,
e) $C_{1-6}$-alkylamino-$C_{1-6}$-alkyl,
f) arylamino-$C_{1-6}$-alkyl,
g) aryl-$C_{1-6}$-alkylamino-$C_{1-6}$-alkyl,
h) 4–10-membered heterocyclyl-$C_{1-6}$-alkylamino-$C_{1-6}$-alkyl,
i) aryl,
j) $C_{1-6}$-alkyl,
k) aryl-$C_{1-6}$-alkyl,
l) heterocyclyl-$C_{1-6}$-alkyl,
m) o $C_{3-6}$-cycloalkyl-$(CH_2)_n$—,
n) —$OR^9$
o) amino-$C_{1-6}$-alkoxy,
p) N-(4–10-membered heterocyclyl-$C_{1-6}$-alkyl)amino,
q) aryl-$C_{1-6}$-alkyl where the alkyl portion is substituted with amino, hydroxy or $C_{1-6}$-alkylamino, and
r) 4–10-membered heterocyclyl-$C_{1-6}$-alkylenyl where the alkylenyl portion is substituted with amino, hydroxy or $C_{1-6}$-alkylamino;

more preferably selected from
a) amino-$C_{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenyl-$C_{1-4}$-amino-$C_{1-4}$-alkyl,
f) phenylamino-$C_{1-4}$-alkyl,
g) 4–10-membered heterocyclyl-$C_{1-4}$-alkylamino-$C_{1-4}$-alkyl,
h) N-(4–10-membered heterocyclyl-$C_{1-4}$-alkyl)amino,
i) $C_{1-4}$-alkyl,
j) $C_{3-6}$-cycloalkyl—$(CH_2)_n$—,
k) aryl-$(CH_2)_n$—,
l) 4–10-membered heterocyclyl-$(CH_2)_n$—,
m) $R^{9a}O$—,
n) amino-$C_{1-4}$-alkoxy,
o) phenyl-$C_{1-4}$-alkyl where the alkyl portion is substituted with amino, hydroxy or $C_{1-4}$-alkylamino, and
p) 4–10-membered heterocyclyl-$C_{1-4}$-alkylenyl where the alkylenyl portion is substituted with amino, hydroxy or $C_{1-4}$-alkylamino;

even more preferably selected from
a) amino-$C_{1-4}$-alkylamino,
b) amino-$C_{1-4}$-alkyl,
c) $C_{1-4}$-alkylamino-$C_{1-4}$-alkylamino,
d) $C_{1-4}$-alkylamino-$C_{1-4}$-alkyl,
e) phenyl-$C_{1-4}$-alkylamino-$C_{1-4}$-alkyl,
f) phenylamino-$C_{1-4}$-alkyl,
g) 4–10-membered heterocyclyl-$C_{1-4}$-alkylamino-$C_{1-4}$-alkyl,
h) N-(4–10-membered heterocyclyl-$C_{1-4}$-alkyl) amino,
i) $C_{1-4}$-alkyl,
j) $C_{3-6}$-cycloalkyl—$(CH_2)_n$—,
k) aryl-$(CH_2)_n$—,
l) 4–10-membered heterocyclyl-$(CH_2)_n$—,
m) amino-$C_{1-4}$-alkoxy,
n) phenyl-$C_{1-4}$-alkyl where the alkyl portion is substituted with amino, hydroxy or —$C_{1-2}$-alkylamino, and
o) 4–10-membered heterocyclyl-$C_{1-4}$-alkylenyl where the alkylenyl portion is substituted with amino, hydroxy or —$C_{1-4}$-alkylamino;
wherein the cycloalkyl and aryl groups are optionally substituted with 1 to 2 groups selected from $R^{4b}$; the heterocyclyl groups are optionally substituted with 1 to 2 groups selected from $R^{4b}$ and oxo; and the alkyl group is optionally substituted with 1 to 2 groups selected from $R^5$;
particularly

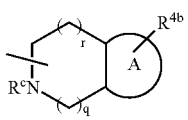

or azetidinyl;
more particularly

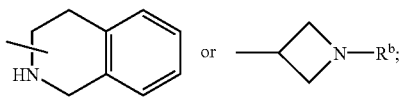

wherein $R^{8a}$ is selected from
a) 5–10-membered heterocyclyl,
b) aryl, and
c) benzyl;
wherein the aryl and heterocyclyl groups are optionally substituted with 1 to 3 radicals selected from $C_{1-6}$-alkyl, halo, hydroxyl, alkoxy, amino, alkylamino, cyano, —NHC(O)$R^7$, —COR$^7$, $C_{1-6}$-haloalkyl and $C_{1-6}$-haloalkoxy;
wherein $R^9$ is selected from H, alkyl, alkenyl, cycloalkyl-$(CH_2)_n$—, heterocyclyl-$(CH_2)_n$—, aryl$(CH_2)_n$—, aminoalkyl, alkylcarbonylaminoalkyl, cycloalkylaminoalkyl, cycloalkylalkylaminoalkyl, heteroarylaminoalkyl, heteroarylalkylaminoalkyl, arylaminoalkyl, arylalkylaminoalkyl, heteroaryloxyalkyl, heteroarylalkyloxyalkyl, arylalkyloxyalkyl, aryloxyalkyl, alkylthioalkyl, alkylaminoalkyl, hydroxyalkyl and alkoxyalkyl;
preferably H, $C_{1-6}$-alkyl, alkenyl, $C_{3-6}$-cycloalkyl-$(CH_2)_n$—, 4–10-membered heterocyclyl-$(CH_2)_n$—, aryl-$(CH_2)_n$—, amino-$C_{1-6}$-alkyl, $C_{1-6}$-alkylcarbonylamino-$C_{1-6}$-alkyl, $C_{3-6}$-cycloalkylamino-$C_{1-6}$-alkyl, $C_{3-6}$-cycloalkyl-$C_{1-6}$-alkylamino-$C_{1-6}$-alkyl, 5–6-membered heteroarylamino-$C_{1-6}$-alkyl, 5–6-membered heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, 5–6-membered heteroaryloxy-$C_{1-6}$-alkyl, 5–6-membered heteroaryl-$C_{1-6}$-alkyloxy-$C_{1-6}$-alkyl, aryl-$C_{1-6}$-alkyloxy-$C_{1-6}$-alkyl, aryloxy-$C_{1-6}$-alkyl, $C_{1-6}$-alkylthio-$C_{1-6}$-alkyl, $C_{1-6}$-alkylamino-$C_{1-6}$-alkyl, $C_{1-6}$-hydroxyalkyl and $C_{1-6}$-alkoxy-$C_{1-6}$-alkyl;
wherein $R^{9a}$ is selected from H, $C_{1-6}$-alkyl, $C_{3-6}$-cycloalkyl-$(CH_2)_n$—, 4–10-membered heterocyclyl-$(CH_2)_n$—, and phenyl-$(CH_2)_n$—;
preferably H, $C_{1-6}$-alkyl, $C_{5-6}$-cycloalkyl-$(CH_2)_n$—, 4–10-membered heterocyclyl-$(CH_2)_n$—, and phenyl-$(CH_2)_n$—;
wherein $R^{9b}$ is selected from H, $C_{1-6}$-alkyl, $C_{2-6}$-alkenyl, $C_{3-6}$-cycloalkyl-$(CH_2)_n$—, 4–10-membered heterocyclyl-$(CH_2)_n$—, phenyl-$(CH_2)_n$—, amino-$C_{1-6}$-alkyl, $C_{1-6}$-alkylcarbonylamino-$C_{1-6}$-alkyl, $C_{3-6}$-cycloalkylamino-$C_{1-6}$-alkyl, $C_{3-6}$-cycloalkyl-$C_{1-6}$-alkylamino-$C_{1-6}$-alkyl, 5–6-membered heteroarylamino-$C_{1-6}$-alkyl, 5–6-membered heteroaryl-$C_{1-6}$-alkylamino-$C_{1-6}$-alkyl, phenylamino-$C_{1-6}$-alkyl, phenyl-$C_{1-6}$-alkylamino-$C_{1-6}$-alkyl, 5–6-membered heteroaryloxy-$C_{1-6}$-alkyl, 5–6-membered heteroaryl-$C_{1-6}$-alkyloxy-$C_{1-6}$-alkyl, phenyl-$C_{1-6}$-alkyloxy-$C_{1-6}$-alkyl, phenyloxy-$C_{1-6}$-alkyl, $C_{1-6}$-alkylthio-$C_{1-6}$-alkyl, $C_{1-6}$-alkylamino-$C_{1-6}$-alkyl, $C_{1-6}$-hydroxyalkyl and $C_{1-6}$-alkoxy-$C_{1-6}$-alkyl;
preferably H, $C_{1-6}$-alkyl, $C_{5-6}$-cycloalkyl-$(CH_2)_n$—, 4–10-membered heterocyclyl-$(CH_2)_n$—, phenyl-$(CH_2)_n$—, amino-$C_{1-3}$-alkyl, $C_{1-3}$-alkylcarbonylamino-$C_{1-3}$-alkyl, $C_{5-6}$-cycloalkylamino-$C_{1-3}$-alkyl, $C_{5-6}$-cycloalkyl-$C_{1-3}$-alkylamino-$C_{1-3}$-alkyl, 5–6-membered heteroarylamino-$C_{1-3}$-alkyl, 5–6-membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6-membered heteroaryloxy-$C_{1-3}$-alkyl, 5–6-membered heteroaryl-$C_{1-3}$-alkyloxy-$C_{1-3}$-alkyl, phenyl-$C_{1-3}$-alkyloxy-$C_{1-3}$-alkyl, phenyloxy-$C_{1-3}$-alkyl, $C_{1-3}$-alkylthio-$C_{1-3}$-alkyl, $C_{1-3}$-alkylamino-$C_{1-3}$-alkyl, $C_{1-3}$-hydroxyalkyl and $C_{1-3}$-alkoxy-$C_{1-3}$-alkyl;
wherein $R^a$ are independently selected from H, and alkyl or the two $R^a$'s together form cycloalkyl;
preferably H, and $C_{1-6}$-alkyl or the two $R^a$ together form $C_{3-4}$-cycloalkyl;
more preferably H, and $C_{1-2}$-alkyl or the two $R^a$'s together form $C_{3-4}$-cycloalkyl;
wherein $R^a$ are H;
wherein $R^b$ is selected from H, $C_{1-6}$-alkyl, $C_{5-6}$-cycloalkyl-$(CH_2)_n$—, 4–10-membered heterocyclyl-$(CH_2)_n$— and phenyl-$(CH_2)_n$—;
wherein $R^c$ is H or methyl;
wherein A is selected from phenyl or 5–6-membered heteroaryl;
wherein k is 0 or 1; preferably 1;
wherein m is 0, 1 or 2; preferably 2;
wherein n is 0, 1, 2 or 3;
wherein p is 1 or 2;
wherein r is 0 or 1; and
wherein q is 0 or 1.

The invention also relates to compounds of Formula II

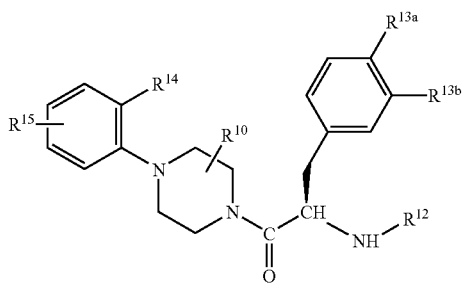

wherein $R^{10}$ is selected from H, chloro or fluoro; or wherein $R^{10}$ is a $C_{1-4}$-alkylene bridge;
preferably H;
wherein $R^{12}$ is selected from optionally substituted phenyl-$C_{1-2}$-alkylenyl, optionally substituted 5–10 membered heteroaryl and

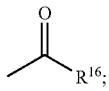

preferably

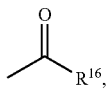

optionally substituted benzyl and optionally substituted 5–10-membered heterocyclyl;
more preferably oxazolylpyridyl, 4-(N,N-dimethylamino)phenylmethyl, 2,2-dimethyloxazolidinyl and

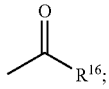

wherein $R^{13a}$ and $R^{13b}$ are independently selected from H, fluoro, iodo, bromo, chloro, $C_{1-2}$-alkyl, $C_{1-2}$-haloalkyl, and $C_{1-2}$-alkoxy; or wherein $R^{13a}$ and $R^{13b}$ together form an $C_{1-4}$-alkenylenyl bridge;
preferably H, chloro, trifluoromethyl and methoxy;
more preferably H and chloro;
wherein $R^{14}$ is selected from $R^{19}R^{20}N—$, $R^{19}R^{20}N—C_{1-4}$-alkyl, $(R^{21}R^{22}N—)(O=)C—$, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;
preferably trifluoromethyl, 2-hydroxyethyl, 1-hydroxyethyl, $R^{19}R^{20}N—$, $R^{19}R^{20}N—C_{1-2}$-alkyl and $(R^{21}R^{22}N—)(O=)C—$;
more preferably N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl,
1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-ylmethyl, 3-pyridyl-oxymethyl, 2-methylimidazol-1-ylmethyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-ylmethyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-methoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl,
N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'-dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(cyclopropylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)

methylsulfonylamino, (2,4,6-trimethylphenyl)
sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

wherein $R^{15}$ is selected from H, $C_{1-2}$-haloalkyl, $C_{1-4}$-alkyl, halo, $-OR^{17}$, and $-N(R^{17})_2$;
preferably H and $C_{1-2}$-haloalkyl;
more preferably H or trifluoromethyl;
wherein $R^{16}$ is selected from
a) 4–6 membered saturated heterocyclyl,
b) 10 membered partially saturated heterocyclyl,
c) 5–10 membered heteroaryl,
d) $C_{1-4}$-aminoalkyl,
e) $C_{1-4}$-aminoalkylamino,
f) $C_{1-4}$-alkylamino-$C_{1-4}$-alkylamino,
g) $C_{1-4}$-alkylamino-$C_{1-4}$-alkyl,
h) arylamino-$C_{1-4}$-alkyl,
i) aryl-$C_{1-4}$-alkylamino-$C_{1-4}$-alkyl,
j) heterocyclyl-$C_{1-4}$-alkylamino-$C_{1-4}$-alkyl,
k) aryl, provided if 2-substituted aryl, is 2-substituted with amino or chloro,
l) $C_{1-4}$-alkyl,
m) aryl-$C_{1-4}$-alkyl,
n) heterocyclyl-$C_{1-4}$-alkyl, provided $R^{16}$ is not 3-methylindol-1-ylethyl,
o) $C_{5-6}$-cycloalkyl,
p) $C_{1-4}$-aminoalkoxy,
q) heterocyclyl-$C_{1-4}$-alkoxy,
r) N-(heterocyclyl-$C_{1-4}$-alkyl)amino,
s) aryl-$C_{1-4}$-alkyl where the alkyl portion is substituted with amino, hydroxy or $C_{1-4}$-alkylamino, and
t) heterocyclyl-$C_{1-4}$-alkylenyl where the alkylenyl portion is substituted with amino, hydroxy or $C_{1-4}$-alkylamino;
preferably selected from
a) 4–6 membered saturated heterocyclyl,
b) 10 membered partially saturated heterocyclyl,
c) 5–10 membered heteroaryl,
d) $C_{1-3}$-aminoalkyl,
e) $C_{1-3}$-aminoalkylamino,
f) $C_{1-3}$-alkylamino-$C_{1-3}$-alkylamino,
g) $C_{1-3}$-alkylamino-$C_{1-3}$-alkyl,
h) phenylamino-$C_{1-3}$-alkyl,
i) phenyl-$C_{1-4}$-alkylamino-$C_{1-3}$-alkyl,
j) heterocyclyl-$C_{1-3}$-alkylamino-$C_{1-3}$-alkyl,
k) phenyl, naphthyl or tetrahydronaphthyl,
l) $C_{1-3}$-alkyl,
m) phenyl-$C_{1-2}$-alkyl,
n) 5–10-membered saturated or partially unsaturated heterocyclylmethyl,
o) 5–6 membered heteroaryl-$C_{1-4}$-alkyl,
p) $C_{5-6}$-cycloalkyl,
q) $C_{1-3}$-aminoalkoxy,
r) [5- or 6-membered heterocyclyl]-$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;
more preferably N-(piperidylmethyl)amino, aminopropylamino, aminomethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl optionally N-substituted with a substituent
selected from methyl, ethyl, propyl, isopropyl, butyl, isobutyl, pentyl, cyclohexylmethyl and benzyl,
6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl)methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino)ethyl, imidazol-4-yl-(1-amino)ethyl, phenyl-1-(methylamino)ethyl and phenyl-1-(amino)ethyl;

wherein $R^{17}$ is selected from H, $C_{1-4}$-alkyl, $C_{3-7}$-cycloalkyl-$(CH_2)_n$—, and aryl-$(CH_2)_n$—;

preferably H, $C_{1-3}$-alkyl, —$(CH_2)_n$—$C_{3-6}$-cycloalkyl, and —$(CH_2)_n$-phenyl;

more preferably H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;

wherein $R^{19}$ is selected from H, $R^{23}SO_2$—, $C_{1-6}$-alkyl, $C_{3-7}$-cycloalkyl-$(CH_2)_n$—, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl $C_{1-6}$-alkylcarbonyl, heteroaryl-$C_{1-6}$-alkylcarbonyl and heteroarylcarbonyl;

preferably H, $R^{23}SO_2$—, $C_{1-6}$-alkyl, amino-$C_{1-3}$-alkyl, $C_{1-5}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and —$(CH_2)_n$—$C_{3-5}$-cycloalkyl optionally substituted with $C_{1-2}$-alkoxycarbonyl;

more preferably H, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-tert-butylmethylaminoethyl, furylmethylaminoethyl, thienylmethylaminoethyl, benzylaminoethyl, di(furylmethyl)aminoethyl, di(cyclopropylmethyl)aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, tert-butylcarbonyl, pentylcarbonyl, cyclopentylcarbonyl, cyclopropylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted benzylcarbonyl, optionally substituted phenylethylcarbonyl, optionally substituted phenylcarbonyl and optionally substituted pyridylcarbonyl;

wherein $R^{20}$ is selected from H, $C_{1-8}$-alkyl, $C_{3-7}$-cycloalkyl-$(CH_2)_n$—, $C_{1-3}$-alkylsulfonyl, amino-$C_{1-3}$-alkylamino, heterocyclyl-$(CH_2)_n$—, and aryl-$(CH_2)_n$—;

preferably H, $C_{1-7}$-alkyl, —$(CH_2)_n$—$C_{5-6}$ cycloalkyl, —$(CH_2)_n$-5–6-membered heterocyclyl, $C_{1-3}$-alkylsulfonyl, amino-$C_{1-3}$-alkyl and —$(CH_2)_n$-phenyl;

more preferably H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a 4–7 membered heterocyclic ring;

preferably a 5 membered heterocyclic ring;

more preferably a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally substituted with one or more substituents selected from methyl, ethyl, propyl, and isopropyl, piperazinyl optionally substituted with one or more substituents selected from methyl, ethyl, propyl, and isopropyl, imidazolyl optionally substituted with one or more substituents selected from methyl, ethyl, propyl, and isopropyl, and pyrrolidinyl optionally substituted with one or more substituents selected from methyl, ethyl, propyl, and isopropyl;

wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n$—, $C_{3-7}$-cycloalkyl-$(CH_2)_n$—, and aryl-$(CH_2)_n$—;

preferably H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;

more preferably H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

more preferably H or methyl;

alternatively $R^{21}$ and $R^{22}$ together with the amide nitrogen atom form a 4–7 membered saturated heterocyclic ring;
  preferably a 5–6 membered heterocyclic ring;
    more preferably a ring selected from pyrrolidinyl, morpholino, piperidinyl, piperazinyl, 4-acetylpiperazinyl and 4-methylpiperazinyl;
wherein $R^{23}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;
  preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;
    more preferably H, methyl, ethyl, propyl, optionally substituted thienyl, optionally substituted phenyl, optionally substituted benzyl, optionally substituted phenylethyl and optionally substituted phenylpropyl;
wherein n is 0, 1, 2 or 3;
wherein m is 0, 1 or 2; and
wherein aryl, heterocyclyl are optionally substituted with one or more substituents selected from $C_{1-2}$-haloalkyl, $C_{1-3}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-3}$-haloalkoxy;
  preferably with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-2}$-haloalkoxy;
    more preferably with one or more substituents selected from trifluoromethyl, methyl, nitro, cyano, chloro, methoxy, phenyloxy, acetyl, amino, dimethylamino and aminomethyl.

The invention also relates to compounds of Formula III

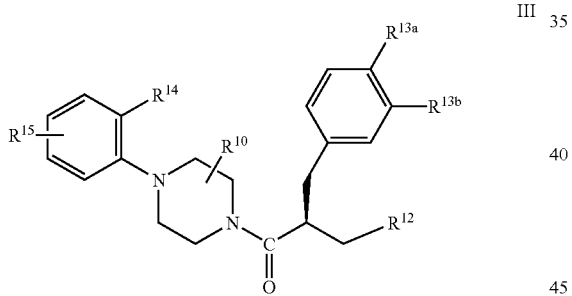

III wherein $R^{10}$ is selected from H, chloro or fluoro; or wherein $R^{10}$ is a $C_{1-4}$-alkylene bridge;
  preferably H;
wherein $R^{12}$ is selected from optionally substituted phenyl-$C_{1-2}$-alkylenyl, optionally substituted 5–10 membered heteroaryl and

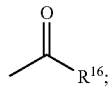

preferably

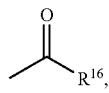

optionally substituted benzyl and optionally substituted 5–10-membered heterocyclyl;

more preferably oxazolylpyridyl, 4-(N,N-dimethylamino)phenylmethyl, 2,2-dimethyl-oxazolidinyl and

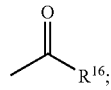

wherein $R^{13a}$ and $R^{13b}$ are independently selected from H, fluoro, iodo, bromo, chloro, $C_{1-2}$-alkyl, $C_{1-2}$-haloalkyl, and $C_{1-2}$-alkoxy; or wherein $R^{13a}$ and $R^{13b}$ together form an $C_{1-4}$-alkenylenyl bridge;
  preferably H, chloro, trifluoromethyl and methoxy;
    more preferably H and chloro;
wherein $R^{14}$ is selected from $R^{19}R^{20}N$—, $R^{19}R^{20}N$—$C_{1-4}$-alkyl, $(R^{21}R^{22}N)(O=)C$—, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;
  preferably trifluoromethyl, 2-hydroxyethyl, 1-hydroxyethyl, $R^{19}R^{20}N$—, $R^{19}R^{20}N$—$C_{1-2}$-alkyl and $(R^{21}R^{22}N)(O=)C$—;
    more preferably N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl, 1-(N-cyclopropylmethylamino)ethyl, 1-(N-methyl-N-methylcarbonylamino)ethyl, 1-(N-isopropylamino) ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-yl-methyl, 3-pyridyl-oxymethyl, 2-methylimidazol-1-ylmethyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)

methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino) ethyl, 1-(N-(4-methoxyphenyl)methyl-N-methylamino)ethyl, 1-(N-benzyl-N-methylamino) ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl, N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'-dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(cyclopropylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6-trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

wherein $R^{15}$ is selected from H, $C_{1-2}$-haloalkyl, $C_{1-4}$-alkyl, halo, —$OR^{17}$, and —$N(R^{17})_2$;

preferably H and $C_{1-2}$-haloalkyl;

more preferably H or trifluoromethyl;

wherein $R^{16}$ is selected from a) 4–6 membered saturated heterocyclyl, b) 10 membered partially saturated heterocyclyl, c) 5–10 membered heteroaryl, d) $C_{1-4}$-aminoalkyl, e) $C_{1-4}$-aminoalkylamino, f) $C_{1-4}$-alkylamino-$C_{1-4}$-alkylamino, g) $C_{1-4}$-alkylamino-$C_{1-4}$-alkyl, h) arylamino-$C_{1-4}$-alkyl, i) aryl-$C_{1-4}$-alkylamino-$C_{1-4}$-alkyl, j) heterocyclyl-$C_{1-4}$-alkylamino-$C_{1-4}$-alkyl, k) aryl, provided if 2-substituted aryl, is 2-substituted with amino or chloro, l) $C_{1-4}$-alkyl, m) aryl-$C_{1-4}$-alkyl, n) heterocyclyl-$C_{1-4}$-alkyl, provided $R^{16}$ is not 3-methylindol-1-ylethyl, o) $C_{5-6}$-cycloalkyl, p) $C_{1-4}$-aminoalkoxy, q) heterocyclyl-$C_{1-4}$-alkoxy, r) N-(heterocyclyl-$C_{1-4}$-alkyl)amino, s) aryl-$C_{1-4}$-alkyl where the alkyl portion is substituted with amino, hydroxy or $C_{1-4}$-alkylamino, and t) heterocyclyl-$C_{1-4}$-alkylenyl where the alkylenyl portion is substituted with amino, hydroxy or $C_{1-4}$-alkylamino;

preferably selected from a) 4–6 membered saturated heterocyclyl, b) 10 membered partially saturated heterocyclyl, c) 5–10 membered heteroaryl, d) $C_{1-3}$-aminoalkyl, e) $C_{1-3}$-aminoalkylamino, f) $C_{1-3}$-alkylamino-$C_{1-3}$-alkylamino, g) $C_{1-3}$-alkylamino-$C_{1-3}$-alkyl, h) phenylamino-$C_{1-3}$-alkyl, i) phenyl-$C_{1-4}$-alkylamino-$C_{1-3}$-alkyl,
j) heterocyclyl-$C_{1-3}$-alkylamino-$C_{1-3}$-alkyl,
k) phenyl, naphthyl or tetrahydronaphthyl,
l) $C_{1-3}$-alkyl,
m) phenyl-$C_{1-2}$-alkyl,
n) 5–10-membered saturated or partially unsaturated heterocyclylmethyl,
o) 5–6 membered heteroaryl-$C_{1-4}$-alkyl,
p) $C_{5-6}$-cycloalkyl,
q) $C_{1-3}$-aminoalkoxy,
r) [5- or 6-membered heterocyclyl]-$C_{1-3}$-alkoxy,
s) N-(5–10-membered heterocyclyl-$C_{1-3}$-alkyl)amino,
t) phenyl-$C_{1-2}$-alkyl where the alkyl portion is substituted with amino, hydroxy or $C_{1-3}$-alkylamino, and
u) 5- or 6-membered heterocyclyl-$C_{1-3}$-alkylenyl where the alkylenyl portion is substituted with amino, hydroxy or $C_{1-3}$-alkylamino;

more preferably N-(piperidylmethyl)amino, aminopropylamino, aminomethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl optionally N-substituted with a substituent
selected from methyl, ethyl, propyl, isopropyl, butyl, isobutyl, pentyl, cyclohexylmethyl and benzyl,
6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl)methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino)ethyl, imidazol-4-yl-(1-amino)ethyl, phenyl-1-(methylamino)ethyl and phenyl-1-(amino)ethyl;

wherein $R^{17}$ is selected from H, $C_{1-4}$-alkyl, $C_{3-7}$-cycloalkyl-$(CH_2)_n$—, and aryl-$(CH_2)_n$—;
preferably H, $C_{1-3}$-alkyl, —$(CH_2)_n$—$C_{36}$-cycloalkyl, and —$(CH_2)_n$-phenyl;
more preferably H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;

wherein $R^{19}$ is selected from H, $R^{23}SO_2$—, $C_{1-6}$-alkyl, $C_{3-7}$-cycloalkyl-$(CH_2)_n$—, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkyl, $C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;

preferably H, $R^{23}SO_2$—, $C_{1-6}$-alkyl, $C_{3-7}$-cycloalkyl-$(CH_2)_n$—, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;

more preferably H, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-tert-butylmethylaminoethyl, furylmethylaminoethyl, thienylmethylaminoethyl, benzylaminoethyl, di(furylmethyl)aminoethyl, di(cyclopropylmethyl)aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, tert-butylcarbonyl, pentylcarbonyl, cyclopentylcarbonyl, cyclopropylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted benzylcarbonyl, optionally substituted phenylethylcarbonyl, optionally substituted phenylcarbonyl and optionally substituted pyridylcarbonyl;

wherein $R^{20}$ is selected from H, $C_{1-8}$-alkyl, $C_{3-7}$-cycloalkyl-$(CH_2)_n$—, $C_{1-3}$-alkylsulfonyl, amino-$C_{1-3}$-alkylamino, heterocyclyl-$(CH_2)_n$—, and aryl-$(CH_2)_n$—;

preferably H, $C_{1-7}$-alkyl, —$(CH_2)_n$—$C_{5-6}$-cycloalkyl, —$(CH_2)_n$-5–6-membered heterocyclyl, $C_{1-3}$-alkylsulfonyl, amino-$C_{1-3}$-alkyl and —$(CH_2)_n$-phenyl;
more preferably H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a 4–8 membered heterocyclic ring;
preferably a 5 membered heterocyclic ring;
more preferably a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally
substituted with one or more substituents selected from methyl, ethyl, propyl, and isopropyl, piperazinyl optionally substituted with one or more substituents selected from methyl, ethyl, propyl, and isopropyl, imidazolyl optionally substituted with one or more substituents selected from methyl, ethyl, propyl, and isopropyl, and pyrrolidinyl optionally substituted with one or more substituents selected from methyl, ethyl, propyl, and isopropyl;

wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n$—, $C_{3-7}$-cycloalkyl-$(CH_2)_n$—, and aryl-$(CH_2)_n$—;

preferably H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;

more preferably H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

more preferably H or methyl;

alternatively $R^{21}$ and $R^{22}$ together with the amide nitrogen atom form a 4–7 membered saturated heterocyclic ring;

preferably a 5–6 membered heterocyclic ring;

more preferably a ring selected from pyrrolidinyl, morpholino, piperidinyl, piperazinyl, 4-acetylpiperazinyl and 4-methylpiperazinyl;

wherein $R^{23}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

more preferably H, methyl, ethyl, propyl, optionally substituted thienyl, optionally substituted phenyl, optionally substituted benzyl, optionally substituted phenylethyl and optionally substituted phenylpropyl;

wherein n is 0, 1, 2 or 3;

wherein m is 0, 1 or 2; and wherein aryl, heterocyclyl are optionally substituted with one or more substituents selected from $C_{1-2}$-haloalkyl, $C_{1-3}$-alkyl, —$(CH_2)_n$—$C_{4-6}$-cycloalkyl, chloro, fluoro, —$OR^{17}$, —$NR^{17}CO_2R^{17}$, —$NR^{17}SO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-3}$-haloalkoxy;

preferably with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$, —$NR^{17}SO_2R^{17}$, —$NR^{17}CO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-2}$-haloalkoxy;

more preferably with one or more substituents selected from trifluoromethyl, methyl, nitro, cyano, chloro, methoxy, phenyloxy, acetyl, amino, dimethylamino and aminomethyl.

The invention also relates to compounds of Formula IV

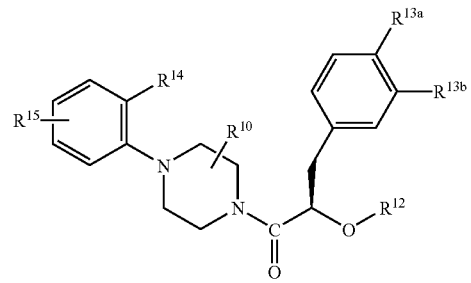

wherein $R^{10}$ is selected from H, chloro or fluoro; or wherein $R^{10}$ is a $C_{1-4}$-alkylene bridge;

preferably H;

wherein $R^{12}$ is selected from optionally substituted phenyl-$C_{1-2}$-alkylenyl, optionally substituted 5–10 membered heteroaryl and

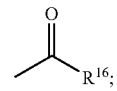

preferably

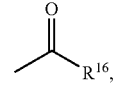

optionally substituted benzyl, and optionally substituted 5–10-membered heteroaryl;

more preferably oxazolylpyridyl, 4-(N,N-dimethylamino)phenylmethyl, 2,2-dimethyl-oxazolidinyl, and

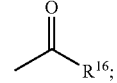

wherein $R^{13a}$ and $R^{13b}$ are independently selected from H, fluoro, iodo, bromo, chloro, $C_{1-2}$-alkyl, $C_{1-2}$-haloalkyl, and $C_{1-2}$-alkoxy; or wherein $R^{13a}$ and $R^{13b}$ together form an $C_{1-4}$-alkenylenyl bridge;

preferably H, chloro, trifluoromethyl and methoxy;

more preferably H and chloro;

wherein $R^{14}$ is selected from $R^{19}R^{20}N$—, $R^{19}R^{20}N$—$C_{1-4}$-alkyl, $(R^{21}R^{22}N)(O=)C$—, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;

preferably trifluoromethyl, 2-hydroxyethyl, 1-hydroxyethyl, $R^{19}R^{20}N$—, $R^{19}R^{20}N$—$C_{1-2}$-alkyl and $(R^{21}R^{22}N)(O=)C$—;

more preferably N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl, 1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-yl-methyl, 3-pyridyl-oxymethyl, 2-methylimidazol-1-yl-methyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl, N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'-dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(cyclopropylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6-trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

wherein $R^{15}$ is selected from H, $C_{1-2}$-haloalkyl, $C_{1-4}$-alkyl, halo, —$OR^{17}$, and —$N(R^{17})_2$;
preferably H and $C_{1-2}$-haloalkyl;
more preferably H or trifluoromethyl;

wherein $R^{16}$ is selected from
  a) 4–6 membered saturated heterocyclyl,
  b) 10 membered partially saturated heterocyclyl,
  c) 5–10 membered heteroaryl,
  d) $C_{1-4}$-aminoalkyl,
  e) $C_{1-4}$-aminoalkylamino,
  f) $C_{1-4}$-alkylamino-$C_{1-4}$-alkylamino,
  g) $C_{1-4}$-alkylamino-$C_{1-4}$-alkyl,
  h) arylamino-$C_{1-4}$-alkyl,
  i) aryl-$C_{1-4}$-alkylamino-$C_{1-4}$-alkyl,
  j) heterocyclyl-$C_{1-4}$-alkylamino-$C_{1-4}$-alkyl,
  k) aryl, provided if 2-substituted aryl, is 2-substituted with amino or chloro,
  l) $C_{1-4}$-alkyl,
  m) aryl-$C_1$–$C_4$-alkyl,
  n) heterocyclyl-$C_{1-4}$-alkyl, provided $R^{16}$ is not 3-methylindol-1-ylethyl,
  o) $C_{5-6}$-cycloalkyl,
  p) $C_{1-4}$-aminoalkoxy,
  q) heterocyclyl-$C_{1-4}$-alkoxy,
  r) N-(heterocyclyl-$C_{1-4}$-alkyl)amino,
  s) aryl-$C_{1-4}$-alkyl where the alkyl portion is substituted with amino, hydroxy or alkylamino, and
  t) heterocyclyl-$C_{1-4}$-alkylenyl where the alkylenyl portion is substituted with amino, hydroxy or $C_1$–$C_4$-alkylamino;
preferably selected from
  a) 4–6 membered saturated heterocyclyl,
  b) 10 membered partially saturated heterocyclyl,
  c) 5–10 membered heteroaryl,
  d) $C_{1-3}$-aminoalkyl,
  e) $C_{1-3}$-aminoalkylamino,
  f) $C_{1-3}$-alkylamino-$C_{1-3}$-alkylamino,
  g) $C_{1-3}$-alkylamino-$C_{1-3}$-alkyl,
  h) phenylamino-$C_{1-3}$-alkyl,
  i) phenyl-$C_{1-4}$-alkylamino-$C_{1-3}$-alkyl,
  j) heterocyclyl-$C_{1-3}$-alkylamino-$C_{1-3}$-alkyl,
  k) phenyl, naphthyl or tetrahydronaphthyl
  l) $C_{1-3}$-alkyl,
  m) phenyl-$C_{1-2}$-alkyl,
  n) 5–10-membered saturated or partially unsaturated heterocyclylmethyl,
  o) 5–6 membered heteroaryl-$C_{1-4}$-alkyl,
  p) $C_{5-6}$-cycloalkyl,
  q) $C_{1-3}$-aminoalkoxy,
  r) [5- or 6-membered heterocyclyl]-$C_{1-3}$-alkoxy,
  s) N-(5–10-membered heterocyclyl-$C_{1-3}$-alkyl)amino,
  t) phenyl-$C_{1-2}$-alkyl where the alkyl portion is substituted with amino, hydroxy or $C_{1-3}$-alkylamino, and
  u) 5- or 6-membered heterocyclyl-$C_{1-3}$-alkylenyl where the alkylenyl portion is substituted with amino, hydroxy or $C_{1-3}$-alkylamino;
    more preferably N-(piperidylmethyl)amino, aminopropylamino, aminomethyl, aminoethyl, aminopropyl, N-methylaminomethyl, N-(4-chlorophenyl)aminoethyl, N-methylaminoethyl, N,N-dimethylaminoethyl, 2-aminoethyl, aminopropoxy, pyrrolidinylmethoxy, N-methylaminoethylamino, 3-aminocyclopentyl, 4-aminocyclohexyl, 1-aminocyclohexyl, 2-indolyl, octahydro-indolyl, 1-methylindol-2-yl, 3-pyridyl, 2-pyridyl, N-methylbenzopyrrolyl, 5-benzopyrrolyl, 2-benzofuran, benzodioxolyl, 2-benzothienyl, 4-imidazolylmethyl, 3-azetidinyl optionally N-substituted with a substituent selected from methyl, ethyl, propyl, isopropyl, butyl, isobutyl, pentyl, cyclohexylmethyl and benzyl, 6-quinolyl, 2-quinolyl, 3-isoquinolyl, tetrahydroisoquinolyl, N-methylpyrrolidin-2-yl, pyrrolidin-2-yl, 5-oxopyrrolidin-2-yl, 3-phenylpyrrolidin-2-yl, (1-methyl-5-oxo-2-(pyridin-3-yl)-pyrrolidin-3-yl)methyl, thienyl, 4-piperidyl, 4-piperidylmethyl, N-methyl-4-piperidyl, N-methyl-2-piperidyl, N-ethyl-4-piperidyl, N-isobutyl-4-piperidyl, 3-piperidyl, 3-(aminomethyl)phenyl, 4-(trifluoromethyl)phenyl, 3-(trifluoromethyl)phenyl, 2-methylphenyl, 4-methoxyphenyl, 4-chlorophenyl, 3-chlorophenyl, 2-chlorophenyl, 3,4-dichlorophenyl, 4-fluorophenyl, 3-fluorophenyl, 2-aminophenyl, 3-aminophenyl, isopropyl, 4-chlorophenylmethyl, benzyl, phenyl-2-hydroxyethyl, 1-(amino)benzyl, 2-(1,2,3,4-tetrahydronaphthyl), naphthyl, (2-benzylamino) ethyl, imidazol-4-yl-(1-amino)ethyl, phenyl-1-(methylamino)ethyl and phenyl-1-(amino)ethyl;
wherein $R^{17}$ is selected from H, $C_{1-4}$-alkyl, $C_{3-7}$-cycloalkyl-$(CH_2)_n$—, and aryl-$(CH_2)_n$—;
  preferably H, $C_{1-3}$-alkyl, —$(CH_2)_n$—$C_{3-6}$-cycloalkyl, and —$(CH_2)_n$-phenyl;
    more preferably H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;
wherein $R^{19}$ is selected from H, $R^{23}SO_2$—, $C_{1-6}$-alkyl, amino-$C_{1-3}$-alkyl, $C_{1-5}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and —$(CH_2)_n$—$C_{3-5}$-cycloalkyl optionally substituted with $C_{1-2}$-alkoxycarbonyl;
  preferably $R^{23}SO_2$—, amino-$C_{1-3}$-alkyl, $C_{1-3}$-alkylcarbonyl, $C_{1-3}$-alkoxycarbonyl, $C_{1-3}$-alkylaminocarbonyl and 5- or 6-membered heteroarylcarbonyl;
    more preferably H, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, $R^{23}SO_2$—, aminomethyl, aminoethyl, dimethylaminoethyl, diethylaminoethyl, dipropylaminoethyl, di-isobutylaminoethyl, di-tert-butylmethylaminoethyl, furylmethylaminoethyl, thienylmethylaminoethyl, benzylaminoethyl, di(furylmethyl)aminoethyl, di(cyclopropylmethyl) aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, tert-butylcarbonyl, pentylcarbonyl, cyclopentylcarbonyl, cyclopropylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted benzylcarbonyl, optionally substituted phenylethylcarbonyl, optionally substituted phenylcarbonyl and optionally substituted pyridylcarbonyl;

wherein $R^{20}$ is selected from H, $C_{1-8}$-alkyl, $C_{3-7}$-cycloalkyl-$(CH_2)_n$—, $C_{1-3}$-alkylsulfonyl, amino-$C_{1-3}$-alkylamino, heterocyclyl-$(CH_2)_n$—, and aryl-$(CH_2)_n$—;

preferably H, $C_{1-7}$-alkyl, —$(CH_2)_n$—$C_{5-6}$-cycloalkyl, —$(CH_2)_n$-5–6-membered heterocyclyl, $C_{1-3}$-alkylsulfonyl, amino-$C_{1-3}$-alkyl and —$(CH_2)_n$-phenyl;

more preferably H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;

alternatively $R^{19}$ and $R^{20}$ together with the nitrogen atom form a 4–8 membered heterocyclic ring;

preferably a 5 membered heterocyclic ring;

more preferably a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally substituted with one or more substituents selected from methyl, ethyl, propyl, and isopropyl, piperazinyl optionally substituted with one or more substituents selected from methyl, ethyl, propyl, and isopropyl, imidazolyl optionally substituted with one or more substituents selected from methyl, ethyl, propyl, and isopropyl, and pyrrolidinyl optionally substituted with one or more substituents selected from methyl, ethyl, propyl, and isopropyl;

wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n$—, $C_{3-7}$-cycloalkyl-$(CH_2)_n$—, and aryl-$(CH_2)_n$—;

preferably H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, —$(CH_2)_n$-[5- or 6-membered heterocyclyl], —$(CH_2)_n$—$C_{5-6}$-cycloalkyl, and —$(CH_2)_n$-phenyl;

more preferably H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;

wherein $R^{22}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

more preferably H or methyl;

alternatively $R^{21}$ and $R^{22}$ together with the amide nitrogen atom form a 4–7 membered saturated heterocyclic ring;

preferably a 5–6 membered heterocyclic ring;

more preferably a ring selected from pyrrolidinyl, morpholino, piperidinyl, piperazinyl, 4-acetylpiperazinyl and 4-methylpiperazinyl;

wherein $R^{23}$ is selected from H, $C_{1-6}$-alkyl, —$(CH_2)_n$—$C_{3-7}$-cycloalkyl, —$(CH_2)_n$-heterocyclyl and —$(CH_2)_n$-aryl;

preferably H, $C_{1-3}$-alkyl, —$(CH_2)_n$—$C_{4-6}$-cycloalkyl, —$(CH_2)_n$-[5- or 6-membered heterocyclyl] and —$(CH_2)_n$-phenyl;

more preferably H, methyl, ethyl, propyl, optionally substituted thienyl, optionally substituted phenyl, optionally substituted benzyl, optionally substituted phenylethyl and optionally substituted phenylpropyl;

wherein n is 0, 1, 2 or 3;

wherein m is 0, 1 or 2; and wherein aryl, heterocyclyl are optionally substituted with one or more substituents selected from $C_{1-2}$-haloalkyl, $C_{1-3}$-alkyl, —$(CH_2)_n$—$C_{4-6}$-cycloalkyl, chloro, fluoro, —$OR^{17}$, —$NR^{17}SO_2R^{17}$, —$NR^{17}CO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-3}$-haloalkoxy;

preferably with one or more substituents selected from $C_{1-2}$-haloalkyl, $C_{1-2}$-alkyl, —$(CH_2)_n$—$C_{4-6}$-cycloalkyl, chloro, fluoro, —$OR^{17}$, —$NR^{17}SO_2R^{17}$, —$NR^{17}CO_2R^{17}$, $N(R^{17})_2$, cyano, —$COR^{17}$, —$C(R^{17})_2N(R^{17})_2$, nitro, —$SO_2N(R^{17})_2$, —$S(O)_mR^{17}$, and $C_{1-2}$-haloalkoxy;

more preferably with one or more substituents selected from trifluoromethyl, methyl, nitro, cyano, chloro, methoxy, phenyloxy, acetyl, amino, dimethylamino and aminomethyl.

Indications

Compounds of the present invention would be useful for, but not limited to, the prevention or treatment of obesity and obesity-related diseases. The compounds of the invention have MCR agonist activity, including MCR4 agonist activity.

Compounds of formula I are MCR agonists and as such are useful in the treatment, control or prevention of diseases, disorders or conditions responsive to the activation of one or more of the MCRs including, but are not limited to, MCR1, MCR2, MCR3, MCR4, and/or MCR5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunomodulation, rheumatoid arthritis, skin tanning, acne and other skin disorders, neuroprotective and cognitive and memory enhancement including the treatment of Alzheimer's disease.

Other conditions that can be treated with the MC receptor agonists of the invention include, but are not limited to, disuse deconditioning; organ damage such as occurs in response to organ transplantation or ischemic injury such as that which can occur after reperfusion or stroke; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas' Disease.

Another aspect of the present invention provides a method for the treatment or prevention of obesity or diabetes in a mammal which comprises administering to said mammal an effective amount of a compound of Formulas I–IV. Compounds of the present invention also are useful as G-protein agonists.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

As used herein, the terms "regulate" or "regulatory" mean to control by enhancing, limiting, restricting, restraining, modulating or moderating. Such regulation includes the pleiotropic, redundant, synergistic or antagonistic effects that occur due to the activity of biological agents such as cytokines, which can affect a variety of biological functions directly or indirectly through cascade or biofeedback mechanisms.

The term "prevention" includes either preventing the onset of disorders altogether or delaying the onset of a pre-clinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

As used herein, "MCR4 agonist" and "MCR3 agonist" refers to a compound with affinity for MCR4 or MCR3, respectively, that results in measurable biological activity in cells, tissues, or organisms which contain MCR4 or MCR3.

As used herein, "MCR3" and "MCR4" mean the known MCR3 and MCR4 receptors, their splice variants, and undescribed receptors. MCR3 is described by Gantz et al., supra (human MCR3), Desarnaud et al., supra (mouse MCR3) and L. Reyfuss et al., Proc. Natl. Acad. Sci. USA, 90, 8856–8860 (1993) (rat MCR3). MCR4 receptors are described by Gantz et al., supra (human MCR4), J. D. Alvaro et al., Mol. Pharmacol., 50, 583–91 (1996) (rat MCR4) and Takeuchi, S. and Takahashi, S., Gen-Comp-Endocrinol., 112(2), 220–31 (1998) (chicken MCR4).

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. The term "impotence" is oftentimes employed to describe this condition.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl (—$CH_2$—) and ethylenyl (—$CH_2CH_2$—).

The term "alkenyl" embraces linear or branched radicals of two to about twelve carbon atoms having at least one carbon-carbon double bond. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having two to about twelve carbon atoms having at least one carbon carbon triple bond. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with one or more halo radicals as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms.

Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocyclyl" also includes bridged heterocyclic groups, having 5–8 members. Examples of such radicals include 8-aza-bicyclo[3.2.1]octyl, 7-aza-bicyclo[2.2.1]heptyl, 5-aza-bicyclo[2.1.1]hexyl, and the like. Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4, -oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The term "alkylsulfonyl" embraces sulfonyl radicals substituted with an alkyl radical. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, and ethylsulfonyl.

The terms "sulfamyl," "aminosulfonyl" and "sulfonamidyl," denotes a sulfonyl radical substituted with an amine radical, (—$SO_2NH_2$).

The term "alkylaminosulfonyl" includes "N-alkylaminosulfonyl" where sulfonyl radicals are substituted with one or two alkylamino radical(s). More preferred alkylaminosulfonyl radicals are "lower alkylaminosulfonyl" radicals having alkyl portions of one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The term "alkoxycarbonyl" denotes an ester group, where a carbonyl radical is substituted with an alkoxy radical. More preferred are "lower alkoxycarbonyl" having lower alkoxy radicals as described above attached to a carbonyl radical.

The terms "N-alkylaminocarbonyl" and "N,N-dialkylaminocarbonyl" denote aminocarbonyl radicals substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkylenyl radicals are "5- or 6-membered heterocyclylalkylenyl" radicals having alkyl portions of one to six carbon atoms and a 5- or 6-membered heterocyclyl radical. Similarly, "heteroarylalkylenyl" and "heteroarylalkyl" embrace heteroaryl-substituted alkyl radicals. Even more preferred are lower heteroarylalkylenyl radicals having alkyl portions of one to three carbon atoms. Examples include such radicals as pyridylmethyl and thienylmethyl.

The terms "aralkyl" and "arylalkyl" embrace aryl-substituted alkyl radicals. Preferable aralkyl radicals are "lower aralkyl" radicals having aryl radicals attached to alkyl radicals having one to six carbon atoms. Even more preferred are "phenylalkylenyl" having alkyl portions of one to three carbon atoms. Examples of such radicals include benzyl, diphenylmethyl and phenylethyl. The aryl in said aralkyl may be additionally substituted, such as with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S—$).

The term "alkylthioalkyl" embraces radicals containing a alkylthio radical, of one to ten carbon atoms, attached to a linear or branched alkyl radical of one to about ten carbon atoms. Even more preferred are lower alkthioalkyl radicals, where each alkyl portion contains one to six carbon atoms. An example of "alkthioalkyl" is meththiomethyl ($CH_3SCH_2—$).

The term "alkoxyalkyl" embrace radicals containing an alkoxy radical, of one to about ten carbon atoms, attached to a linear or branched alkyl radical of one to about ten carbon atoms. More preferred alkoxyalkyl radicals are "lower alkoxyalkyl" radicals having alkyl portions each with one to six carbon atoms. Examples of such radicals include methoxyethyl, ethoxymethyl, methoxymethyl, and the like. Even more preferred are lower alkoxyalkyl radicals where each alkyl portion has one to three carbon atoms.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "aminoalkylamino" embraces aminoalkyl radicals having one to about ten carbon atoms any one of which are substituted on an amino radical. More preferred aminoalkylamino radicals are "lower aminoalkylamino" radicals having one to six carbon atoms. Examples of such radicals include aminomethylamino, aminoethylamino, aminopropylamino and aminobutylamino. Even more preferred are lower aminoalkylamino radicals having one to three carbon atoms.

The term "aminoalkoxy" embraces alkoxy radicals having one to about ten carbon atoms any one of which may be substituted with one or more amino radicals. More preferred aminoalkoxy radicals are "lower aminoalkoxy" radicals having one to six carbon atoms and one or more amino radicals. Examples of such radicals include aminomethoxy, and aminopropoxy. Even more preferred are lower aminoalkoxy radicals having one to three carbon atoms.

The term "alkylcarbonylaminoalkyl" embraces aminoalkyl radicals which are substituted with an alkylcarbonyl radical. More preferred alkylcarbonylaminoalkyl radicals are "lower alkylcarbonylaminoalkyl" radicals having alkyl portions each containing one to six carbon atoms. Examples of such radicals include methylcarbonylmethylamino, and the like. Even more preferred are lower alkylcarbonylaminoalkyl radicals having alkyl portions each containing one to three carbon atoms.

The term "alkylcarbonyl" denotes carbonyl groups which have been substituted with an alkyl radical. More preferred are $C_1$–$C_6$-alkylcarbonyl radicals, such as methylcarbonyl, ethlcarbonyl and propylcarbonyl.

The term "alkoxyalkylcarbonyl" denotes alkylcarbonyl groups which have been substituted with one or more alkoxy radicals. More preferred are $C_1$–$C_6$-alkoxy-$C_1$–$C_6$-alkylcarbonyl radicals, such as methoxymethylcarbonyl, and the like.

The tern "arylcarbonyl" denotes carbonyl groups which have been substituted with aryl radicals, such as phenylcarbonyl. The arylcarbonyl radicals may be further substituted on the aryl ring portion of the radical.

The term "heteroarylcarbonyl" denotes carbonyl groups which have been substituted with a heteroaryl radical, such as thienylcarbonyl. The "heteroarylcarbonyl" radicals may be further substituted on the heteroaryl ring portion of the radical.

The terms "aralkylcarbonyl" and "arylalkylcarbonyl" denote carbonyl groups which have been substituted with aralkyl radicals. More preferred are phenyl-$C_1$–$C_3$-alkylcarbonyl radicals, such as benzylcarbonyl. The aralkylcarbonyl radicals may be further substituted on the aryl ring portion.

The term "heterocyclylalkylcarbonyl" denotes carbonyl groups which have been substituted with heterocyclylalkyl radicals. More preferred are heterocyclyl-$C_1$–$C_3$-alkylcarbonyl radicals, such as thienylmethylcarbonyl, and, the like. The "heterocyclylalklylcarbonyl" radicals may be further substituted on the heterocyclyl ring portion of the radical.

The term "heteroarylalkylcarbonyl" denotes carbonyl groups which have been substituted heteroarylalkyl radicals. More preferred are heteroaryl-$C_1$–$C_3$-alkylcarbonyl radicals, such as pyridylmethylcarbonyl, and the like. The "heteroarylalklylcarbonyl" radicals may be further substituted on the heteroaryl ring portion of the radical.

The term "cycloalkylcarbonyl" denotes carbonyl groups which have been substituted with cycloalkyl radicals, such as cyclopropylcarbonyl. More preferred contain $C_3$–$C_6$ cycloalkyl radicals. The "cycloalkylcarbonyl" radicals may be further substituted on the cycloalkyl ring portion of the radical.

The term "cycloalkylalkylcarbonyl" denotes carbonyl groups which have been substituted with cycloalkylalkyl radicals. More preferred are $C_3$–$C_6$ cycloalkyl-$C_1$–$C_3$-alkylcarbonyl radicals, such as cyclpentylmethylcarbonyl. The cycloalkylalkylcarbonyl radicals may be further substituted on the aryl ring portion.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl, such as N-methylaminomethyl, N,N-dimethylaminoethyl, N,N-diethylaminomethyl and the like.

The term "alkylaminoalkylamino" embraces alkylamino radicals substituted with alkylamino radicals. More preferred alkylaminoalkylamino radicals are "lower alkylaminoalkylamino" radicals having alkyl radicals of one to six carbon atoms. Even more preferred are radicals having alkyl radicals of one to three carbon atoms. Suitable alkylaminoalkylamino radicals may be mono or dialkyl, such as N-methylaminomethylamino, N,N-dimethylaminoethylamino, N,N-diethylaminomethylamino or the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms, attached to a amino group. Even more preferred are lower alkylamino radicals having alkyl radicals of one to three carbon atoms. Suitable alkylamino radicals may be mono or dialkylamino such as N-methylaminomethyl, N,N-dimethylaminoethyl, N,N-diethylaminomethyl or the like.

The term "cycloalkylaminoalkyl" denotes aminoalkyl groups which have been substituted with one or two cycloalkyl radicals. More preferred are $C_3$–$C_6$-cycloalkylamino-$C_1$–$C_3$-alkyl radicals, such as N-cyclohexylmethylaminomethyl. The cycloalkylalkylaminoalklyl radicals may be further substituted on the cycloalkyl ring portion of the radical.

The term "cycloalkylalkylaminoalkyl" denotes aminoalkyl groups which have been substituted with one or two cycloalkylalkyl radicals. More preferred are $C_3$–$C_6$-cycloalkyl-$C_1$–$C_3$-alkylamino-$C_1$–$C_3$-alkyl radicals, such as N-cyclohexylmethylaminomethyl. The cycloalkylalkylaminoalkyl radicals may be further substituted on the cycloalkyl ring portion.

The terms "aralkylamino" and "arylalkylamino" denote amino groups which have been substituted with one or two aralkyl radicals. More preferred are phenyl-$C_1$–$C_3$-alkylamino radicals, such as N-benzylamino. The aralkylamino radicals may be further substituted on the aryl ring portion.

The term "heterocyclylalkylamino" denotes amino groups which have been substituted with one or two heterocyclylalkyl radicals. More preferred include heterocyclyl-$C_1$–$C_3$-alkylamino, such as N-thienylmethylamino, and the like. The "heterocyclylalklylamino" radicals may be further substituted on the heterocyclyl ring portion of the radical.

The term "heteroarylalkylamino" denotes amino groups which have been substituted with one or two heteroarylalkyl radicals. More preferred are heteroaryl-$C_1$–$C_3$-alkylamino, such as N-thienylmethylamino, and the like. The "heteroarylalklylamino" radicals may be further substituted on the heteroaryl ring portion of the radical.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The tern "arylaminoalkyl" denotes aminoalkyl groups which have been substituted with one or two aryl radicals. More preferred are arylamino-$C_1$–$C_3$-alkyl radicals, such as N-phenylaminomethyl. The arylaminoalkyl radicals may be further substituted on the aryl ring portion of the radical.

The term "heteroarylaminoalkyl" denotes aminoalkyl groups which have been substituted with one or two heteroaryl radicals. More preferred are heteroarylamino-$C_1$–$C_3$-alkyl radicals, such as N-thienylaminomethyl. The "heteroarylaminoalkyl" radicals may be further substituted on the heteroaryl ring portion of the radical.

The terms "aralkylaminoalkyl" and "arylalkylaminoalkyl" denote aminoalkyl groups which have been substituted with one or two aralkyl radicals. More preferred are phenyl-$C_1$–$C_3$-alkylamino-$C_1$–$C_3$-alkyl radicals, such as N-benzylaminomethyl. The aralkylaminoalkyl radicals may be further substituted on the aryl ring portion.

The term "arylthio" embraces aryl radicals of six to ten carbon atoms, attached to a divalent sulfur atom. An example of "arylthio" is phenylthio. The aryl portion may be further substituted.

The term "aralkylthio" embraces aralkyl radicals as described above, attached to a divalent sulfur atom. More preferred are phenyl-$C_1$–$C_3$-alkylthio radicals. An example of "aralkylthio" is benzylthio. The aryl portion may be further substituted.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above. The aryl portion may be further substituted.

The term "heteroaryloxy" embraces optionally substituted heteroaryl radicals, as defined above, attached to an oxygen atom.

The term "heteroarylalkoxy" embraces heteroarylalkyl radicals attached through an oxygen atom. More preferred heteroarylalkoxy radicals are "lower heteroarylalkoxy" radicals having optionally substituted heteroarylalkyl radicals attached to lower alkoxy radical as described above.

The term "aryloxyalkyl" embraces radicals containing an aryloxy radical attached to a linear or branched alkyl radical of one to about ten carbon atoms. More preferred aryloxyalkyl radicals are "lower phenyloxyalkyl" radicals having alkyl portions of one to six carbon atoms. Examples of such radicals include phenoxyethyl, phenoxymethyl, and the like. Even more preferred are lower aryloxyalkyl radicals having alkyl portions of one to three carbon atoms.

The term "heteroaryloxyalkyl" embraces radicals containing an heteroaryloxy radical attached to a linear or branched alkyl radical of one to about ten carbon atoms. More preferred heteroaryloxyalkyl radicals are "lower heteroaryloxyalkyl" radicals having alkyl portions of one to six carbon atoms. Examples of such radicals include pyridyloxyethyl, and the like. Even more preferred are lower heteroaryloxyalkyl radicals having alkyl portions of one to three carbon atoms.

The term "heteroarylalkyloxyalkyl" embraces radicals containing an heteroarylalkyloxy radical attached to a linear or branched alkyl radical of one to about ten carbon atoms. More preferred heteroarylalkyloxyalkyl radicals are "lower heteroarylalkyloxyalkyl" radicals having alkyl portions of one to six carbon atoms. Examples of such radicals include pyridylmethyloxymethyl, and the like. Even more preferred are lower heteroarylalkyloxyalkyl radicals having alkyl portions of one to three carbon atoms.

The term "aralkyloxyalkyl" embraces radicals containing an aralkyloxy radical attached to a linear or branched alkyl radical of one to about ten carbon atoms. More preferred aralkyloxyalkyl radicals are "lower phenylalkyloxyalkyl" radicals having alkyl portions of one to six carbon atoms each. Examples of such radicals include benzyloxyethyl, phenylethyloxymethyl, and the like. Even more preferred are lower aralkyloxyalkyl radicals having alkyl portions of one to three carbon atoms each.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "comprising" is meant to be open ended, including the indicated component but not excluding other elements.

The present invention preferably includes compounds that are agonists of the melanocortin-4 receptor.

The present invention also comprises the use of a compound of the invention, or pharmaceutically acceptable salt thereof, in the manufacture of a medicament for the treatment either acutely or chronically of an obesity mediated disease state, including those described previously. The compounds of the present invention are useful in the manufacture of an anti-obesity medicament. The compounds of the present invention are also useful in the manufacture of a medicament to attenuate or prevent disorders through antagonism of melanocortin receptor.

The present invention comprises a pharmaceutical composition comprising a therapeutically-effective amount of a compound of Formulas I–IV in association with a least one pharmaceutically-acceptable carrier, adjuvant or diluent.

The present invention also comprises a method of treating obesity related disorders, in a subject, the method comprising treating the subject having or susceptible to such disorder with a therapeutically-effective amount of a compound of Formulas I–IV.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

If formulated as a fixed dose, such combination products employ the compounds of this invention within the accepted dosage ranges. Compounds of Formula I may also be administered sequentially with known agents when a combination formulation is inappropriate. The invention is not limited in the sequence of administration; compounds of formula I–IV may be administered either prior to or after administration of the known agents.

Specifically, the administration of compounds of the present invention may be in conjunction with additional antiobesity agents or appetite regulating agents, therapies known to those skilled in the art.

Such agents may be selected from the group consisting of CART (cocaine amphetamine regulated transcript) agonists, NPY (neuropeptide Y) antagonists, MC4 (melanocortin-4) agonists, orexin antagonists, TNF (tumor necrosis factor) agonists, CRF (corticotropin releasing factor) agonists, CRF BP (corticotropin releasing factor binding protein) antagonists, urocortin agonists, P3 agonists, IVISH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators or TR P agonists.

Specifically such agents include leptin, topiramate, bupropion, dexamphetamine or amphetamine, fenfluramine, dexfenfluramine or sibutramine, orlistat, mazindol or phentermine.

Furthermore, the present compounds may be administered in combination with one or more anti hypertensive agents. Examples of anti-hypertensive agents are P-blockers such as alprenolol, atenolol, timolol, pindolol, propranolol and metoprotol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazern and verapamil, and a-blockers such as doxazosin, urapidil, prazosin and terazosin, insulin sensitizers including PPARy agonists [such as the glitazones (e.g. troglitazone, ploglitazone, englitazone, MCC-555, BRL49653 and the like)] and biguanides such as metformin and phenformin, insulin or insulin mimetics, sulfonylureas such as tolbutamide and glipizide, glucosidase inhibitors (such as acarbose), cholesterol lowering agents such as [HMG-CoA reductase inhibitors (lovastatin, slmvastatin and pravastatin, fluvastatin, atorvastatin, and other statins), sequestrants (cholestyramine, colestipol and a dialkylaminoalkyl derivatives of a cross-linked dextran), nicotinyl alcohol nicotinic acid or a salt thereof, proliferator-activater receptor (x agonists such as fenofibric acid derivatives (gemfibrozil, clofibrate, fenofibrate and benzafibrate), inhibitors of cholesterol absorption for example beta-sitosterol and (acyl CoA:cholesterol acyltransferase) inhibitors for example melinamide, probucol, vitamin E, and thyromimetics] PPAR8 agonists, antiobesity compounds such as fenfluramine, dexfenfluramine, phentermine, sibutramine, orlistat, or P3 adrenergic receptor agonists, feeding behavior modifying agents such as neuropeptide Y antagonists (e.g. neuropeptide Y5), PPARu. agonists by Glaxo, PPARy antagonists, serotonin reuptake inhibitors such as fluoxetine and sertraline, growth hormone secretagogues such as MK-0677; and agents useful in the treatment of male and/or female sexual dysfunction which include phosphodiesterase V (PDE-V) inhibitors, such as sildenafil and IC-351; (x2-adrenergic receptor antagonists, such as phentolamine mesylate; and dopamine-receptor agonists, such as apomorphine. Further reference can be made to Remington: The Science and Practice of Pharmacy, 19th Edition, Gennaro, Ed., Mack Publishing Co., Easton, Pa., 1995.

The present invention comprises a process for the preparation of a compound of Formula I–IV.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, dituoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I–IV.

Also included in the family of compounds of Formula I–IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–IV include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I–IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Additional examples of such salts can be found in Berge et al., J. Pharm. Sci., 66, 1 (1977).

General Synthetic Procedures

The compounds of the invention can be synthesized according to the following procedures of Schemes 1–14, wherein the substituents are as defined for Formulas I–IV, above, except where further noted.

Scheme 1

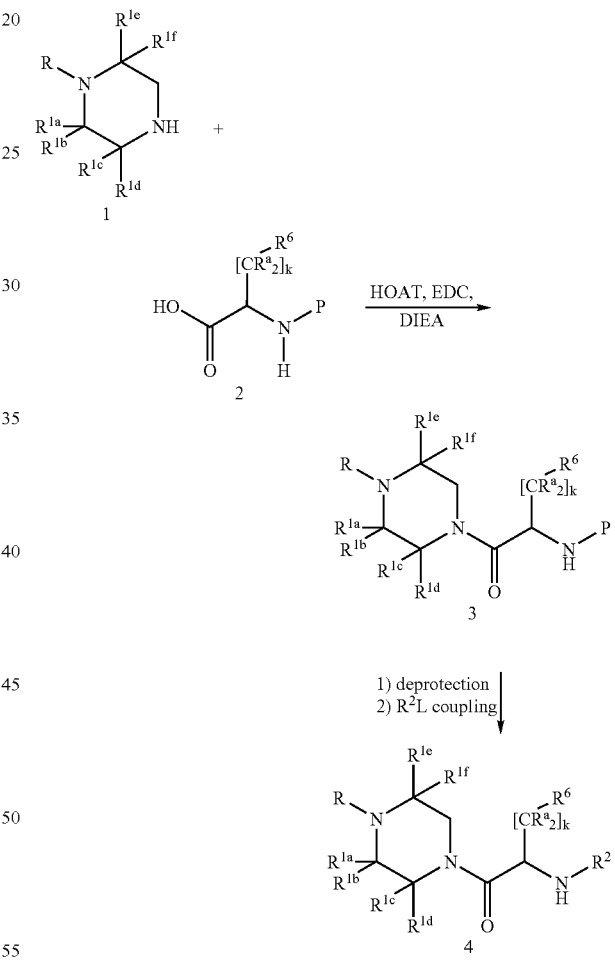

Compounds of Formula I may be prepared in a convergent manner as described in Scheme 1. Protected amino acids 2 (where P is a protecting group) are coupled with the substituted piperazine 1 using standard peptide coupling conditions, such as with HOAT EDC, and DIEA in a solvent, such as MeCl$_2$, and reacted at RT, to afford the protected piperazine amino acid 3. The protected amino acid derivatives 2 are commercially available or may be prepared by literature methods (R. M. Williams, Synthesis of Optically Active α-Amino Acids, Pergamon Press: Oxford, 1989). Similarly, substituted piperazines 1 are either commercially available, can be prepared via literature methods, or may be prepared following literature methods described for analogous compounds. Some of these methods are illustrated in the subsequent schemes. Removal of the protecting group P (CBZ, BOC, etc.) is accomplished using conventional methods, such as with a solution of 50% TFA and $CH_2Cl_2$ to remove a Boc group, to yield the free amine. The free amine is treated with base, such as DIEA in a solvent, such as $MeCl_2$. The reaction mixture is coupled with $R^2L$ (where L is a leaving group), such as a substituted acid using standard peptide coupling conditions, such as with HOAT, EDC, and DIEA in a solvent, at a temperature such as of about RT, to yield the desired compound 4.

Scheme 2

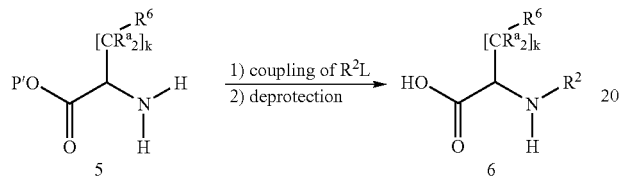

Amino acid ester intermediate 5, wherein P' is an acid protecting group including $C_{1-4}$ alkyl (such as methyl or ethyl), benzyl or allyl group, can be synthesized by well documented methods in the literature. Coupling of $R^2L$ (where L is a leaving group) and ester 5, such as with a substituted acid under standard peptide coupling conditions followed by removal of the ester group P' yields the intermediate 6.

Scheme 3

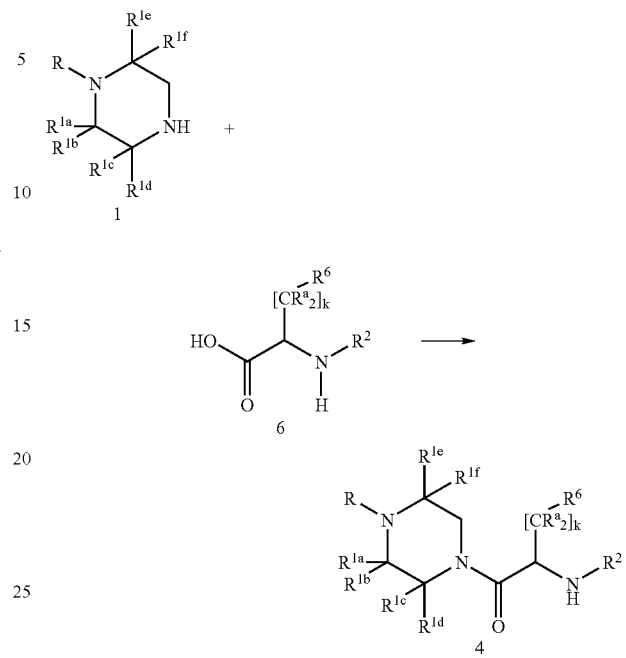

Compounds of Formula I may also be prepared in a convergent manner as described in Scheme 3. Compounds 4 are obtained by coupling intermediates 6 to piperidines 1 under standard peptide coupling reaction conditions.

Scheme 4

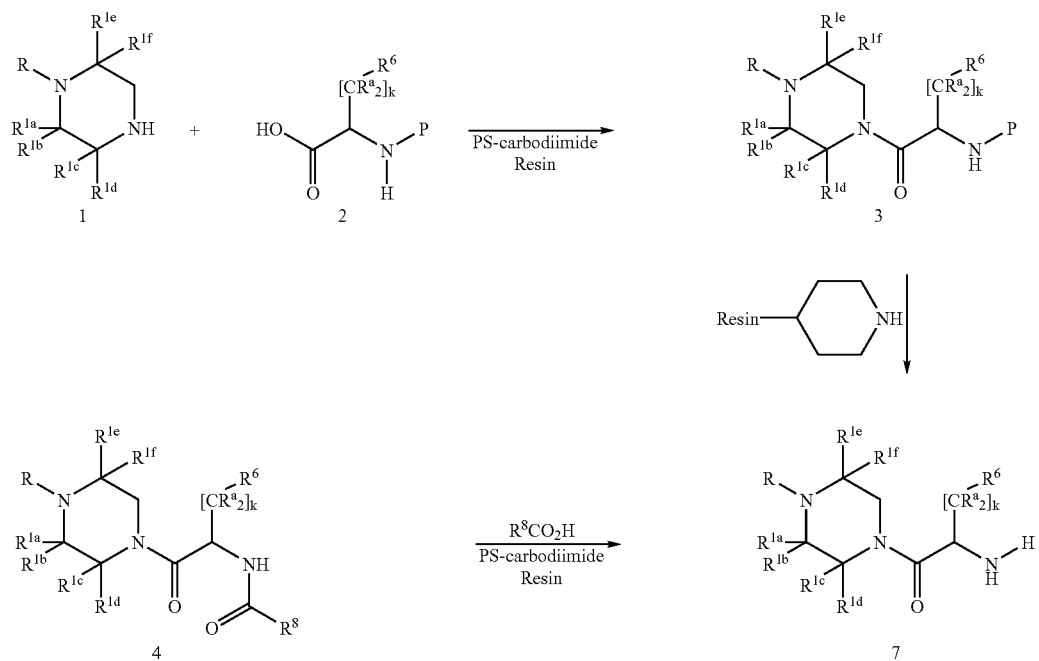

Chemical libraries can be made using variations of the above described chemistry to make compounds of Formula I as described in Scheme 4. Piperazine 1 is added to PS-carbodiimide resin, and an FMOC protected amino acid. Excess piperazine 1 is scavenged, such as with PS-isocyanate resin. The reaction mixture is filtered into vials containing DMAP and piperidine-4-carboxylic acid polyamine resin HL. PS-carbodiimide resin and $R^8CO_2H$ are added. The reactions are filtered and excess amine is scavenged, such as with PS-isocyanate resin. The compounds are deprotected if needed to yield compounds 4. Other conditions and resins known to one skilled in the art can be used.

Scheme 5

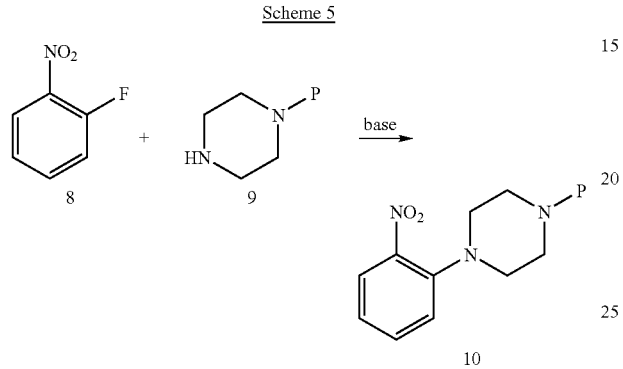

Substituted piperazines can be prepared such as by the method described in Scheme 5. 2-Fluoronitrobenzene 8, DIEA, 1-benzylpiperazine 9 and a solvent such as DMF are reacted to yield the nitrophenylpiperazine 10.

Benzenesulfonamide piperazines are prepared by the method described in Scheme 6. An excess of $SnCl_2 \cdot 2H_2O$ is added to a solution of protected 1-(2-nitrophenyl)piperazine 10 in a solvent, such as an alcohol, preferably EtOH. The reaction mixture is warmed, such as at a temperature of about 60° C. and then treated with base, such as with 1N NaOH and $CH_2Cl_2$, to afford the protected amine 11. Alternatively, the nitro compound may be hydrogenated, such as with $H_2$ in the presence of 10% Pd/C.

Substituted sulfonyl chloride is added to a mixture of protected 2-piperazinylphenylamine 11 and a base, such as pyridine, in a non-protic solvent such as $CH_2Cl_2$. The reaction is heated, such as at a temperature greater than RT, more preferably at reflux. After cooling to RT, base is added, such as a satd soln of $NaHCO_3$, to afford the protected sulfone 12.

The sulfone 12 is deprotected to form the free piperazine 13. For example, where the piperazine is benzyl protected, the benzyl group is removed by 10% Pd/C and $HCO_2NH_4$ in a solvent such as MeOH, and heating, such as at reflux to yield the sulfonamide 13. One skilled in the art knows how to remove other protecting groups.

Scheme 6

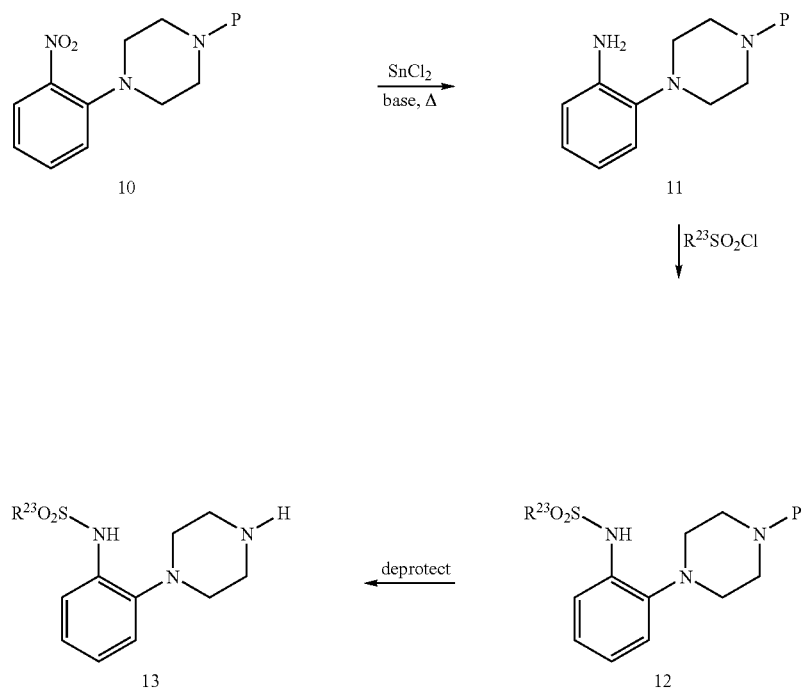

Scheme 7

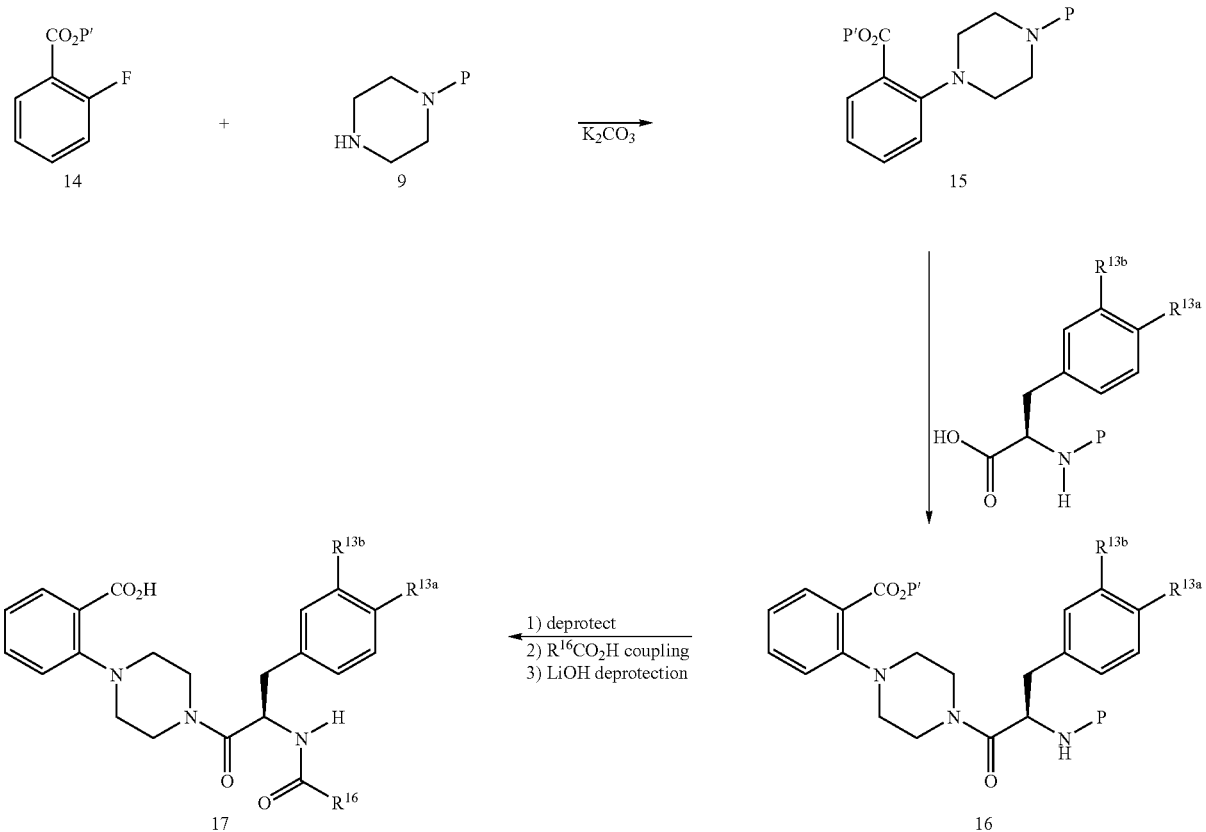

Benzoic derivatives may be prepared by a process similar to that shown in Scheme 7. A mixture of ester 14, protected piperazine 9 and base, such as $K_2CO_3$, is heated, such as at a temperature of about greater then 100° C., more preferably at about 150° C., to yield benzoate 15. The protected piperazinyl benzoate 15 is deprotected, such as with 10% Pd/C and $HCO_2NH_4$ for benzyl protection, and coupled with the appropriate amino acid using traditional coupling chemistry to yield ester 16. After further deprotection and coupling with $R^{16}CO_2H$ (with standard peptide conditions), the free acid 17 is formed by treatment with an aqueous solution of LiOH at a temperature greater than about RT and preferably at about 60° C.

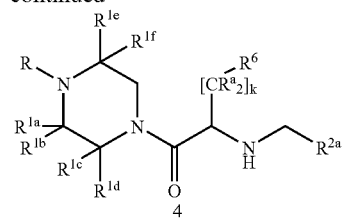

Compounds of Formula I, where $R^2$ is $-CH_2R^{2a}$, may also be prepared in a convergent manner as described in Scheme 8. To a free amine 7 in a solvent, such as $ClCH_2CH_2Cl$, and base, such as DIEA, an aldehyde and a reducing agent, such as $NaBH(OAc)_3$ are added, to form the substituted amine 4, where $R^{2a}$, is aryl, heterocyclyl or cycloalkyl. The reaction is preferably kept at about RT.

Scheme 8

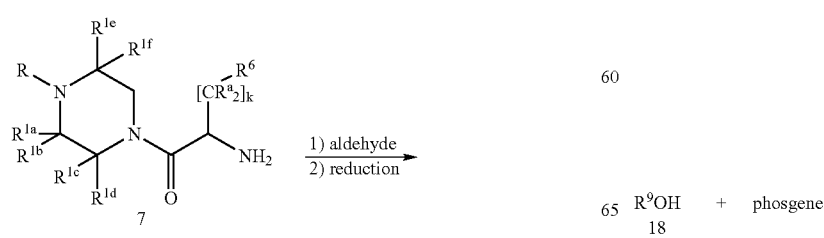

Scheme 9

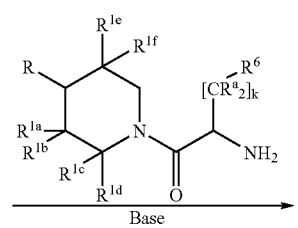

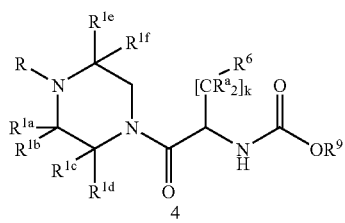

Compounds of Formula I, where R² is —C(=O)OR⁹, may also be prepared as described in Scheme 9. Alcohol 18 is converted to the anhydride, such as with phosgene and base, such as DIEA, at a temperature between −23° C. and reflux, preferably at about 0° C. and reflux, in a suitable solvent, such as CH₂Cl₂. To the mixture is added the piperazine derivative 7 and base to afford the amide 4. A similar procedure can be used for the reactions of amines to form the corresponding ureas.

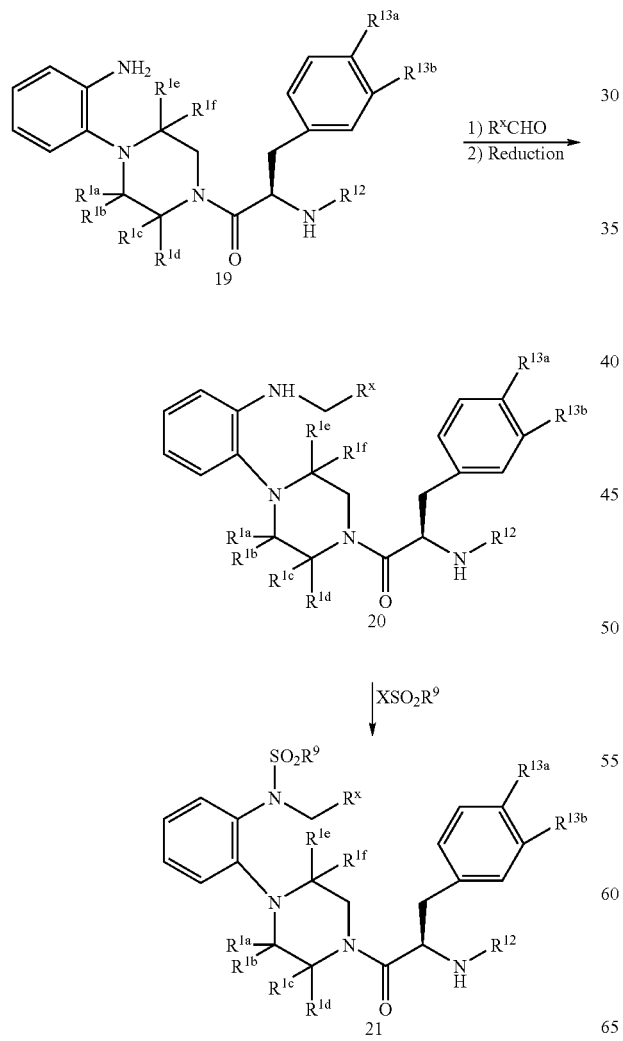

Compounds of Formula I may also be prepared in a convergent manner as described in Scheme 10. Following the procedure for the synthesis of Scheme 9, the aniline 20 was prepared from the corresponding amine 19, aldehyde and reducing agent, such as NaBH(OAc)₃. The aniline 20 may be further substituted using, for example methylsulfonyl chloride, base such as pyridine, and DMAP (cat.), in a suitable solvent, such as ClCH₂CH₂Cl to yield the sulfonamide 21.

Scheme 11

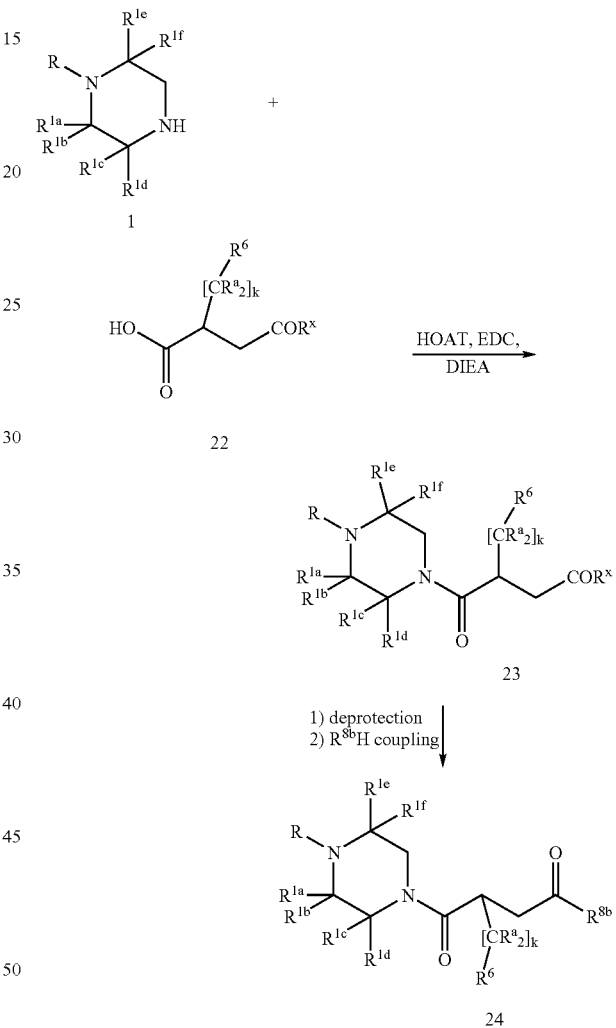

Compounds of Formula I, where R² is —C(=O)R⁸ and Y is CH₂ may be prepared as described in Scheme 11. Piperazine 1 is coupled with acid 22 (where Rˣ is an acid protecting group, such as alkoxy, aryloxy, benzyloxy, and the like) to form the piperazinyl amide 23. The amide 23 is deprotected to form the free acid which can be coupled with appropriate reagents (where R⁸ᵇ is capable of reacting with an acid, such as an optionally substituted amine) to form compounds 24. Such coupling can be normal amino acid coupling reagents.

Scheme 12

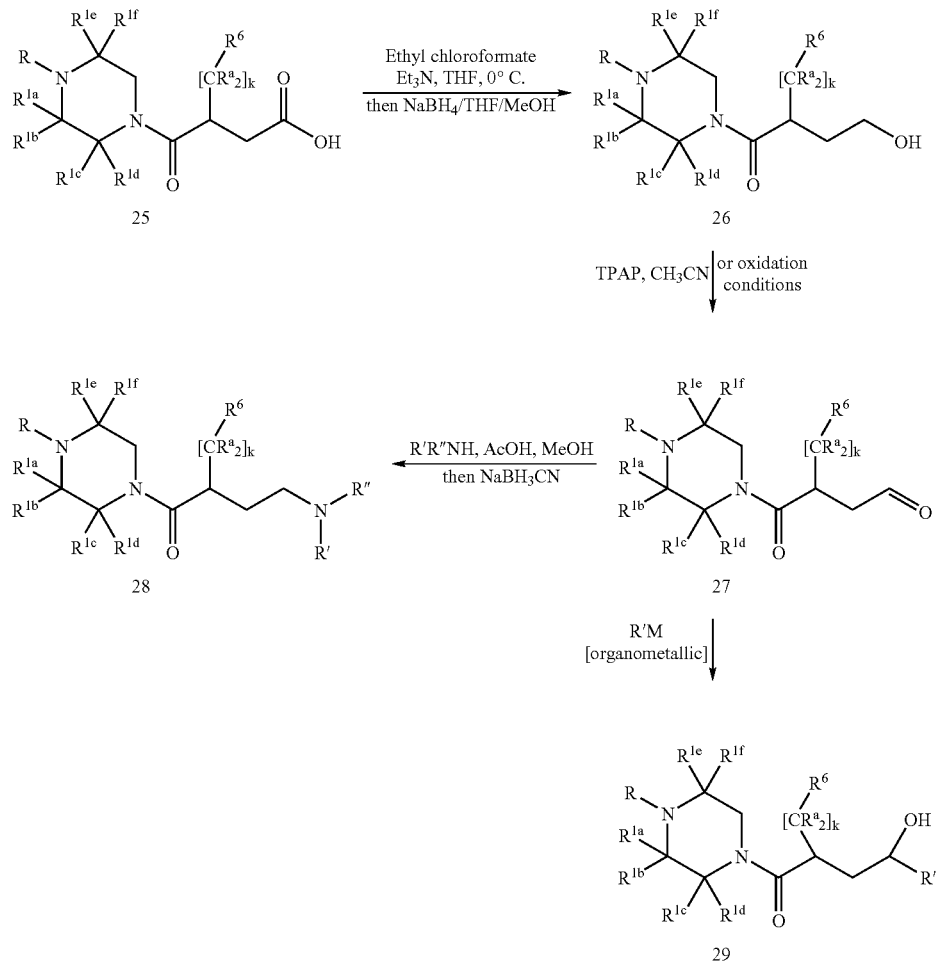

Alternatively, several types of compounds of Formula I, where R² is —COR⁸ and Y is CH₂ may be prepared as described in Scheme 12. The free acid 25 can be reduced to the alcohol 26, for example using a two step procedure that converts the acid 25 first to the mixed carbonate, such as with ethyl chloroformate, then is reduced to the alcohol 26, such as with NaBH₄. The alcohol 26 can be converted to the aldehyde 27 (using reagents such as with Dess Martin reagent, TPAP or Swern oxidation) which can be further reacted with substituted amines, such as in the presence of acetic acid, then reduced, such as with NaBH₃CN to form amines 28. Alternatively the aldehyde 27 can react with organometallic agents to form the alcohols 29.

Scheme 13

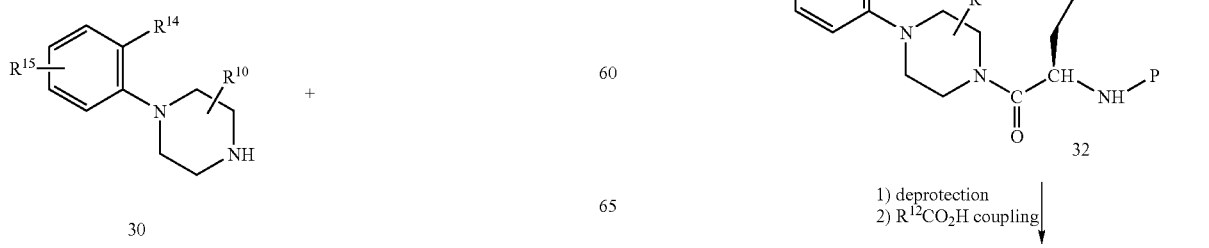

-continued

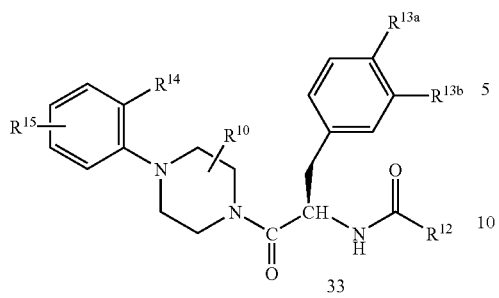

33

-continued

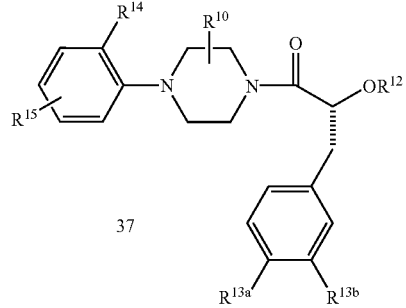

37

Compounds of Formula II may be prepared as described in Scheme 13. Protected D-phenylalanine derivatives 31 (where P is a protecting group) are coupled with the substituted phenyl piperazine 30 using standard peptide coupling conditions, such as with HOAT, EDC, and DIEA in a solvent, such as MeCl$_2$, and reacted at RT, to afford the protected piperazine phenylalanine compounds 32. Removal of the protecting group P (CBZ, BOC, FMOC etc.) is accomplished using conventional methods, such as with a solution of 50% TFA and CH$_2$Cl$_2$ (to remove a Boc group), to yield the free amine. The free amine is treated with base, such as DIEA in a solvent, such as MeCl$_2$. The reaction mixture is coupled with a substituted acid, using standard peptide coupling conditions, such as with HOAT, EDC, and DIEA in a solvent, such as at a temperature of about RT, to yield the desired compound 33.

Scheme 14

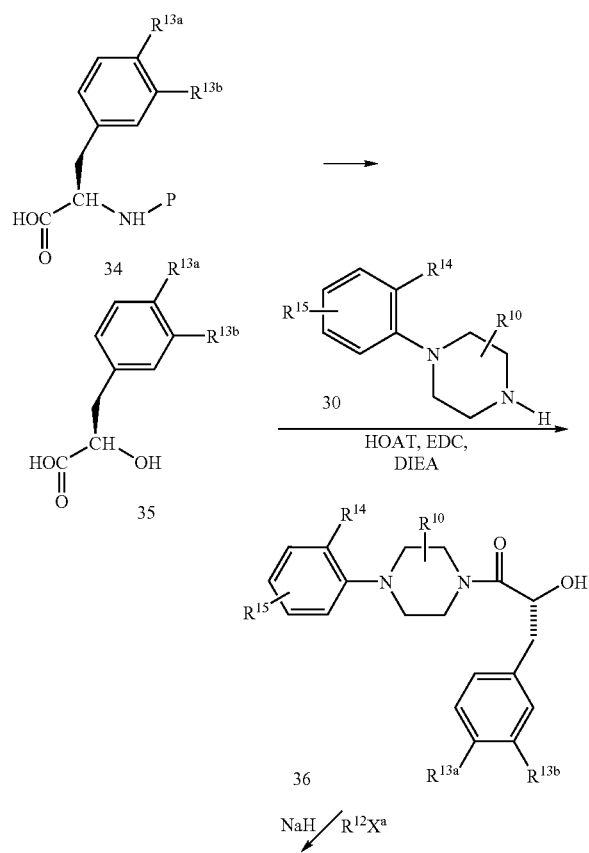

Compounds of Formula I (where Y is O) may be prepared as described in Scheme 14. A protected phenylalanine derivative 34 was treated with acid, such as H$_2$SO$_4$. To the solution was added an oxidizer, such as NaNO$_2$, such as at a temperature of about 0° C., and reacted at about RT to afford the alcohol 35. The alcohol 35 is coupled with the substituted phenyl-piperazine 20 similar to the procedures previously described to afford the coupled alcohol 36. The coupled alcohol 36 is converted to the ether 37, such as by treatment with an alkali metal and a substituted halide.

The protected D-phenylalanine derivatives are commercially available or may be prepared by literature methods (R. M. Williams, Synthesis of Optically Active α-Amino Acids, Pergamon Press: Oxford, 1989). Similarly, substituted piperazines are either commercially available, can be prepared via literature methods, or may be prepared following literature methods described for analogous compounds. TIC derivatives can be prepared such as by methods described in WO00/74679. Piperazine derivatives can be prepared such as by methods described in WO95/34311.

The starting compounds defined in Schemes 1–14 may also be present with functional groups in protected form if necessary and/or in the form of salts, provided a salt-forming group is present and the reaction in salt form is possible. If so desired, one compound of formula I can be converted into another compound of formula I or a N-oxide thereof; a compound of formula I can be converted into a salt; a salt of a compound of formula I can be converted into the free compound or another salt; and/or a mixture of isomeric compounds of formula I can be separated into the individual isomers.

N-Oxides can be obtained in a known matter by reacting a compound of formula I with hydrogen peroxide or a peracid, e.g. 3-chloroperoxy-benzoic acid, in an inert solvent, e.g. dichloromethane, at a temperature between about −10–35° C., such as about 0° C.—RT.

If one or more other functional groups, for example carboxy, hydroxy, amino, or mercapto, are or need to be protected in a compound of formulas I–IV, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from about 130 to about 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150° C., for example at about −80° C. to about 60° C., at room temperature, at about −20° C. to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g diethyl acetate, ethers, typically aliphatic ethers, e.g. diethylether, or cyclic ethers, e.g. THF, liquid aromatic hydrocarbons, typically benzene or toluene, alcohols, typically MeOH, EtOH or 1- or 2-propanol, nitrites, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention are known, are commercially available, or can be synthesized in analogy to or according to methods that are known in the art.

The skills required in carrying out the reaction and purification of the resulting reaction products are known to those in the art. Purification procedures include crystallization and normal-phase or reverse-phase chromatography.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I–IV. These detailed descriptions fall within the scope, and serve to exemplify, the above described General Synthetic Procedures which form part of the invention.

These detailed descriptions are presented for illustrative purposes only and are not intended as a restriction on the scope of the invention.

Unless otherwise noted, all materials were obtained from commercial suppliers and used without further purification. All reactions involving air- or moisture-sensitive compounds were performed under a nitrogen atmosphere. All parts are by weight and temperatures are in Degrees centigrade unless otherwise indicated. All compounds showed NMR spectra consistent with their assigned structures. Unless otherwise stated, reactions were run at room temperature.

The following abbreviations are used:

| | |
|---|---|
| AcOH | acetic acid |
| AlH$_3$ | aluminum hydride |
| Bn | benzyl |
| Boc | tert-(butoxycarbonyl)- |
| Boc-D-Phe-OH | N-tert-(butoxycarbonyl)-D-phenylalanine |
| Boc-L-Tic-OH | N-tert-(butoxycarbonyl)-L-1,2,3,4-tetrahydroisoquinoline-3-carboxylic acid |
| Boc-p-Cl-D-Phe-OH | N-tert-(butoxycarbonyl)-para-chloro-D-phenylalanine |
| BOP-Cl | bis(2-oxo-3-oxazolidinyl)phosphinic chloride |
| CBZ-N | Carbobenzyloxy |
| CH$_2$Cl$_2$ | dichloromethane |
| ClCH$_2$CH$_2$Cl | ethylene dichloride |
| CH$_3$CN | acetonitrile |
| chxl | cyclohexyl |
| Cond | concentrated |
| cyp | cyclopropyl |
| DIEA | N,N-diisopropylethylamine |
| DMAP | 4-dimethylaminopyridine |
| DME | ethylene glycol dimethylether |
| DMF | dimethylformamide |
| EDC | 1-ethyl-3-[3-(dimethylamino)propyl] carbodiimide hydrochloride |
| Et$_2$O | diethyl ether |
| EtOAc | ethyl acetate |
| EtOH | ethyl alcohol |
| Fmoc | N-(9-fluorenylmethoxycarbonyl)- |
| g | gram |
| h | hour |
| H$_2$ | hydrogen |
| H$_2$O | water |
| H$_2$O$_2$ | hydrogen peroxide |
| HCO$_2$NH$_4$ | ammonium formate |
| HCl | hydrochloric acid |
| HOAT | 1-hydroxy-7-azabenzotriazole |
| HOBT | 1-hydroxybenzotriazole hydrate |
| H$_3$PO$_4$ | Phosphoric acid |
| HPLC | high pressure liquid chromatography |
| K$_2$CO$_3$ | potassium carbonate |
| LDA | lithium diisopropylamide |
| LiOH | lithium hydroxide |
| LiAlH$_4$ | lithium aluminum hydride |
| mg | milligram |
| ml | milliliter |
| min | minutes |
| MeOH | methyl alcohol |
| Na$_2$CO$_3$ | sodium carbonate |
| NaH | sodium hydride |
| NaOH | sodium hydroxide |
| NaBH$_3$CN | sodium cyanoborohydride |
| NaBH(OAc)$_3$ | sodium triacetoxyborohydride |
| NaHCO$_3$ | sodium bicarbonate |
| NaHMDS | sodium bis(trimethylsilyl)amide |
| NaH$_2$PO$_4$ | sodium phosphate monobasic |
| Na$_2$SO$_4$ | sodium sulfate |
| N$_2$ | nitrogen |
| NH$_3$ | ammonia |
| (NH$_4$)$_2$SO$_4$ | ammonium sulfate |
| NH$_4$OAc | ammonium acetate |
| NH$_4$Cl | ammonium chloride |
| Pd/C | palladium on carbon |
| ps | polystyrene |
| phe | phenylalanine |
| RT | room temperature |
| Satd | saturated |

| | |
|---|---|
| SiO$_2$ | silica |
| SnCl$_2$.2H$_2$O | stannous chloride dihydrate |
| soln | solution |
| TEA | triethylamine |
| TFA | trifluoroacetic acid |
| THF | tetrahydrofuran |
| TIC | tetrahydroisoquinoline carboxylic acid |
| TPAP | tetrapropyl ammonium perruthenate |
| TLC | thin layer chromatography |

Preparative HPLC (TFA Buffer): Unless otherwise stated, compounds that were purified by preparative HPLC using a TFA buffer were run on a YMC-ODS AM (150×20 mm, 5 micron particle size) column, with a flowrate of 20 mL/min. The eluant used was 10 to 100% CH$_3$CN in H$_2$O over 7 min then 3.5 min at 100% CH$_3$CN. Both solvents were buffered with 0.1% TFA.

Preparative HPLC (AcOH Buffer): The following method was used when AcOH was used as a buffer. YMC-ODS AM (150×20 mm, 5 micron particle size) column, with a flowrate of 20 mL/min. The eluant used was 10 to 100% CH$_3$CN in H$_2$O over 6 min then 3.5 min at 100% CH$_3$CN. Both solvents were buffered with 0.1% AcOH.

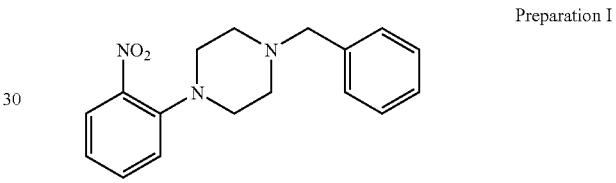

Preparation I 1-(2-Nitrophenyl)-4-benzylpiperazine

To a 500 mL round-bottomed flask equipped with magnetic stirring was added 1-(2-nitrophenyl)piperazine (Emka-Chemie) (30 g, 145 mmol) in CH$_2$Cl$_2$ (300 mL). A solution of Na$_2$CO$_3$ in H$_2$O (61.2 g in 100 mL) was added, and the reaction mixture was stirred for 5 min. Stirring was stopped, benzyl bromide (18.6 mL, 159 mmol) was added, and the reaction was heated at reflux for 4 h. The organic layer was separated, and the aqueous layer was extracted with CH$_2$Cl$_2$ (2×50 mL). All organic fractions were combined, washed with brine, dried over Na$_2$SO$_4$, filtered and concentrated in vacuo to afford 1-(2-nitrophenyl)-4-benzylpiperazine as an orange oil (42 g). MS (ESI, pos. Ion) m/z: 298 (M+H); MS (ESI, neg. Ion) m/z: 296 (M−H). Calc'd for C$_{17}$H$_{19}$N$_3$O$_2$: 297.15.

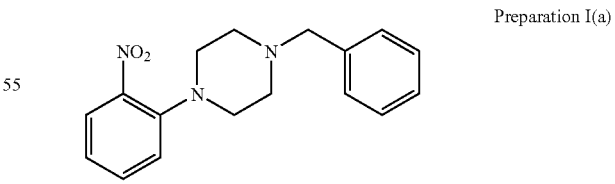

Preparation I(a)

1-(2-Nitrophenyl)-4-benzylpiperazine

To a 500 mL round-bottomed flask equipped with magnetic stirring was added 2-fluoronitrobenzene (14 g, 101 mmol), DIEA (19 mL, 110 mmol), 1-benzylpiperazine (18 mL, 110 mmol) (Aldrich) and DMF (250 mL). The reaction was stirred for 18 h, diluted with 400 mL of EtOAc and washed with 300 mL each of 10% NaHCO₃, H₂O, and brine. The organic layer was separated, dried over Na₂SO₄, filtered, and concentrated in vacuo to yield 1-(2-nitrophenyl)-4-benzylpiperazine (30 g). Calc'd for C₁₇H₁₉N₃O₂: 297.15.

Preparation II

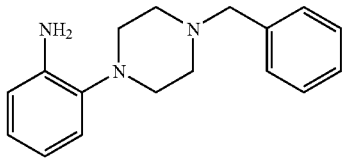

2-[4-Benzylpiperazinyl]phenylamine

To a round-bottomed flask equipped with magnetic stirring was added 1-(2-nitrophenyl)-4-benzylpiperazine (42 g, 160 mmol), EtOH (300 mL), and SnCl₂·2H₂O (Aldrich) (141 g, 624 mmol), and the reaction mixture was warmed to 60° C. for 5 h. The reaction mixture was treated with 1N NaOH (30 mL) and CH₂Cl₂. The organic layer was separated, and the aqueous layer was extracted with CH₂Cl₂ (2×30 mL). All organic fractions were combined, washed with brine, dried over Na₂SO₄, filtered and concentrated in vacuo to afford the amine as a light yellow oil (34 g). MS (ESI, pos. Ion) m/z: 268 (M+H); MS (ESI, neg. Ion) m/z: 266 (M−H). Calc'd for C₁₇H₂₁N₃: 267.17.

Preparation III

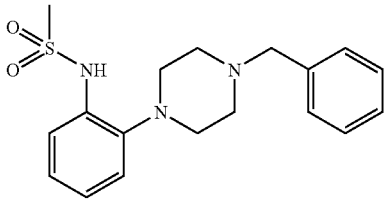

(Methylsulfonyl){2-[4-benzylpiperazinyl]phenyl}amine

To a round-bottomed flask equipped with magnetic stirring was added 2-[4-benzylpiperazinyl]phenylamine (34 g, 127 mmol) in ClCH₂CH₂Cl (100 mL) and pyridine (12 mL, 140 mmol). The reaction mixture was stirred for 5 min. To the reaction was added methanesulfonyl chloride (Aldrich) (11 mL, 139 mmol), and the reaction mixture was heated at reflux for 18 h. After cooling to RT a satd soln of NaHCO₃ (50 mL) was added. The organic layer was separated, and the aqueous layer was extracted with CH₂Cl₂ (2×50 mL). All organic fractions were combined, washed with brine, dried over Na₂SO₄, filtered and concentrated in vacuo to afford the sulfonamide as yellow oil (42 g). MS (ESI, pos. Ion) m/z: 346 (M+H); MS (ESI, neg. Ion) m/z: 344 (M−H). Calc'd for C₁₈H₂₃N₃O₂S: 345.15.

Preparation IV

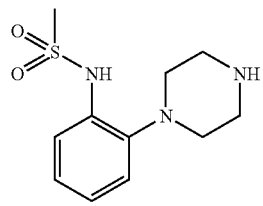

(Methylsulfonyl) (2-piperazinylphenyl)amine

To a round-bottomed flask equipped with stirring was added (methylsulfonyl){2-[4-benzylpiperazinyl]phenyl}amine (42 g, 120 mmol), MeOH, 10% Pd/C (Aldrich)(25 g), and HCO₂NH₄ (38 g, 610 mmol). After heating at reflux for 2 h, the mixture was filtered through Celite® and washed with CH₂Cl₂. The combined organic layers were washed with NaHCO₃ and concentrated in vacuo to afford a light yellow solid. This was treated with a soln of EtOAc and HCl to afford the salt of the desired compound as the hydrochloride salt (20 g). MS (ESI, pos. Ion) m/z: 256 (M+H); MS (ESI, neg. Ion) m/z: 254 (M−H). Calc'd for C₁₁H₁₇N₃O₂S: 255.10.

Preparation V

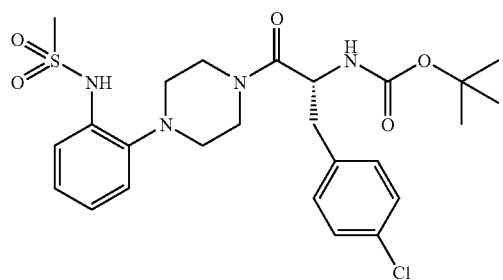

(2R)-{1-(4-Chlorobenzyl)-2-[4-(2-methylsulfonylamino-phenyl)piperazin-1-yl]-2-oxo-ethyl}-carbamic acid tert-butyl ester To a round-bottomed flask equipped with magnetic stirring was added (methylsulfonyl)(2-piperazinyl-phenyl)amine hydrochloride (3.0 g, 10 mmol) and CH₂Cl₂ (20 mL) followed by DIEA (2.1 mL, 11.72 mmol). The reaction was stirred for 5 min. To the mixture was added N-Boc-p-Cl-D-Phe-OH (Peptech Corp.) (3.2 g, 10.6 mmol), HOAT (Aldrich) (1.8 g, 13 mmol) and EDC (4.1 g, 21 mmol), and the reaction mixture was stirred at RT for 2.5 h. A satd soln of NaHCO₃ was added, the organic layer was separated, and the aqueous layer was extracted with CH₂Cl₂ (2×50 mL). All organic fractions were combined, washed with brine, dried over Na₂SO₄, filtered and concentrated in vacuo to afford an orange oil. MS (ESI, pos. ion) m/z: 537 (M+H); MS (ESI, neg. ion) m/z: 535 (M−H). Calc'd for C₂₅H₃₃ClN₄O₅S: 536.19.

Preparation VI

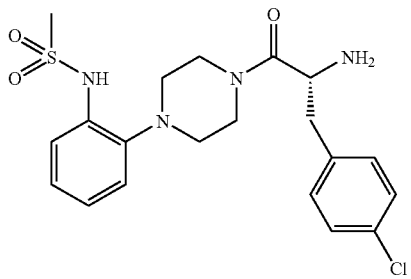

(2R)-2-Amino-3-(4-chlorophenyl)-1-(4-{2-[(methylsulfonyl)-amino]phenyl}piperazinyl)propan-1-one To a round-bottomed flask equipped with magnetic stirring was added (2R)-{1-(4-chlorobenzyl)-2-[4-(2-methylsulfonylamino-phenyl)-piperazin-1-yl]-2-oxoethyl}-carbamic acid tert-butyl ester (12 g, 22 mmol) and a soln of $CH_2Cl_2$ (10 mL), and TFA (10 mL). This was stirred at RT for 2 h. The organic solvent was concentrated in vacuo to give the amine as the TFA salt (6.1 g). MS (ESI, pos. ion) m/z: 437 (M+H); MS (ESI, neg. ion) m/z: 435 (M–H). Calc'd for $C_{20}H_{25}ClN_4O_3S$: 436.13.

Preparation VII

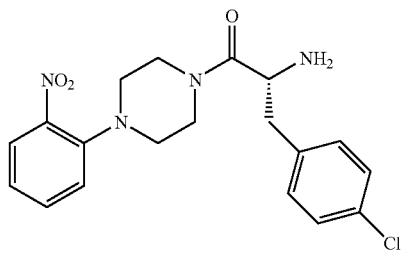

(2R)-2-Amino-3-(4-chlorophenyl)-1-[4-(2-nitrophenyl)piperazinyl]propan-1-one

To a round-bottomed flask equipped with magnetic stirring was added a solution of 1-(2-nitrophenyl)-piperazine (Emka-Chemie) (1.0 g, 4.8 mmol) $CH_2Cl_2$ (10 mL), and the reaction mixture was stirred for 5 min. N-Boc-p-Cl-D-Phe-OH (Peptech Corporation) (1.6 g, 5.3 mmol), HOAT (Aldrich)(660 mg, 4.8 mmol) and EDC (Aldrich)(2.9 g, 9.7 mmol) were added, and the reaction mixture was stirred at RT for 2.5 h. A satd soln of $NaHCO_3$ (10 mL) was added, the organic layer was separated, and the aqueous layer was extracted with $CH_2Cl_2$ (2×50 mL). All organic fractions were combined, washed with brine, dried over $Na_2SO_4$, filtered and concentrated in vacuo to afford an orange oil. The Boc protecting group was removed using the procedure described for Preparation VI with a soln of 50% TFA and $CH_2Cl_2$ (2 mL). The organic solvent was removed in vacuo to give the desired compound as the TFA salt (1.4 g). MS (ESI, pos. ion) m/z: 389 (M+H); MS (ESI, neg. ion) m/z: 387 (M–H). Calc'd for $C_{19}H_{21}ClN_4O_3$: 388.13.

Preparation VIII

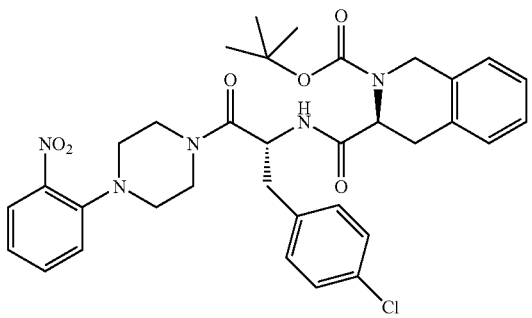

tert-Butyl 3-(N-{(1R)-1-[(4-chlorophenyl)methyl]-2-[4-(2-nitrophenyl) piperazinyl]-2-oxoethyl}carbamoyl-(3S)-1,2,3,4-tetrahydroisoquinoline-2-carboxylate To a round-bottomed flask equipped with stirring was added (2R)-2-amino-3-(4-chlorophenyl)-1-[4-(2-nitrophenyl)piperazinyl]propan-1-one trifluoroacetate (1.7 g, 3.4 mmol) and $CH_2Cl_2$ (10 mL), and the reaction was stirred for 5 min. Boc-L-Tic-OH (Bachem) (1.6 g, 5.3 mmol), HOAT (Aldrich) (1.2 g, 4.7 mmol), EDC (Aldrich) (2.6 g, 8.7 mmol), and DIEA (Aldrich) (0.75 mL, 4.3 mmol) were added, and the mixture was stirred at RT for 2.5 h. A satd soln of $NaHCO_3$ (10 mL) was added. The organic layer was separated, and the aqueous layer was extracted with $CH_2Cl_2$ (2×50 mL). All organic fractions were combined, washed with brine, dried over $Na_2SO_4$, filtered and concentrated in vacuo to afford an orange oil (2.1 g). MS (ESI, pos. ion) m/z: 648 (M+H); MS (ESI, neg. ion) m/z: 646 (M–H). Calc'd for $C_{34}H_{38}ClN_5O_6$: 647.25.

Preparation IX

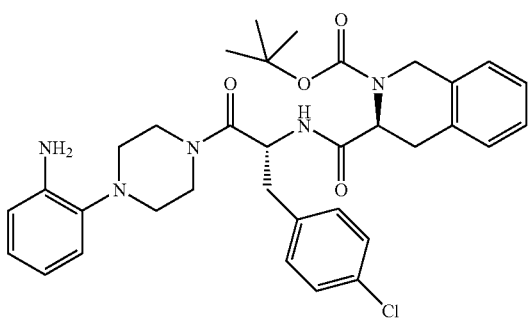

tert-Butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate Following the procedure of Preparation II, tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate was prepared from tert-butyl 3-(N-{(1R)-1-[(4-chlorophenyl)methyl]-2-[4-(2-nitrophenyl)piperazinyl]-2-oxoethyl}carbamoyl)(3S)-1,2,3,4-tetrahydroisoquinoline-2-carboxylate (2.5 g, 3.9 mmol) in EtOH (10 mL), and $SnCl_2.2H_2O$ (Aldrich) (3.6 g, 16 mmol). A light yellow solid was isolated (2.1 g). MS (ESI, pos. ion)

m/z: 618 (M+H); MS (ESI, neg. ion) m/z: 616 (M–H). Calc'd for $C_{34}H_{40}ClN_5O_4$: 617.28.

Preparation X

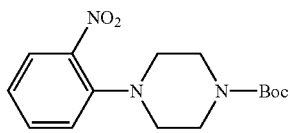

tert-Butyl 4-(2-nitrophenyl)piperazinecarboxylate

To a 1 L round-bottomed flask equipped with magnetic stirring was added 1-(2-nitrophenyl)-piperazine (Emkachem) (7.2 g, 35 mmol), di-tert-butyl dicarbonate (11 g, 52 mmol) (Aldrich), and DMAP (cat.) (Aldrich) in THF (500 mL), and the reaction was stirred 18 h and then concentrated in vacuo. The resulting crude material was dissolved in 500 mL EtOAc and washed with 400 mL each of 10% citric acid (2×), 10% NaHCO$_3$, H$_2$O and brine. The organic layer was separated, dried over Na$_2$SO$_4$, filtered, and concentrated in vacuo to afford the desired material (6.4 g). MS (ESI, pos. ion) m/z: 308 (M+H), (ESI, neg. ion) m/z: 306 (M–H). Calc'd for $C_{15}H_{21}N_3O_4$: 307.15.

Preparation XI

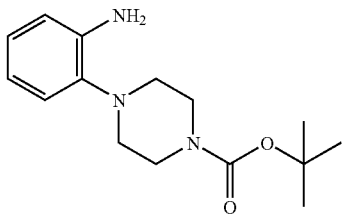

tert-Butyl 4-(2-aminophenyl)piperazinecarboxylate

Into a 500 mL round bottomed flask equipped with magnetic stirring was added tert-butyl 4-(2-nitrophenyl) piperazinecarboxylate (5.0 g, 16 mmol) in 95% EtOH (250 mL), and 10% Pd/C (2.0 g, 1.9 mmol) (Aldrich). The flask was equipped with a balloon filled with H$_2$, and the reaction was stirred for 18 h. After filtering through a pad of Celite®, the crude material was concentrated in vacuo to afford the desired compound (4.4 g). MS (ESI, pos. ion) m/z: 278 (M+H), (ESI, neg. ion) m/z: 276 (M–H). Calc'd for $C_{15}H_{23}N_3O_2$: 277.18.

Preparation XII

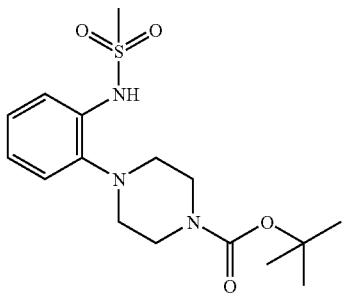

tert-Butyl 4-{2-[(methylsulfonyl)amino]phenyl}-piperazinecarboxylate tert-Butyl 4-{2-[(methylsulfonyl)amino]phenyl}-piperazinecarboxylate was prepared following the procedure for Preparation III using, tert-butyl 4-(2-aminophenyl) piperazinecarboxylate (4.4 g, 16 mmol), methanesulfonyl chloride (1.4 mL, 18 mmol) and DIEA (instead of pyridine) (3.1 mL, 18 mmol). The crude material was purified by flash chromatography (SiO$_2$, 4:1 hexane:EtOAc) and concentrated in vacuo to afford the desired compound (4.1 g). MS (ESI, pos. ion) m/z: 356 (M+H), (ESI, neg. ion) m/z: 354 (M–H). Calc'd for $C_{16}H_{25}N_3O_4S$: 355.16.

Preparation XIII

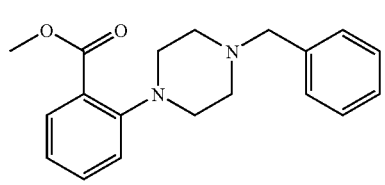

Methyl 2-[4-benzylpiperazinyl]benzoate

To a 250 mL pressure bottle equipped with magnetic stirring was added methyl 2-fluorobenzoate (Lancaster Synthesis Inc.) (3.0 g, 20 mmol), 1-benzylpiperazine (Aldrich) (3.8 g, 22 mmol) and K$_2$CO$_3$ (3.0 g, 22 mmol) in DMF (100 mL) The mixture was heated at 150° C. for 12 h. After cooling to RT the reaction was diluted with EtOAc (100 mL) and H$_2$O was added. The organic layer was separated and washed with H$_2$O, brine, dried over Na$_2$SO$_4$, filtered and concentrated in vacuo to afford a brown oil. The crude material was purified by column chromatography (4:1 hexanes-EtOAc) to give the title compound as a white foam (3.6 g). MS (ESI, pos. ion) m/z: 311 (M+H). Calc'd for $C_{19}H_{22}N_2O_2$: 310.17.

Preparation XIV

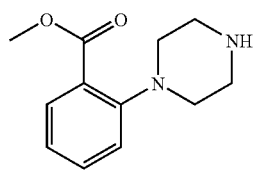

Methyl 2-piperazinylbenzoate

The title compound was prepared according to the procedure described in Preparation IV by using methyl 2-[4-benzylpiperazinyl]benzoate (2.8 g, 8.9 mmol), 10% Pd/C (Aldrich) (940 mg), and HCO$_2$NH$_4$ (2.8, 44 mmol). The title compound was isolated as a colorless oil (1.75 g). (MS (ESI, pos. ion) m/z: 221 (M+H). Calc'd for $C_{12}H_{16}N_2O_2$: 220.12.

Preparation XV

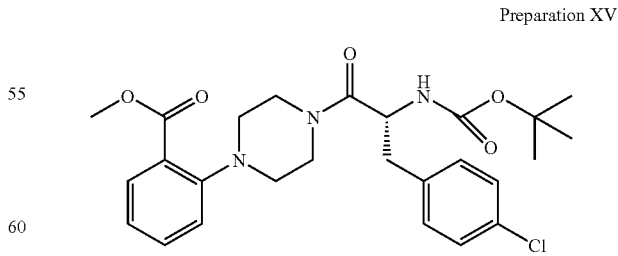

Methyl 2-(4-{(2R)-2-[(tert-butoxy)carbonylamino]-3-(4-chlorophenyl)propanoyl}piperazinyl)benzoate The title compound was prepared according to the procedure described in Preparation V (without DIEA) by using methyl 2-piperazinylbenzoate (2.5 g, 11 mmol), N-Boc-p-Cl-D-Phe-OH (Peptech Corporation) (3.8 g, 13 mmol), HOAT (Aldrich) (1.6 g, 11 mmol), and EDC (Aldrich) (4.4 g, 23 mmol). The title compound was isolated as a crude white foam (4.8 g). MS (ESI, pos. ion) m/z: 502 (M+H). Calc'd for $C_{26}H_{32}ClN_3O_5$: 501.20.

Preparation XVI

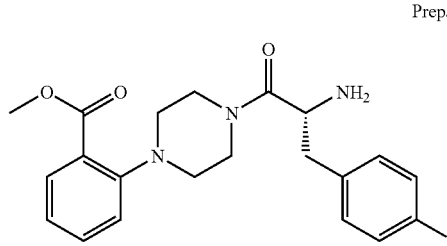

Methyl 2-(4-[(2R)-2-amino-3-(4-chlorophenyl) propanoyl]piperazinyl)benzoate

To a 25 mL round-bottomed flask equipped with magnetic stirring was added methyl 2-(4-{(2R)-2-[(tert-butoxy) carbonylamino]-3-(4-chlorophenyl) propanoyl}-piperazinyl)benzoate (3.2 g, 6.4 mmol). A satd soln of HCl in EtOAc (15 mL) was added, and the mixture was stirred at RT for 1 h. The title compound, as the hydrochloride salt, was isolated by filtration as a white solid (2.6 g). MS (ESI, pos. ion) m/z: 402 (M+H). Calc'd for $C_{21}H_{24}ClN_3O_3$: 401.15.

Preparation XVII

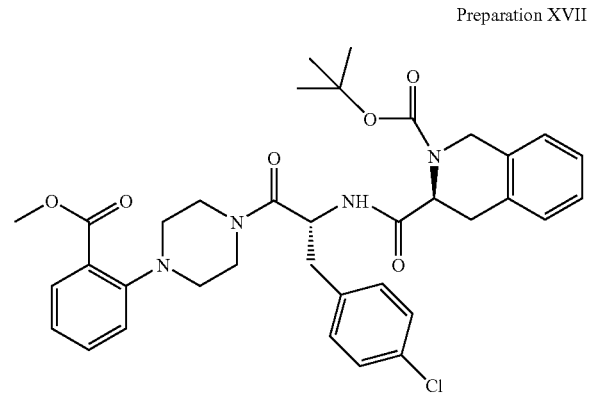

Methyl 2-{4-[(2R)-2-({(3S)-2-[(tert-butyl) oxycarbonyl](3-1,2,3,4-tetrahydroisoquinolyl) }carbonylamino)-3-(4-chlorophenyl)propanoyl] piperazinyl}benzoate The title compound was prepared according to the procedure described in Preparation V by using methyl 2-{4-[(2R)-2-amino-3-(4-chlorophenyl)propanoyl] piperazinyl}-benzoate hydrochloride (2.6 g, 5.9 mmol), Boc-L-Tic-OH (Bachem) (1.8 g, 6.5 mmol), HOAT (Aldrich) (810 mg, 5.9 mmol), and EDC (Aldrich) (2.3 g, 12 mmol) and DIEA (Aldrich) (1.0 mL, 5.9 mmol). The title compound was isolated and purified by column chromatography ($CH_2Cl_2$ with 1.5% $NH_3$ 2M in MeOH) (2.8 g). MS (ESI, pos. ion) m/z: 661 (M+H). Calc'd for $C_{36}H_{41}ClN_4O_6$: 660.27.

Preparation XVIII

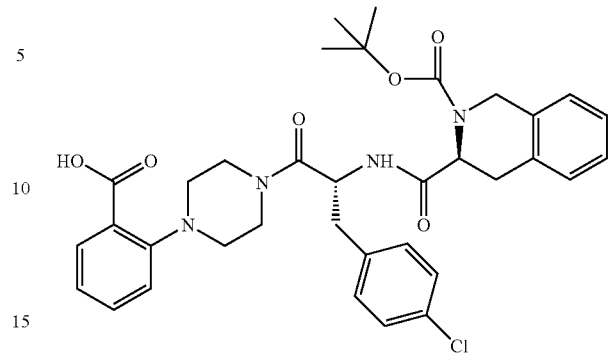

2-{4-[(2R)-2-({(3S)-2-[(tert-Butyl)oxycarbonyl](3-1, 2,3,4-tetrahydroisoquinolyl)}carbonylamino)-3-(4-chlorophenyl)propanoyl]piperazinyl}benzoic acid To a 150 mL round-bottomed flask equipped with magnetic stirring was added methyl 2-{4-[(2R)-2-({(3S)-2-[(tert-butyl)oxycarbonyl](3-1,2,3,4-tetrahydroisoquinolyl) }carbonylamino)-3-(4-chlorophenyl)propanoyl] piperazinyl}benzoate (1.6 g, 2.4 mmol) in THF (30 mL). A soln of LiOH (Aldrich) (303 mg, 7.14 mmol) in $H_2O$ (ca. 10 mL) was added and the reaction was heated at 60° C. for 12 h. After cooling to RT, the mixture was concentrated in vacuo and diluted with EtOAc (100 mL). A 10% soln of citric acid (25 mL) was added, the organic layer was separated, and the aqueous layer was extracted with EtOAc (2×25 mL). The organic layers were combined, washed with $H_2O$, and brine, dried over $Na_2SO_4$, filtered and concentrated in vacuo to afford the title compound as a white solid (960 mg). MS (ESI, pos. ion) m/z: 647 (M+H). Calc'd for $C_{35}H_{39}ClN_4O_6$: 646.26.

Preparation XIX

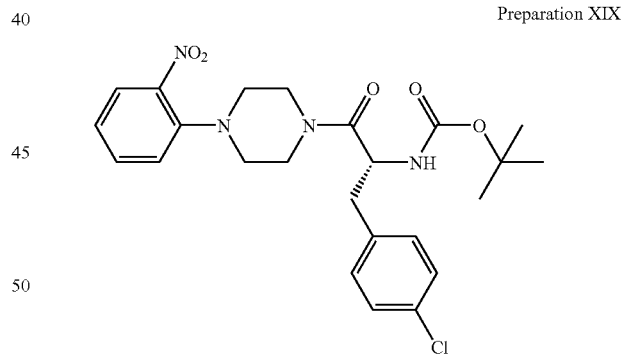

N-{(1R)-1-[(4-Chlorophenyl)methyl]-2-[4-(2-nitrophenyl)piperazinyl]-2-oxoethyl}(tert-butoxy) carboxamide To a 500 mL round-bottomed flask equipped with magnetic stirring was added N-BOC-p-Cl-D-Phe-OH (5.28 g, 17.6 mmol) (Nova Biochem), 1-[3-(dimethylamino)-propyl]-3-ethylcarbodiimide methiodide (10.0 g, 34 mmol) (Aldrich), and HOAT (2.7 g, 20 mmol) (Aldrich). DMF (100 mL) was added and the solution was stirred for 5 min. 1-(2-Nitrophenyl)piperazine (3.5 g, 17 mmol) (Emka-Chemie) was added and the solution was stirred for 2 h. The reaction was diluted with EtOAc (150 mL) and washed with satd NaHCO₃, H₂O, and brine (75 mL each). The organic layer was collected, dried over Na₂SO₄, filtered, and concentrated in vacuo. MS (ESI, pos. ion) m/z: 489 (M+H), (ESI, neg. ion) m/z: 487 (M−H). Calc'd for C₂₄H₂₉ClN₄O₅:488.18.

Preparation XX

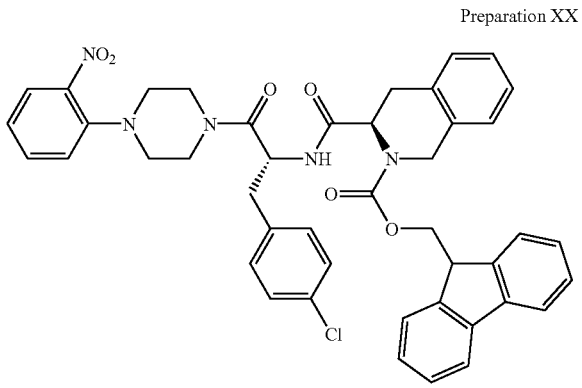

Fluoren-9-ylmethyl (3R)-3-(N-{(1R)-1-[(4-chlorophenyl)methyl]-2-[4-(2-nitrophenyl)piperazinyl]-2-oxoethyl}carbamoyl)-1,2,3,4-tetrahydroisoquinoline-2-carboxylate N-{(1R)-1-[(4-Chlorophenyl)methyl]-2-[4-(2-nitrophenyl)piperazinyl]-2-oxoethyl}(tert-butoxy)-carboxamide (1.4 g, 2.8 mmol) was treated with satd HCl in EtOAc as described in Preparation XVI. The resulting crude material was diluted with EtOAc and washed with satd NaHCO₃ soln. The organic layer was separated, dried over Na₂SO₄, filtered and concentrated in vacuo. This sample (1.05 g, 2.50 mmol), was coupled to N-Fmoc-D-1,2,3,4-tetrahydroisoquinoline-3-carboxylic acid (1.1 g, 2.7 mmol) (Peptech), by the procedure for Preparation XIX using 1-(3-dimethylaminopropyl)-3-ethylcarbodiimide methiodide (Aldrich) (1.6 g, 5.5 mmol) and HOAT (370 mg, 2.7 mmol). The crude compound was obtained in a quantitative yield (2.2 g). MS (ESI, pos. ion) m/z: 770 (M+H), (ESI, neg. ion) m/z: 768 (M−H). Calc'd for C₄₄H₄₀ClN₅O₆: 769.27.

Preparation XXI

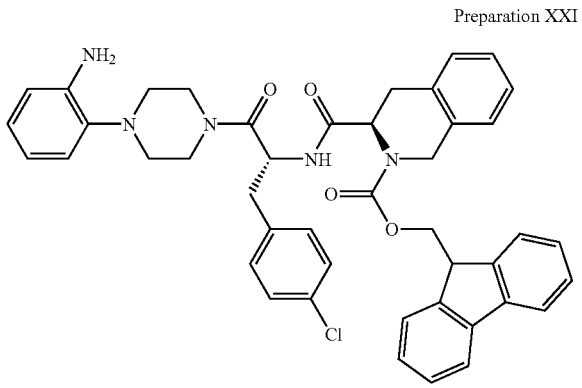

Fluoren-9-ylmethyl (3R)-3-(N-{(1R)-2-[4-(2-aminophenyl)piperazinyl]-1-[(4-chlorophenyl)methyl]-2-oxoethyl}carbamoyl)-1,2,3,4-tetrahydroisoquinoline-2-carboxylate Fluoren-9-ylmethyl (3R)-3-(N-{(1R)-2-[4-(2-aminophenyl)piperazinyl]-1-[(4-chlorophenyl)methyl]-2-oxoethyl}carbamoyl)-1,2,3,4-tetrahydroisoquinoline-2-carboxylate was prepared according to the procedure for Preparation II using fluoren-9-ylmethyl (3R)-3-(N-{(1R)-1-[(4-chlorophenyl)methyl]-2-[4-(2-nitrophenyl)-piperazinyl]-2-oxoethyl}carbamoyl)-1,2,3,4-tetrahydroisoquinoline-2-carboxylate (1.4 g, 1.8 mmol) and SnCl₂.2H₂O (1.7 g, 7.3 mmol) (Aldrich). The crude product was purified by flash chromatography (SiO₂, 1:1 EtOAc:hexane) and concentrated in vacuo to afford the desired compound (770 mg). MS (ESI, pos. ion) m/z: 740 (M+H), (ESI, neg. ion) m/z: 738 (M−H). Calc'd for C₄₄H₄₂ClN₅O₄: 739.29.

Preparation XXII

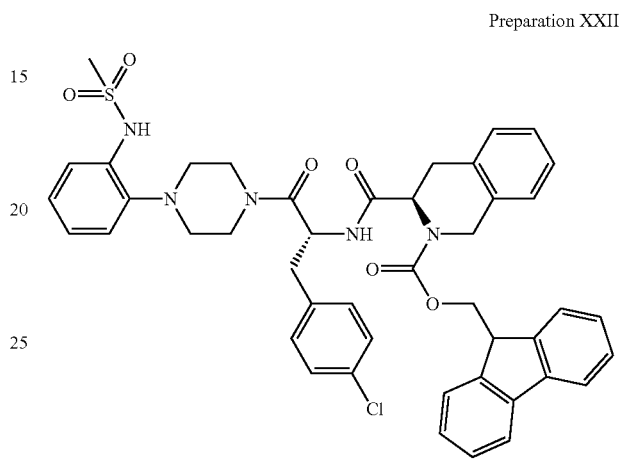

Fluoren-9-ylmethyl (3R)-3-{N-[(1R)-1-[(4-chlorophenyl)methyl]-2-(4-{2-[(methylsulfonyl)amino]phenyl}piperazinyl)-2-oxoethyl]carbamoyl}-1,2,3,4-tetrahydroisoquinoline-2-carboxylate Fluoren-9-ylmethyl (3R)-3-{N-[(1R)-1-[(4-chlorophenyl)methyl]-2-(4-{2-[(methylsulfonyl)amino]phenyl}piperazinyl)-2-oxoethyl]carbamoyl}-1,2,3,4-tetrahydroisoquinoline-2-carboxylate was prepared from fluoren-9-ylmethyl (3R)-3-(N-{(1R)-2-[4-(2-aminophenyl)piperazinyl]-1-[(4-chlorophenyl)methyl]-2-oxoethyl}carbamoyl)-1,2,3,4-tetrahydroisoquinoline-2-carboxylate (250 mg, 0.34 mmol) according to the procedure for Preparation III using methanesulfonyl chloride (30 µl, 0.39 mmol) and 2,6-di-tert-butyl-pyridine (80 µl, 0.36 mmol) (Aldrich). The crude product was concentrated in vacuo and purified by flash chromatography (SiO₂, 15% EtOAc in CH₂Cl₂), to afford the desired compound (240 mg). MS (ESI, pos. ion) m/z: 818 (M+H), (ESI, neg. ion) m/z: 816 (M−H). Calc'd for C₄₅H₄₄ClN₅O₆S: 817.27.

Preparation XXIII

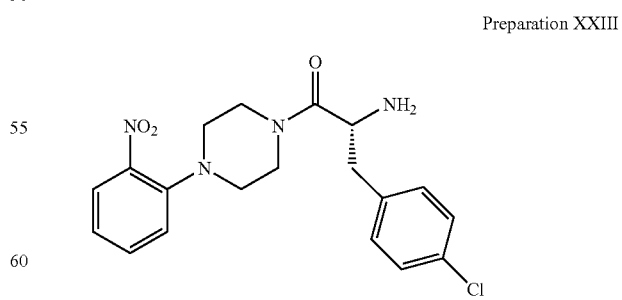

(2R)-2-Amino-3-(4-chlorophenyl)-1-[4-(2-nitrophenyl)piperazinyl]propan-1-one

Using the procedure described for the synthesis of Preparation XVI, (2R)-2-amino-3-(4-chlorophenyl)-1-[4-(2- nitrophenyl)piperazinyl]propan-1-one hydrochloride was prepared from N-{(1R)-1-[(4-chlorophenyl)methyl]-2-[4-(2-nitrophenyl)piperazinyl]-2-oxoethyl}(tert-butoxy) carboxamide (660 mg, 1.4 mmol) and a satd soln of HCl in EtOAc (10 mL). The yellow solid was filtered to give the target compound isolated as the HCl salt, as a white solid (530 mg). MS (ESI, pos. ion) m/z: 389 (M+H). Calc'd for $C_{19}H_{12}ClN_4O_5$: 388.13.

Preparation XXIV

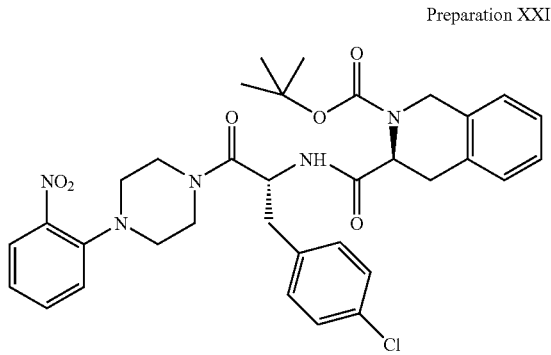

tert-Butyl 3-(N-{(1R)-1-[(4-chlorophenyl)methyl]-2-[4-(2-nitrophenyl) piperazinyl]-2-oxoethyl) carbamoyl)(3S)-1,2,3,4-tetrahydroisoquinoline-2-carboxylate Using the procedure described for the synthesis of Preparation V, tert-butyl 3-(N-{(1R)-1-[(4-chlorophenyl)methyl]-2-[4-(2-nitrophenyl) piperazinyl]-2-oxoethyl{carbamoyl) (3S)-1,2,3,4-tetrahydroisoquinoline-2-carboxylate was prepared from (2R)-2-amino-3-(4-chlorophenyl)-1-[4-(2-nitrophenyl)piperazinyl]propan-1-one hydrochloride (570 mg, 1.3 mmol) in DMF (10 mL), Boc-L-Tic-OH (Bachem) (410, 1.5 mmol), HOAT (Aldrich) (180 mg, 1.4 mmol), EDC (Aldrich) (520 mg, 2.70 mmol), and DIEA (Aldrich) (240 μL, 1.4 mmol). The crude material was purified by column chromatography (1:1 hexanes-EtOAc) to give the title compound as a white foam (716 mg). MS (ESI, pos. ion) m/z: 648 (M+H). Calc'd for $C_{34}H_{38}ClN_5O_6$: 647.25.

EXAMPLE 1

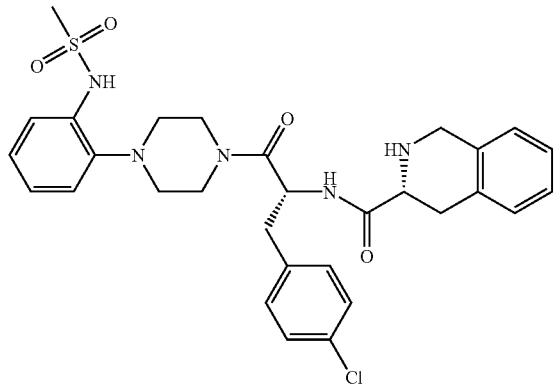

((3R)(3-1,2,3,4-Tetrahydroisoquinolyl))-N-[(1R)-1-[(4-chlorophenyl)methyl]-2-(4-(2-[(methylsulfonyl) amino]-phenyl}piperazinyl)-2-oxoethyl] carboxamide In a 50 mL round bottomed flask equipped with magnetic stirring was added fluoren-9-ylmethyl (3R)-3-{N-[(1R)-1-[(4-chlorophenyl)methyl]-2-(4-(2-[(methylsulfonyl)amino] phenyl}piperazinyl)-2-oxoethyl]carbamoyl}-1,2,3,4-tetrahydroisoquinoline-2-carboxylate (240 mg, 0.290 mmol) in $CH_2Cl_2$ (5 mL). This solution was treated with tris(2-aminoethyl)amine (220 μl, 1.4 mmol) (Aldrich) and stirred for 1.5 h. The reaction was diluted with $CH_2Cl_2$ and washed with brine. The organic layer was separated and washed with sodium phosphate buffer (1M, pH 5.5), dried over $Na_2SO_4$, filtered and concentrated in vacuo. The crude product was purified by flash chromatography (SiO2, 1% MeOH in $CH_2Cl_2$) and to afford the desired material (150 mg). The purified compound was dissolved in $H_2O$, treated with excess AcOH and lyophilized to yield the acetate salt. MS (ESI, pos. ion) m/z: 596 (M+H), (ESI, neg. ion) m/z: 594 (M−H). Calc'd for $C_{30}H_{34}ClN_5O_4S$: 595.20. Anal. Calc'd for $C_{30}H_{34}ClN_5O_4S—C_2H_4O_2H_4O_2$-0.5$H_2O$: C, 57.78; H, 5.91; N, 10.53; Cl, 5.33. Found C, 58.01; H, 5.63; N, 10.83; Cl, 5.49.

EXAMPLE 2

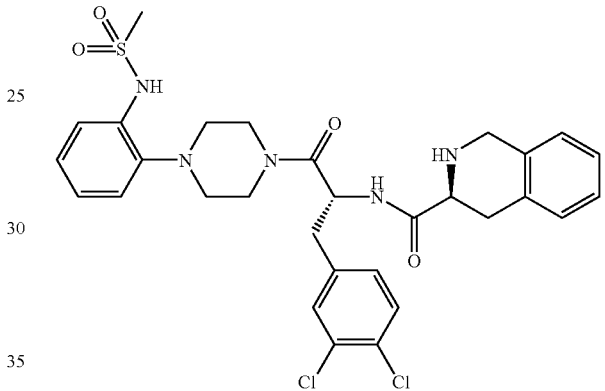

N-[(1R)-1-[(3,4-Dichlorophenyl)methyl]-2-(4-{2-[(methylsulfonyl)amino]phenyl}piperazinyl)-2-oxoethyl]((3S)(3-1,2,3,4-tetrahydroisoquinolyl))-carboxamide Step 1

N-[(1R)-1-[(3,4-Dichlorophenyl)methyl]-2-(4-{2-[(methylsulfonyl)amino]phenyl}piperazinyl)-2-oxoethyl] (tert-butoxy)carboxamide was prepared according to the procedure for Preparation XIX using (methylsulfonyl)(2-piperazinylphenyl)amine hydrochloride (800 mg, 2.8 mmol), N-Boc-D-3,4-dichlorophenylalanine (930 mg, 2.80 mmol) (Peptech), DIEA (480 μl, 2.80 mmol), EDC (1.66 g, 5.60 mmol), HOAT (400 mg, 3.0 mmol) and DMF (10 mL). The crude product was purified by flash chromatography (SiO$_2$, 1:1 hexane:EtOAc) and concentrated in vacuo to afford the desired compound (1.0 g). MS (ESI, pos. ion) m/z: 571 (M+H), (ESI, neg. ion) m/z: 569 (M−H). Calc'd for $C_{25}H_{32}Cl_2N_4O_5S$: 570.15.

Step 2

(2R)-2-Amino-3-(3,4-dichlorophenyl)-1-(4-{2-[(methylsulfonyl)amino]phenyl}piperazinyl)propan-1-one was prepared according to the procedure for Preparation XVI using N-[(1R)-1-[(3,4-dichlorophenyl)methyl]-2-(4-{2-[(methylsulfonyl)amino]phenyl}piperazinyl)-2-oxoethyl](tert-butoxy)carboxamide (Step 1) (1.0 g, 1.8 mmol) and satd HCL in EtOAC. The resulting crude material was diluted with EtOAc and washed with satd NaHCO$_3$ soln. The organic layer was separated, dried over Na$_2$SO$_4$, filtered and concentrated in vacuo (700 mg). MS (ESI, pos.

ion) m/z: 471 (M+H), (ESI, neg. ion) m/z: 469 (M−H). Calc'd for $C_{20}H_{24}Cl_2N_4O_3S$: 470.09. Anal. Calc'd for $C_{20}H_{24}Cl_2N_4O_3S$: C, 50.96; H, 5.13; N, 11.88; Cl, 15.04. Found C, 50.66; H, 5.14; N, 11.51; Cl, 15.11.

Step 3 tert-Butyl 3-{N-[(1R)-1-[(3,4-dichlorophenyl)methyl]-2-(4-{2-[(methylsulfonyl)amino]phenyl}piperazinyl)-2-oxoethyl]carbamoyl}(3S)-1,2,3,4-tetrahydroisoquinoline-2-carboxylate was prepared from (2R)-2-amino-3-(3,4-dichlorophenyl)-1-(4-{2-[(methylsulfonyl)amino]phenyl}-piperazinyl)propan-1-one (Step 2) (350 mg, 0.750 mmol) according to the procedure for Preparation XIX using Boc-L-Tic-OH (220 mg, 0.78 mmol), 1-(3-dimethylaminopropyl)-3-ethylcarbodiimide methiodide (450 mg, 1.5 mmol), HOAT (100 mg, 0.764 mmol), and DMF (5 mL) (590 mg crude). MS (ESI, pos. ion) m/z: 730 (M+H), (ESI, neg. ion) m/z: 728 (M−H). Calc'd for $C_{35}H_{41}Cl_2N_5O_6S$: 729.22.

Step 4

N-[(1R)-1-[(3,4-Dichlorophenyl)methyl]-2-(4-{2-[(methylsulfonyl)amino]phenyl}piperazinyl)-2-oxoethyl] ((3S)(3-1,2,3,4-tetrahydroisoquinolyl)) carboxamide was prepared from tert-butyl 3-{N-[(1R)-1-[(3,4-dichlorophenyl) methyl]-2-(4-{2-[(methylsulfonyl)amino] phenyl}piperazinyl)-2-oxoethyl]carbamoyl}(3S)-1,2,3,4-tetrahydroisoquinoline-2-carboxylate (Step 3) (590 mg, 0.80 mmol) according to the procedure for Preparation XVI. The resulting crude material was diluted with EtOAc and washed with satd NaHCO₃ soln. The organic layer was separated, dried over Na₂SO₄, filtered and concentrated in vacuo. The material was purified by preparative HPLC to give the title compound (477 mg) as the TFA salt. MS (ESI, pos. ion) m/z: 630 (M+H), (ESI, neg. ion) m/z: 628 (M−H). Calc'd for $C_{30}H_{33}Cl_2N_5O_4S$: 629.16. Anal. Calc'd for $C_{30}H_{33}Cl_2N_5O_4S \cdot 1.5C_2HF_3O_2 \cdot 0.5H_2O$: C, 48.89; H, 4.41; N, 8.64; Cl, 8.75. Found C, 49.33; H, 4.47; N, 8.94; Cl, 8.61.

EXAMPLE 3

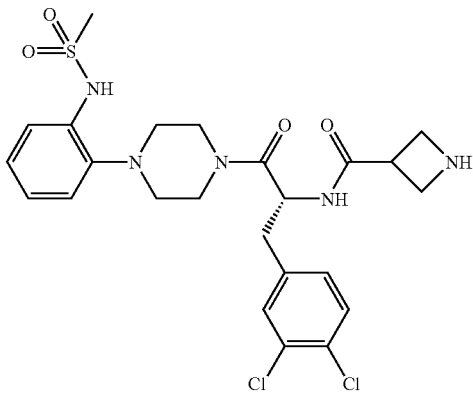

N-[(1R)-1-[(3,4-Dichlorophenyl)methyl]-2-(4-{2-[(methylsulfonyl)amino]phenyl}piperazinyl)-2-oxoethyl]azetidin-3-ylcarboxamide Step 1 tert-Butyl 3-{N-[(1R)-1-[(3,4-dichlorophenyl)methyl]-2-(4-{2-[(methylsulfonyl)amino]phenyl}piperazinyl)-2-oxoethyl]carbamoyl}azetidinecarboxylate was prepared from (2R)-2-amino-3-(3,4-dichlorophenyl)-1-(4-{2-[(methylsulfonyl)amino]phenyl}-piperazinyl)propan-1-one (Example 2, Step 2) (320 mg, 0.67 mmol), according to the procedure for Preparation XIX using Boc-azetidine-3-carboxylic acid (140 mg, 0.71 mmol), 1-(3-dimethylaminopropyl)-3-ethylcarbodiimide methiodide (400 mg, 1.3 mmol), HOAT (96 mg, 0.71 mmol), and DMF (5 mL) (448 mg crude). MS (ESI, pos. ion) m/z: 654 (M+H), (ESI, neg. ion) m/z: 652 (M−H). Calc'd for $C_{29}H_{37}Cl_2N_5O_6S$: 653.18.

Step 2

N-[(1R)-1-[(3,4-Dichlorophenyl)methyl]-2-(4-{2-[(methylsulfonyl)amino]phenyl}piperazinyl)-2-oxoethyl] azetidin-3-ylcarboxamide was prepared from tert-butyl 3-{N-[(1R)-1-[(3,4-dichlorophenyl)methyl]-2-(4-{2-[(methylsulfonyl)amino]phenyl}piperazinyl)-2-oxoethyl] carbamoyl}azetidinecarboxylate (440 mg, 0.67 mmol) according to the procedure for Preparation XVI. The resulting crude material was diluted with EtOAc and washed with satd NaHCO₃ soln. The organic layer was separated, dried over Na₂SO₄, filtered and concentrated in vacuo. Purification by preparative HPLC (TFA buffer) gave the title compound as the TFA salt (10 mg). MS (ESI, pos. ion) m/z: 554 (M+H), (ESI, neg. ion) m/z: 552 (M−H). Calc'd for $C_{24}H_{29}Cl_2N_5O_4S$: 553.13.

EXAMPLE 4

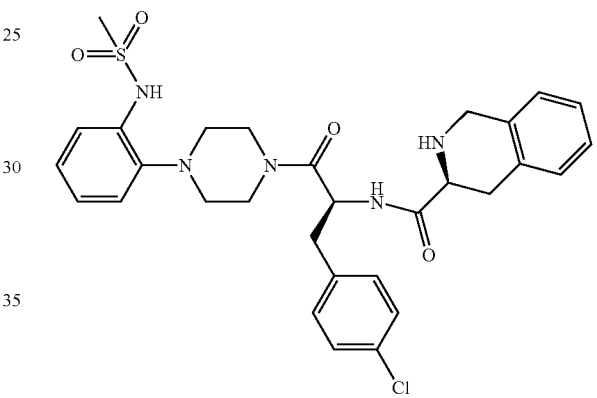

((3S)(3-1,2,3,4-Tetrahydroisoquinolyl))-N-[(1S)-1-[(4-chlorophenyl)methyl]-2-(4-{2-[(methylsulfonyl) amino]phenyl}piperazinyl)-2-oxoethyl]carboxamide Step 1

N-[(1S)-1-[(4-Chlorophenyl)methyl]-2-(4-{2-[(methylsulfonyl)amino]phenyl}piperazinyl)-2-oxoethyl] (tert-butoxy)carboxamide was prepared according to the procedure for Preparation XIX using (methylsulfonyl) (2-piperazinylphenyl)amine hydrochloride (913 mg, 3.13 mmol), N-Boc-4-chloro-L-phenylalanine (960 mg, 3.2 mmol) (Bachem), DIEA (550 μl, 3.16 mmol), 1-(3-dimethylaminopropyl)-3-ethylcarbodiimide methiodide (1.9 g, 6.5 mmol), HOAT (440 mg, 3.2 mmol) and DMF (30 mL). The crude was purified by flash chromatography (SiO₂, 1:1 hexane:EtOAc) to afford the desired compound (1.1 g). MS (ESI, pos. ion) m/z: 537 (M+H), (ESI, neg. ion) m/z: 535 (M−H). Calc'd for $C_{25}H_{33}ClN_4O_5S$: 536.19.

Step 2

(2S)-2-Amino-3-(4-chlorophenyl)-1-(4-{2-[(methylsulfonyl)amino]phenyl}piperazinyl)propan-1-one (1.1 g, 2.1 mmol) was prepared from the material of Step 1, according to the procedure for Preparation XVI. The resulting crude material was diluted with EtOAc and washed with satd NaHCO₃ soln. The organic layer was separated, dried over Na₂SO₄, filtered, and concentrated in vacuo to afford the desired compound (823 mg). MS (ESI, pos. ion) m/z: 437 (M+H), (ESI, neg. ion) m/z: 435 (M−H). Calc'd for $C_{20}H_{25}ClN_4O_3S$: 436.13. Anal. Calc'd for $C_{20}H_{25}ClN_4O_3S$: C, 54.98; H, 5.77; N, 12.82; Cl, 8.11. Found C, 55.05; H, 5.82; N, 12.68.

Step 3 tert-Butyl (3S)-3-{N-[(1S)-1-[(4-chlorophenyl)methyl]-2-(4-{2-[(methylsulfonyl)amino]phenyl}piperazinyl)-2-oxoethyl]carbamoyl}-1,2,3,4-tetrahydroisoquinoline-2-carboxylate was prepared from (2S)-2-amino-3-(4-chlorophenyl)-1-(4-{2-[(methylsulfonyl)amino]phenyl}-piperazinyl)propan-1-one (Step 2) (380 mg, 0.87 mmol), according to the procedure for Preparation XIX using Boc-L-Tic-OH (250 mg, 0.91 mmol), 1-(3-dimethylaminopropyl)-3-ethylcarbodiimide methiodide (540 mg, 1.8 mmol), HOAT (140 mg, 1.0 mmol), and DMF (25 mL). Crude material was obtained in a quantitative yield and used without further purification. MS (ESI, pos. ion) m/z: 696 (M+H), (ESI, neg. ion) m/z: 694 (M–H). Calc'd for $C_{35}H_{42}ClN_5O_6S$: 695.25.

Step 4

((3S) (3-1,2,3,4-Tetrahydroisoquinolyl))-N-[(1S)-1-[(4-chlorophenyl)methyl]-2-(4-{2-[(methylsulfonyl)amino] phenyl}piperazinyl)-2-oxoethyl]carboxamide (600 mg, 0.86 mmol) was prepared from the compound of Step 3 according to the procedure for Preparation XVI. The resulting crude material was diluted with EtOAc and washed with satd $NaHCO_3$ soln. The organic layer was separated, dried over $Na_2SO_4$, filtered, and concentrated in vacuo. The resulting crude was purified by preparative HPLC (AcOH buffer) to afford the title compound (240 mg) as the acetate salt. MS (ESI, pos. ion) m/z: 596 (M+H), (ESI, neg. ion) m/z: 594 (M–H). Calc'd for $C_{30}H_{34}ClN_5O_4S$: 595.20 Anal. Calc'd for $C_{30}H_{34}ClN_5O_4S-C_2H_4O_2-H_2O$: C, 57.01; H, 5.98; N, 10.39; Cl, 5.26. Found C, 57.69; H, 5.82; N, 10.54; Cl, 5.20.

EXAMPLES 5–7

General Procedure:

(a) To 25 mL peptide vessels were added PS-carbodiimide resin (Argonaut Technologies) (1 mmol/g) (800 mg, 0.8 mmol), an Fmoc-protected amino acid (0.4 mmol) and (methylsulfonyl)(2-piperazinylphenyl)amine hydrochloride (0.2 mmol) previously free based. The vessels were shaken for 48 h, and PS-isocyanate resin (Argonaut Technologies) was added to each vessel (1.76 mmol/g) (500 mg, 0.9 mmol). After shaking for 48 h, the mixture was filtered into scintillation vials containing DMAP (50 mg, 0.5 mmol) and piperidine-4-carboxylic acid polyamine resin HL (Nova Biochem) (0.7 mmol/g) (1 g, 0.7 mmol) and shaken for another 48 h. These reaction mixtures were filtered into 10 mL scintillation vials containing PS-carbodiimide resin (Argonaut Technologies) (1 mmol/g) (800 mg, 0.8 mmol) and Boc-L-Tic-OH (100 mg, 0.36 mmol).

(b) These vials were shaken for 48 h. To each vial was added PS-isocyanate resin (Argonaut Technologies) (1.76 mmol/g) (1 g, 1.76 mmol) and shaking continued for 48 h. The solutions were filtered, concentrated in vacuo, and treated with 30% TFA in $CH_2Cl_2$ for 1.5 h. The solvent was eliminated in vacuo, and the resulting crude products were purified by preparative HPLC to yield the TFA salts of the products.

EXAMPLE 5

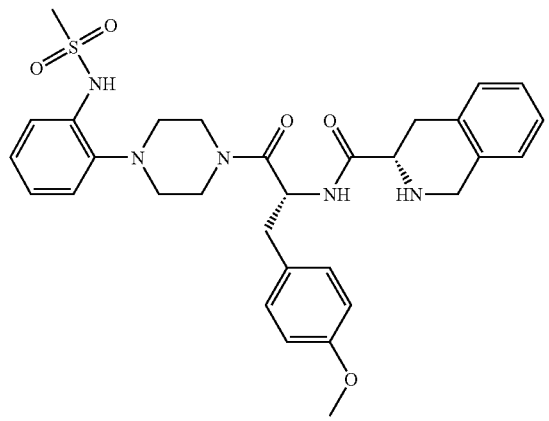

N-[(1R)-1-[(4-Methoxyphenyl)methyl]-2-(4-{2-[(methylsulfonyl)amino]phenyl}piperazinyl)-2-oxoethyl]((3S)(3-1,2,3,4-tetrahydroisoquinolyl))-carboxamide MS (ESI, pos. ion) m/z: 592 (M+H), (ESI, neg. ion) m/z: 590 (M–H). Calc'd for $C_{31}H_{37}N_5O_5S$: 591.25.

EXAMPLE 6

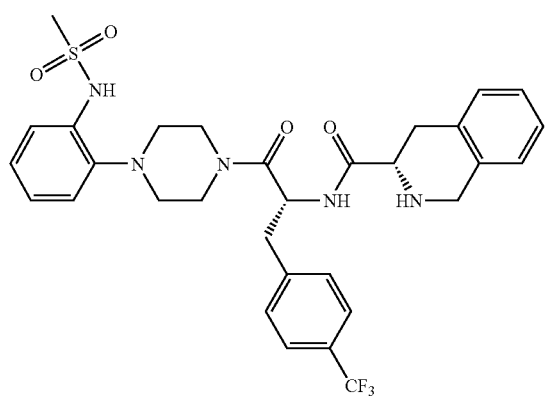

N-[(1R)-2-(4-{2-[(Methylsulfonyl)amino] phenyl}piperazinyl)-2-oxo-1-{[4-(trifluoromethyl) phenyl]methyl}ethyl]((3S)(3-1,2,3,4-tetrahydroisoquinolyl))carboxamide MS (ESI, pos. ion) m/z: 630 (M+H), (ESI, neg. ion) m/z: 628 (M–H). Calc'd for $C_{31}H_{34}F_3N_5O_4S$: 629.23.

EXAMPLE 7

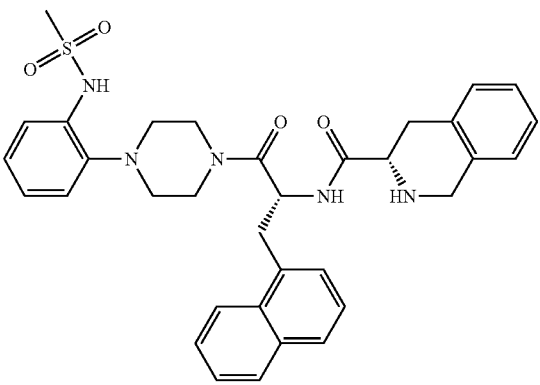

N-[(1R)-2-(4-{2-[(Methylsulfonyl)amino]phenyl}piperazinyl)-1-(naphthylmethyl)-2-oxoethyl]((3S)(3-1,2,3,4-tetrahydroisoquinolyl))carboxamide MS (ESI, pos. ion) m/z: 612 (M+H), (ESI, neg. ion) m/z: 610 (M−H). Calc'd for $C_{34}H_{37}N_5O_4S$: 611.26.

EXAMPLES 8–16

General Procedure:

To 10 mL scintillation vials were added PS-carbodiimide resin (Argonaut Technologies) (1 mmol/g) (400 mg, 0.4 mmol) and the appropriate Boc protected amino acid (0.2 mmol). DMF (5 mL) was added followed by a stock solution of (2R)-2-amino-3-(4-chlorophenyl)-1-(4-{2-[(methylsulfonyl) amino]phenyl}piperazinyl)propan-1-one TFA salt (0.1 mmol) (previously free-based) in DMF. The vials were shaken over night. The reactions were filtered and the resins were washed with a 2:1 mixture of $CH_2Cl_2$:DMF (2×2 mL). The solutions were concentrated in vacuo and the Boc groups were removed by dissolving the crude product in $CH_2Cl_2$ (1 mL) and adding TFA (1 mL). The vials were shaken for 2 h and the solvent was removed in vacuo. Each compound was purified by preparative HPLC (TFA buffer) to yield the TFA salt of the desired product.

EXAMPLE 8

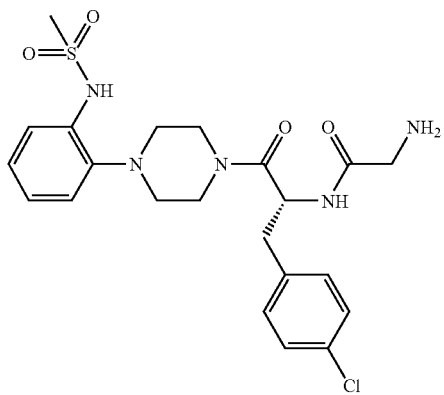

N-[(1R)-1-[(4-Chlorophenyl)methyl]-2-(4-{2-[(methylsulfonyl)amino]phenyl}piperazinyl)-2-oxoethyl]-2-aminoacetamide MS (ESI, pos. ion) m/z: 494 (M+H), (ESI, neg. ion) m/z: 492 (M−H). Calc'd for $C_{22}H_{28}ClN_5O_4S$: 493.16.

EXAMPLE 9

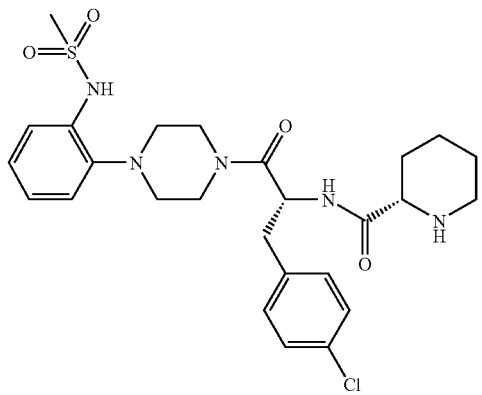

N-[(1R)-1-[(4-Chlorophenyl)methyl]-2-(4-{2-[(methylsulfonyl)amino]phenyl}piperazinyl)-2-oxoethyl]((2S)(2-piperidyl))carboxamide MS (ESI, pos. ion) m/z: 548 (M+H), (ESI, neg. ion) m/z: 546 (M−H). Calc'd for $C_{26}H_{34}ClN_5O_4S$: 547.20.

EXAMPLE 10

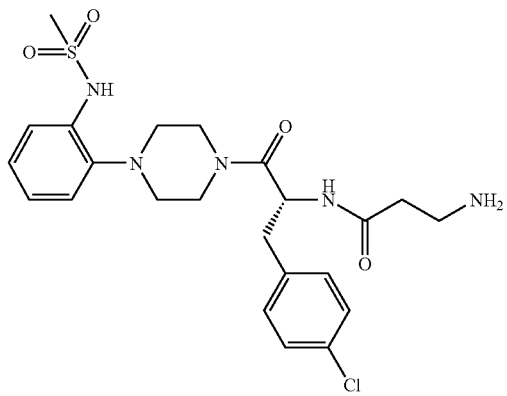

N-[(1R)-1-[(4-Chlorophenyl)methyl]-2-(4-{2-[(methylsulfonyl)amino]phenyl}piperazinyl)-2-oxoethyl]-3-aminopropanamide MS (ESI, pos. ion) m/z: 508 (M+H), (ESI, neg. ion) m/z: 506 (M−H). Calc'd for $C_{23}H_{30}ClN_5O_4S$: 507.17.

EXAMPLE 11

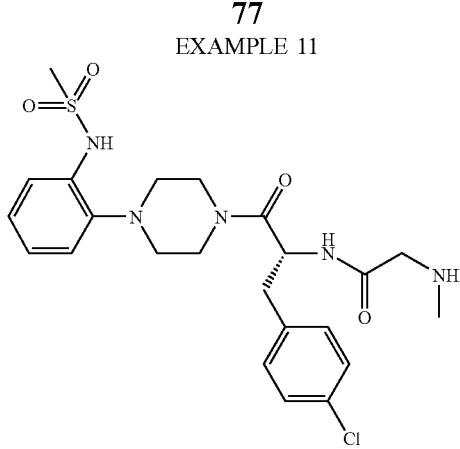

N-[(1R)-1-[(4-Chlorophenyl)methyl]-2-(4-{2-[(methylsulfonyl)amino]phenyl}piperazinyl)-2-oxoethyl]-2-(methylamino)acetamide MS (ESI, pos. ion) m/z: 508 (M+H), (ESI, neg. ion) m/z: 506 (M−H). Calc'd for $C_{23}H_{30}ClN_5O_4S$: 507.17.

EXAMPLE 12

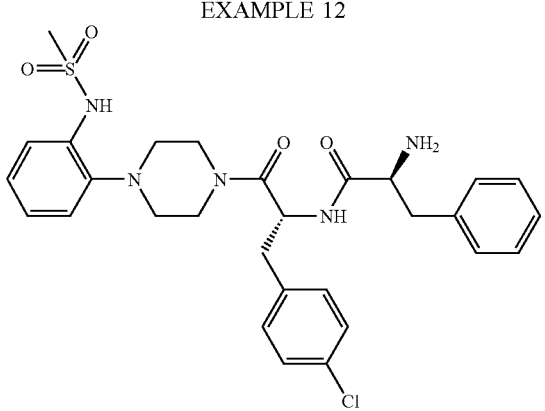

N-[(1R)-1-[(4-Chlorophenyl)methyl]-2-(4-{2-[(methylsulfonyl)amino]phenyl}piperazinyl)-2-oxoethyl](2S)-2-amino-3-phenylpropanamide MS (ESI, pos. ion) m/z: 584 (M+H), (ESI, neg. ion) m/z: 582 (M−H). Calc'd for $C_{29}H_{34}ClN_5O_4S$: 583.20.

EXAMPLE 13

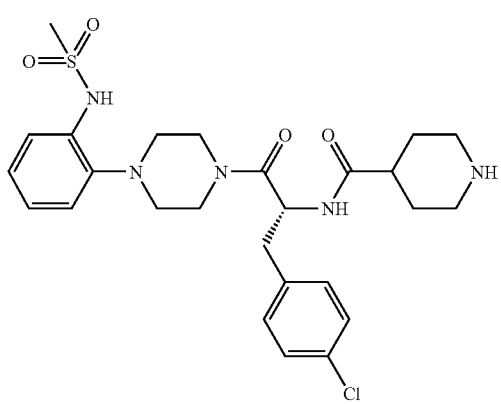

N-[(1R)-1-[(4-Chlorophenyl)methyl]-2-(4-{2-[(methylsulfonyl)amino]phenyl}piperazinyl)-2-oxoethyl]-4-piperidylcarboxamide MS (ESI, pos. ion) m/z: 548 (M+H), (ESI, neg. ion) m/z: 546 (M−H). Calc'd for $C_{26}H_{34}ClN_5O_4S$: 547.20.

EXAMPLE 14

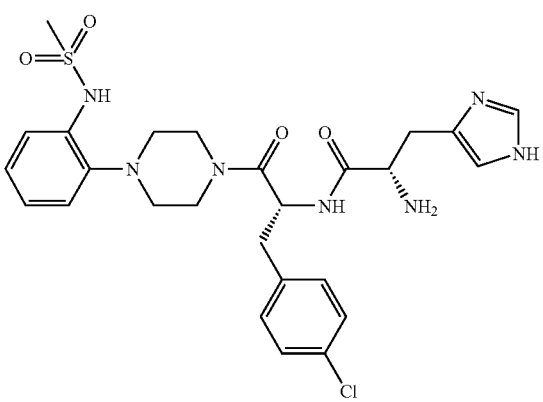

N-[(1R)-1-[(4-Chlorophenyl)methyl]-2-(4-{2-[(methylsulfonyl)amino]phenyl}piperazinyl)-2-oxoethyl](2S)-2-amino-3-imidazol-4-ylpropanamide MS (ESI, pos. ion) m/z: 574 (M+H), (ESI, neg. ion) m/z: 572 (M−H). Calc'd for $C_{26}H_{32}ClN_7O_4S$: 573.19.

EXAMPLE 15

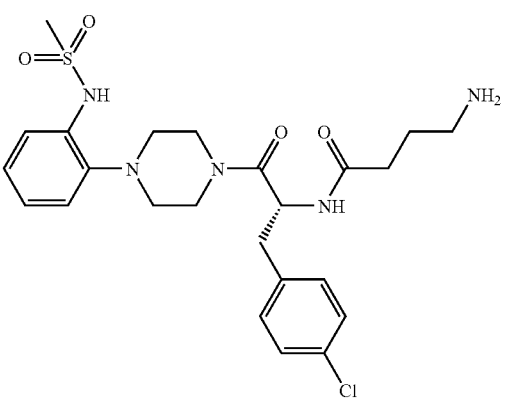

N-[(1R)-1-[(4-Chlorophenyl)methyl]-2-(4-{2-[(methylsulfonyl)amino]phenyl}piperazinyl)-2-oxoethyl]-4-aminobutanamide MS (ESI, pos. ion) m/z: 522 (M+H), (ESI, neg. ion) m/z: 520 (M−H). Calc'd for $C_{24}H_{32}ClN_5O_4S$: 521.19.

EXAMPLE 16

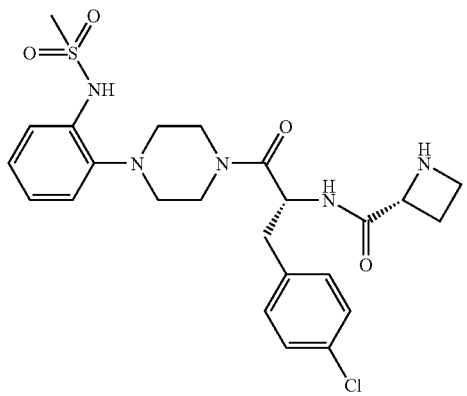

((2R)Azetidin-2-yl)-N-[(1R)-1-[(4-chlorophenyl)
methyl]-2-(4-{2-[(methylsulfonyl)amino]
phenyl}piperazinyl)-2-oxoethyl]carboxamide MS (ESI, pos. ion) m/z: 520 (M+H), (ESI, neg. ion) m/z: 518 (M−H). Calc'd for $C_{24}H_{30}ClN_5O_4S$: 519.17.

EXAMPLES 17–18

General Procedure:

To 10 mL scintillation vials were added tetrafluorophenol resin (TFP) (IRORI Inc.) (0.96 mmol/g) (125 mg, 0.12 mmol) loaded with the appropriate acid and (2R)-2-amino-3-(4-chlorophenyl)-1-(4-{2-[(methylsulfonyl)amino]phenyl)piperazinyl)propan-1-one TFA salt (0.1 mmol, previously free based) in DMF (2 mL). After shaking at RT for 16 h, the reactions were filtered and the resin was washed with 2:1 $CH_2Cl_2$:DMF (2×2 mL). The solutions were concentrated in vacuo and each compound was purified by preparative HPLC (TFA buffer).

EXAMPLE 17

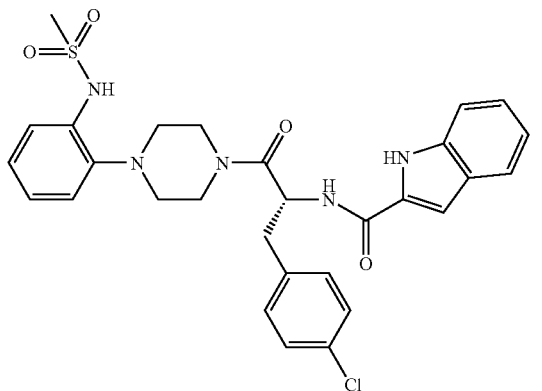

N-[(1R)-1-[(4-Chlorophenyl)methyl]-2-(4-{2-[(methylsulfonyl)amino]phenyl}piperazinyl)-2-oxoethyl]indol-2-ylcarboxamide MS (ESI, pos. ion) m/z: 580 (M+H), (ESI, neg. ion) m/z: 578 (M−H). Calc'd for $C_{29}H_{30}ClN_5O_4S$: 579.17.

EXAMPLE 18

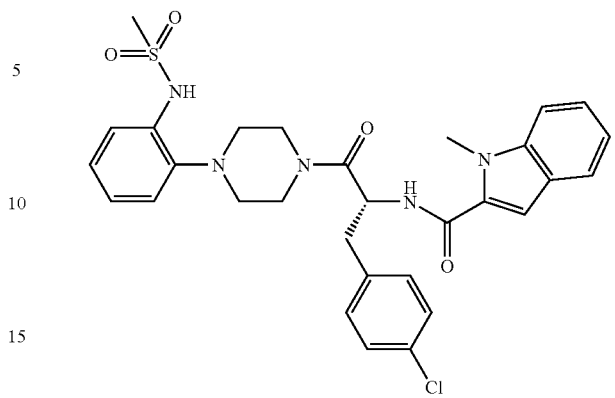

N-[(1R)-1-[(4-Chlorophenyl)methyl]-2-(4-{2-[(methylsulfonyl)amino]phenyl}piperazinyl)-2-oxoethyl](1-methylindol-2-yl)carboxamide MS (ESI, pos. ion) m/z: 594 (M+H), (ESI, neg. ion) m/z: 592 (M−H). Calc'd for $C_{30}H_{32}ClN_5O_4S$: 593.19.

EXAMPLES 19–32

General Procedure:

To 10 mL scintillation vials were added PS-carbodiimide resin (Argonaut Technologies) (1 mmol/g) (400 mg, 0.4 mmol) and the appropriate acid (0.2 mmol) in DMF (2 mL). After shaking at RT for 0.5 h, a solution of (2R)-2-amino-3-(4-chlorophenyl)-1-(4-{2-[(methylsulfonyl)amino]phenyl}piperazinyl)propan-1-one TFA salt (0.1 mmol, previously free-based) dissolved in 1:1 $CH_2Cl_2$:DMF was added to each vial, and the vials were shaken for 48 h. PS-isocyanate resin (Argonaut Technologies) (1.76 mmol/g) (500 mg, 0.9 mmol) was added to each reaction vial, and shaking was continued for 48 h. The reactions were filtered and concentrated in vacuo. The crude products were purified by preparative HPLC (TFA buffer).

EXAMPLE 19

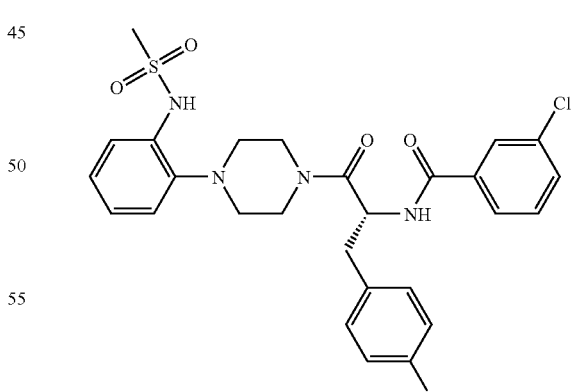

N-[(1R)-1-[(4-Chlorophenyl)methyl]-2-(4-{2-[(methylsulfonyl)amino]phenyl}piperazinyl)-2-oxoethyl](3-chlorophenyl)carboxamide MS (ESI, pos. ion) m/z: 575 (M+H), (ESI, neg. ion) m/z: 573 (M−H). Calc'd for $C_{27}H_{28}Cl_2N_4O_4S$: 574.12.

EXAMPLE 20

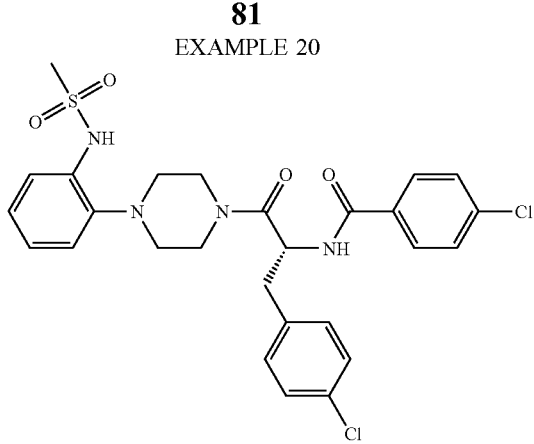

N-[(1R)-1-[(4-Chlorophenyl)methyl]-2-(4-{2-[(methylsulfonyl)amino]phenyl}piperazinyl)-2-oxoethyl](4-chlorophenyl)carboxamide MS (ESI, pos. ion) m/z: 575 (M+H), (ESI, neg. ion) m/z: 573 (M−H). Calc'd for $C_{27}H_{28}Cl_2N_4O_4S$: 574.12.

EXAMPLE 21

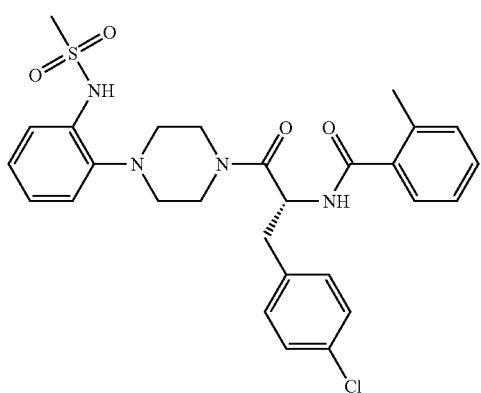

N-[(1R)-1-[(4-Chlorophenyl)methyl]-2-(4-{2-[(methylsulfonyl)amino]phenyl}piperazinyl)-2-oxoethyl](2-methylphenyl)carboxamide MS (ESI, pos. ion) m/z: 555 (M+H), (ESI, neg. ion) m/z: 553 (M−H). Calc'd for $C_{28}H_{31}ClN_4O_4S$: 554.18.

EXAMPLE 22

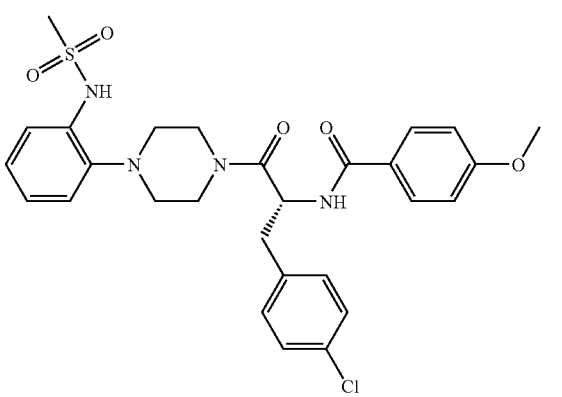

N-[(1R)-1-[(4-Chlorophenyl)methyl]-2-(4-{2-[(methylsulfonyl)amino]phenyl}piperazinyl)-2-oxoethyl](4-methoxyphenyl)carboxamide MS (ESI, pos. ion) m/z: 571 (M+H), (ESI, neg. ion) m/z: 569 (M−H). Calc'd for $C_{28}H_{31}ClN_4O_5S$: 570.17.

EXAMPLE 23

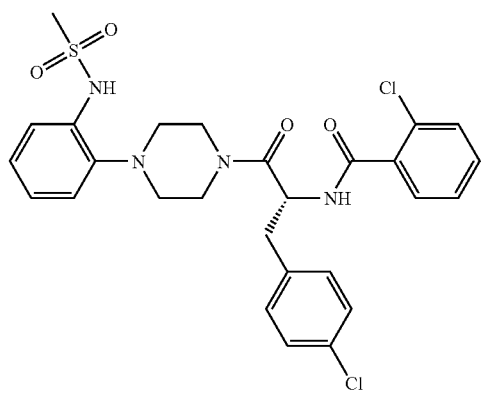

N-[(1R)-1-[(4-Chlorophenyl)methyl]-2-(4-{2-[(methylsulfonyl)amino]phenyl}piperazinyl)-2-oxoethyl](2-chlorophenyl)carboxamide MS (ESI, pos. ion) m/z: 575 (M+H), (ESI, neg. ion) m/z: 573 (M−H). Calc'd for $C_{27}H_{28}Cl_2N_4O_4S$: 574.12.

EXAMPLE 24

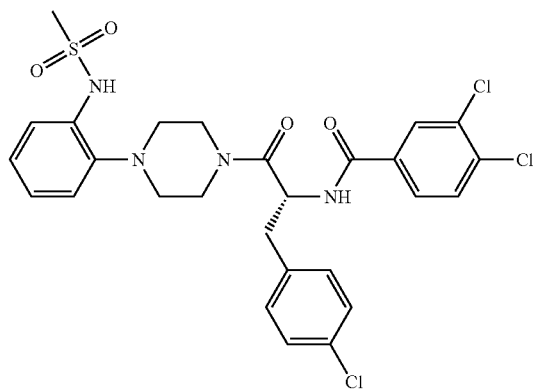

N-[(1R)-1-[(4-Chlorophenyl)methyl]-2-(4-{2-[(methylsulfonyl)amino]phenyl}piperazinyl)-2-oxoethyl](3,4-dichlorophenyl)carboxamide MS (ESI, pos. ion) m/z: 609 (M+H), (ESI, neg. ion) m/z: 607 (M−H). Calc'd for $C_{27}H_{27}Cl_3N_4O_4S$: 608.08.

EXAMPLE 25

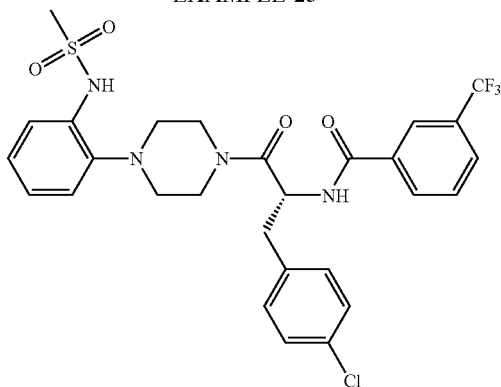

N-[(1R)-1-[(4-Chlorophenyl)methyl]-2-(4-{2-[(methylsulfonyl)amino]phenyl}piperazinyl)-2-oxoethyl][3-(trifluoromethyl)phenyl]carboxamide MS (ESI, pos. ion) m/z: 609 (M+H), (ESI, neg. ion) m/z: 607 (M−H). Calc'd for $C_{28}H_{28}ClF_3N_4O_4S$: 608.15.

EXAMPLE 26

2H-Benzo[d]1,3-dioxolan-5-yl-N-[(1R)-1-[(4-chlorophenyl)methyl]-2-(4-{2-[(methylsulfonyl)amino]phenyl}piperazinyl)-2-oxoethyl]carboxamide MS (ESI, pos. ion) m/z: 585 (M+H), (ESI, neg. ion) m/z: 583 (M−H). Calc'd for $C_{28}H_{29}ClN_4O_6S$: 584.15.

EXAMPLE 27

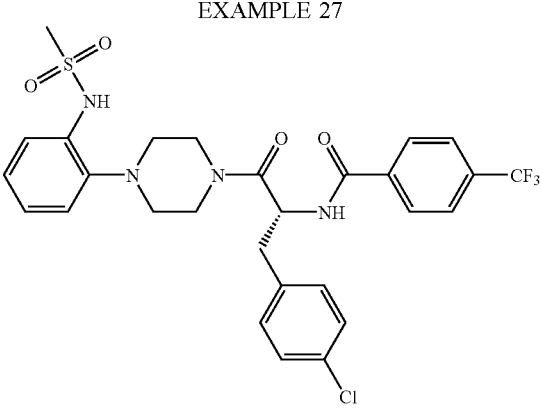

EXAMPLE 28

N-[(1R)-1-[(4-Chlorophenyl)methyl]-2-(4-{2-[(methylsulfonyl)amino]phenyl}piperazinyl)-2-oxoethyl][4-(trifluoromethyl)phenyl]carboxamide MS (ESI, pos. ion) m/z: 609 (M+H), (ESI, neg. ion) m/z: 607 (M−H). Calc'd for $C_{28}H_{28}ClF_3N_4O_4S$: 608.15.

EXAMPLE 28

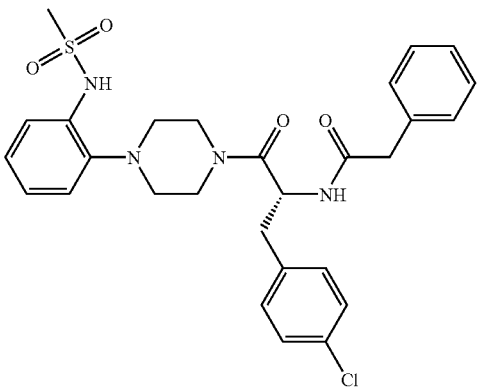

N-[(1R)-1-[(4-Chlorophenyl)methyl]-2-(4-{2-[(methylsulfonyl)amino]phenyl}piperazinyl)-2-oxoethyl]-2-phenylacetamide MS (ESI, pos. ion) m/z: 555 (M+H), (ESI, neg. ion) m/z: 553 (M−H). Calc'd for $C_{28}H_{31}ClN_4O_4S$: 554.15. Anal. Calc'd for $C_{28}H_{31}ClN_4O_4S \cdot 1.5 \ H_2O$: C, 57.77; H, 5.89; N, 9.62. Found: C, 58.11; H, 6.18; N, 9.59.

EXAMPLE 29

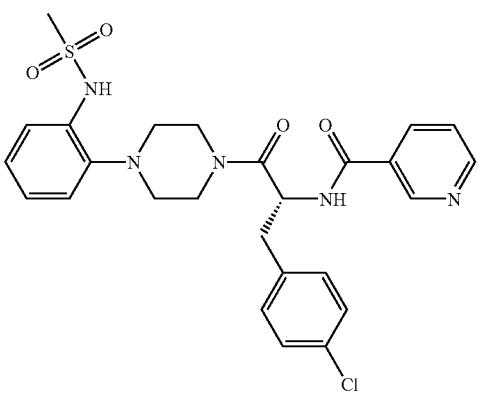

N-[(1R)-1-[(4-Chlorophenyl)methyl]-2-(4-{2-[(methylsulfonyl)amino]phenyl}piperazinyl)-2-oxoethyl]-3-pyridylcarboxamide MS (ESI, pos. ion) m/z: 542 (M+H), (ESI, neg. ion) m/z: 540 (M−H). Calc'd for $C_{26}H_{28}ClN_5O_4S$: 541.16.

EXAMPLE 30

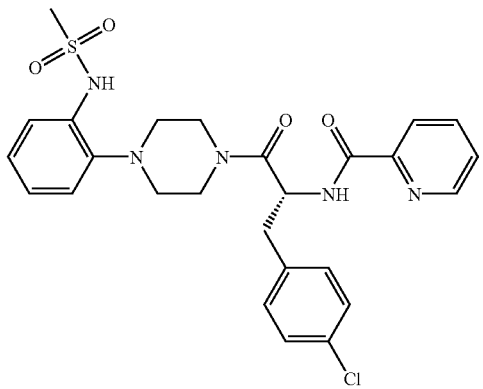

N-[(1R)-1-[(4-Chlorophenyl)methyl]-2-(4-{2-[(methylsulfonyl)amino]phenyl}piperazinyl)-2-oxoethyl]-2-pyridylcarboxamide MS (ESI, pos. ion) m/z: 542 (M+H), (ESI, neg. ion) m/z: 540 (M−H). Calc'd for $C_{26}H_{28}ClN_5O_4S$: 541.16.

EXAMPLE 31

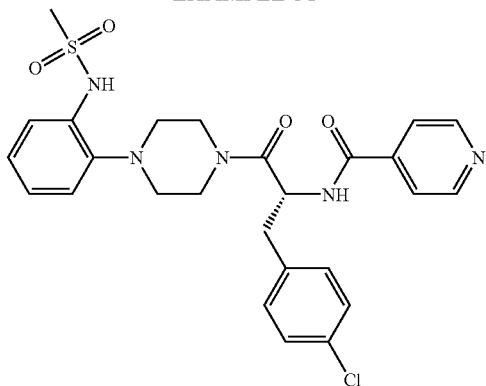

N-[(1R)-1-[(4-Chlorophenyl)methyl]-2-(4-{2-[(methylsulfonyl)amino]phenyl}piperazinyl)-2-oxoethyl]-4-pyridylcarboxamide MS (ESI, pos. ion) m/z: 542 (M+H), (ESI, neg. ion) m/z: 540 (M−H). Calc'd for $C_{26}H_{28}ClN_5O_4S$: 541.16.

EXAMPLE 32

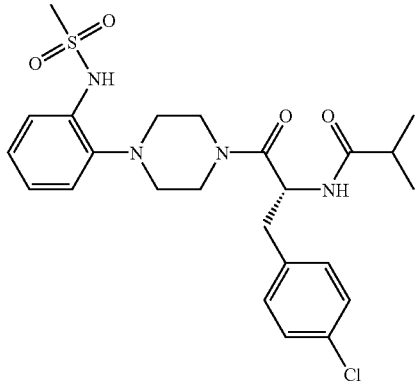

N-[(1R)-1-[(4-Chlorophenyl)methyl]-2-(4-{2-[(methylsulfonyl)amino]phenyl}piperazinyl)-2-oxoethyl]-2-methylpropanamide MS (ESI, pos. ion) m/z: 507 (M+H), (ESI, neg. ion) m/z: 505 (M−H). Calc'd for $C_{24}H_{31}ClN_4O_4S$: 506.18.

EXAMPLE 33

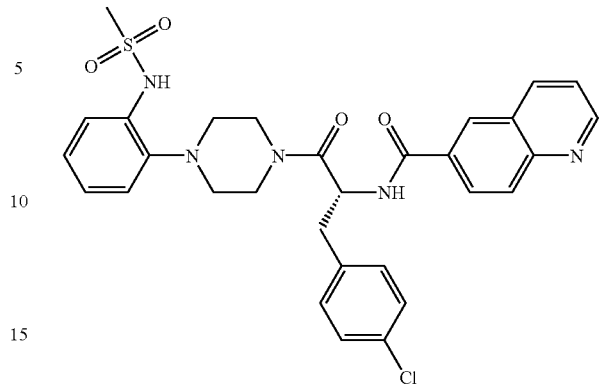

N-[(1R)-1-[(4-Chlorophenyl)methyl]-2-(4-{2-[(methylsulfonyl)amino]phenyl}piperazinyl)-2-oxoethyl]-6-quinolylcarboxamide (2R)-2-Amino-3-(4-chlorophenyl)-1-(4-{2-[(methylsulfonyl)amino]phenyl}piperazinyl)propan-1-one, TFA salt (850 mg, 1.6 mmol) was diluted with EtOAc and washed with satd $NaHCO_3$ soln. The organic layer was separated, dried over $Na_2SO_4$, filtered and concentrated in vacuo. This material was used to prepare the title compound according to the procedure for Preparation XIX using quinoline-6-carboxylic acid (240 mg, 1.40 mmol) (Acros), HOAT (190 mg, 1.40 mmol), 1-(3-dimethylaminopropyl)-3-ethylcarbodiimide methiodide (810 mg, 2.7 mmol) and DMF (50 mL). The crude material was purified by flash chromatography, ($SiO_2$, 3% MeOH in $CH_2Cl_2$) and concentrated in vacuo to provide 500 mg. The purified product was dissolved in $H_2O$ with $CH_3CN$ and AcOH, then lyophilized to yield the acetate salt. MS (ESI, pos. ion) m/z: 592 (M+H), (ESI, neg. ion) m/z: 590 (M−H). Calc'd for $C_{30}H_{30}ClN_5O_4S$: 591.17. Anal. Calc'd for $C_{30}H_{30}ClN_5O_4S$-$0.5C_2H_4O_2$-$0.5H_2O$: C, 58.99; H, 5.27; N 11.10; Cl, 5.62. Found C, 59.32; H, 5.23; N, 11.25; Cl, 5.89.

EXAMPLE 34

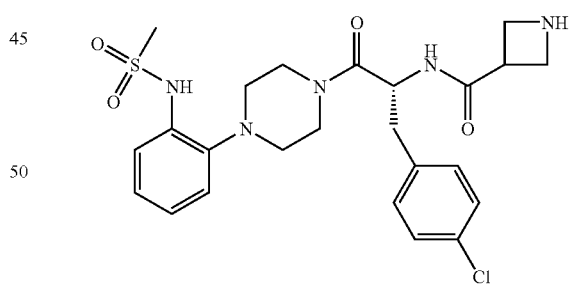

N-[(1R)-1-[(4-Chlorophenyl)methyl]-2-(4-{2-[(methylsulfonyl)amino]phenyl}piperazinyl)-2-oxoethyl]azetidin-3-ylcarboxamide Step 1

Following the procedure of Preparation V, tert-butyl 3-{N-[(1R)-1-[(4-chlorophenyl)methyl]-2-(4-{2-[(methylsulfonyl)amino]phenyl}piperazinyl)-2-oxoethyl]-carbamoyl}azetidinecarboxylate was prepared from (2R)-2-amino-3-(4-chlorophenyl)-1-(4-{2-[(methylsulfonyl)-amino]phenyl}piperazinyl)propan-1-one TFA salt (200 mg, 0.36 mmol) in DMF (1 mL), DIEA (Aldrich) (0.18 mL, 1.05 mmol), Boc-azetidine-3-carboxylic acid (PepTech Corp.) (73 mg, 0.36 mmol), HOAT (Aldrich) (41 mg, 0.30 mmol), and EDC (Sigma) (86 mg, 0.45 mmol). The crude was purified by flash column chromatography (silica gel, 1:1 EtOAc-hexane) to give the protected compound as an off-white solid (88 mg). MS (ESI, pos. ion) m/z: 620 (M+H); (ESI, neg. ion) m/z: 618 (M−H). Calc'd for $C_{29}H_{38}ClN_5O_6S$: 619.22.

Step 2

Following the procedure of Preparation VI, N-[(1R)-1-[(4-chlorophenyl)methyl]-2-(4-{2-[(methylsulfonyl)-amino]phenyl}piperazinyl)-2-oxoethyl]azetidin-3-ylcarboxamide was prepared from tert-butyl 3-{N-[(1R)-1-[(4-chlorophenyl)methyl]-2-(4-(2-[(methylsulfonyl)-amino]phenyl}piperazinyl)-2-oxoethyl]carbamoyl}-azetidinecarboxylate (Step 1) (88 mg, 0.14 mmol) and 1 mL of 1:1 TFA-CH₂Cl₂. The crude product was purified by preparative HPLC (TFA buffer) to afford the title compound (TFA salt) as a white solid (44 mg). MS (ESI, pos. ion) m/z: 520 (M+H). Calc'd for $C_{24}H_{30}ClN_5O_4S$: 519.17.

EXAMPLE 35

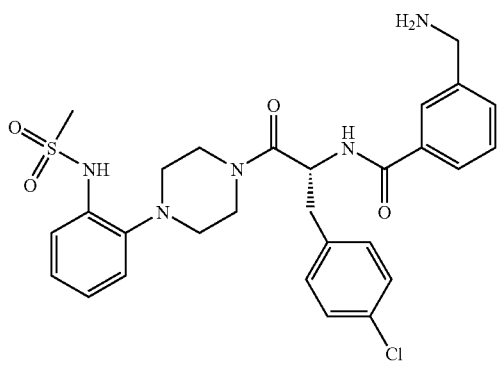

N-[(1R)-1-[(4-Chlorophenyl)methyl]-2-(4-{2-[(methylsulfonyl)amino]phenyl}piperazinyl)-2-oxoethyl][3-(aminomethyl)phenyl]carboxamide The title compound was prepared according to the procedure described in Example 34 by using 3-Boc-aminomethyl-benzoic acid (Chem-Impex International Inc.) (91 mg, 0.36 mmol). The title compound, TFA salt, was isolated as a white solid (133 mg). MS (ESI, pos. ion) m/z: 570 (M+H); (ESI, neg. ion) m/z: 568 (M−H). Calc'd for $C_{28}H_{32}ClN_5O_4S$: 569.19.

EXAMPLE 36

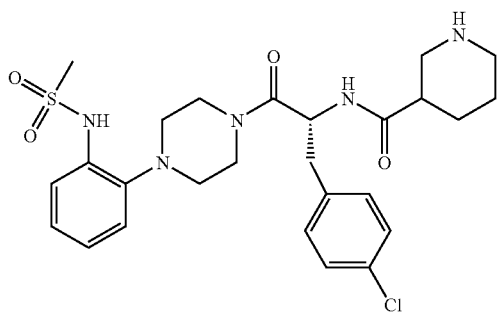

N-[(1R)-1-[(4-Chlorophenyl)methyl]-2-(4-{2-[(methylsulfonyl)amino]phenyl}piperazinyl)-2-oxoethyl]-3-piperidylcarboxamide The title compound was prepared according to the procedure described in Example 34 by using piperidine-1,3-dicarboxylic acid 1-tert-butyl ester (Aldrich) (82 mg, 0.36 mmol). The title compound as the TFA salt, was isolated as a white solid (83 mg) containing two diastereomers. MS (ESI, pos. ion) m/z: 548 (M+H); (ESI, neg. ion) m/z: 546 (M−H). Calc'd for $C_{26}H_{34}ClN_5O_4S$: 547.20.

EXAMPLE 37

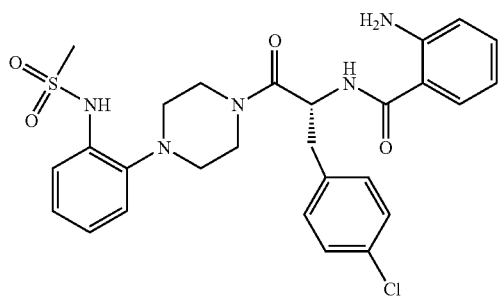

N-[(1R)-1-[(4-Chlorophenyl)methyl]-2-(4-{2-[(methylsulfonyl)amino]phenyl}piperazinyl)-2-oxoethyl](2-aminophenyl)carboxamide The title compound was prepared according to the procedure described in Example 34 by using 2-tert-butoxycarbonylaminobenzoic acid (Advanced ChemTech) (85 mg, 0.36 mmol). The title compound, as the TFA salt, was isolated as a white solid (36 mg). MS (ESI, pos. ion) m/z: 556 (M+H); (ESI, neg. ion) m/z: 554 (M−H). Calc'd for $C_{27}H_{30}ClN_5O_4S$: 555.17.

EXAMPLE 38

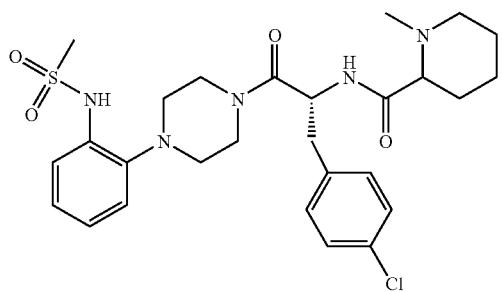

N-[(1R)-1-[(4-Chlorophenyl)methyl]-2-(4-{2-[(methylsulfonyl)amino]phenyl}piperazinyl)-2-oxoethyl](1-methyl(2-piperidyl))carboxamide Step 1 tert-Butyl 2-{N-[(1R)-1-[(4-chlorophenyl)methyl]-2-(4-{2-[(methylsulfonyl)amino]phenyl}piperazinyl)-2-oxoethyl]carbamoyl}piperidinecarboxylate was prepared according to the procedure described in Preparation V by using piperidine-1,2-dicarboxylic acid 1-tert-butyl ester (Aldrich) (82 mg, 0.36 mmol) and (2R)-2-Amino-3-(4-chlorophenyl)-1-(4-{2-[(methylsulfonyl}-amino]phenyl}piperazinyl)propan-1-one. The desired compound was isolated as a white solid (106 mg). MS (ESI, pos. ion) m/z: 648 (M+H); (ESI, neg. ion) m/z: 646 (M−H). Calc'd for $C_{31}H_{42}ClN_5O_6S$: 647.25.

Step 2

N-[(1R)-1-[(4-Chlorophenyl)methyl]-2-(4-{2-[(methylsulfonyl)amino]phenyl}piperazinyl)-2-oxoethyl]-2-piperidylcarboxamide, trifluoroacetate was prepared according to the procedure described in Preparation VI by using tert-butyl 2-{N-[(1R)-1-[(4-chlorophenyl) methyl]-2-(4-{2-[(methylsulfonyl)amino]phenyl}piperazinyl)-2-oxoethyl]carbamoyl}piperidinecarboxylate (Step 1). The crude material was used directly in the next step without further purification. MS (ESI, pos. ion) m/z: 548 (M+H); (ESI, neg. ion) m/z: 546 (M−H). Calc'd for $C_{26}H_{34}ClN_5O_4S$: 547.20.

Step 3

To a round-bottomed flask equipped with magnetic stirring was added N-[(1R)-1-[(4-chlorophenyl)methyl]-2-(4-{2-[(methylsulfonyl)amino]phenyl}piperazinyl)-2-oxoethyl]-2-piperidylcarboxamide, trifluoroacetate (Step 2) (0.16 mmol), $ClCH_2CH_2Cl$ (1 mL) and DIEA (Aldrich) (0.06 mL, 0.32 mmol). Formaldehyde (Aldrich, 37% aqueous soln) (0.03 mL, 0.33 mmol) was added to the reaction mixture, followed by $NaBH(OAc)_3$ (Aldrich Chemical Company) (52 mg, 0.25 mmol), and the reaction mixture was stirred at RT 18 h. The mixture was diluted with $CH_2Cl_2$, and the organic solution was washed with satd $NaHCO_3$ and brine. The organic layer was dried over $Na_2SO_4$, filtered and concentrated in vacuo. The crude product was purified by flash column chromatography (silica gel, 5:95 $MeOH-CH_2Cl_2$) to give N-[(1R)-1-[(4-chlorophenyl)methyl]-2-(4-{2-[(methylsulfonyl)amino]phenyl}piperazinyl)-2-oxoethyl]-(1-methyl(2-piperidyl))carboxamide as a white solid, (71 mg) (two diastereomers). MS (ESI, pos. ion) m/z: 562 (M+H); (ESI, neg. ion) m/z: 560 (M−H). Calc'd for $C_{27}H_{36}ClN_5O_4S$: 561.22.

EXAMPLE 39

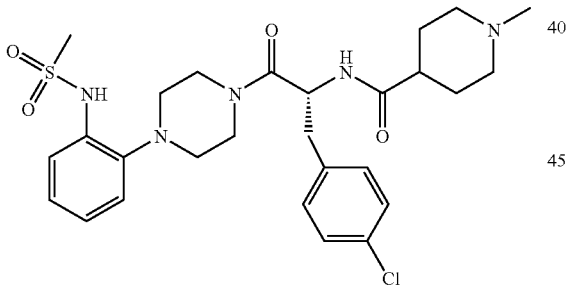

N-[(1R)-1-[(4-Chlorophenyl)methyl]-2-(4-{2-[(methylsulfonyl)amino]phenyl}piperazinyl)-2-oxoethyl](1-methyl(4-piperidyl))carboxamide The title compound was prepared according to the procedure of Example 38 by using piperidine-1,4-dicarboxylic acid mono-tert-butyl ester (Aldrich) (82 mg, 0.36 mmol). The title compound was isolated as a white solid (63 mg MS (ESI, pos. ion) m/z: 562 (M+H); (ESI, neg. ion) m/z: 560 (M−H). Calc'd for $C_{27}H_{36}ClN_5O_4S$: 561.22.

EXAMPLE 40

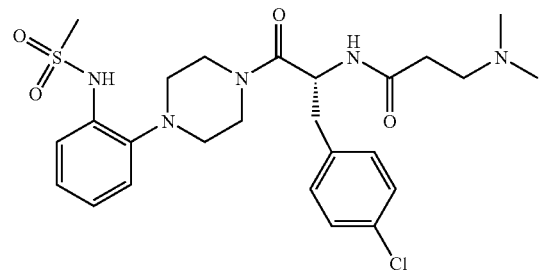

N-[(1R)-1-[(4-Chlorophenyl)methyl]-2-(4-{2-[(methylsulfonyl)amino]phenyl}piperazinyl)-2-oxoethyl]-3-(dimethylamino)propanamide The title compound was prepared according to the procedure of Example 40 by using 3-tert-butoxycarbonyl-aminopropionic acid (Novabiochem). The title compound was isolated as a white solid. MS (ESI, pos. ion) m/z: 536 (M+H); (ESI, neg. ion) m/z: 534 (M−H). Calc'd for $C_{25}H_{34}ClN_5O_4S$: 535.20.

EXAMPLE 41

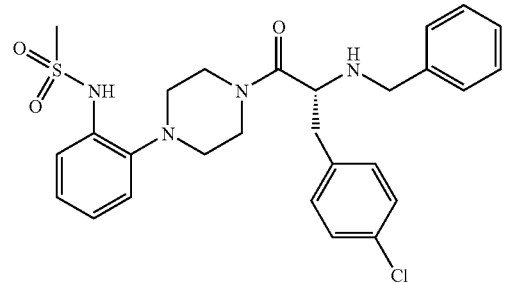

(2R)-3-(4-Chlorophenyl)-1-(4-{2-[(methylsulfonyl)amino]phenyl}piperazinyl)-2-[benzylamino]propan-1-one Following the procedure of Example 38, Step 3, (2R)-3-(4-chlorophenyl)-1-(4-{2-[(methylsulfonyl)-amino]phenyl}-piperazinyl)-2-[benzylamino]propan-1-one, hydrochloride was prepared from (2R)-2-amino-3-(4-chlorophenyl)-1-(4-{2-[(methylsulfonyl)amino]phenyl}-piperazinyl)propan-1-one TFA salt (0.6 g, 1.1 mmol) in $ClCH_2Cl_2Cl$ (10 mL), benzaldehyde (Aldrich) (0.14 mL, 1.4 mmol) and $NaBH(OAc)_3$ (Aldrich) (340 mg, 1.9 mmol). The desired compound was purified by preparative TLC (60% Hexane, 38% $CH_2Cl_2$, and 2% 2N $NH_3$ in MeOH), and treated with a soln of EtOAc satd with HCl. A precipitate formed (HCl salt), was filtered and dried in vacuo to afford the desired product as a white solid (130 mg). MS (ESI, pos. ion) m/z: 527 (M+H); MS (ESI, neg. ion) m/z: 525 (M−H). Calc'd for $C_{27}H_{31}ClN_4O_3S$. 526.18. Anal. Calcd for $C_{27}H_{31}ClN_4O_3S.1.1$ HCl. $0.9H_2O$: C, 55.59; H, 5.86; N, 9.60; Cl, 12.76. Found: C, 55.91; H, 5.61; N, 9.33; Cl, 12.92.

EXAMPLE 42

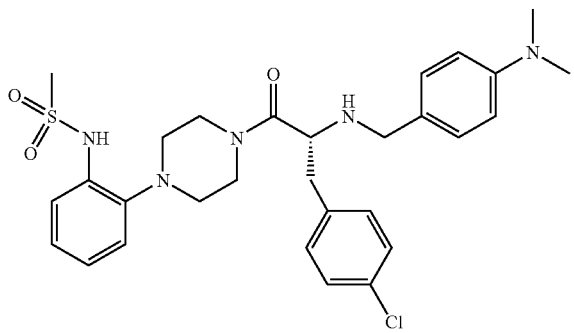

(2R)-2-({[4-(Dimethylamino)phenyl]
methyl}amino)-3-(4-chlorophenyl)-1-(4-{2-
[(methylsulfonyl)amino]-phenyl}piperazinyl)
propan-1-one Following the procedure of Example 38, Step 3, (2R)-2-({[4-(dimethylamino)phenyl]methyl}amino)-3-(4-chlorophenyl)-1-(4-{2-[(methylsulfonyl)amino]-phenyl}piperazinyl)propan-1-one was prepared from (2R)-2-amino-3-(4-chlorophenyl)-1-(4-{2-[(methylsulfonyl)amino]phenyl}piperazinyl)propan-1-one TFA salt (0.6 g, 1.1 mmol) in ClCH$_2$Cl$_2$Cl (10 mL), 4-dimethylaminobenzaldehyde (Aldrich) (170 mg, 1.1 mmol) and NaBH(OAc)$_3$ (Aldrich) (340 mg, 1.6 mmol). The desired compound was purified by preparative TLC (60% Hexane, 38% CH$_2$Cl$_2$, and 2% 2N NH$_3$ in MeOH), and treated with a soln of EtOAc satd with HCl. The precipitate (HCl salt) which formed was filtered and dried in vacuo to afford the desired product as a white solid (75 mg). MS (ESI, pos. ion) m/z: 570 (M+H); MS (ESI, neg. ion) m/z: 568 (M−H). Calc'd for C$_{29}$H$_{36}$ClN$_5$O$_3$S: 569.22.

EXAMPLE 43

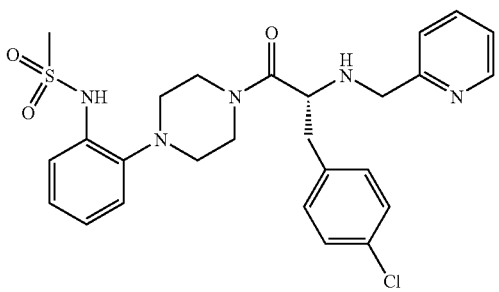

(2R)-3-(4-Chlorophenyl)-1-(4-{2-[(methylsulfonyl)
amino]phenyl}piperazinyl)-2-[(2-pyridylmethyl)
amino]propan-1-one Following the procedure of Example 38, Step 3, (2R)-3-(4-chlorophenyl)-1-(4-{2-[(methylsulfonyl)-amino]phenyl}piperazinyl)-2-[(2-pyridylmethyl)amino]-propan-1-one was prepared from (2R)-2-amino-3-(4-chlorophenyl)-1-(4-{2-[(methylsulfonyl)amino]phenyl}piperazinyl)propan-1-one TFA salt (0.6 g, 1.1 mmol) in ClCH$_2$Cl$_2$Cl (10 mL), 2-pyridine carboxaldehyde (Aldrich) (0.1 mL, 1.1 mmol) and NaBH(OAc)$_3$ (Aldrich) (340 mg, 1.6 mmol). The desired compound was purified by preparative TLC (60% Hexane, 38% CH$_2$Cl$_2$, and 2% 2N NH$_3$ in MeOH), and treated with a soln of EtOAc satd with HCl. The precipitate (HCl salt) which formed was filtered and dried in vacuo to afford the desired product as a white solid (102 mg). MS (ESI, pos. ion) m/z: 528 (M+H); MS (ESI, neg. ion) m/z: 526 (M−H). Calc'd for C$_{26}$H$_{30}$ClN$_5$O$_3$S: 527.18. Anal. Calc'd for C$_{26}$H$_{30}$ClN$_5$O$_3$S.1.8H$_2$O.2.6 HCl: C, 47.66; H, 5.57; N, 10.69; Cl, 19.48. Found: C, 47.59; H, 5.62; N, 10.4; Cl, 19.47.

EXAMPLE 44

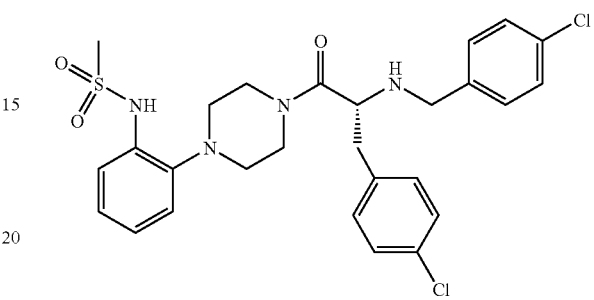

(2R)-3-(4-Chlorophenyl)-2-{[(4-chlorophenyl)
methyl]amino}-1-(4-{2-[(methyl sulfonyl)amino]
phenyl}piperazinyl)propan-1-one Following the procedure of Example 38, Step 3, (2R)-3-(4-chlorophenyl)-2-{[(4-chlorophenyl)methyl]amino}-1-(4-{2-[(methyl sulfonyl)amino]phenyl}piperazinyl)propan-1-one was prepared from (2R)-2-amino-3-(4-chlorophenyl)-1-(4-{2-[(methylsulfonyl)amino]phenyl}piperazinyl)propan-1-one TFA salt (0.6 g, 1.1 mmol) in ClCH$_2$Cl$_2$Cl (10 mL), 4-chlorobenzaldehyde (Aldrich) (270 mg, 1.40 mmol) and NaBH(OAc)$_3$ (Aldrich) (340 mg, 1.9 mmol). The desired compound was purified by preparative TLC (60% Hexane, 38% CH$_2$Cl$_2$, and 2% 2N NH$_3$ in MeOH), and treated with a soln of EtOAc satd with HCl. A precipitate formed (HCl salt), was filtered and dried in vacuo to afford the desired product as a white solid (80 mg, 12%). MS (ESI, pos. ion) m/z: 561 (M+H); MS (ESI, neg. ion) m/z: 559 (M−H). Calc'd for C$_{27}$H$_{30}$Cl$_2$N$_4$O$_3$S: 560.14.

EXAMPLE 45

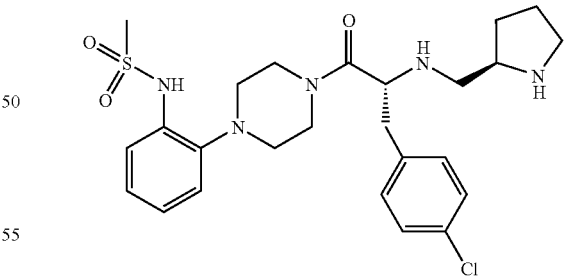

(2R)-2-{[((2R)-Pyrrolidin-2-yl)methyl]amino}-3-(4-
chlorophenyl)-1-(4-{2-[(methyl sulfonyl)amino]
phenyl}-piperazinyl)propan-1-one Following the procedure of Example 38, Step 3, (2R)-2-{[(2R)-pyrrolidin-2-yl)methyl]amino}-3-(4-chlorophenyl)-1-(4-{2-[(methylsulfonyl)amino]phenyl}piperazinyl)propan-1-one was prepared from (2R)-2-amino-3-(4-chlorophenyl)-1-(4-{2-[(methylsulfonyl)-amino]

phenyl}piperazinyl)propan-1-one TFA salt (0.6 g, 1.1 mmol) in ClCH$_2$Cl$_2$Cl (10 mL), N-Boc-L-prolinal (Aldrich) (280 mg, 1.4 mmol), and NaBH(OAc)$_3$ (Aldrich) (340 mg, 1.9 mmol). The desired compound (TFA salt) was purified by preparative TLC (60% Hexane, 38% CH$_2$Cl$_2$ and 2% 2N NH$_3$ in MeOH), followed by preparative HPLC (TFA buffer) yielding a white solid (14.8 mg). MS (ESI, pos. ion) m/z: 520 (M+H); MS (ESI, neg. ion) m/z: 518 (M–H). Calc'd for C$_{25}$H$_{34}$ClN$_5$O$_3$S: 519.21.

EXAMPLE 46

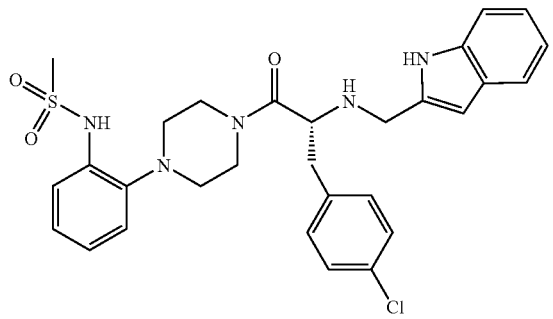

(2R)-3-(4-Chlorophenyl)-2-[(indol-2-ylmethyl)amino]-1-(4-{2-[(methylsulfonyl)amino]phenyl}piperazinyl)propan-1-one Following the procedure of Example 38, Step 3, (2R)-3-(4-chlorophenyl)-2-[(indol-2-ylmethyl)amino]-1-(4-{2-[(methylsulfonyl)amino]phenyl}piperazinyl)propan-1-one was prepared from (2R)-2-amino-3-(4-chlorophenyl)-1-(4-{2-[(methylsulfonyl)amino]phenyl}piperazinyl)propan-1-one TFA salt (0.5 g, 0.91 mmol) in ClCH$_2$Cl$_2$Cl (10 mL), indole-3-carboxaldehyde (Aldrich) (150 mg, 0.930 mmol) and NaBH(OAc)$_3$ (Aldrich) (280 mg, 1.30 mmol). The desired compound was purified by preparative TLC (60% hexane, 38% CH$_2$Cl$_2$ and 2% 2N NH$_3$ in MeOH), followed by preparative HPLC (TFA buffer) to afford the TFA salt as a white solid (10.8 mg). MS (ESI, pos. ion) m/z: 566 (M+H); MS (ESI, neg. ion) m/z: 564 (M–H). Calc'd for C$_{29}$H$_{32}$ClN$_5$O$_3$S: 565.19.

EXAMPLE 47

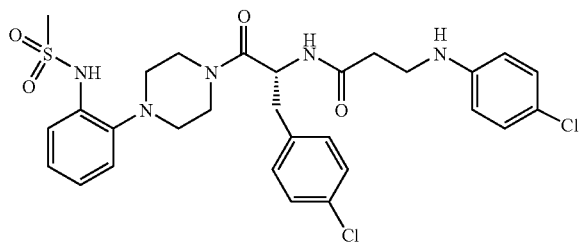

N-[(1R)-1-[(4-Chlorophenyl)methyl]-2-(4-{2-[(methylsulfonyl)amino]phenyl}piperazinyl)-2-oxoethyl]-3-[(4-chlorophenyl)amino]propanamide Following the procedure of Preparation V, N-[(1R)-1-[(4-chlorophenyl)methyl]-2-(4-{2-[(methylsulfonyl)-amino]phenyl}piperazinyl)-2-oxoethyl]-3-[(4-chlorophenyl)amino]propanamide was prepared from (2R)-2-amino-3-(4-chlorophenyl)-1-(4-{2-[(methylsulfonyl)-amino]phenyl}piperazinyl)propan-1-one TFA salt (200 mg, 0.36 mmol) in CH$_2$Cl$_2$ (3 mL), DIEA (0.12 mL, 0.66 mmol), 3-(4-chloroanilino)-propionic acid (Maybridge) (66 mg, 0.33 mmol), HOAT (Aldrich) (53 mg, 0.39 mmol) and EDC (Aldrich) (130 mg, 0.66 mmol). The desired compound was purified by preparative TLC (60% hexane, 38% CH$_2$Cl$_2$, and 2% 2N NH$_3$ in MeOH), followed by preparative HPLC (TFA buffer) to afford the desired compound (TFA salt) as a white solid (9.8 mg). MS (ESI, pos. ion) m/z: 618 (M+H); MS (ESI, neg. ion) m/z: 616 (M–H). Calc'd for C$_{29}$H$_{33}$Cl$_2$N$_5$O$_4$S: 617.16.

EXAMPLE 48

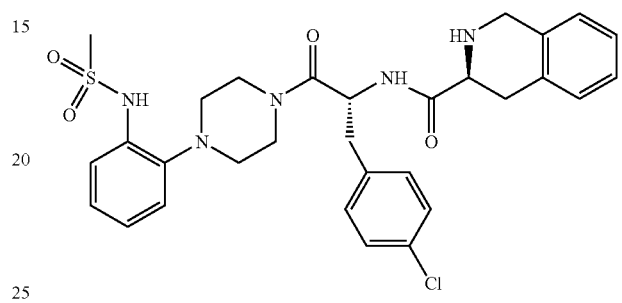

N-[(1R)-1-[(4-Chlorophenyl)methyl]-2-(4-{2-[(methylsulfonyl)amino]phenyl}piperazinyl)ethyl]((3S)(3-1,2,3,4-tetrahydroisoquinolyl))carboxamide Step 1

To a round-bottomed flask equipped with stirring was added (2R)-{1-(4-chlorobenzyl)-2-[4-(2-methylsulfonyl-aminophenyl)-piperazin-1-yl]-2-oxo-ethyl}-carbamic acid tert-butyl ester (3.0 g, 5.59 mmol) and THF (6 mL). AlH$_3$ (prepared according to the method of H. C. Brown and N. M. Yoon, J. Am. Chem. Soc., 1968, 90, 2927) (28 mL, 27 mmol) was added to the reaction mixture drop-wise, and the reaction mixture was stirred at RT for 2 h. The organic layer was washed with satd aqueous NaHCO$_3$ soln, dried over Na$_2$SO$_4$, filtered and concentrated in vacuo. The residue was treated with a soln of EtOAc satd with HCl. The precipitate was filtered and dried in vacuo to afford (2-{4-[(2R)-2-amino-3-(4-chlorophenyl)propyl]piperazinyl}phenyl)(methylsulfonyl)-amine hydrochloride (HCl salt) as a white solid (2.8 g). MS (ESI, pos. ion) m/z: 423 (M+H); MS (ESI, neg. ion) m/z: 421 (M–H). Calc'd for C$_{20}$H$_{27}$ClN$_4$O$_2$S: 422.15.

Step 2

Following the procedure of Preparation V, N-[(1R)-1-[(4-chlorophenyl)methyl]-2-(4-{2-[(methylsulfonyl)amino]phenyl}piperazinyl)ethyl]((3S)(3-1,2,3,4-tetrahydroisoquinolyl))carboxamide was prepared from (2-{4-[(2R)-2-amino-3-(4-chlorophenyl)propyl]-piperazinyl}phenyl)(methylsulfonyl)amine hydrochloride (Step 1) (600 mg, 1.3 mmol) in CH$_2$Cl$_2$ (3 mL), DIEA (0.30 mL, 1.5 mmol), Boc-L-Tic-OH (Bachem) (390 mg, 1.4 mmol), HOAT (Aldrich) (230 mg, 1.70 mmol), and EDC (Aldrich) (540 mg, 2.8 mmol). The desired compound was purified by preparative TLC (60% hexane, 38% CH$_2$Cl$_2$, and 2% 2N NH$_3$ in MeOH), followed by preparative HPLC to afford the TFA salt as a white solid (35 mg). MS (ESI, pos. ion) m/z: 582 (M+H); MS (ESI, neg. ion) m/z: 580 (M–H). Calc'd for C$_{30}$H$_{36}$ClN$_5$O$_3$S: 581.22.

EXAMPLE 49

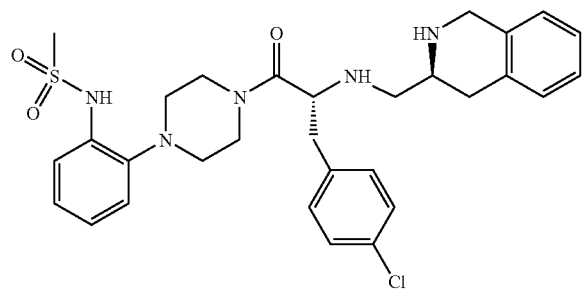

(2R)-2-{[((3S)(3-(1,2,3,4-Tetrahydroisoquinolyl))methyl]-amino}-3-(4-chloro phenyl)-1-(4-{2-[(methylsulfonyl)amino]-phenyl}piperazinyl)propan-1-one

Step 1

To a round-bottomed flask equipped with stirring was added Boc-L-Tic-OH (Bachem) (1 g, 3.6 mmol) and CH₂Cl₂ (20 mL), followed by TEA (0.5 mL, 3.6 mmol) and N,O-dimethylhydroxylamine hydrochloride. The reaction mixture was cooled to 0° C., EDC (690 mg, 3.6 mmol) and HOBT (550 mg, 3.6 mmol) were added, and the reaction mixture was stirred at 0° C. for 1 h then at RT for 18 h. The organic layer was washed with 0.5N HCl, satd NaHCO₃, and brine. The organic layer was dried over Na₂SO₄, filtered and concentrated in vacuo to afford a colorless oil. Into a round bottomed flask equipped with magnetic stirring, was added the oil dissolved in Et₂O (15 mL), and the flask was cooled to −78° C. LiAlH₄ (1M in Et₂O, Aldrich) (3.2 mL, 3.2 mmol) was added, and after 30 min the reaction was warmed to RT. The organic layer was washed with 0.5N HCl, satd NaHCO₃, and brine. After drying the organic layer over Na₂SO₄, it was filtered and concentrated in vacuo to afford (3S)-N-Boc-1,2,3,4-tetrahydroisoquinoline-3-carbaldehyde as a colorless oil (588 mg).

Step 2

Following the procedure of Example 38, Step 3, (2R)-2-{[((3S)(3-(1,2,3,4-tetrahydroisoquinolyl))methyl]-amino}-3-(4-chloro phenyl)-1-(4-{2-[(methylsulfonyl)-amino]phenyl}-piperazinyl)propan-1-one was prepared from (2R)-2-amino-3-(4-chlorophenyl)-1-(4-{2-[(methylsulfonyl)amino]phenyl}piperazinyl)propan-1-one TFA salt (0.52 g, 0.94 mmol) in ClCH₂CH₂Cl (10 mL), (3S)-N-Boc-1,2,3,4-tetrahydroisoquinoline-3-carbaldehyde (310 mg, 1.2 mmol), and NaBH(OAc)₃ (Aldrich) (350 mg, 1.70 mmol). The desired compound was purified by preparative TLC (60% hexane, 38% CH₂Cl₂, and 2% 2N NH₃ in MeOH), followed by preparative HPLC (TFA buffer) to afford the desired material (TFA salt) as a white solid (59 mg). MS (ESI, pos. ion) m/z: 582 (M+H); MS (ESI, neg. ion) m/z: 580 (M−H). Calc'd for C₃₀H₃₆ClN₅O₃S: 581.22.

EXAMPLE 50

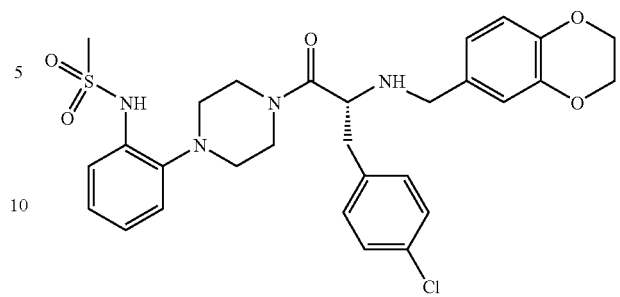

(2R)-2-[(2H,3H-Benzo[3,4-e]1,4-dioxin-6-ylmethyl)amino]-3-(4-chlorophenyl)-1-(4-{2-[(methylsulfonyl)amino]phenyl}-piperazinyl)propan-1-one Following the procedure of Example 38, Step 3, (2R)-2-[(2H,3H-benzo[3,4-e]1,4-dioxin-6-ylmethyl)-amino]-3-(4-chlorophenyl)-1-(4-{2-[(methylsulfonyl)-amino]phenyl}-piperazinyl)propan-1-one was prepared from (2R)-2-amino-3-(4-chlorophenyl)-1-(4-{2-[(methylsulfonyl)amino]phenyl}piperazinyl)propan-1-one TFA salt (0.6 g, 1.1 mmol) in ClCH₂CH₂Cl (10 mL), 1,4-benzodioxan-6-carboxaldehyde (Aldrich) (184 mg, 1.12 mmol) and NaBH(OAc)₃ (Aldrich) (340 mg, 1.6 mmol). The desired compound was purified by preparative TLC (60% Hexane, 38% CH₂Cl₂, and 2% 2N NH₃ in MeOH), and treated with a soln of EtOAc satd with HCl. The precipitate which formed was filtered and dried in vacuo to afford the title compound (HCl salt) as a white solid (330 mg). MS (ESI, pos. ion) m/z: 585 (M+H); MS (ESI, neg. ion) m/z: 583 (M−H). Calc'd for C₂₉H₃₃ClN₄O₅S: 584.19. Anal. Calcd for C₂₉H₃₃ClN₄O₅S.HCl: C, 56.04; H, 5.51; N, 9.01; Cl, 11.41. Found: C, 55.57 (+/−0.46); H, 5.45; N, 8.99; Cl, 11.25.

EXAMPLE 51

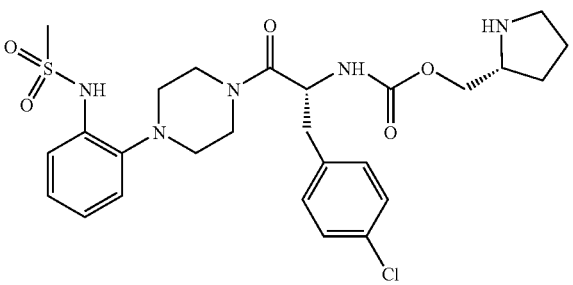

N-[(1R)-1-[(4-Chlorophenyl)methyl]-2-(4-{2-[(methylsulfonyl)amino]phenyl}piperazinyl)-2-oxoethyl][((2R)pyrrolidin-2-yl)methoxy]carboxamide To a round-bottomed flask equipped with stirring was added Boc-D-prolinol (Aldrich) (46 mg, 0.23 mmol) and CH₂Cl₂ (1 mL), and the reaction flask was cooled to −23° C. A soln of triphosgene (Avocado) (30 mg, 0.1 mmol) in CH₂Cl₂ (0.5 mL) was added drop-wise followed by DIEA (0.040 mL, 0.230 mmol). The reaction mixture was stirred at 0° C. for 4 h, at RT for 16 h, and then at reflux for 1.5 h. The reaction mixture was concentrated in vacuo. This was then stirred with (2R)-2-amino-3-(4-chlorophenyl)-1-(4-{2-[(methylsulfonyl)amino]phenyl}piperazinyl)propan-1-one TFA salt (200 mg, 0.36 mmol) and DIEA (0.34 mL, 2.0 mmol) in CH$_2$Cl$_2$ (1.5 mL) for 18 h. The organic layer was washed with 10% citric acid, dried over Na$_2$SO$_4$, filtered and concentrated in vacuo to afford a yellow oil. The Boc protecting group was removed by treating the compound with a soln of 50% TFA in CH$_2$Cl$_2$ (2 mL) for 2 h. The desired compound was purified by preparative TLC (60% hexane, 38% CH$_2$Cl$_2$, and 2% 2N NH$_3$ in MeOH), followed by preparative HPLC to afford the TFA salt as a white solid (10 mg). MS (ESI, pos. ion) m/z: 564 (M+H); MS (ESI, neg. ion) m/z: 562 (M−H). Calc'd for C$_{26}$H$_{34}$ClN$_5$O$_5$S: 563.20.

EXAMPLE 52

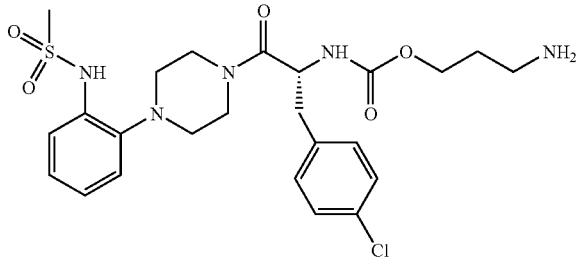

N-[(1R)-1-[(4-Chlorophenyl)methyl]-2-(4-{2-[(methylsulfonyl)amino]phenyl}piperazinyl)-2-oxoethyl](3-aminopropoxy)carboxamide Following the procedure of Example 51, N-[(1R)-1-[(4-chlorophenyl)methyl]-2-(4-{2-[(methylsulfonyl)-amino]phenyl}piperazinyl)-2-oxoethyl] (3-aminopropoxy) carboxamide, was prepared from N-(3-hydroxypropyl)-carbamic acid tert-butyl ester (Aldrich) (40 mg, 0.230 mmol), triphosgene (Avocado) (30 mg, 0.1 mmol), DIEA (0.040 mL, 0.230 mmol), (2R)-2-amino-3-(4-chlorophenyl)-1-(4-{2-[(methylsulfonyl)amino]phenyl}piperazinyl)propan-1-one TFA salt (200 mg, 0.36 mmol), and more DIEA (0.34 mL, 2.0 mmol). The Boc protecting group was removed by treating with a soln of 50% TFA in CH$_2$Cl$_2$ (2 mL) for 2 h. The crude product was purified by preparative TLC (60% hexane, 38% CH$_2$Cl$_2$ and 2% 2N NH$_3$ in MeOH) and then by preparative HPLC (TFA buffer) to afford the title compound (TFA salt) as a white solid (10 mg). MS (ESI, pos. ion) m/z: 538 (M+H); MS (ESI, neg. ion) m/z: 536 (M−H). Calc'd for C$_{24}$H$_{32}$ClN$_5$O$_5$S: 537.18.

EXAMPLE 53

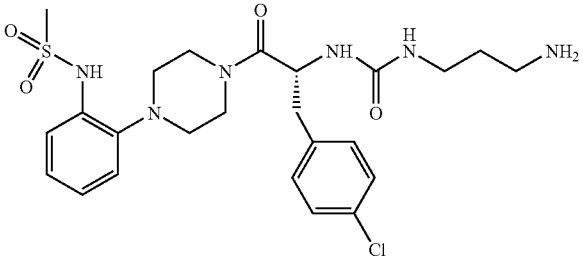

N-[(1R)-1-[(4-Chlorophenyl)methyl]-2-(4-{2-[(methylsulfonyl)amino]phenyl}piperazinyl)-2-oxoethyl][(3-aminopropyl)amino]carboxamide Following the procedure of Example 51, N-[(1R)-1-[(4-chlorophenyl)methyl]-2-(4-{2-[(methylsulfonyl)amino]phenyl}piperazinyl)-2-oxoethyl][(3-aminopropyl)amino]carboxamide, TFA salt was prepared from triphosgene (Avocado Chemical Company) (45 mg, 0.152 mmol), (2R)-2-amino-3-(4-chlorophenyl)-1-(4-{2-[(methylsulfonyl)amino]phenyl}piperazinyl)propan-1-one TFA salt (200 mg, 0.36 mmol), DIEA (0.32 mL, 0.916 mmol), and tert-butyl-N-(3-aminopropyl)carbamate (Aldrich Chemical Company) (96 mg, 0.55 mmol). The Boc protecting group was removed by treating the compound with a soln of 50% TFA and CH$_2$Cl$_2$ (2 mL) for 2 h. The organic solvent was removed in vacuo to give the desired product. Preparative TLC purification with 60% Hexane, 35% CH$_2$Cl$_2$ and 5% 2N NH$_3$ in MeOH afforded 90% pure compound. This was further purified by preparative HPLC (TFA buffer) to afford the title compound (TFA salt) as a white solid (10 mg). MS (ESI, pos. ion) m/z: 537 (M+H); MS (ESI, neg. ion) m/z: 535 (M−H). Calc'd for C$_{24}$H$_{33}$ClN$_6$O$_4$S: 536.20.

EXAMPLE 54

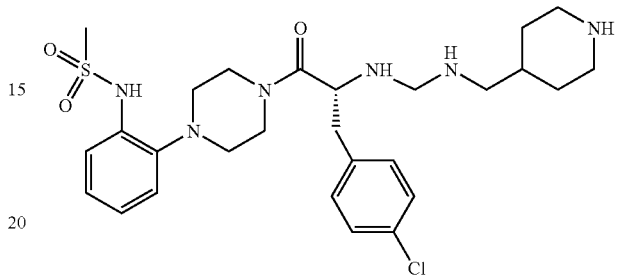

N-[(1R)-1-[(4-Chlorophenyl)methyl]-2-(4-{2-[(methylsulfonyl)amino]phenyl}piperazinyl)-2-oxoethyl][(4-piperidylmethyl)amino]carboxamide Following the procedure of Example 51, N-[(1R)-1-[(4-chlorophenyl)methyl]-2-(4-{2-[(methylsulfonyl)amino]phenyl}piperazinyl)-2-oxoethyl][(4-piperidyl-methyl)amino]-carboxamide, was prepared from triphosgene (Avocado Chemical Company) (45 mg, 0.152 mmol), (2R)-2-amino-3-(4-chlorophenyl)-1-(4-{2-[(methylsulfonyl)amino]phenyl}piperazinyl)propan-1-one TFA salt (200 mg, 0.36 mmol), DIEA (0.32 mL, 0.916 mmol), and 4-(aminomethyl)-1-BOC-piperidine (Aldrich Chemical Company) (118 mg, 0.55 mmol). The Boc protecting group was removed by treating the compound with a soln of 50% TFA and CH$_2$Cl$_2$ (2 mL) for 2 h. The organic solvent was removed in vacuo to give the desired product. Preparative TLC purification with 60% Hexane, 35% CH$_2$Cl$_2$ and 5% 2N NH$_3$ in MeOH afforded 90% pure compound. This was further purified by preparative HPLC (TFA buffer) to afford the title compound (TFA salt) as a white solid (10 mg). MS (ESI, pos. ion) m/z: 577 (M+H); MS (ESI, neg. ion) m/z: 575 (M−H). Calc'd for C$_{27}$H$_{37}$ClN$_6$O$_4$S: 576.23.

EXAMPLE 55

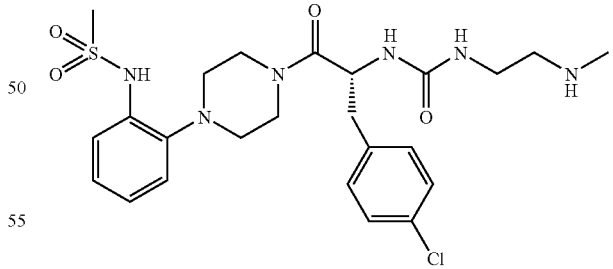

N-[(1R)-1-[(4-Chlorophenyl)methyl]-2-(4-{2-[(methylsulfonyl)amino]phenyl}piperazinyl)-2-oxoethyl]{[2-(methylamino)ethyl]amino}carboxamide Following the procedure of Example 51, N-[(1R)-1-[(4-chlorophenyl)methyl]-2-(4-{2-[(methylsulfonyl)-amino]phenyl}piperazinyl)-2-oxoethyl]{[2-(methylamino)ethyl]amino}carboxamide was prepared from triphosgene (Avocado Chemical Company) (45 mg, 0.152 mmol), N-[(1R)-1-[(4-chlorophenyl)-methyl]-2-(4-{2-[(methylsulfonyl)amino]phenyl}piperazinyl)-2-oxoethyl]-{[2-(methylamino)ethyl]-amino}carboxamide (200 mg, 0.36 mmol), DIEA (0.32 mL, 0.916 mmol), N-Boc-N-methylethylenediamine (Astatech Inc.) (96 mg, 0.55 mmol). The Boc protecting group was removed by treating compound with a soln of 50% TFA and $CH_2Cl_2$ (2 mL) for 2 h. The organic solvent was removed in vacuo to give the desired product. Preparative TLC purification with 60% Hexane, 35% $CH_2Cl_2$ and 5% 2N $NH_3$ in MeOH afforded 90% pure compound. This was further purified by preparative HPLC (TFA buffer) to afford the title compound (TFA salt) as a white solid (10 mg). MS (ESI, pos. ion) m/z: 537 (M+H); MS (ESI, neg. ion) m/z: 535 (M−H). Calc'd for $C_{24}HN_6O_4ClS$: 536.

EXAMPLE 56

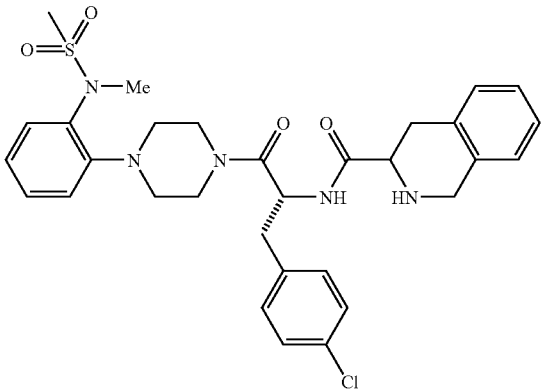

N-[(1R)-1-[(4-Chlorophenyl)methyl]-2-(4-{2-[methyl(methylsulfonyl)amino]phenyl}piperazinyl)-2-oxoethyl]-3-1,2,3,4-tetrahydroisoquinolylcarboxamide Step 1

In a 100 mL round bottomed flask equipped with magnetic stirring was added tert-butyl 4-{2-[(methylsulfonyl)-amino]phenyl}-piperazinecarboxylate (Preparation III) (692 mg, 1.947 mmol) and DMF (5 mL). After stirring 5 min, NaH (60% oil dispersion) (100 mg, 2.5 mmol) (Aldrich) in DMF (10 mL) was added. The reaction was stirred 20 min, then iodomethane (190 μl, 3.05 mmol) (Aldrich) was added via syringe. After stirring 2.5 h, the reaction was diluted with 150 mL EtOAc and washed 75 mL each, satd $NH_4Cl$, $H_2O$, 10% $NaHCO_3$ and brine. The organic layer was separated, dried over $Na_2SO_4$, filtered and concentrated in vacuo to give tert-butyl 4-{2-[methyl(methylsulfonyl)amino]phenyl}piperazine-carboxylate (700 mg). MS (ESI, pos. ion) m/z: 370(M+H), (ESI, neg. ion) m/z: 368 (M−H). Calc'd for $C_{17}H_{27}N_3O_4S$: 369.48.

Step 2 tert-Butyl 4-{2-[methyl(methylsulfonyl)amino]phenyl}piperazinecarboxylate (Step 1) (700 mg, 1.9 mmol) was stirred with 25 mL of HCl satd EtOAc. The resulting crude material was diluted with EtOAc and washed with a satd $NaHCO_3$ soln. The organic layer was separated, dried over $Na_2SO_4$, filtered and concentrated in vacuo. This material was treated with DIEA (400 μl, 2.295 mmol), Boc-p-Cl-D-Phe-OH (672 mg, 2.241 mmol), 1-(3-dimethylaminopropyl)-3-ethylcarbodiimide methiodide (1.25 g, 4.206 mmol), HOAT (345 mg, 2.535 mmol), and DMF (15 mL) according to the procedure for preparation XIX. The crude material was purified by flash chromatography ($SiO_2$, 1.5:1 hexane:EtOAc) to yield N-[(1R)-1-[(4-chlorophenyl)methyl]-2-(4-{2-[methyl-(methylsulfonyl)amino]phenyl}piperazinyl)-2-oxoethyl]-(tert-butoxy)carboxamide (327 mg). MS (ESI, pos. ion) m/z: 551 (M+H), (ESI, neg. ion) m/z: 549 (M−H). Calc'd for $C_{26}H_{35}ClN_4O_5S$: 551.10.

Step 3

N-[(1R)-1-[(4-Chlorophenyl)methyl]-2-(4-{2-[methyl-(methylsulfonyl)amino]phenyl}piperazinyl)-2-oxoethyl]--(tert-butoxy)carboxamide (Step 2) (327 mg, 0.593 mmol) was stirred with 25 mL of HCl satd EtOAc. The resulting crude material was diluted with EtOAc and washed with a satd $NaHCO_3$ soln. The organic layer was separated, dried over $Na_2SO_4$, filtered and concentrated in vacuo. This material was treated with DIEA (115 μl, 0.660 mmol), Boc-L-Tic-OH (167 mg, 0.602 mmol), 1-(3-dimethylaminopropyl)-3-ethylcarbodiimide methiodide (500 mg, 1.68 mmol), and HOAT (99 mg, 0.727 mmol) according to the procedure for preparation XIX. The crude was purified by flash chromatography ($SiO_2$, 10% EtOAc in $CH_2Cl_2$) and concentrated in vacuo to yield tert-butyl 3-{N-[(1R)-1-[(4-chlorophenyl)methyl]-2-(4-{2-[methyl(methylsulfonyl)amino]phenyl}piperazinyl)-2-oxoethyl]carbamoyl}-1,2,3,4-tetrahydroisoquinoline-2-carboxylate (219 mg). MS (ESI, pos. ion) m/z: 710 (M+H), (ESI, neg. ion) m/z: 708 (M−H). Calc'd for $C_{36}H_{44}ClN_5O_6S$: 710.28.

Step 4

N-[(1R)-1-[(4-Chlorophenyl)methyl]-2-(4-{2-[methyl-(methylsulfonyl)amino]phenyl}piperazinyl)-2-oxoethyl]-3-1,2,3,4-tetrahydroisoquinolylcarboxamide was prepared according to the procedure for Preparation XVI tert-butyl 3-{N-[(1R)-1-[(4-chlorophenyl)methyl]-2-(4-{2-[methyl(methylsulfonyl)amino]phenyl}piperazinyl)-2-oxoethyl]carbamoyl}-1,2,3,4-tetrahydroisoquinoline-2-carboxylate (220 mg, 0.310 mmol). The crude material was purified by preparative HPLC (TFA buffer) to afford N-[(1R)-1-[(4-Chlorophenyl)methyl]-2-(4-{2-[methyl(methylsulfonyl)amino]phenyl}piperazinyl)-2-oxoethyl]-3-1,2,3,4-tetrahydroisoquinolylcarboxamide as the TFA salt (20 mg). MS (ESI, pos. ion) m/z: 610 (M+H), (ESI, neg. ion) m/z: 608 (M−H). Calc'd for $C_{31}H_{36}ClN_5O_4S$ 609. Anal. Calcd for $C_{31}H_{36}ClN_5O_4S$—$C_2HF_3O_2$-$2H_2O$: C, 52.14; H, 5.44; Cl, 4.66; F, 7.50; N, 9.21; 0, 16.84; S, 4.22. Found C, 52.51; H, 5.10; N, 8.85.

EXAMPLE 57

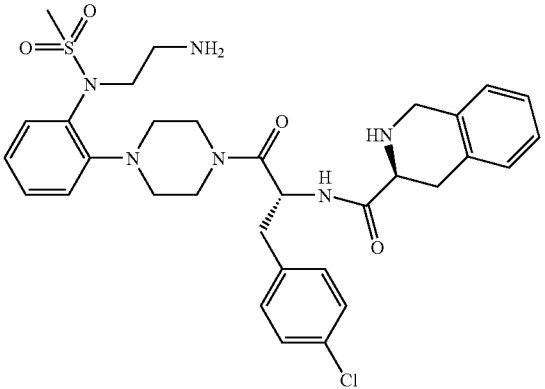

N-[(1R)-2-(4-{2-[(2-Aminoethyl)(methylsulfonyl)amino]-phenyl}piperazinyl)-1-[(4-chlorophenyl)methyl]-2-oxoethyl]((3S)(3-1,2,3,4-tetrahydroisoquinolyl))carboxamide Step 1

Following the procedure for the synthesis of Example 38, Step 3, (without DIEA), tert-butyl 3-[N-((1R)-2-{4-[2-({2-

[(tert-butoxy)carbonylamino]ethyl}amino)phenyl]-piperazinyl}-1-[(4-chlorophenyl)methyl]-2-oxoethyl)-carbamoyl](3S)-1,2,3,4-tetrahydroisoquinoline-2-carboxylate was prepared from tert-butyl 3-(N-{(1R)-2-[4-(2-aminophenyl)piperazinyl]-1-[(4-chlorophenyl)-methyl]-2-oxoethyl}carbamoyl)(3S)-1,2,3,4-tetrahydroisoquinoline-2-carboxylate (633 mg, 1.024 mmol), (Preparation IX) tert-butyl-N-(2-oxoethyl)-carbamate (179 mg, 1.126 mmol) (Aldrich) and NaBH(OAc)₃ (330 mg, 1.557 mmol) (Aldrich) The compound was purified by flash chromatography, (SiO₂, 2:1 hexane:EtOAc) and concentrated in vacuo yielding (578 mg). MS (ESI, pos. ion) m/z: 761 (M+H), (ESI, neg. ion) m/z: 759 (M–H). Calc'd for C₄₁H₅₃ClN₆O₆: 761.35. Anal. Calc'd for C₄₁H₅₃ClN₆O₆-0.5C₄H₈O₂-0.5H₂O: C, 63.42; H, 7.18; N, 10.32; Cl, 4.35. Found C, 62.96; H, 7.14; N, 10.26; Cl, 4.06.

Step 2 tert-Butyl 3-[N-((1R)-2-{4-[2-({2-[(tert-butoxy)carbonylamino]ethyl}(methylsulfonyl)amino)phenyl]piperazinyl}-1-[(4-chlorophenyl)methyl]-2-oxoethyl)-carbamoyl](3S)-1,2,3,4-tetrahydroisoquinoline-2-carboxylate was prepared according to the procedure for Preparation III using tert-butyl 3-[N-((1R)-2-{4-[2-({2-[(tert-butoxy)carbonylamino]ethyl}amino)phenyl]piperazinyl}-1-[(4-chlorophenyl)methyl]-2-oxoethyl)carbamoyl](3S)-1,2,3,4-tetrahydroisoquinoline-2-carboxylate (Step 1) (370 mg, 0.45 mmol), methanesulfonyl chloride (41 µl, 0.530 mmol), pyridine (40 µl, 0.495 mmol), DMAP (cat.), and ClCH₂CH₂Cl (15 mL). The crude material was purified by flash chromatography, (SiO₂, 1:1 hexane:EtOAc) to afford the desired material (155 mg). MS (ESI, pos. ion) m/z: 839 (M+H), (ESI, neg. ion) m/z: 837 (M–H). Calc'd for C₄₂H₅₅ClN₆O₈S: 839.44.

Step 3 tert-Butyl 3-[N-((1R)-2-{4-[2-({2-[(tert-butoxy)carbonylamino]ethyl}(methylsulfonyl)amino)phenyl]piperazinyl}-1-[(4-chlorophenyl)methyl]-2-oxoethyl)-carbamoyl](3S)-1,2,3,4-tetrahydroisoquinoline-2-carboxylate (Step 2) (150 mg, 0.179 mmol) was treated with 30% TFA in CH₂Cl₂, for 1.5 h, in a 50 mL round-bottomed flask equipped with magnetic stirring. The reaction was concentrated in vacuo and purified by preparative HPLC (TFA buffer) to afford N-[(1R)-2-(4-{2-[(2-aminoethyl)(methylsulfonyl)amino]phenyl}-piperazinyl)-1-[(4-chlorophenyl)methyl]-2-oxoethyl]((3S) (3-1,2,3,4-tetrahydroisoquinolyl))carboxamide as the TFA salt (35 mg). MS (ESI, pos. ion) m/z: 639 (M+H), (ESI, neg. ion) m/z: 637 (M–H). Calc'd for C₃₂H₃₉ClN₆O₄S: 638.24. Anal. Calcd for C₃₂H₃₉ClN₆O₄S-2C₂HF₃O₂—H₂O: C, 48.84; H, 4.90; N, 9.49; Cl, 4.00. Found C, 48.52; H, 4.77; N, 9.36; Cl, 4.13.

EXAMPLE 58

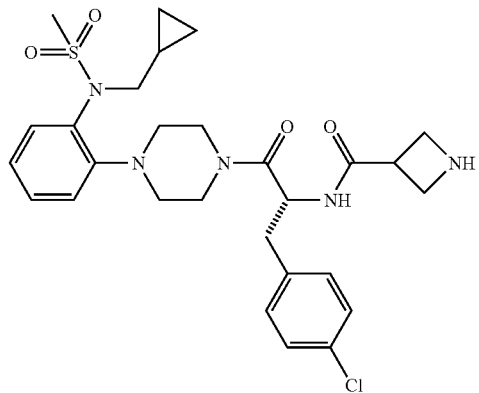

N-[(1S)-1-[(4-Chlorophenyl)methyl]-2-(4-{2-[(cyclopropylmethyl)(methylsulfonyl)amino]phenyl}piperazinyl)-2-oxoethyl]azetidin-3-ylcarboxamide Step 1 tert-Butyl 4-{2-[(cyclopropylmethyl)(methylsulfonyl)aminophenyl}piperazinecarboxylate was prepared according to the procedure for Example 56, Step 1, using tert-butyl 4-{2-[(methylsulfonyl)amino]phenyl}piperazinecarboxylate (393 mg, 1.11 mmol), NaH (65 mg, 1.625 mmol), cyclopropylmethyl bromide (140 µl, 1.44 mmol) (Aldrich), and DMF (15 mL). The product was isolated in a quantitative yield (458 mg). MS (ESI, pos. ion) m/z: 410 (M+H), (ESI, neg. ion) m/z: 408 (M–H). Calc'd for C₂₀H₃₁N₃O₄S: 409.54.

Step 2 tert-Butyl 4-{2-[(cyclopropylmethyl)(methylsulfonyl)amino]phenyl}piperazinecarboxylate (450 mg, 1.099 mmol) was treated with satd HCl in EtOAc as described in Preparation XVI. The resulting crude material was diluted with EtOAc and washed with 10% Na₂CO₃ soln. The organic layer was separated, dried over Na₂SO₄, filtered and concentrated in vacuo. This material was used to prepare N-[(1R)-1-[(4-chlorophenyl)methyl]-2-(4-{2-[(cyclopropylmethyl) (methylsulfonyl)amino]phenyl}piperazinyl)-2-oxoethyl](tert-butoxy)carboxamide according to the procedure for Preparation XIX using p-Cl-D-Phe-OH (301 mg, 1.0 mmol), HOAT (130 mg, 0.955 mmol), 1-(3-dimethylaminopropyl)-3-ethylcarbodiimide methiodide (595 mg, 2.00 mmol) and DMF (10 mL). The compound was concentrated in vacuo to yield 581 mg. MS (ESI, pos. ion) m/z: 591 (M+H), (ESI, neg. ion) m/z: 589 (M–H). Calc'd for C₂₉H₃₉ClN₄O₅S: 591.16.

Step 3

(2R)-2-Amino-3-(4-chlorophenyl)-1-(4-{2-[(cyclopropylmethyl) (methylsulfonyl)amino]phenyl}piperazinyl)propan-1-one was prepared according to the procedure for Preparation XVI using N-[(1R)-1-[(4-chlorophenyl)methyl]-2-(4-{2-[(cyclopropylmethyl)-(methylsulfonyl)amino]phenyl}-piperazinyl)-2-oxoethyl](tert-butoxy)carboxamide (Step 2) (560 mg, 0.95 mmol). The resulting crude material was diluted with EtOAc and washed with satd NaHCO₃ soln. The organic layer was separated, dried over Na₂SO₄, filtered and concentrated in vacuo to afford 449 mg. MS (ESI, pos. ion) m/z: 491 (M+H), (ESI, neg. ion) m/z: 489 (M−H). Calc'd for $C_{24}H_{31}ClN_4O_3S$: 491.05.

Step 4 tert-Butyl 3-{N-[(1R)-1-[(4-chlorophenyl)methyl]-2-(4-{2-[(cyclopropylmethyl)(methylsulfonyl)amino]phenyl}-piperazinyl)-2-oxoethyl]carbamoyl}-azetidine-carboxylate was prepared from (2R)-2-amino-3-(4-chlorophenyl)-1-(4-{2-[(cyclopropylmethyl)-(methylsulfonyl)amino]phenyl}piperazinyl)propan-1-one (Step 3) (220 mg, 0.46 mmol), according to the procedure for Preparation XIX using Boc-azetidine-3-carboxylic acid (100 mg, 0.50 mmol) (Peptech), 1-(3-dimethylaminopropyl)-3-ethylcarbodiimide methiodide (275 mg, 0.925 mmol), HOAT (64 mg, 0.470 mmol), and DMF (7 mL). The compound was isolated (294 mg). MS (ESI, pos. ion) m/z: 674 (M+H), (ESI, neg. ion) m/z: 672 (M−H). Calc'd for $C_{33}H_{44}ClN_5O_6S$: 674.25.

Step 5

N-[(1S)-1-[(4-Chlorophenyl)methyl]-2-(4-{2-[(cyclopropylmethyl)(methylsulfonyl)amino]phenyl}piperazinyl)-2-oxoethyl]azetidin-3-ylcarboxamide was prepared from tert-butyl 3-{N-[(1R)-1-[(4-chlorophenyl)methyl]-2-(4-{2-[(cyclopropylmethyl)(methylsulfonyl)amino]phenyl}piperazinyl)-2-oxoethyl]carbamoyl}azetidine carboxylate (250 mg, 0.371 mmol) according to the procedure for Preparation XVI. The product was purified using preparative HPLC (TFA buffer) (3 mg). MS (ESI, pos. ion) m/z: 574 (M+H), (ESI, neg. ion) m/z: 572 (M−H). Calc'd for $C_{28}H_{36}ClN_5O_4S$: 573.

EXAMPLE 59

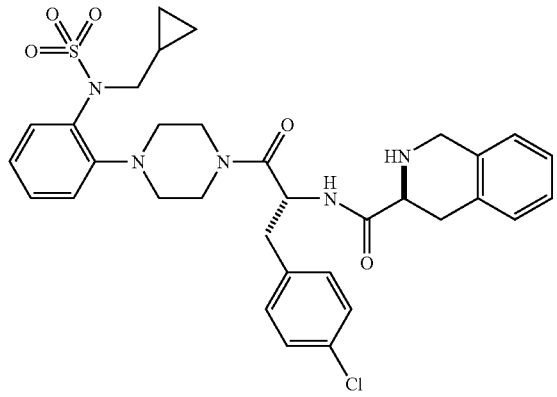

N-[(1R)-1-[(4-Chlorophenyl)methyl]-2-(4-{2-[(cyclopropylmethyl)(methylsulfonyl)amino]phenyl}piperazinyl)-2-oxoethyl]((3S)(3-1,2,3,4-tetrahydroisoquinolyl))carboxamide Step 1 tert-Butyl 3-{N-[(1R)-1-[(4-chlorophenyl)methyl]-2-(4-{2-[(cyclopropylmethyl) (methylsulfonyl)amino] phenyl}piperazinyl)-2-oxoethyl]carbamoyl}(3S)-1,2,3,4-tetrahydroisoquinoline-2-carboxylate was prepared from (2R)-2-amino-3-(4-chlorophenyl)-1-(4-{2-[(cyclopropylmethyl)(methylsulfonyl)amino]phenyl}-piperazinyl)propan-1-one (Example 58, Step 3) (224 mg, 0.457 mmol), according to the procedure for Preparation XIX using Boc-L-Tic-OH (135 mg, 0.487 mmol), 1-(3-dimethylaminopropyl)-3-ethylcarbodiimide methiodide (285 mg, 0.959 mmol), HOAT (68 mg, 0.50 mmol), and DMF (7 mL). The compound was isolated (339 mg). MS (ESI, pos. ion) m/z: 750 (M+H), (ESI, neg. ion) m/z: 748 (M−H). Calc'd for $C_{39}H_{48}ClN_5O_6S$: 750.35.

Step 2

N-[(1R)-1-[(4-Chlorophenyl)methyl]-2-(4-{2-[(cyclopropylmethyl)(methylsulfonyl)amino]phenyl}piperazinyl)-2-oxoethyl]((3S)(3-1,2,3,4-tetrahydroisoquinolyl))carboxamide was prepared from tert-butyl 3-{N-[(1R)-1-[(4-chlorophenyl)methyl]-2-(4-{2-[(cyclopropylmethyl)(methylsulfonyl)amino]phenyl}piperazinyl)-2-oxoethyl]carbamoyl}(3S)-1,2,3,4-tetrahydroisoquinoline-2-carboxylate (Step 1)(315 mg, 0.420 mmol) according to the procedure for Preparation XVI. The crude was concentrated in vacuo, purified by preparative HPLC (TFA buffer) to afford the desired product as the TFA salt (120 mg). MS (ESI, pos. ion) m/z: 650 (M+H), (ESI, neg. ion) m/z: 648 (M−H). Calc'd for $C_{34}H_{40}ClN_5O_4S$: 649. Anal. Calcd for $C_{34}H_{40}ClN_5O_4S$-2 $C_2HF_3O_2$: C, 51.97; H, 4.82; N, 7.97; Cl, 4.04. Found C, 52.05; H, 4.99; N, 8.04; Cl, 3.84.

EXAMPLES 60–61

General Procedure

Step 1 tert-Butyl 4-{2-[(methylsulfonyl)amino]phenyl}-piperazinecarboxylate (Preparation XII) (650 mg, 1.1 mmol) was treated according to the procedure for tert-butyl 4-{2-[methyl-(methylsulfonyl)amino]phenyl}-piperazinecarboxylate (Example 56, Step 1) with NaH (88 mg, 2.2 mmol) in DMF. This solution was divided evenly into two 10 mL scintillation vials equipped with magnetic stirring. To one vial was added 1-iodo-2-methylpropane (77 mg, 0.418 mmol) (Aldrich) for Example 60, and to the other vial was added 2-(bromoethyl)-benzene (79 mg, 0.427 mmol) (Aldrich) for Example 61. The reaction mixtures were stirred 24 h. The reaction mixtures were diluted with EtOAc, washed with 10% $NaHCO_3$, $H_2O$ and brine. The organic layers were dried over $Na_2SO_4$, filtered and concentrated in vacuo, in scintillation vials.

Step 2

To each vial was added $CH_2Cl_2$ (5 mL) followed by TFA (2 mL). The mixtures were stirred 1.5 h, and the reaction mixtures were concentrated in vacuo. To each vial was added $CH_2Cl_2$ (5 mL) and MP-carbonate resin (300 mg, 3.23 mmol/g, 0.97 mmol, Argonaut). The reaction mixtures were stirred 4 h.

Step 3

The samples from Step 2 were filtered into the vials containing PS-carbodiimide resin (700 mg, 1 mmol/g, 0.70 mmol, Argonaut) and p-Cl-D-Phe-OH (150 mg, 0.5 mmol) and the reaction mixtures were stirred for 60 h. To each vial was added PS-isocyanate resin (300 mg, 1.76 mmol/g, 0.53 mmol, Argonaut), and the reaction mixtures were stirred for 24 h. The reactions were filtered and concentrated in vacuo into new scintillation vials.

Step 4

The reaction mixtures from Step 3 were treated according to the procedure for Step 2.

Step 5

The samples from step (4) were filtered into the vials containing PS-carbodiimide resin (800 mg, 1 mmol/g, 0.80 mmol, Argonaut) and Boc-L-Tic-OH (100 mg, 360 mmol, Bachem) and the reaction mixtures were stirred for 48 h. To each vial was added PS-isocyante resin (300 mg, 1.76 mmol/g, 0.53 mmol, Argonaut) and stirring was continued for 48 h. The reaction mixtures were filtered, concentrated in vacuo, and treated with $CH_2Cl_2$ (5 mL) followed by TFA (2 mL). After stirring 1.5 h, the reaction mixtures were concentrated in vacuo and purified by preparative HPLC (TFA buffer) to yield the TFA salts of the desired products.

EXAMPLE 60

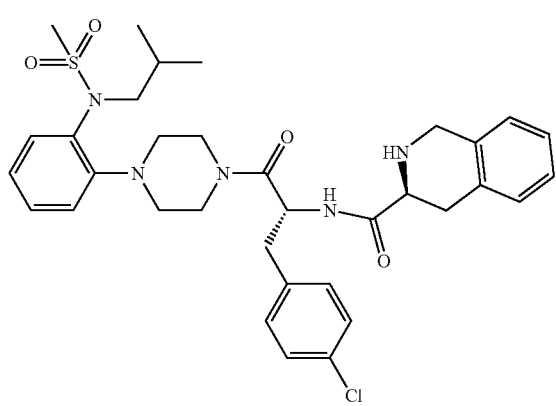

N-[(1R)-1-[(4-Chlorophenyl)methyl]-2-(4-{2-[(2-methylpropyl)(methylsulfonyl)amino]phenyl}piperazinyl)-2-oxoethyl]((3S)(3-1,2,3,4-tetrahydroisoquinolyl))carboxamide MS (ESI, pos. ion) m/z: 652 (M+H), (ESI, neg. ion) m/z: 650 (M−H). Calc'd for $C_{34}H_{42}ClN_5O_4S$: 651.

EXAMPLE 61

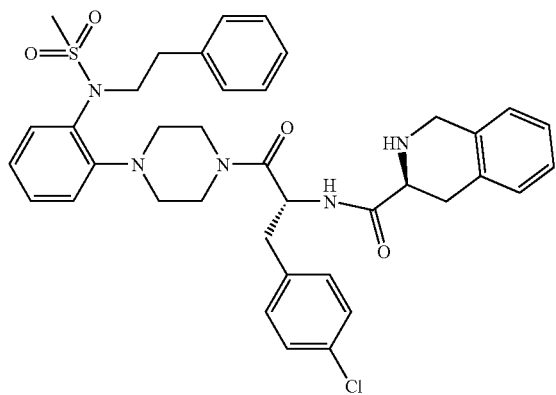

N-[(1R)-1-[(4-Chlorophenyl)methyl]-2-(4-{2-[(methylsulfonyl)(2-phenylethyl)amino]phenyl}piperazinyl)-2-oxoethyl]((3S)(3-1,2,3,4-tetrahydroisoquinolyl))carboxamide MS (ESI, pos. ion) m/z: 700 (M+H), (ESI, neg. ion) m/z: 698 (M−H). Calc'd for $C_{38}H_{42}ClN_5O_4S$: 699.

EXAMPLE 62

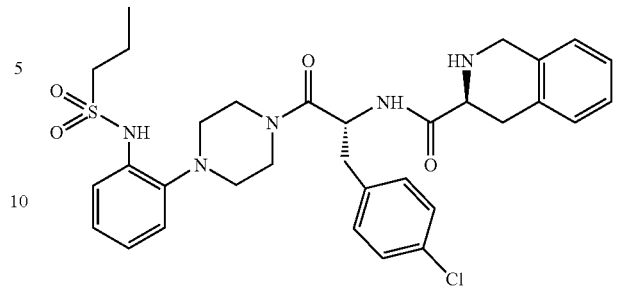

N-[(1R)-1-[(4-Chlorophenyl)methyl]-2-oxo-2-(4-{2-[(propylsulfonyl)amino]phenyl}piperazinyl)ethyl]((3S)(3-1,2,3,4-tetrahydroisoquinolyl))carboxamide Following the procedure for the synthesis of Preparation III, N-[(1R)-1-[(4-chlorophenyl)methyl]-2-oxo-2-(4-{2-[(propylsulfonyl)amino]phenyl}-piperazinyl)ethyl]((3S)(3-1,2,3,4-tetrahydroisoquinolyl))carboxamide was prepared from tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (200 mg, 0.32 mmol) in ClCH$_2$CH$_2$Cl (1.3 mL), pyridine (0.030 mL, 0.16 mmol), and propanesulfonyl chloride (Aldrich) (0.04 mL, 0.18 mmol). The material was treated with a soln of HCl satd EtOAc, which resulted in the precipitation of the salt. This was filtered and placed in vacuo to afford the desired crude as a white solid. After recrystallization from MeOH, the desired product was isolated as the HCl salt (10 mg). MS (ESI, pos. ion) m/z: 624 (M+H); MS (ESI, neg. ion) m/z: 622 (M−H). Calc'd for $C_{32}H_{38}ClN_5O_4S$: 623.23.

EXAMPLE 63

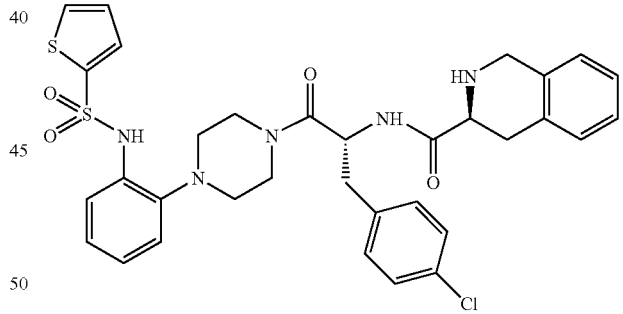

N-[(1R)-1-[(4-Chlorophenyl)methyl]-2-oxo-2-(4-{2-[(2-thienylsulfonyl)amino]phenyl}piperazinyl)ethyl]((3S) (3-1,2,3,4-tetrahydroisoquinolyl))carboxamide Following the procedure for the synthesis of Preparation III, N-[(1R)-1-[(4-chlorophenyl)methyl]-2-oxo-2-(4-{2-[(2-thienylsulfonyl)amino]phenyl}-piperazinyl)ethyl]((3S)(3-1,2,3,4-tetrahydro-isoquinolyl))carboxamide was prepared from tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (100 mg, 0.17 mmol) in ClCH$_2$CH$_2$Cl (5.0 mL), TEA (0.047 mL, 0.32 mmol) and 2-thiophenesulfonyl chloride (Aldrich) (34 mg, 0.188 mmol). The crude product from this reaction was treated with a soln of HCl satd EtOAc that resulted in the precipitation of the salt. This material was collected by filtration, dried in vacuo, and recrystallized from MeOH to afford the desired product as the HCl salt (55 mg). MS (ESI, pos. ion) m/z: 664 (M+H); MS (ESI, neg. ion) m/z: 662 (M−H). Calc'd for $C_{33}H_{34}ClN_5O_4S_2$: 663.

EXAMPLE 64

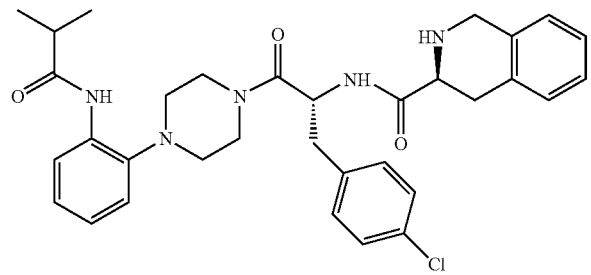

N-[2-(4-{(2R)-2-[((3S)(3-1,2,3,4-Tetrahydroisoquinolyl))carbonylamino]-3-(4-chlorophenyl)propanoyl{piperazinyl}phenyl]-2-methylpropanamide Following the procedure for the synthesis of Preparation III, N-[2-(4-{(2R)-2-[((3S)(3-1,2,3,4-tetrahydroisoquinolyl))carbonylamino]-3-(4-chlorophenyl)propanoyl}piperazinyl)phenyl]-2-methyl-propanamide was prepared from tert-butyl 3-(N-{(1R)-2-[4-(2-aminophenyl)piperazinyl]-1-[(4-chlorophenyl)-methyl]-2-oxoethyl}carbamoyl)(3S)-1,2,3,4-tetrahydro-isoquinoline-2-carboxylate (Preparation IX) (200 mg, 0.32 mmol) in ClCH$_2$CH$_2$Cl (1.3 mL), pyridine (0.040 mL, 0.32 mmol), and isobutyryl chloride (Aldrich Chemical Company) (37 mg, 0.36 mmol). The crude was treated with a soln of HCl satd EtOAc, which resulted in the precipitation of the salt. This material was collected by filtration, dried in vacuo, and recrystallized from MeOH to afford the desired product as the HCl salt (75 mg). MS (ESI, pos. ion) m/z: 588 (M+H); MS (ESI, neg. ion) m/z: 586 (M−H). Calc'd for $C_{33}H_{38}ClN_5O_3$: 587.

EXAMPLE 65

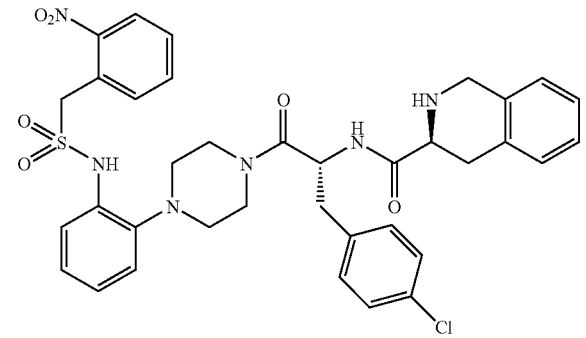

N-((1R)-1-[(4-Chlorophenyl)methyl]-2-{4-[2-({[(2-nitrophenyl)methyl]sulfonyl}amino)phenyl]piperazinyl}-2-oxoethyl)((3S)(3-1,2,3,4-tetrahydroisoquinolyl))carboxamide Following the procedure for the synthesis of Preparation III, the title compound was prepared from tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (250 mg, 0.40 mmol) in ClCH$_2$CH$_2$Cl (1.5 mL), pyridine (0.040 mL, 0.44 mmol), and 2-nitro-α-toluenesulfonyl chloride (Aldrich) (104 mg, 0.44 mmol). The crude was treated with a soln of HCl satd EtOAc, which resulted in the precipitation of the salt. This material was collected by filtration, dried in vacuo, and recrystallized from MeOH to afford the product as the HCl salt (18 mg). MS (ESI, pos. ion) m/z: 717 (M+H). Calc'd for $C_{36}H_{37}ClN_6O_4S$: 716.

EXAMPLE 66

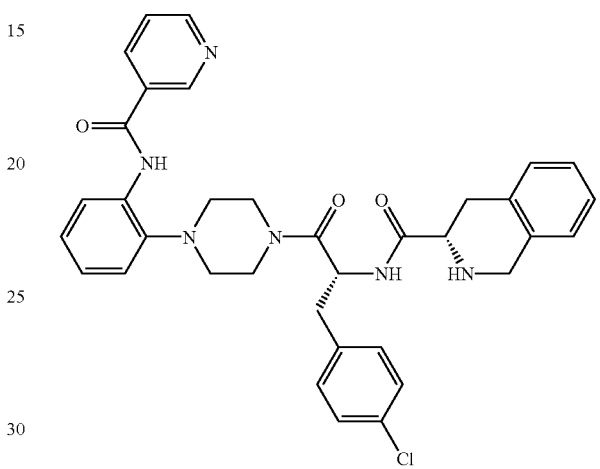

N-((1R)-1-[(4-Chlorophenyl)methyl]-2-oxo-2-{4-[2-(3-pyridylcarbonylamino)phenyl]piperazinyl}ethyl)((3S)(3-1,2,3,4-tetrahydroisoquinolyl))carboxamide Step 1

Following the procedure for the synthesis of Preparation XIX, tert-butyl 3-[N-((1R)-1-[(4-chlorophenyl)methyl]-2-oxo-2-{4-[2-(3-pyridylcarbonyl-amino)phenyl]piperazinyl}-ethyl)carbamoyl](3S)-1,2,3,4-tetrahydroisoquinoline-2-carboxylate was prepared from tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (250 mg, 0.40 mmol), nicotinic acid (54 mg, 0.44 mmol) (Aldrich), 1-(3-dimethylamino-propyl)-3-ethylcarbodiimide methiodide (227 mg; 0.76 mmol) and HOAT (62 mg; 0.46 mmol). The crude was concentrated in vacuo to afford of the desired compound (286 mg). MS (ESI, pos. ion) m/z: 723 (M+H), (ESI, neg. ion) m/z: 721 (M−H). Calc'd for $C_{40}H_{43}ClN_6O_5$: 723.26

Step 2

Following the procedure for the synthesis of Preparation XVI, N-((1R)-1-[(4-Chlorophenyl)methyl]-2-oxo-2-{4-[2-(3-pyridylcarbonylamino)phenyl]-piperazinyl}ethyl)((3S)(3-1,2,3,4-tetrahydro-isoquinolyl))carboxamide was prepared from tert-butyl 3-[N-(1R)-1-[(4-chlorophenyl)methyl]-2-oxo-2-{4-[2-(3-pyridylcarbonylamino)phenyl]piperazinyl}-ethyl)-carbamoyl](3S)-1,2,3,4-tetrahydroisoquinoline-2-carboxylate (280 mg, 0.39 mmol) and 15 mL of EtOAc satd with HCl. The crude was purified by flash chromatography (SiO$_2$, 3% MeOH in CH$_2$Cl$_2$) to afford 150 mg. The product was dissolved in H$_2$O (5 mL), CH$_3$CN (2 mL) and AcOH was added. The resulting solution was lyophilized to form the acetate salt. MS (ESI, pos. ion) m/z: 623 (M+H), MS (ESI, neg. ion) m/z: 621 (M−H).

Calc'd for $C_{35}H_{35}ClN_6O_3$: 622.25. Anal. Calc'd for $C_{35}H_{35}ClN_6O_3$—$C_2H_4O_2$: C, 65.05; H, 5.75; N, 12.30; Cl, 5.19. Found C, 64.79; H, 5.84; N, 12.55; Cl, 5.40.

EXAMPLE 67

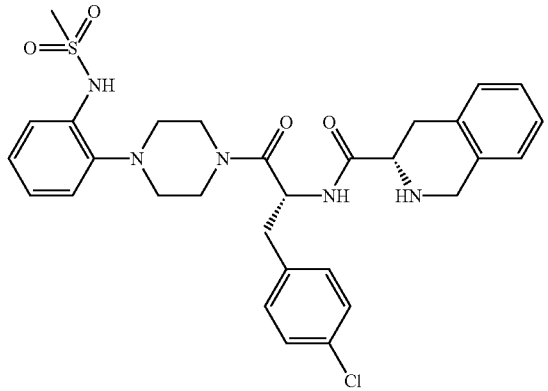

N-[(1R)-1-[(4-Chlorophenyl)methyl]-2-(4-{2-[(methylsulfonyl)amino]phenyl}piperazinyl)-2-oxoethyl]((3S)(3-1,2,3,4-tetrahydroisoquinolyl))carboxamide Step 1

Following the procedure for the synthesis of Preparation III, tert-butyl 3-{N-[(1R)-1-[(4-chlorophenyl)methyl]-2-(4-{2-[(methylsulfonyl)amino]phenyl}piperazinyl)-2-oxoethyl]carbamoyl}(3S)-1,2,3,4-tetrahydroisoquinoline-2-carboxylate was prepared from tert-butyl 3-(N-{(1R)-2-[4-(2-aminophenyl)piperazinyl]-1-[(4-chlorophenyl)methyl]-2-oxoethyl}carbamoyl) (3S)-1,2,3,4-tetrahydroisoquinoline-2-carboxylate (Preparation IX) (1.3 g, 2.0 mmol) in 20 mL of $ClCH_2CH_2Cl$, pyridine (200 μl, 2.5 mmol) (Aldrich) and methanesulfonyl chloride (180 μl, 2.3 mmol) (Aldrich) to give 1.4 g of the compound. MS (ESI, pos. ion) m/z: 695 (M+H), (ESI, neg. ion) m/z: 693 (M−H). Calc'd for $C_{35}H_{42}ClN_5O_6S$: 696.26. Anal. Calcd for $C_{35}H_{42}ClN_5O_6S$-0.5 $C_4H_8O_2$: C, 60.03; H, 6.26; N, 9.46; Cl, 4.79. Found C, 59.68; H, 6.33; N, 9.50; Cl, 4.99.

Step 2

Following the procedure for the synthesis of Preparation XVI,) N-[(1R)-1-[(4-chlorophenyl)methyl]-2-(4-{2-[(methylsulfonyl)amino]phenyl}piperazinyl)-2-oxoethyl]((3S) (3-1,2,3,4-tetrahydroisoquinolyl))carboxamide was prepared from tert-butyl 3-{N-[(1R)-1-[(4-chlorophenyl)methyl]-2-(4-{2-[(methylsulfonyl) amino] phenyl}piperazinyl)-2-oxoethyl]carbamoyl}(3S)-1,2,3,4-tetrahydroisoquinoline-2-carboxylate (Step 1) (1.42 g, 2.04 mmol) and 50 mL of EtOAc satd with HCl. The crude product was purified by preparative HPLC (AcOH buffer) yielding the desired product as the acetate salt (250 mg). MS (ESI, pos. ion) m/z: 596 (M+H), (ESI, neg. ion) m/z: 594 (M−H). Calc'd for $C_{30}H_{34}ClN_5O_4S$: 595. Anal. Calcd for $C_{30}H_{34}ClN_5O_4S$—$C_2H_4O_2 \cdot H_2O$: C, 57.01; H, 5.98; N, 10.39; Cl, 5.26. Found C, 56.83; H, 6.05; N, 10.25; Cl, 5.25.

EXAMPLE 68

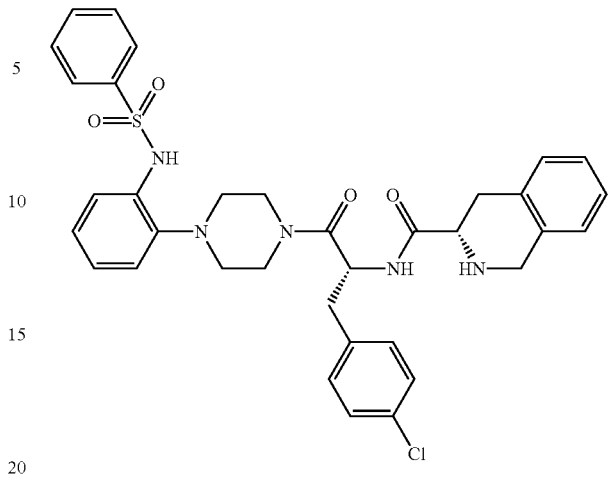

N-[(1R)-1-[(4-Chlorophenyl)methyl]-2-oxo-2-(4-{2-[(phenylsulfonyl)amino]phenyl}piperazinyl)ethyl] ((3S)(3-1,2,3,4-tetrahydroisoquinolyl))carboxamide Step 1

Following the procedure for the synthesis of Preparation III, tert-butyl 3-{N-[(1R)-1-[(4-chlorophenyl)methyl]-2-oxo-2-(4-{2-[(phenylsulfonyl)-amino]phenyl}piperazinyl) ethyl]carbamoyl}(3S)-1,2,3,4-tetrahydroisoquinoline-2-carboxylate was prepared from tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (771 mg, 1.247 mmol), pyridine (110 μl, 1.4 mmol) and benzenesulfonyl chloride (160 μl, 1.3 mmol) (Aldrich). The crude was purified by flash chromatography ($SiO_2$, 10% EtOAc in $CH_2Cl_2$) to afford 330 mg of the desired compound. MS (ESI, pos. ion) m/z: 758 (M+H), (ESI, neg. ion) m/z: 756 (M−H). Calc'd for $C_{40}H_{44}ClN_5O_6S$: 758.33. Anal. Calcd for $C_{40}H_{44}ClN_5O_6S$-0.5 $C_4H_8O_2$: C, 62.87; H, 6.03; N, 8.73; Cl, 4.42. Found C, 62.49; H, 6.03; N, 8.52.

Step 2

N-[(1R)-1-[(4-Chlorophenyl)methyl]-2-oxo-2-(4-{2-[(phenylsulfonyl)amino]phenyl}piperazinyl)ethyl]((3S)(3-1,2,3,4-tetrahydroisoquinolyl))carboxamide was prepared from tert-butyl 3-{N-[(1R)-1-[(4-chlorophenyl)methyl]-2-oxo-2-(4-{2-[(phenylsulfonyl)amino]phenyl}piperazinyl) ethyl]carbamoyl}(3S)-1,2,3,4-tetrahydroisoquinoline-2-carboxylate (Step 1) (300 mg, 0.40 mmol) according to the procedure for Preparation XVI. The product was concentrated in vacuo (66 mg) dissolved in $H_2O$ and $CH_3CN$, treated with AcOH and lyophilized. MS (ESI, pos. ion) m/z: 658 (M+H), (ESI, neg. ion) m/z: 656 (M−H). Calc'd for $C_{35}H_{36}ClN_5O_4S$: 657. Anal. Calcd for $C_{35}H_{36}ClN_5O_4S$-0.5$C_2H_4O_2$-0.5 $H_2O$: C, 62.01; H, 5.64; N, 10.04; Cl, 5.08. Found C, 62.36; H, 5.54; N, 10.06; Cl, 5.05.

EXAMPLE 69

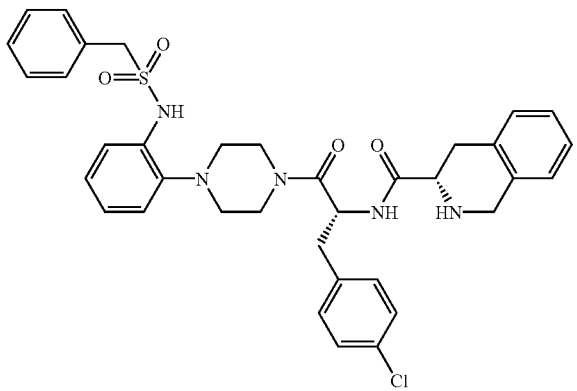

N-{(1R)-1-[(4-Chlorophenyl)methyl]-2-oxo-2-[4-(2-{[benzylsulfonyl]amino}phenyl)piperazinyl]ethyl}((3S)(3-1,2,3,4-tetrahydroisoquinolyl))carboxamide

Step 1 tert-Butyl 3-(N-{(1R)-1-[(4-chlorophenyl)methyl]-2-oxo-2-[4-(2-{[benzylsulfonyl]amino}phenyl)piperazinyl]ethyl}carbamoyl)(3S)-1,2,3,4-tetrahydroisoquinoline-2-carboxylate was prepared according to the procedure for Preparation III using tert-butyl 3-(N-{(1R)-2-[4-(2-aminophenyl)piperazinyl]-1-[(4-chlorophenyl)methyl]-2-oxoethyl}carbamoyl)(3S)-1,2,3,4-tetrahydroisoquinoline-2-carboxylate (Preparation IX) (730 mg, 1.2 mmol), pyridine (100 μl, 1.2 mmol) and α-toluenesulfonyl chloride (240 mg, 1.2 mmol) (Aldrich). The crude material was purified by flash chromatography (SiO$_2$ 10% EtOAc in CH$_2$Cl$_2$) to afford the desired compound (387 mg). MS (ESI, pos. ion) m/z: 772 (M+H), (ESI, neg. ion) m/z: 770 (M−H). Calc'd for C$_{41}$H$_{46}$ClN$_5$O$_6$S: 772.35. Anal. Calcd for C$_{41}$H$_{46}$ClN$_5$O$_6$S-0.5 C$_4$H$_8$O$_2$: C, 63.26; H, 6.17; N, 8.58; Cl, 4.34. Found C, 62.98; H, 6.09; N, 8.36.

Step 2

N-{(1R)-1-[(4-Chlorophenyl)methyl]-2-oxo-2-[4-(2-{[benzylsulfonyl]amino}phenyl)piperazinyl]ethyl}((3S)(3-1,2,3,4-tetrahydroisoquinolyl))carboxamide was prepared from tert-butyl 3-(N-{(1R)-1-[(4-chlorophenyl)methyl]-2-oxo-2-[4-(2-{[benzylsulfonyl]amino}phenyl)piperazinyl]ethyl}carbamoyl)(3S)-1,2,3,4-tetrahydroisoquinoline-2-carboxylate (Step 1) (300 mg, 0.39 mmol) according to the procedure for Preparation XVI. The crude product was purified by flash chromatography (SiO$_2$ 3% MeOH in CH$_2$Cl$_2$) to afford the desired material (130 mg). The compound was dissolved in H$_2$O and CH$_3$CN, treated with AcOH and freeze-dried to yield the acetate salt. MS (ESI, pos. ion) m/z: 672 (M+H), (ESI, neg. ion) m/z: 670 (M−H). Calc'd for C$_{36}$H$_{38}$ClN$_5$O$_4$S: 671.23.

EXAMPLE 70

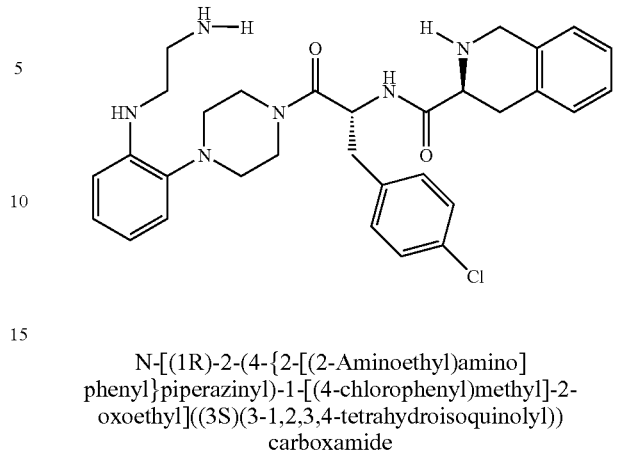

N-[(1R)-2-(4-{2-[(2-Aminoethyl)amino]phenyl}piperazinyl)-1-[(4-chlorophenyl)methyl]-2-oxoethyl]((3S)(3-1,2,3,4-tetrahydroisoquinolyl))carboxamide

Step 1

Following the procedure for the synthesis of Example 40 Step 3 (without DIEA), tert-butyl 3-[N-((1R)-2-{4-[2-({2-[(tert-butoxy)carbonylamino]ethyl}amino)phenyl]-piperazinyl}-1-[(4-chlorophenyl)methyl]-2-oxoethyl)-carbamoyl](3S)-1,2,3,4-tetrahydroisoquinoline-2-carboxylate was prepared from tert-butyl 3-(N-{(1R)-2-[4-(2-aminophenyl)piperazinyl]-1-[(4-chlorophenyl)-methyl]-2-oxoethyl}carbamoyl)(3S)-1,2,3,4-tetrahydroisoquinoline-2-carboxylate (Preparation IX) (630 mg, 1.0 mmol) in 2 mL of ClCH$_2$CH$_2$Cl, tert-butyl-N-(2-oxoethyl)carbamate (179 mg, 1.126 mmol) (Aldrich) in ClCH$_2$CH$_2$Cl (10 mL), and NaBH(OAc)$_3$ (330 mg, 1.557 mmol) (Aldrich). The crude was purified by flash chromatography (SiO$_2$, 2:1 hexane:EtOAc) to afford the desired compound (578 mg). MS (ESI, pos. ion) m/z: 761 (M+H), (ESI, neg. ion) m/z: 759 (M−H). Calc'd for C$_{41}$H$_{53}$ClN$_6$O$_6$: 761.35. Anal. Calc'd for C$_{41}$H$_{53}$ClN$_6$O$_6$-0.5 C$_4$H$_8$O$_2$-0.5 H$_2$O: C, 63.42; H, 7.18; N, 10.32; Cl, 4.35. Found C, 62.96 (±0.46); H, 7.14; N, 10.26; Cl, 4.06.

Step 2

N-[(1R)-2-(4-{2-[(2-Aminoethyl)amino]phenyl}piperazinyl)-1-[(4-chlorophenyl)methyl]-2-oxoethyl]((3S)(3-1,2,3,4-tetrahydroisoquinolyl))carboxamide was prepared according to Preparation XVI using tert-butyl 3-[N-((1R)-2-{4-[2-({2-[(tert-butoxy)carbonylamino]-ethyl}amino)phenyl]-piperazinyl}-1-[(4-chlorophenyl)-methyl]-2-oxoethyl)-carbamoyl](3S)-1,2,3,4-tetrahydro-isoquinoline-2-carboxylate (150 mg, 0.18 mmol) and 25 mL of EtOAc satd with HCl. The crude product was concentrated to provide the desired product (90 mg). MS (ESI, pos. ion) m/z: 561 (M+H), (ESI, neg. ion) m/z: 559 (M−H). Calc'd for C$_{31}$H$_{37}$ClN$_6$O$_2$: 560.27.

EXAMPLE 71

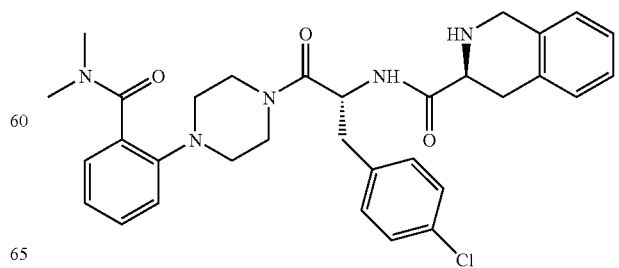

[2-(4-((2R)-2-[((3S)(3-1,2,3,4-Tetrahydroisoquinolyl))carbonylamino]-3-(4-chlorophenyl)propanoyl}piperazinyl)phenyl]-N,N-dimethylcarboxamide

Step 1

To a 150 mL round-bottomed flask equipped with magnetic stirring was added methyl 2-[4-benzylpiperazinyl] benzoate (Preparation XIII) (2.3 g, 7.4 mmol) in THF (60 mL). A soln of LiOH (Aldrich) (940 mg, 22 mmol) in $H_2O$ (20 mL), was added and the reaction mixture was heated at 60° C. for 12 h. After cooling to RT, the reaction mixture was concentrated in vacuo and diluted with EtOAc (100 mL). A 10% soln of citric acid (25 mL) was added, the organic layer was separated and the aqueous layer was extracted with EtOAc (2×25 mL). The organic layers were combined, washed with $H_2O$, satd NaCl, dried over $Na_2SO_4$, filtered and concentrated in vacuo to afford 2-[4-benzylpiperazinyl] benzoic acid as a white solid (2.05 g). MS (ESI, pos.ion) m/z: 297 (M+H). Calc'd for $C_{18}H_{20}N_2O_2$: 296.15 : 296.15.

Step 2

To a 100 mL round-bottomed flask equipped with magnetic stirring was added 2-[4-benzylpiperazinyl] benzoic acid (Step 1) (1.1 g, 3.7 mmol) in $CH_2Cl_2$ (40 mL) under a $N_2$ atmosphere. Oxalyl chloride (Aldrich) (390 µL, 1.32 mmol) was added, the mixture was stirred at RT for 5 min. and several drops of DMF were added. After stirring at RT for 2 h, the reaction mixture was concentrated in vacuo and re-dissolved in $CH_2Cl_2$ (40 mL). N,N-Dimethylamine (Aldrich) (5.6 mL of a 2M soln in THF, 11 mmol) was added and the mixture was stirred at RT for 12 h. The reaction was washed with $H_2O$, brine, dried over $Na_2SO_4$, filtered, concentrated in vacuo, and purified by column chromatography (4:1 hexanes-EtOAc) affording N,N-dimethyl{2-[4-benzylpiperazinyl]phenyl}carboxamide (558 mg). MS (ESI, pos. ion) m/z: 324 (M+H). Calc'd for $C_{20}H_{25}N_3O$: 323.43.

Step 3

To a round-bottomed flask equipped with stirring was added N,N-dimethyl{2-[4-benzylpiperazinyl]phenyl} carboxamide (Step 2) (420 mg, 1.3 mmol), MeOH (10 mL), 10% Pd/C (Aldrich) (138 mg), and $HCO_2NH_4$ (409 mg, 6.5 mmol), and the reaction mixture was heated at reflux for 2 h. The reaction mixture was filtered through Celite®, concentrated in vacuo, and redissolved in $CH_2Cl_2$ (20 mL). The reaction mixture was washed with a $Na_2CO_3$ (10%, 2×), $H_2O$, brine, dried over $Na_2SO_4$, filtered and concentrated in vacuo yielding N,N-dimethyl(2-piperazinylphenyl) carboxamide (255 mg). MS (ESI, pos.ion) m/z: 234 (M+H). Calc'd for $C_{13}H_{19}N_3O$: 233.31.

Step 4

[2-(4-{(2R)-2-[(tert-Butoxy)carbonylamino]-3-(4-chlorophenyl)propanoyl}piperazinyl)phenyl]-N,N-dimethylcarboxamide was prepared according to the procedure described in Preparation V by using N,N-dimethyl(2-piperazinylphenyl)carboxamide (Step 3) (260 mg, 1.1 mmol), Boc-p-Cl-D-Phe-OH (Peptech Corporation) (370 mg, 1.2 mmol), HOAT (Aldrich) (151 mg, 1.11 mmol), and EDC (Aldrich Chemical Company) (430 mg, 2.2 mmol). The compound was isolated as a crude white foam (480 mg) and used in the next step without further purification. MS (ESI, pos.ion) m/z: 515 (M+H). Calc'd for $C_{27}H_{35}ClN_4O_4$: 515.04.

Step 5

(2-{4-[(2R)-2-Amino-3-(4-chlorophenyl)propanoyl]-piperazinyl}phenyl)-N,N-dimethylcarboxamide HCl salt was prepared according to the procedure described in Preparation XVI by using [2-(4-{(2R)-2-[(tert-butoxy) carbonylamino]-3-(4-chlorophenyl)propanoyl]-piperazinyl}phenyl]-N,N-dimethylcarboxamide (Step 4) (240 mg, 0.46 mmol) and a satd soln of HCl in EtOAc (10 mL). The white solid that formed was isolated by filtration (200 mg). MS (ESI, pos.ion) m/z: 415 (M+H). Calc'd for $C_{22}H_{28}Cl_2N_4O_2$: 451.39.

Step 6 tert-Butyl 3-[N-((1R)-2-{4-[2-(N,N-dimethylcarbamoyl)-phenyl]piperazinyl}-1-[(4-chlorophenyl)methyl]-2-oxoethyl)carbamoyl](3S)-1,2,3,4-tetrahydro-isoquinoline-2-carboxylate was prepared according to the procedure described in Preparation V by using (2-{4-[(2R)-2-amino-3-(4-chlorophenyl)-propanoyl]-piperazinyl}phenyl)-N,N-dimethylcarboxamide HCl salt (Step 5) (230 mg, 0.50 mmol), Boc-L-Tic-OH (Bachem Company) (150 mg, 0.55 mmol), HOAT (Aldrich) (68 mg, 0. 50 mmol), EDC (Aldrich) (190 mg, 1.00 mmol) and DIEA (Aldrich) (87 µL, 0.50 mmol). The compound was isolated and purified by column chromatography ($CH_2Cl_2$: 1.5% 2M $NH_3$ in MeOH). (255 mg). MS (ESI, pos. ion) m/z: 674 (M+H). Calc'd for $C_{37}H_{44}ClN_5O_5$: 674.23.

Step 7

[2-(4-{(2R)-2-[((3S)(3-1,2,3,4-Tetrahydro-isoquinolyl))carbonylamino]-3-(4-chlorophenyl)-propanoyl}piperazinyl) phenyl]-N,N-dimethylcarboxamide was prepared according to the procedure described in Preparation XVI by using tert-butyl 3-[N-((1R)-2-{4-[2-(N,N-dimethylcarbamoyl)-phenyl]piperazinyl}-1-[(4-chlorophenyl)methyl]-2-oxoethyl)carbamoyl](3S)-1,2,3,4-tetrahydro-isoquinoline-2-carboxylate (Step 6) (156 mg, 0.23 mmol) and a satd soln of HCl in EtOAc (5 mL). The title compound was isolated by filtration as a white solid, and purified by preparative HPLC (TFA buffer) (125 mg). MS (ESI, pos.ion) m/z: 574 (M+H). Calc'd for $C_{32}H_{36}ClN_5O_3$: 573.25.

EXAMPLE 72

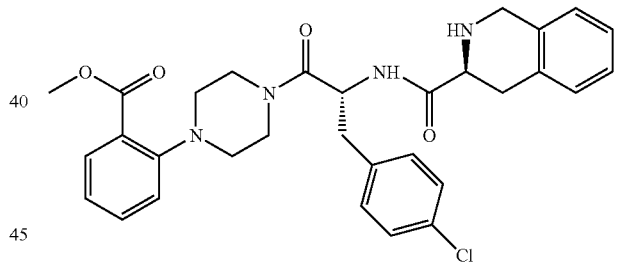

Methyl 2-(4-{(2R)-2-[((3S)(3-1,2,3,4-tetrahydroisoquinolyl))carbonylamino]-3-(4-chlorophenyl)propanoyl}piperazinyl)benzoate The title compound was prepared according to the procedure described in Preparation XVI by using methyl 2-{4-[(2R)-2-({(3S)-2-[(tert-butyl)oxycarbonyl](3-1,2,3,4-tetrahydroisoquinolyl)}carbonylamino)-3-(4-chlorophenyl) propanoyl]piperazinyl}benzoate (Preparation XVII) (140 mg, 0.21 mmol) and a satd soln of HCl in EtOAc (5 mL). The title compound was isolated by filtration as a white solid, and purified by preparative HPLC (62 mg). MS (ESI, pos.ion) m/z: 561 (M+H). Calc'd for $C_{31}H_{33}ClN_4O_4$: 560.22.

EXAMPLES 73–90

Parallel Synthesis of Amide Library: General Procedure

To eighteen 10 mL scintillation vials were added PS-carbodiimide resin (Argonaut Technologies) (1 mmol/g) (80 mg, 0.08 mmol), HOAT (Aldrich) (8 mg, 0.06 mmol)

and 2-{4-[(2R)-2-({(3S)-2-[(tert-butyl)oxycarbonyl](3-1,2,3,4-tetrahydroisoquinolyl)}carbonylamino)-3-(4-chlorophenyl)propanoyl]-piperazinyl}benzoic acid (Preparation XVIII) (40 mg, 0.06 mmol) in $CH_2Cl_2$ (3 mL), and the reaction mixtures were shaken at RT for 10 min. The corresponding amine (0.05 mmol) was added, and the vials were shaken at RT for 12 h. Resin was filtered off and washed with $CH_2Cl_2$, and the solutions were concentrated in vacuo. A satd soln of HCl in EtOAc (2 mL) was added. After 1 h at RT, the solutions were concentrated in vacuo, and the products were purified by preparative HPLC (TFA buffer) to yield the TFA salts of the desired product.

EXAMPLE 73

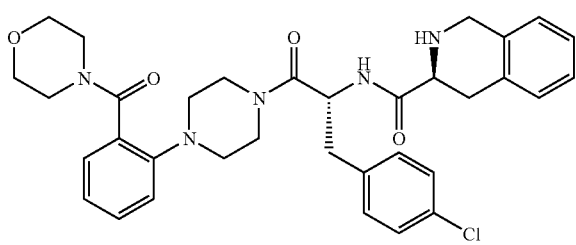

N-((1R)-1-[(4-Chlorophenyl)methyl]-2-{4-[2-(morpholin-4-ylcarbonyl)phenyl]piperazinyl}-2-oxoethyl)((3S)(3-1,2,3,4-tetrahydroisoquinolyl))carboxamide MS (ESI, pos.ion) m/z: 616 (M+H). Calc'd for $C_{34}H_{38}N_5O_4Cl$: 615.26.

EXAMPLE 74

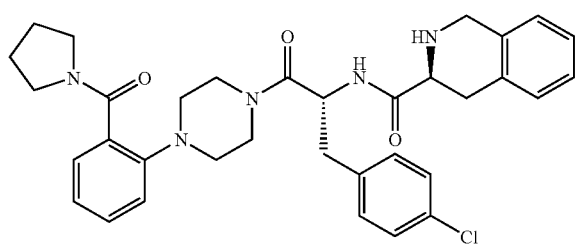

N-((1R)-1-[(4-Chlorophenyl)methyl]-2-oxo-2-{4-[2-(pyrrolidinylcarbonyl)phenyl]piperazinyl}ethyl)((3S)(3-1,2,3,4-tetrahydroisoquinolyl))carboxamide MS (ESI, pos.ion) m/z: 600 (M+H). Calc'd for $C_{34}H_{38}ClN_5O_3$: 599.27.

EXAMPLE 75

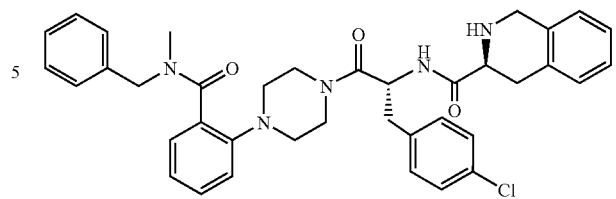

N-[(1R)-1-[(4-Chlorophenyl)methyl]-2-(4-{2-[N-methyl-N-benzylcarbamoyl]phenyl}piperazinyl)-2-oxoethyl]((3S)(3-1,2,3,4-tetrahydroisoquinolyl))carboxamide MS (ESI, pos.ion) m/z: 650 (M+H). Calc'd for $C_{38}H_{40}ClN_5O_3$: 649.28.

EXAMPLE 76

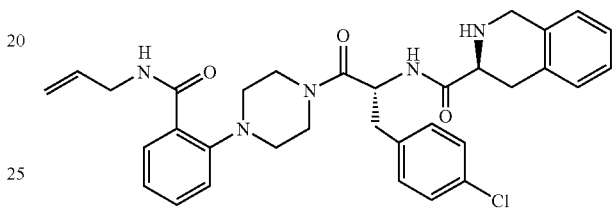

N-((1R)-1-[(4-Chlorophenyl)methyl]-2-oxo-2-{4-[2-(N-prop-2-enylcarbamoyl)phenyl]piperazinyl}ethyl)((3S)(3-1,2,3,4-tetrahydroisoquinolyl))carboxamide MS (ESI, pos.ion) m/z: 586 (M+H). Calc'd for $C_{33}H_{36}ClN_5O_3$: 585.25.

EXAMPLE 77

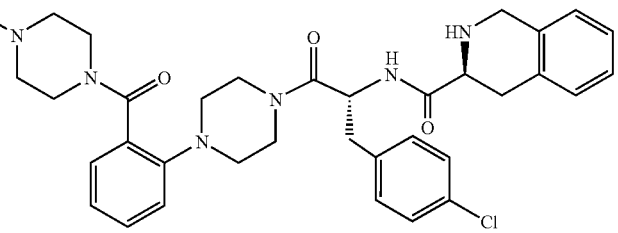

N-{(1R)-1-[(4-Chlorophenyl)methyl]-2-oxo-2-[4-(2-{[4-benzylpiperazinyl]carbonyl}phenyl)piperazinyl]ethyl}((3S) (3-1,2,3,4-tetrahydroisoquinolyl))carboxamide MS (ESI, pos.ion) m/z: 705 (M+H). Calc'd for $C_{41}H45ClN_6O_3$: 704.32.

EXAMPLE 78

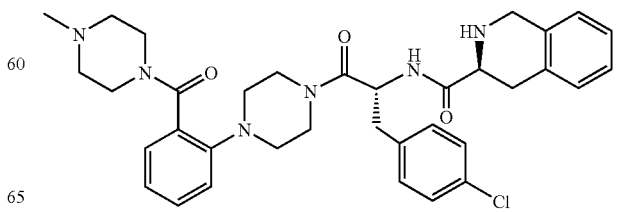

N-[(1R)-1-[(4-Chlorophenyl)methyl]-2-(4-(2-[(4-methylpiperazinyl)carbonyl]phenyl)piperazinyl)-2-oxoethyl]((3s)(3-1,2,3,4-tetrahydroisoquinolyl))carboxamide MS (ESI, pos.ion) m/z: 629 (M+H). Calc'd for $C_{35}H_{41}ClN_6O_3$: 628.29.

EXAMPLE 79

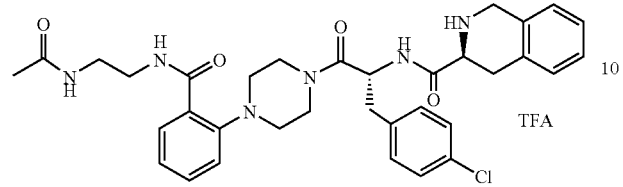

N-(2-{[2-(4-{(2R)-2-[((3S)(3-1,2,3,4-tetrahydroisoquinolyl))carbonylamino]-3-(4-chlorophenyl)propanoyl}piperazinyl)phenyl]carbonylamino}ethyl)acetamide MS (ESI, pos.ion) m/z: 631 (M+H). Calc'd for $C_{34}H_{39}ClN_6O_4$: 630.27.

EXAMPLE 80

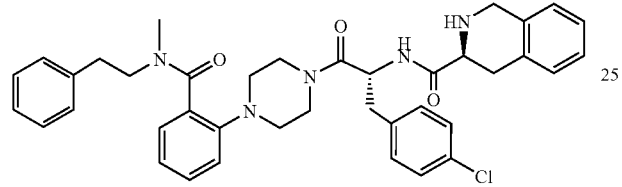

N-[(1R)-1-[(4-Chlorophenyl)methyl]-2-(4-{2-[N-methyl-N-(2-phenylethyl)carbamoyl]phenyl}piperazinyl)-2-oxoethyl]((3S)(3-1,2,3,4-tetrahydroisoquinolyl)) carboxamide MS (ESI, pos.ion) m/z: 664 (M+H). Calc'd for $C_{39}H_{42}ClN_5O_3$: 663.30.

EXAMPLE 81

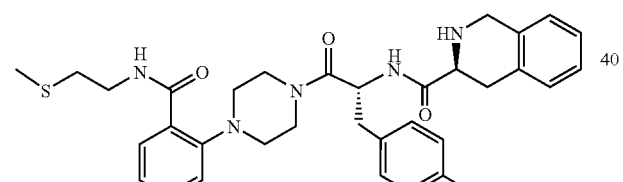

N-[(1R)-1-[(4-Chlorophenyl)methyl]-2-(4-{2-[N-(2-methylthioethyl)carbamoyl]phenyl}piperazinyl)-2-oxoethyl]((3S)(3-1,2,3,4-tetrahydroisoquinolyl)) carboxamide MS (ESI, pos.ion) m/z: 620 (M+H). Calc'd for $C_{33}H_{38}ClN_5O_3S$: 619.24.

EXAMPLE 82

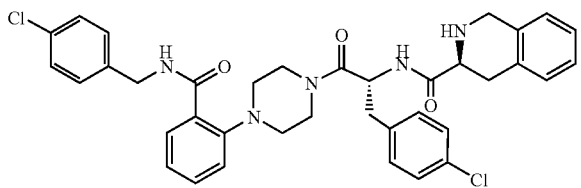

N-{(1R)-1-[(4-Chlorophenyl)methyl]-2-[4-(2-{N-[(4-chlorophenyl)methyl]carbamoyl}phenyl)piperazinyl]-2-oxoethyl}((3S)(3-1,2,3,4-tetrahydroisoquinolyl))carboxamide MS (ESI, pos.ion) m/z: 670 (M+H). Calc'd for $C_{37}H37Cl_2N_5O_3$: 669.23.

EXAMPLE 83

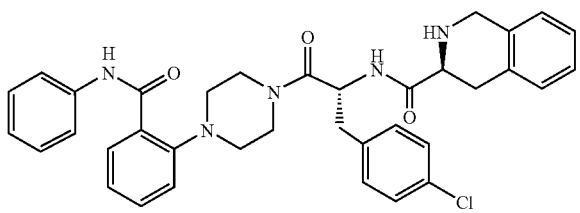

N-((1R)-1-[(4-Chlorophenyl)methyl]-2-oxo-2-{4-[2-(N-phenylcarbamoyl)phenyl]piperazinyl}ethyl)((3S)(3-1,2,3,4-tetrahydroisoquinolyl))carboxamide MS (ESI, pos.ion) m/z: 622 (M+H). Calc'd for $C_{36}H_{36}ClN_5O_3$: 621.25.

EXAMPLE 84

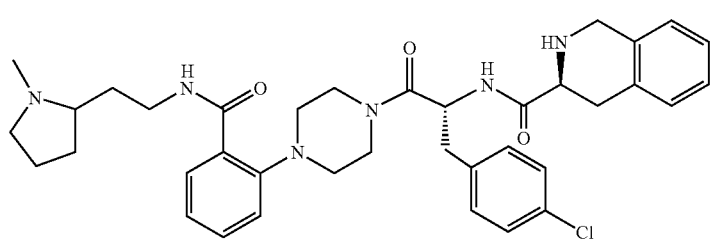

N-{(1R)-1-[(4-Chlorophenyl)methyl]-2-[4-(2-{N-[2-(1-methylpyrrolidin-2-yl)ethyl]carbamoyl}phenyl)piperazinyl]-2-oxoethyl}((3S)(3-1,2,3,4-tetrahydroisoquinolyl))carboxamide MS (ESI, pos.ion) m/z: 657 (M+H). Calc'd for $C_{37}H_{45}ClN_6O_3$: 656.32.

EXAMPLE 85

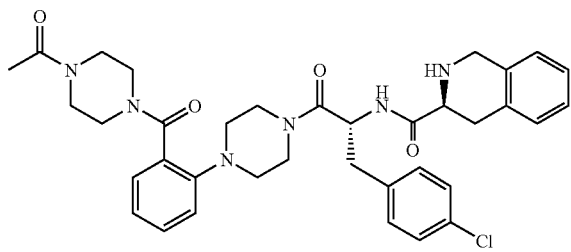

N-[(1R)-2-(4-{2-[(4-Acetylpiperazinyl)carbonyl]phenyl}piperazinyl)-1-[(4-chlorophenyl)methyl]-2-oxoethyl]((3S)(3-1,2,3,4-tetrahydroisoquinolyl))carboxamide MS (ESI, pos.ion) m/z: 657 (M+H). Calc'd for $C_{36}H_4lClN_6O_4$: 656.29.

EXAMPLE 86

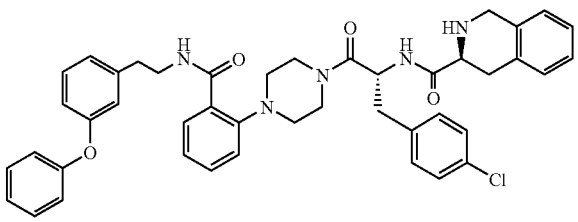

N-{(1R)-1-[(4-Chlorophenyl)methyl]-2-oxo-2-[4-(2-{N-[2-(3-phenoxyphenyl)ethyl]carbamoyl}phenyl)piperazinyl]ethyl}((3S)(3-1,2,3,4-tetrahydroisoquinolyl))carboxamide MS (ESI, pos.ion) m/z: 742 (M+H). Calc'd for $C_{44}H_{44}ClN_5O_4$: 741.31.

EXAMPLE 87

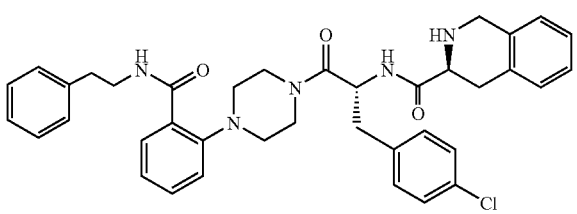

N-[(1R)-1-[(4-Chlorophenyl)methyl]-2-oxo-2-(4-{2-[N-(2-phenylethyl)carbamoyl]phenyl}piperazinyl)ethyl]-((3S)(3-1,2,3,4-tetrahydroisoquinolyl))carboxamide MS (ESI, pos.ion) m/z: 650 (M+H). Calc'd for $C_{38}H_{40}ClN_5O_3$: 646.28.

EXAMPLE 88

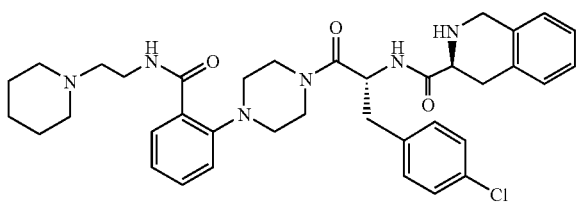

N-[(1R)-1-[(4-Chlorophenyl)methyl]-2-oxo-2-(4-{2-[N-(2-piperidylethyl)carbamoyl]phenyl}piperazinyl)ethyl]((3S)(3-1,2,3,4-tetrahydroisoquinolyl))carboxamide MS (ESI, pos.ion) m/z: 657 (M+H). Calc'd for $C_{37}H_{45}ClN_6O_3$: 656.32.

EXAMPLE 89

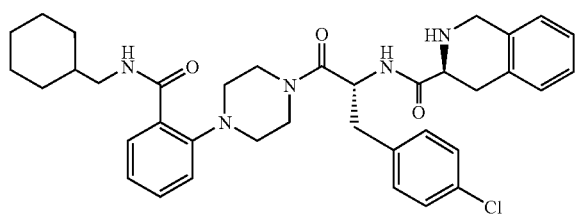

N-[(1R)-1-[(4-Chlorophenyl)methyl]-2-(4-{2-[N-(cyclohexylmethyl)carbamoyl]phenyl}piperazinyl)-2-oxoethyl]((3S)(3-1,2,3,4-tetrahydroisoquinolyl))carboxamide MS (ESI, pos.ion) m/z: 642 (M+H). Calc'd for $C_{37}H_{44}ClN_5O_3$: 641.31.

EXAMPLE 90

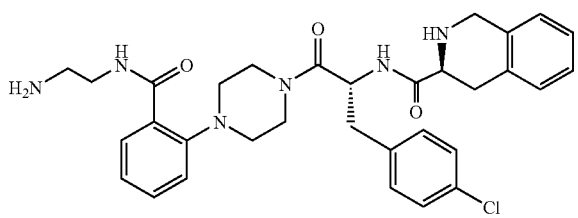

N-[(1R)-2-(4-{2-[N-(2-Aminoethyl)carbamoyl]phenyl}piperazinyl)-1-[(4-chlorophenyl)methyl]-2-oxoethyl]((3S)(3-1,2,3,4-tetrahydroisoquinolyl))carboxamide MS (ESI, pos.ion) m/z: 589 (M+H). Calc'd for $C_{32}H_{37}ClN_6O_3$: 588.26.

EXAMPLE 91

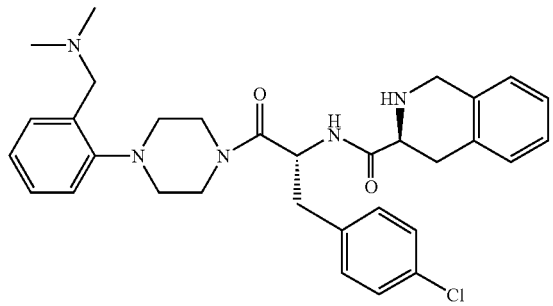

N-[(1R)-2-(4-{2-[(dimethylamino)methyl]
phenyl}piperazinyl)-1-[(4-chlorophenyl)methyl]-2-
oxoethyl]-((3S)(3-1,2,3,4-tetrahydroisoquinolyl))
carboxamide Step 1

To a solution of 2-fluorobenzaldehyde (Aldrich) (1 g, 8.1 mmol) in DMF (14 mL) was added 1-Boc-piperazine (Lancaster) (2.3 g, 12 mmol). The resulting solution was treated with copper (Aldrich Chemical Company) (50 mg, 0.8 mmol) and $K_2CO_3$ (Aldrich) (5.1 g, 37 mmol) The suspension was heated in a sealed tube at 150° C. for 18 h. After cooling to RT, the reaction mixture was partitioned between EtOAc and brine. The aqueous layer was extracted twice with EtOAc and the combined EtOAc layers were washed with water, dried over $Na_2SO_4$, filtered and concentrated in vacuo. The crude compound was purified on a Biotage 40M column (12% EtOAc in hexanes) to give tert-butyl 4-(2-formylphenyl)piperazinecarboxylate (0.66 g) as a yellow oil. MS m/z: 291 (M+H). Calc'd for $C_{16}H_{22}N_2O_3$: 290.36.

Step 2

To tert-butyl 4-(2-formylphenyl)piperazinecarboxylate (Step 1)(0.6 g, 2.1 mmol), was added dimethylamine (Aldrich) (1.6 mL of a 2.0 M soln in THF, 3.2 mmol) in $ClCH_2CH_2Cl$ (15 mL) and $NaBH(OAc)_3$ (Aldrich) (0.66 g, 3.2 mmol). The reaction was stirred at RT for 2 h. The mixture was partitioned between $CH_2Cl_2$ and satd $NaHCO_3$. The organic layer was washed with brine, dried over $Na_2SO_4$, filtered and concentrated in vacuo to give tert-butyl 4-{2-[(dimethylamino)methyl]phenyl}piperazinecarboxylate (0.68 g) as a yellow oil. MS m/z: 320 (M+H). Calc'd for $C_{18}H_{29}N_3O_2$: 319.44.

Step 3

To tert-butyl 4-{2-[(dimethylamino)methyl]phenyl}-piperazinecarboxylate (Step 2) (0.68 g, 2.1 mmol) dissolved in $CH_2Cl_2$ (12 mL) was added TFA (6 mL). After stirring the reaction at RT for 1 h, the solvent was concentrated in vacuo and the residue was partitioned between $CH_2Cl_2$ and satd $NaHCO_3$. The organic layer was washed with brine and the combined aqueous layer were extracted with a mixture of $CH_2Cl_2$ and 30% MeOH. The combined organic layer was dried over $Na_2SO_4$, filtered and concentrated in vacuo to give dimethyl[(2-piperazinylphenyl)methyl]amine as a yellow oil (0.35 g). MS m/z: 220 (M+H). Calc'd for $C_{13}H_{21}N_3$: 219.33.

Step 4

(2R)-2-Amino-1-(4-{2-[(dimethylamino)methyl]phenyl}piperazinyl)-3-(4-chlorophenyl)propan-1-one was prepared according to the procedure described in Preparation V using dimethyl[(2-piperazinylphenyl)methyl]amine (Step 3)(0.35 g, 1.4 mmol), Boc-p-Cl-D-Phe-OH (Peptech Corp)(0.53 g, 1.8 mmol) in $CH_2Cl_2$ (7 mL), EDC (Aldrich Chemical Company) (0.37 g, 1.9 mmol) and HOBT (used in place of HOAT) (Bachem) (0.27 g, 1.8 mmol). After workup as described in Preparation V, the crude compound was dissolved in $CH_2Cl_2$ (10 mL) and treated with TFA (5 mL). After stirring the reaction at RT for 1 h, the solvent was concentrated in vacuo and the residue was partitioned between $CH_2Cl_2$ and satd $NaHCO_3$. The organic layer was washed with brine, dried over $Na_2SO_4$, filtered and concentrated in vacuo to give (2R)-2-amino-1-(4-{2-[(dimethylamino)methyl]phenyl}piperazinyl)-3-(4-chlorophenyl)propan-1-one as a yellow oil (0.53 g). MS m/z: 401 (M+H). Calc'd for $C_{22}H_{29}ClN_4O$: 400.94.

Step 5 tert-Butyl 3-{N-[(1R)-2-(4-{2-[(dimethylamino)methyl]phenyl}piperazinyl)-1-[(4-chlorophenyl)methyl]-2-oxoethyl]carbamoyl}(3S)-1,2,3,4-tetrahydroisoquinoline-2-carboxylate was prepared according to the procedure described in Preparation V, (2R)-2-amino-1-(4-{2-[(dimethylamino)methyl]phenyl}piperazinyl)-3-(4-chlorophenyl)propan-1-one (0.34 g, 0.85 mmol), Boc-L-Tic-OH (Peptech Corp.) (0.26 g, 0.93 mmol), EDC (0.2 g, 1.0 mmol), HOBT (used in place of HOAT) (Bachem) (0.14 g, 0.93 mmol) and $CH_2Cl_2$ (4 mL). The crude compound was purified on a Biotage 40S column ($CH_2Cl_2$/MeOH 95:5) to give tert-butyl 3-{N-[(1R)-2-(4-{2-[(dimethylamino)methyl]phenyl}piperazinyl)-1-[(4-chlorophenyl)methyl]-2-oxoethyl]carbamoyl}(3S)-1,2,3,4-tetrahydro-isoquinoline-2-carboxylate as a white foam (0.32 g). MS m/z: 660 (M+H). Calc'd for $C_{37}H_{46}ClN_5O_4$: 660.25.

Step 6

To tert-butyl 3-{N-[(1R)-2-(4-{2-[(dimethylamino)methyl]phenyl}piperazinyl)-1-[(4-chlorophenyl)methyl]-2-oxoethyl]carbamoyl}(3S)-1,2,3,4-tetrahydro-isoquinoline-2-carboxylate (Step 5) (0.31 g, 0.47 mmol) dissolved in dioxane (0.5 mL) was added 4N HCl in dioxane (1 mL). After stirring at RT for 6 h, the solvent was removed in vacuo, and the residue was purified by preparative HPLC (Waters Xterra C18 5 micron 100×20 mm, 10% to 80% $CH_3CN$ in $H_2O$ over 6.0 min, 4.63 min) to give N-[(1R)-2-(4-{2-[(dimethylamino)methyl]phenyl}piperazinyl)-1-[(4-chlorophenyl)methyl]-2-oxoethyl]((3S)(3-1,2,3,4-tetrahydroisoquinolyl))carboxamide (TFA salt) as a white solid (0.27 g). MS m/z: 560 (M+H). Calc'd for $C_{32}H_{38}ClN_5O_2$: 559.27. Anal. Calcd for $C_{32}H_{38}ClN_5O_2$·2.5 TFA·0.1 $H_2O$: C, 52.47; H, 4.84; N, 8.27; Cl, 4.19. Found: C, 52.26; H, 4.75; N, 8.14; Cl, 4.41.

EXAMPLE 92

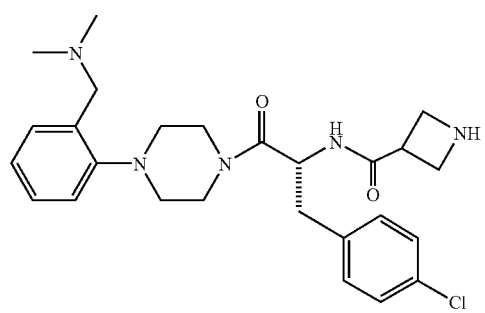

N-[(1R)-2-(4-{2-[(Dimethylamino)methyl]phenyl}-
piperazinyl)-1-[(4-chlorophenyl)methyl]-2-oxoethyl]
azetidin-3-ylcarboxamide Step 1 tert-Butyl 3-{N-[(1S)-2-(4-{2-[(dimethylamino)methyl]phenyl}piperazinyl)-1-[(4-chlorophenyl)methyl]-2- oxoethyl]carbamoyl}azetidinecarboxylate was prepared according to the procedure described in Preparation V by using (2R)-2-amino-1-(4-{2-[(dimethylamino)methyl]-phenyl}piperazinyl)-3-(4-chlorophenyl)propan-1-one (Example 91, Step 4) (0.17 g, 0.42 mmol), Boc-azetidine (Peptech Corp.) (0.094 g, 0.47 mmol), EDC (Aldrich) (0.097 g, 0.51 mmol), HOBT (used in place of HOAT) (Bachem) (0.071 g, 0.47 mmol) and $CH_2Cl_2$ (2 mL). The crude was purified on a Biotage 40S column ($CH_2Cl_2$/MeOH=95:5) to give tert-butyl 3-{N-[(1S)-2-(4-{2-[(dimethylamino) methyl]phenyl}piperazinyl)-1-[(4-chlorophenyl)methyl]-2-oxoethyl]carbamoyl}azetidine carboxylate as a white solid (0.15 g). MS m/z: 584 (M+H). Calc'd for $C_{31}H_{42}ClN_5O_4$: 584.15.

Step 2

To tert-butyl 3-{N-[(1S)-2-(4-{2-[(dimethylamino) methyl]phenyl}piperazinyl)-1-[(4-chlorophenyl)methyl]-2-oxoethyl]carbamoyl}azetidinecarboxylate (Step 1) (0.12 g, 0.2 mmol) dissolved in dioxane (0.2 mL) was added 4N HCl in dioxane (0.4 mL). After stirring at RT for 6 h, the solvent was concentrated in vacuo and the residue was purified by preparative HPLC (Waters Xterra $C_{18}$ 5 micron 100×20 mm, 10% to 80% $CH_3CN$ in $H_2O$ over 6.0 min) to yield the TFA salt of the desired compound. MS m/z: 520 (M+HCl). Calc'd for $C_{26}H34ClN_5O_2$: 483.24.

EXAMPLE 93

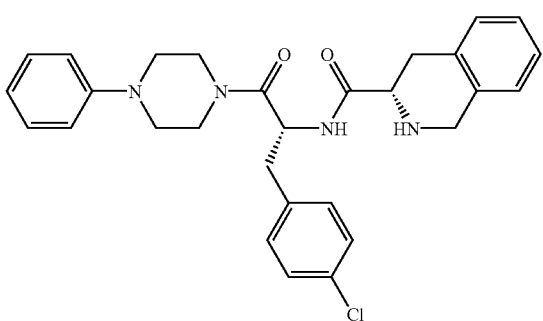

N-{(1R)-1-[(4-Chlorophenyl)methyl]-2-oxo-2-(4-phenylpiperazinyl)ethyl}((3S)(3-1,2,3,4-tetrahydroisoquinolyl))carboxamide Step 1

Following the procedure for the synthesis of Preparation XIX, N-{(1R)-1-[(4-chlorophenyl)methyl]-2-oxo-2-(4-phenylpiperazinyl)ethyl}(tert-butoxy)-carboxamide was prepared from Boc-p-Cl-D-Phe-OH (380 mg, 1.3 mmol) (Nova Biochem), 1-[3-(dimethylamino)-propyl]-3-ethylcarbodiimide methiodide, (770 mg, 2.6 mmol) (Aldrich), HOAT (180 mg, 1.30 mmol) (Aldrich) and 1-phenylpiperazine (200 µl, 1.28 mmol) (Aldrich), (570 mg). MS (ESI, pos. ion) m/z: 444 (M+H), (ESI, neg. ion) m/z: 442 (M−H). Calc'd for $C_{24}H_{30}ClN_3O_3$: 443.97.

Step 2

To N-{(1R)-1-[(4-chlorophenyl)methyl]-2-oxo-2-(4-phenylpiperazinyl)ethyl}(tert-butoxy)carboxamide (Step 1) (573 mg, 1.30 mmol) in 50 mL round bottomed flask equipped with magnetic stirring was added 25 mL of EtOAc satd with HCl, and the reaction mixture was stirred for 1 h. The resulting solid was filtered and washed with hexane. The solid was dried further in vacuo and then added to a 50 mL round bottomed flask equipped with magnetic stirring. DMF (10 mL), DIEA (110 µl, 0.631 mmol) (Aldrich), Boc-L-Tic-OH (90 mg, 0.68 mmol) (Peptech), 1-(3-dimethylaminopropyl)-3-ethylcarbodiimide methiodide (396 mg, 1.33 mmol), and HOAT (90 mg, 0.661 mmol) were added to the reaction flask. The resulting solution was stirred 2 h then worked up as in Preparation XIX. The resulting crude was purified by flash chromatography ($Sio_2$, 1:1, hexane-EtOAc) to afford tert-butyl 3-(N-{(1R)-1-[(4-chlorophenyl)methyl]-2-oxo-2-(4-phenylpiperazinyl) ethyl}carbamoyl)(3S)-1,2,3,4-tetrahydroisoquinoline-2-carboxylate (130 mg). MS (ESI, pos. ion) m/z: 603 (M+H), (ESI, neg. ion) m/z: 601 (M−H). Calc'd for $C_{34}H_{39}ClN_4O_4$: 603.15.

Step 3 tert-Butyl 3-(N-{(1R)-1-[(4-chlorophenyl)methyl]-2-oxo-2-(4-phenylpiperazinyl)ethyl}carbamoyl)(3S)-1,2,3,4-tetrahydroisoquinoline-2-carboxylate (Step 2) (127 mg, 0.211 mmol) was treated with 10 mL of EtOAc satd with HCl in a 50 mL round bottomed flask equipped with magnetic stirring. The resulting solid was filtered, washed with hexane and dried in vacuo to yield N-{(1R)-1-[(4-chlorophenyl)methyl]-2-oxo-2-(4-phenyl-piperazinyl) ethyl}((3S)(3-1,2,3,4-tetrahydro-isoquinolyl))carboxamide (40 mg). MS (ESI, pos. ion) m/z: 503 (M+H), (ESI, neg. ion) m/z: 501 (M−H). Calc'd for $C_{29}H_{31}ClN_4O_2$: 502 21.

EXAMPLE 94

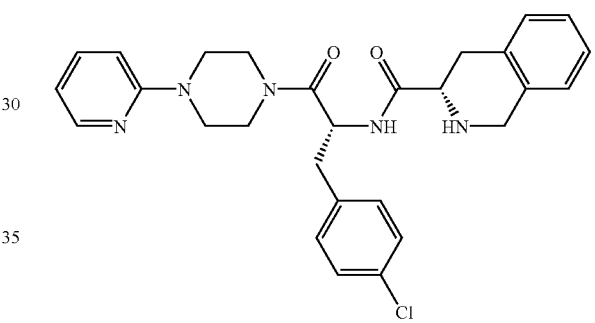

N-{(1R )-1-[(4-Chlorophenyl)methyl]-2-oxo-2-(4-(2-pyridyl)piperazinyl)ethyl}((3S)(3-1,2,3,4-tetrahydroisoquinolyl))carboxamide Step 1

N-{(1R)-1-[(4-Chlorophenyl)methyl]-2-oxo-2-(4-(2-pyridyl)piperazinyl)ethyl}(tert-butoxy)carboxamide was prepared according to the procedure for Preparation XIX using Boc-p-Cl-D-Phe-OH (550 mg, 1.8 mmol), 1-(3-dimethylaminopropyl)-3-ethylcarbodiimide methiodide (1.1 g, 3.80 mmol), HOAT (260 mg, 1.9 mmol), DMF (15 mL), and 1-(2-piperidyl)piperazine (280 µl, 1.8 mmol) (Aldrich). The crude material was concentrated in vacuo to yield 810 mg. MS (ESI, pos. ion) m/z: 445 (M+H), (ESI, neg. ion) m/z: 443 (M−H). Calc'd for $C_{23}H_{29}ClN_4O_3$: 444.95.

Step 2 tert-Butyl 3-(N-{(1R)-1-[(4-chlorophenyl)methyl]-2-oxo-2-(4-(2-pyridyl)piperazinyl)ethyl}carbamoyl)(3S)-1,2,3,4-tetrahydroisoquinoline-2-carboxylate was prepared from N-{(1R)-1-[(4-chlorophenyl)methyl]-2-oxo-2-(4-(2-pyridyl)piperazinyl)ethyl}(tert-butoxy)-carboxamide (Step 1) (800 mg, 1.80 mmol), following the procedure for Example 93, Step 2 using 25 mL of EtOAc satd with HCl for the first step, and DIEA (240 µl, 1.38 mmol), Boc-L-Tic-OH (340 mg, 1.2 mmol), 1-(3-dimethylaminopropyl)-3-ethylcarbodiimide methiodide (740 mg, 2.5 mmol), HOAT (184 mg, 1.35 mmol) and DMF (15 mL) for the second step. The crude was purified by flash chromatography ($SiO_2$, 1:1, hexane:EtOAc) to yield the title compound (460 mg). MS (ESI, pos. ion) m/z: 604 (M+H), (ESI, neg. ion) m/z: 602 (M−H). Calc'd for $C_{33}H_{38}ClN_5O_4$: 604.14.

Step 3

N-{(1R)-1-[(4-Chlorophenyl)methyl]-2-oxo-2-(4-(2-pyridyl)piperazinyl)ethyl}((3S)(3-1,2,3,4-tetrahydroisoquinolyl))carboxamide was prepared according to the procedure used for Preparation XVI using tert-butyl 3-(N-{(1R)-1-[(4-chlorophenyl)methyl]-2-oxo-2-(4-(2-pyridyl)piperazinyl)ethyl}carbamoyl)(3S)-1,2,3,4-tetrahydroisoquinoline-2-carboxylate (Step 2) (450 mg, 0.745 mmol) and 10 mL HCl satd EtOAc. The resulting solid was purified by preparative HPLC (AcOH buffer) and freeze-dried yielding the acetate salt (410 mg). Mass Spec. m/z: 504 (M+H), (ESI, neg. ion) m/z: 502 (M−H). Calc'd for $C_{28}H_{30}ClN_5O_2$: 503.21. Anal. Calcd for $C_{28}H_{30}ClN_5O_2$—$C_2H_4O_2$: C, 63.88; H, 6.08; N, 12.42. Found C, 63.66; H, 6.02; N, 12.64.

EXAMPLE 95

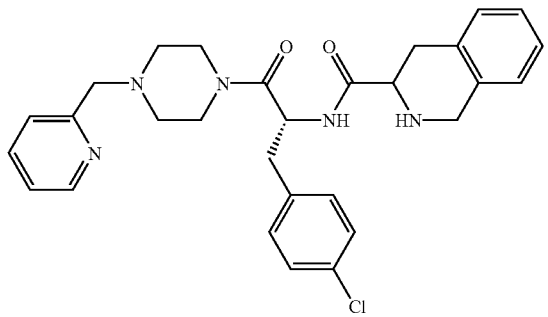

N-{(1R)-1-[(4-Chlorophenyl)methyl]-2-oxo-2-[4-(2-pyridylmethyl)piperazinyl]ethyl}-3-1,2,3,4-tetrahydroisoquinolylcarboxamide Step 1

N-{(1R)-1-[(4-Chlorophenyl)methyl]-2-oxo-2-[4-(2-pyridylmethyl)piperazinyl]ethyl}(tert-butoxy) carboxamide was prepared according to the procedure for Preparation XIX using (2-pyridylmethyl)piperazine (650 mg. 3.7 mmol) (Array), Boc-p-Cl-D-Phe-OH (1.1 g, 3.7 mmol), 1-(3-dimethylaminopropyl)-3-ethylcarbodiimide methiodide (2.2 g, 7.2 mmol), HOAT (560 mg, 4.10 mmol) and DMF (15 mL) (730 mg). MS (ESI, pos. ion) m/z: 459 (M+H), (ESI, neg. ion) m/z: 457 (M−H). Calc'd for $C_{24}H_{31}ClN_4O_3$: 458.98.

Step 2 tert-Butyl 3-(N-{(1R)-1-[(4-chlorophenyl)methyl]-2-oxo-2-[4-(2-pyridylmethyl)-piperazinyl]ethyl}carbamoyl)-(3S)-1,2,3,4-tetrahydroisoquinoline-2-carboxylate was prepared from N-{(1R)-1-[(4-chlorophenyl)methyl]-2-oxo-2-[4-(2-pyridylmethyl)piperazinyl]ethyl}(tert-butoxy) carboxamide (Step 1) (270 mg, 0.58 mmol) according to the procedure used for Example 93, Step 2 using 25 mL HCl satd EtOAc, for the first step, then DIEA (100 µl, 0.574 mmol), Boc-L-Tic-OH (82 mg, 0.296 mmol), 1-(3-dimethylaminopropyl)-3-ethylcarbodiimide methiodide (101 mg, 0.340 mmol), and HOAT (50 mg, 0.367 mmol) for the second step (139 mg). MS (ESI, pos. ion) m/z: 618 (M+H), (ESI, neg. ion) m/z: 616 (M−H). Calc'd for $C_{34}H_{40}ClN_5O_4$: 618.17.

Step 3

N-{(1R)-1-[(4-Chlorophenyl)methyl]-2-oxo-2-[4-(2-pyridylmethyl)piperazinyl]ethyl}-3-1,2,3,4-tetrahydroisoquinolylcarboxamide was prepared from tert-butyl 3-(N-{(1R)-1-[(4-chlorophenyl)methyl]-2-oxo-2-[4-(2-pyridylmethyl)piperazinyl]ethyl}carbamoyl)(3S)-1,2,3,4-tetrahydroisoquinoline-2-carboxylate (Step 2) (140 mg, 0.230 mmol) according to the procedure for Preparation XVI. The crude was purified by preparative HPLC (TFA buffer) to afford the desired product (20 mg) as a TFA salt. MS (ESI, pos. ion) m/z: 518 (M+H), (ESI, neg. ion) m/z: 516 (M−H). Calc'd for $C_{29}H_{32}ClN_5O_2$: 517.22.

EXAMPLE 96

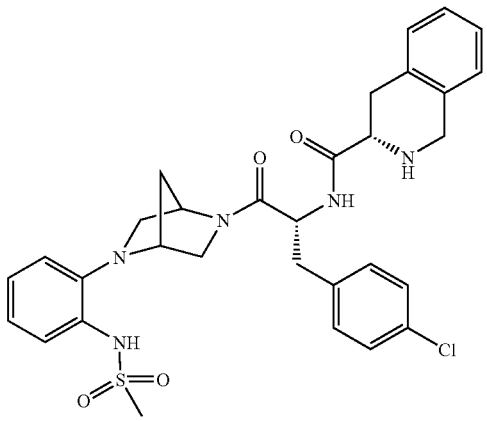

N-[(1R)-2-(2,5-Diaza-5-{2-[(methylsulfonyl)amino] phenyl}bicyclo[2.2.1]hept-2-yl)-1-[(4-chlorophenyl) methyl]-2-oxoethyl]((3S)(3-1,2,3,4-tetrahydroisoquinolyl))carboxamide Step 1

2,5-Diaza-2-(2-nitrophenyl)-5-benzylbicyclo[2.2.1] heptane was prepared according to the procedure for Preparation Ia using, 2-fluoronitrobenzene (860 µl, 8.2 mmol), DIEA (5.3 mL, 30 mmol), and (1S, 4S)-2-benzyl-2,5-diazabicyclo[2.2.1]heptane dihydrobromide (3.0 g, 8.6 mmol) (Aldrich) and DMF (100 mL). The crude was purified by flash chromatography ($SiO_2$, 2:1 hexane:EtOAc) to yield 685 mg. MS (ESI, pos. ion) m/z: 310 (M+H), (ESI, neg. ion) m/z: 308 (M−H). Calc'd for $C_{18}H_{19}N_3O_2$: 309.36.

Step 2

2-[2,5-Diaza-5-benzylbicyclo[2.2.1]hept-2-yl]-phenylamine was prepared according to the procedure for Preparation II using 2,5-diaza-2-(2-nitrophenyl)-5-benzylbicyclo[2.2.1]heptane (Step 1) (690 mg, 2.2 mmol) and $SnCl_2$—$H_2O$ (2.2 g, 9.8 mmol). MS (ESI, pos. ion) m/z: 280 (M+H), (ESI, neg. ion) m/z: 278 (M−H). Calc'd for $C_{18}H_2N_3$: 279.38.

Step 3

{2-[2,5-Diaza-5-benzylbicyclo[2.2.1]hept-2-yl]phenyl}-(methylsulfonyl)amine was prepared from 2-[2,5-diaza-5-benzylbicyclo[2.2.1]hept-2-yl]phenylamine (Step 2) (690 mg, 2.5 mmol) according to the procedure for Preparation III using methanesulfonyl chloride (190 µl, 2.46 mmol) and pyridine (220 µl, 2.72 mmol). The crude mix was purified by flash chromatography ($SiO_2$, 3% MeOH in $CH_2Cl_2$) to afford the desired sulfonamide (533 mg). MS (ESI, pos. ion) m/z: 358 (M+H), (ESI, neg. ion) m/z: 356 (M−H). Calc'd for $C_{19}H_{23}N_3O_2S$: 357.47.

Step 4

[2-(2,5-Diazabicyclo[2.2.1]hept-2-yl)phenyl] (methylsulfonyl)amine (180 mg) was prepared according to the procedure for Preparation IV using {2-[2,5-diaza-5-benzylbicyclo[2.2.1]hept-2-yl]phenyl}-(methylsulfonyl)

amine (Step 3) (530 mg, 1.5 mmol), 10% Pd/C (450 mg) and HCO$_2$NH$_4$ (520 mg, 8.30 mmol). MS (ESI, pos. ion) m/z: 268 (M+H), (ESI, neg. ion) m/z: 266 (M–H). Calc'd for C$_{12}$H17N$_3$O$_2$S: 267.10.

Step 5

N-[(1R)-2-(2,5-Diaza-5-{2-[(methylsulfonyl)amino] phenyl}bicyclo[2.2.1]hept-2-yl)-1-[(4-chlorophenyl) methyl]-2-oxoethyl](tert-butoxy)carboxamide was prepared according to the procedure for Preparation XIX using [2-(2,5-diazabicyclo[2.2.1]hept-2-yl)phenyl](methylsulfonyl) amine (Step 4) (176 mg, 0.658 mmol), p-Cl-D-Phe-OH (210 mg, 0.700 mmol), 1-(3-dimethylamino-propyl)-3-ethylcarbodiimide methiodide (351 mg, 1.181 mmol) and HOAT (92 mg, 0.676 mmol). The crude was concentrated in vacuo to yield 369 mg, and used as is in the next step. MS (ESI, pos. ion) m/z: 549 (M+H), (ESI, neg. ion) m/z: 547 (M–H). Calc'd for C$_{26}$H$_{33}$ClN$_4$O$_5$S: 549.08.

Step 6

N-[(1R)-2-(2,5-Diaza-5-}2-[(methylsulfonyl)amino]-phenyl}bicyclo[2.2.1]hept-2-yl)-1-[(4-chlorophenyl)-methyl]-2-oxoethyl](tert-butoxy)carboxamide (Step 5) (369 mg, 0.672 mmol) was treated with satd HCl in EtOAc as described in Preparation XVI. The resulting crude material was diluted with EtOAc and washed with 10% Na$_2$CO$_3$ soln. The organic layer was separated, dried over Na$_2$SO$_4$, filtered and concentrated in vacuo. Using this material, tert-butyl 3-{N-[(1R)-2-(2,5-diaza-5-{2-[(methylsulfonyl)amino] phenyl}bicyclo [2.2.1]hept-2-yl)-1-[(4-chlorophenyl) methyl]-2-oxoethyl]carbamoyl}(3S)-1,2,3,4-tetrahydroisoquinoline-2-carboxylate was prepared according to the procedure for Preparation XIX from Boc-L-Tic-OH (194 mg, 0.699 mmol), HOAT (94 mg, 0.691 mmol), 1-(3-dimethylamino-propyl)-3-ethylcarbodiimide methiodide (415 mg, 1.396 mmol) and DMF (5 mL). The crude was purified by flash chromatography (SiO$_2$, 20% EtOAc in CH$_2$Cl$_2$) to afford the desired compound (250 mg). MS (ESI, pos. ion) m/z: 708 (M+H), (ESI, neg. ion) m/z: 706 (M–H). Calc'd for C$_{36}$H$_{42}$ClN$_5$O$_6$S: 708.27.

Step 7

N-[(1R)-2-(2,5-Diaza-5-{2-[(methylsulfonyl)amino] phenyl}bicyclo[2.2.1]hept-2-yl)-1-[(4-chlorophenyl) methyl]-2-oxoethyl]((3S)(3-1,2,3,4-tetrahydro-isoquinolyl))carboxamide was prepared from tert-butyl 3-{N-[(1R)-2-(2,5-diaza-5-{2-[(methylsulfonyl)amino]-phenyl}bicyclo[2.2.1]hept-2-yl)-1-[(4-chlorophenyl)-methyl]-2-oxoethyl]carbamoyl}(3S)-1,2,3,4-tetrahydro-isoquinoline-2-carboxylate (Step 6) (250 mg, 0.35 mmol) according to the procedure for Preparation XVI. The crude was purified by preparative HPLC (TFA buffer) to afford the desired product as the TFA salt (50 mg). MS (ESI, pos. ion) m/z: 608 (M+H), (ESI, neg. ion) m/z: 606 (M–H). Calc'd for C$_{31}$H$_{34}$ClN$_5$O$_4$S: 607.20. Anal. Calcd for C$_{31}$H$_{34}$ClN$_5$O$_4$S·1.5C$_2$HF$_3$O$_2$—H$_2$O: C, 51.23; H, 4.74; N, 8.78; Cl, 4.45; Found C, 50.96; H, 4.56; N, 8.57; Cl, 4.46.

EXAMPLE 97

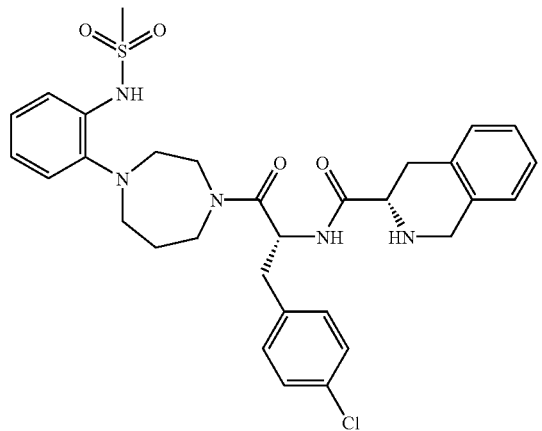

N-[(1R)-1-[(4-Chlorophenyl)methyl]-2-(4-{2-[(methylsulfonyl)amino]phenyl}(1,4-diazaperhydroepinyl))-2-oxoethyl]((3S)(3-1,2,3,4-tetrahydroisoquinolyl))carboxamide Step 1

To a 500 mL round-bottomed flask equipped with magnetic stirring was added homopiperazine (8.315 g, 83 mmol) (Aldrich) and DMF (200 mL). This solution was heated in a 45° C. oil bath and 2-fluoronitrobenzene (1.8 mL, 17 mmol) was added over 5 min. The reaction was stirred for 16 h, diluted with 400 mL EtOAc and washed with 1N NaOH (2×300 mL). The organic layer was concentrated in vacuo to afford 1-(2-nitrophenyl)-1,4-diaza-perhydroepine (3.8 g). MS (ESI, pos. ion) m/z: 222 (M+H), (EST, neg. ion) m/z: 220 (M–H). Calc'd for C$_{11}$H$_5$N$_3$O$_2$: 221.26.

Step 2

1-(2-Nitrophenyl)-1,4-diazaperhydroepine (Step 1) (1.7 g, 7.8 mmol) was treated according to the procedure for Preparation XIX using p-Cl-D-Phe-OH (2.4 g, 7.8 mmol), 1-(3-dimethylaminopropyl)-3-ethylcarbodiimide methiodide (4.82 g, 16.2 mmol), HOAT (1.09 g, 7.99 mmol), and DMF (50 mL) to yield N-{(1R)-1-[(4-chlorophenyl) methyl]-2-[4-(2-nitrophenyl)(1,4-diaza-perhydroepinyl)]-2-oxoethyl}(tert-butoxy)-carboxamide. MS (ESI, pos. ion) m/z: 503 (M+H), (ESI, neg. ion) m/z: 501 (M–H). Calc'd for C$_{25}$H$_{31}$ClN$_4$O$_5$: 502.99.

Step 3

N-{(1R)-1-[(4-Chlorophenyl)methyl]-2-[4-(2-nitrophenyl)(1,4-diazaperhydroepinyl)]-2-oxoethyl(tert-butoxy)carboxamide (Step 2) (1.37 g, 2.72 mmol) was treated with EtOAc satd with HCl as described in Preparation XVI. The resulting crude material was diluted with EtOAc and washed with satd NaHCO$_3$ soln. The organic layer was separated, dried over Na$_2$SO$_4$, filtered and concentrated in vacuo. Using this material, tert-butyl 3-(N-{ (1R)-1-[(4-chlorophenyl)-methyl]-2-[4-(2-nitrophenyl)(1,4-diazaperhydroepinyl)]-2-oxoethyl}carbamoyl)(3S)-1,2,3,4-tetrahydro-isoquinoline-2-carboxylate was prepared according to the procedure for Preparation XIX using Boc-L-Tic-OH (790 mg, 2.85 mmol), HOAT (385 mg, 2.83 mmol) and 1-(3-dimethylaminopropyl)-3-ethylcarbodiimide methiodide (1.695 g, 5.70 mmol). The crude material was purified by flash chromatography (SiO$_2$, 2:1 Hexane:EtOAc) to afford the desired material (1.2 g). MS (ESI, pos. ion) m/z: 662 (M+H), (ESI, neg. ion) m/z: 660 (M–H). Calc'd for C$_{35}$H$_{40}$ClN$_4$O$_6$: 662.17.

Step 4 tert-Butyl 3-(N-{(1R)-2-[4-(2-aminophenyl)(1,4-diazaperhydroepinyl)]-1-[(4-chlorophenyl)methyl]-2-oxoethyl}carbamoyl)(3S)-1,2,3,4-tetrahydroisoquinoline-2-carboxylate was prepared from tert-butyl 3-(N-{(1R)-1-[(4-chlorophenyl)methyl]-2-[4-(2-nitrophenyl)(1,4-diazaperhydroepinyl)]-2-oxoethyl}carbamoyl)(3S)-1,2,3,4-tetrahydroisoquinoline-2-carboxylate (Step 3) (1.2 g, 1.8 mmol) and $SnCl_2 \cdot 2H_2O$ (1.6 g, 7.2 mmol), according to the procedure for Preparation II. The crude was purified by flash chromatography ($SiO_2$, 20% EtOAc in $CH_2Cl_2$) to afford the desired material (590 mg). MS (ESI, pos. ion) m/z: 632 (M+H), (ESI, neg. ion) m/z: 630 (M–H). Calc'd for $C_{35}H_{42}ClN_5O_4$: 632.19.

Step 5 tert-Butyl 3-{N-[(1R)-1-[(4-chlorophenyl)methyl]-2-(4-{2-[(methylsulfonyl)amino]phenyl}(1,4-diazaperhydroepinyl))-2-oxoethyl]carbamoyl}(3S)-1,2,3,4-tetrahydroisoquinoline-2-carboxylate was prepared according to the procedure for Preparation III using tert-butyl 3-(N-{(1R)-2-[4-(2-aminophenyl)(1,4-diazaperhydroepinyl)]-1-[(4-chlorophenyl)methyl]-2-oxoethyl}carbamoyl)(3S)-1,2,3,4-tetrahydroisoquinoline-2-carboxylate (Step 4) (390 mg, 0.61 mmol), methanesulfonyl chloride (52 µl, 0.67 mmol) and pyridine (60 µl, 0.74 mmol). The crude was isolated (400 mg). MS (ESI, pos. ion) m/z: 710 (M+H), (ESI, neg. ion) m/z: 708 (M–H). Calc'd for $C_{36}H_{44}ClN_5O_6$: 710.28.

Step 6

N-[(1R)-1-[(4-Chlorophenyl)methyl]-2-(4-{2-[(methylsulfonyl)amino]phenyl}(1,4-diaza-perhydroepinyl))-2-oxoethyl]((3S)(3-1,2,3,4-tetrahydroisoquinolyl))carboxamide was prepared from tert-butyl 3-{N-[(1R)-1-[(4-chlorophenyl)methyl]-2-(4-{2-[(methylsulfonyl)amino]phenyl}(1,4-diaza-perhydroepinyl))-2-oxoethyl]carbamoyl}(3S)-1,2,3,4-tetrahydroisoquinoline-2-carboxylate (Step 5) (400 mg, 0.56 mmol) according to the procedure for Preparation XVI. The crude product was purified by preparative HPLC to yield the desired material as the acetate salt (7 mg). MS (EST, pos. ion) m/z: 610 (M+H), (ESI, neg. ion) m/z: 608 (M–H). Calc'd for $C_{31}H_{36}ClN_5O_4S$: 609.22.

Other compounds included in this invention are set forth in Tables 1–8 below.

TABLE 1

| # | $R^{14}$ | $R^{15}$ | $R^{10}$ | $R^{13a}$ | $R^{13b}$ |
|---|---|---|---|---|---|
| 98. | methylsulfonylamino | H | H | Cl | H |
| 99. | N-propyl-N-(CypCH$_2$)aminomethyl | H | H | Cl | H |
| 100. | N-propyl-N-(CypCH$_2$)aminomethyl | H | H | Br | H |
| 101. | N,N-di(CypCH$_2$)aminomethyl | H | H | Cl | H |
| 102. | N-(methylsulfonyl)-N-(aminoethyl)amino | H | H | Cl | Cl |
| 103. | methylsulfonylamino | H | 3-cypCH$_2$NHC=OCH$_2$— | Cl | H |
| 104. | 2-pyridylcarbonylamino | H | H | Cl | H |
| 105. | benzylaminocarbonyl | H | H | Cl | H |
| 106. | (isothiazolidine-1,1-dioxide, N-substituted) | H | H | Cl | H |
| 107. | N-methyl-N-methylcarbonylamino | H | H | Cl | H |
| 108. | N-propyl-N-methylsulfonylamino | H | H | Cl | H |
| 109. | methylsulfonylamino | H | 3-NH$_2$—(CH)$_2$NHC=OCH$_2$— | Cl | H |
| 110. | N-(CypCH$_2$)-N-(MeSO$_2$)aminomethyl | H | H | Cl | H |
| 111. | N-(CypCH$_2$)-N-propylaminomethyl | F | H | Cl | H |
| 112. | N-(phenylpropyl)-N-(MeSO$_2$)amino | H | H | Cl | H |
| 113. | methylsulfonylamino | 4-CF$_3$ | H | Cl | H |
| 114. | methylcarbonyl | H | H | Cl | H |
| 115. | CH$_3$C=ONH | H | H | Cl | H |
| 116. | MeSO$_2$NH— | H | 3-phenyl(CH$_2$)$_2$NHC=OCH$_2$— | Cl | H |
| 117. | methoxy | H | H | Cl | H |
| 118. | amino | H | H | Cl | H |

TABLE 2

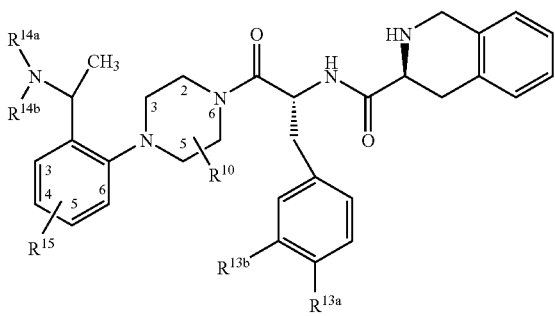

| # | R14a | R14b | R15 | R10 | R13a | R13b |
|---|---|---|---|---|---|---|
| 119. | cyclopropylmethyl | methyl | H | H | Cl | H |
| 120. | cyclopropylmethyl | H | H | H | Cl | H |
| 121. | methylcarbonyl | methyl | H | H | Cl | H |
| 122. | isobutyl | methyl | H | H | Cl | H |
| 123. | propyl | methyl | H | H | Cl | H |
| 124. | methylsulfonyl | methyl | H | H | Cl | H |
| 125. | ethyl | methyl | H | H | Cl | H |
| 126. | ethoxycarbonylcyclopropylmethyl | methyl | H | H | Cl | H |
| 127. | isopentyl | methyl | H | H | Cl | H |
| 128. | 4-methylcarbonylaminobenzyl | methyl | H | H | Cl | H |
| 129. | methyl | H | 4-Br | H | Cl | H |
| 130. | methyl | methyl | H | H | Cl | H |
| 131. | 3-thienylmethyl | methyl | H | H | Cl | H |
| 132. | benzyloxyethyl | methyl | H | H | Cl | H |
| 133. | 2-methoxybenzyl | methyl | H | H | Cl | H |
| 134. | methyl | H | H | H | Cl | H |
| 135. | 4-pyridylmethyl | methyl | H | H | Cl | H |
| 136. | 2-pyrrolidinylmethyl | methyl | H | H | Cl | H |
| 137. | 3-methoxybenzyl | methyl | H | H | Cl | H |
| 138. | benzyl | methyl | H | H | Cl | H |
| 139. | aminoethyl | methyl | H | H | Cl | H |
| 140. | 4-methoxybenzyl | methyl | H | H | Cl | H |
| 141. | cyclohexylmethyl | methyl | H | H | Cl | H |
| 142. | 2-aminopropyl | methyl | H | H | Cl | H |
| 143. | methylamino | methyl | H | H | Cl | H |
| 144. | 3-cyanobenzyl | methyl | H | H | Cl | H |
| 145. | isopropyl | methyl | H | H | Cl | H |
| 146. | CypCH2— | methylcarbonyl | H | H | Cl | H |
| 147. | methylcarbonyl | methyl | H | H | Cl | H |

TABLE 3

| # | R14 | R10 | R15 | R13a | R13b | Rb |
|---|---|---|---|---|---|---|
| 148. | N—(CH3SO2)—N-(CypCH2)amino | H | H | Cl | H | isobutyl |
| 149. | N—(CH3SO2)—N-(CypCH2)amino | H | H | Cl | H | —CH2C(CH3)3 |
| 150. | N—(CH3SO2)—N-(CypCH2)amino | H | H | Cl | H | —CH2cyp |
| 151. | N—(CH3SO2)—N-(CypCH2)amino | H | H | Cl | H | butyl |
| 152. | N—(CH3SO2)—N-(CypCH2)amino | H | H | Cl | H | pentyl |
| 153. | N—(CH3SO2)—N-(CypCH2)amino | H | H | Cl | H | —CH2chxl |
| 154. | N—(CH3SO2)—N-(CypCH2)amino | H | H | Cl | H | ethyl |
| 155. | N—(CH3SO2)—N-(CypCH2)amino | H | H | Cl | H | methyl |
| 156. | N—(CH3SO2)—N-(CypCH2)amino | H | H | Cl | H | isopropyl |
| 157. | N—(CH3SO2)—N-(CypCH2)amino | H | H | Cl | H | benzyl |
| 158. | N—(CH3SO2)amino | H | H | Cl | H | H |
| 159. | N—(CH3SO2)—N-(CypCH2)amino- | H | H | Cl | H | propyl |
| 160. | 1,2,3-triazol-2-yl-CH2— | H | H | Cl | H | H |
| 161. | N-(CypCH2)—N-propylaminoCH2— | H | H | Cl | H | Boc |
| 162. | N-(CypCH2)—N-propylaminoCH2— | H | H | Cl | H | H |
| 163. | 1-imidazolylCH2 | H | H | Cl | H | H |
| 164. | 1-tetrazolylCH2 | H | H | Cl | H | H |
| 165. | 2,5-dimethylpyrrolidin-1-yl | H | H | Cl | H | H |
| 166. | 2-oxo-pyrrolidin-1-ylmethyl | H | H | Cl | H | H |
| 167. | 2-oxo-pyrrolidin-5-ylmethyl | H | H | Cl | H | isopropyl |
| 168. | 2-oxo-pyrrolidin-1-ylmethyl | H | H | Cl | H | ethyl |
| 169. | 2-oxo-pyrrolidin-1-ylmethyl | H | H | Cl | H | CypCH2— |
| 170. | 2-oxo-pyrrolidin-1-ylmethyl | H | H | Cl | H | —CH2C(CH3)3 |
| 171. | 8-aza-bicyclo[3.2.1]oct-8-ylmethyl | H | H | Cl | H | H |
| 172. | 8-aza-bicyclo[3.2.1]oct-8-ylmethyl | H | H | Cl | H | isopropyl |
| 173. | 8-aza-bicyclo[3.2.1]oct-8-ylmethyl | H | H | Cl | H | ethyl |

TABLE 3-continued

| # | R¹⁴ | R¹⁰ | R¹⁵ | R¹³ᵃ | R¹³ᵇ | Rᵇ |
|---|---|---|---|---|---|---|
| 174. | 8-aza-bicyclo[3.2.1]oct-8-ylmethyl | H | H | Cl | H | CypCH₂— |
| 175. | 8-aza-bicyclo[3.2.1]oct-8-ylmethyl | H | H | Cl | H | —CH₂C(CH₃)₃ |
| 176. | phenoxymethyl | H | H | Cl | H | H |
| 177. | 1-methylpiperazin-4-ylCH₂— | H | H | Cl | H | H |
| 178. | 2,6-dimethylpiperdin-1-ylCH₂— | H | H | Cl | H | H |
| 179. | 3-pyridyloxymethyl | H | H | Cl | H | H |
| 180. | 1,2,3-triazol-2-ylCH₂— | H | H | Cl | H | isopropyl |
| 181. | 1,2,3-triazol-2-ylCH₂— | H | H | Cl | H | H |
| 182. | 1,2,3-triazol-2-ylCH₂— | H | H | Cl | H | CypCH₂— |
| 183. | 1,2,4-triazol-1-ylCH₂— | H | H | Cl | H | H |
| 184. | pyridyl-2-one-CH₂— | H | H | Cl | H | H |
| 185. | 1,2,3-triazol-2-ylCH₂— | H | H | Cl | H | isobutyl |
| 186. | 4-morpholinoCH₂— | H | H | Cl | H | H |
| 187. | 2-CH₃-imidazol-1-ylCH₂— | H | H | Cl | H | H |
| 188. | 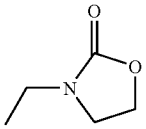 | H | H | Cl | H | H |
| 189. | 2-propylimidazol-1-yl-CH₂— | H | H | Cl | H | H |
| 190. | 1-piperidylCH₂— | H | H | Cl | H | H |
| 191. | 1-pyrrolidinylCH₂— | H | H | Cl | H | H |
| 192. | N—(MeSO₂)—N-(CypCH₂)aminomethyl | H | H | Cl | H | H |
| 193. | 2-isopropylimidazol-1-ylCH₂— | H | H | Cl | H | H |
| 194. | 1,2,3-triazol-2-ylCH₂— | H | H | Cl | H | —CH₂C(CH₃)₃ |
| 195. | 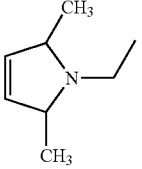 | H | H | Cl | H | H |
| 196. | 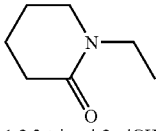 | H | H | Cl | H | H |
| 197. | 1,2,3-triazol-2-ylCH₂ | H | H | Cl | H | chxl |
| 198. | N—(MeSO₂)—N-(CypCH₂)aminomethyl | H | H | Cl | H | cycloheptyl |
| 199. | N—(MeSO₂)—N-(CypCH₂)aminomethyl | H | H | Cl | H | morpholino |
| 200. | N—(MeSO₂)—N-(CypCH₂)aminomethyl | H | H | Cl | H | 2-(ethyl)butyl |
| 201. | N—(MeSO₂)—N-(CypCH₂)aminomethyl | H | H | Cl | H | chxl |
| 202. | 1-pyrazolyl-CH₂— | H | H | Cl | H | CypCH₂— |
| 203. | 1-pyrazolyl-CH₂— | H | H | Cl | H | ethyl |
| 204. | 1-pyrazolyl-CH₂— | H | H | Cl | H | H |
| 205. | 1-pyrazolyl-CH₂— | H | H | Cl | H | isopropyl |
| 206. | 1,2,3-triazol-1-ylCH₂— | H | H | Cl | H | isopropyl |
| 207. | N-propyl-N-(CypCH₂)aminoCH₂— | H | H | Cl | H | isobutyl |
| 208. | N-propyl-N-(CypCH₂)aminoCH₂— | H | H | Cl | H | ethyl |
| 209. | N-(CypCH₂)—N-propylaminoCH₂ | H | H | Cl | H | —CH₂C(CH₃)₃ |
| 210. | 1,2,3-triazol-1-ylCH₂ | H | H | Cl | H | isobutyl |
| 211. | N—(CH₃SO₂)—N-(CypCH₂)amino | H | H | Br | H | isobutyl |
| 212. | N—(CH₃SO₂)—N-(CypCH₂)amino | H | H | Br | H | —CH₂C(CH₃)₃ |
| 213. | N—(CH₃SO₂)—N-(CypCH₂)amino | H | H | Br | H | —CH₂cyp |
| 214. | N—(CH₃SO₂)—N-(CypCH₂)amino | H | H | Br | H | butyl |
| 215. | N—(CH₃SO₂)—N-(CypCH₂)amino | H | H | Br | H | pentyl |
| 216. | N—(CH₃SO₂)—N-(CypCH₂)amino | H | H | Br | H | —CH₂chxl |
| 217. | N—(CH₃SO₂)—N-(CypCH₂)amino | H | H | Br | H | ethyl |
| 218. | N—(CH₃SO₂)—N-(CypCH₂)amino | H | H | Br | H | methyl |
| 219. | N—(CH₃SO₂)—N-(CypCH₂)amino | H | H | Br | H | isopropyl |
| 220. | N—(CH₃SO₂)—N-(CypCH₂)amino | H | H | Br | H | H |
| 221. | N-(CypCH₂)—N-(MeSO₂)amino- | H | H | Cl | H | cyclopentyl |
| 222. | N-(CypCH₂)—N-(MeSO₂)amino- | H | H | Cl | H | 2-butyl |
| 223. | 1,2,3-triazol-1-ylCH₂ | H | H | Cl | H | ethyl |
| 224. | 1,2,3-triazol-1-ylCH₂ | H | H | Cl | H | —CH₂C(CH₃)₃ |
| 225. | N-(CypCH₂)—N-propylaminoCH₂— | H | H | Br | H | Boc |
| 226. | N-(CypCH₂)—N-propylaminoCH₂— | H | H | Br | H | H |
| 227. | N-(CypCH₂)—N-propylaminoCH₂— | H | 4-F | Cl | H | H |

TABLE 4

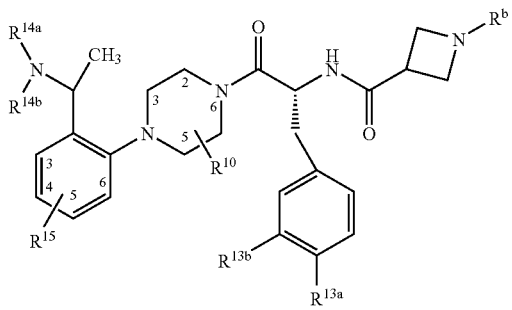

| # | R14a | R14b | R15 | R10 | R13a | R13b | Rb |
|---|---|---|---|---|---|---|---|
| 228. | cyclopropylmethyl | methyl | H | H | Cl | H | H |
| 229. | cyclopropylmethyl | H | H | H | Cl | H | H |
| 230. | methylcarbonyl | methyl | H | H | Cl | H | CypCH2 |
| 231. | isobutyl | methyl | H | H | Cl | H | H |
| 232. | propyl | methyl | H | H | Cl | H | H |
| 233. | methylsulfonyl | methyl | H | H | Cl | H | H |
| 234. | ethyl | methyl | H | H | Cl | H | H |
| 235. | ethoxycarbonylcyclopropylmethyl | methyl | H | H | Cl | H | H |
| 236. | isopentyl | methyl | H | H | Cl | H | H |
| 237. | 4-methylcarbonylaminobenzyl | methyl | H | H | Cl | H | H |
| 238. | methyl | H | 4-Br | H | Cl | H | H |
| 239. | methylcarbonyl | methyl | H | H | Cl | H | isobutyl |
| 240. | methylcarbonyl | methyl | H | H | Cl | H | ethyl |
| 241. | methylcarbonyl | methyl | H | H | Cl | H | H |
| 242. | methylcarbonyl | methyl | H | H | Cl | H | isopropyl |
| 243. | cyclohexylmethyl | methyl | H | H | Cl | H | H |
| 244. | methyl | methyl | H | H | Cl | H | H |
| 245. | 3-thienylmethyl | methyl | H | H | Cl | H | H |
| 246. | benzyloxyethyl | methyl | H | H | Cl | H | H |
| 247. | 2-methoxybenzyl | methyl | H | H | Cl | H | H |
| 248. | methyl | H | H | H | Cl | H | H |
| 249. | 4-pyridylmethyl | methyl | H | H | Cl | H | H |
| 250. | 2-pyrrolidinylmethyl | methyl | H | H | Cl | H | H |
| 251. | 3-methoxybenzyl | methyl | H | H | Cl | H | H |
| 252. | benzyl | methyl | H | H | Cl | H | H |
| 253. | aminoethyl | methyl | H | H | Cl | H | H |
| 254. | 4-methoxybenzyl | methyl | H | H | Cl | H | H |

TABLE 5

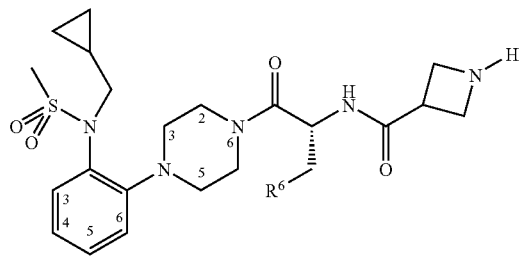

| # | R6 |
|---|---|
| 255. | 4-bromophenyl |
| 256. | 2-naphthyl |
| 257. | 1,4-biphenyl |
| 258. | 1-naphthyl |
| 259. | 3,4-dichlorophenyl |
| 260. | 4-methoxyphenyl |
| 261. | 4-iodophenyl |
| 262. | 3-chlorophenyl |
| 263. | 4-trifluoromethylphenyl |
| 264. | 3-pyridyl |

TABLE 6

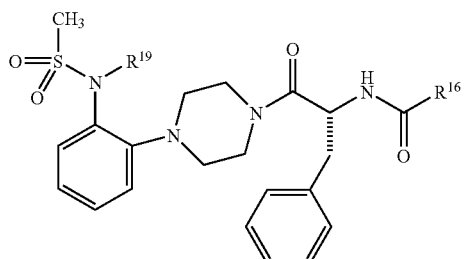

| # | R19 | R16 |
|---|---|---|
| 265. | —CH2cyp | 6-quinolyl |
| 266. | —CH2cyp | 4-(benzyloxy)phenyl |
| 267. | —CH2cyp | —CH2CH2NHCH3 |
| 268. | —CH2cyp | 3,4-dimethoxyphenyl |
| 269. | —CH2cyp | 4-(phenoxy)phenyl |
| 270. | —CH2cyp | —CH2CH2NH2 |
| 271. | —CH2cyp | 4-piperidyl |
| 272. | —CH2cyp | 4-fluorophenyl |

TABLE 6-continued

| # | R19 | R16 |
|---|---|---|
| 273. | —CH2cyp | 4-(1-pyrrolyl)phenyl |
| 274. | —CH2cyp | 5-methoxyindol-2-yl |
| 275. | —CH2cyp | 3-quinolyl |
| 276. | —CH2cyp | 3-cyanophenyl |
| 277. | —CH2cyp | 4-(1-isobutyl)piperidyl |
| 278. | —CH2cyp | 4-(1-ethyl)piperidyl |
| 279. | propyl | 3-fluorophenyl-CH2— |
| 280. | —CH2cyp | 3-methoxyphenyl |
| 281. | propyl | 2-CF3-phenyl-CH2— |
| 282. | —CH2cyp | 2-methylthiophenyl |
| 283. | —CH2cyp | —CH(CH3)phenyl |
| 284. | —CH2cyp | 3,4-dimethoxyphenyl-CH2CH2 |
| 285. | —CH2cyp | 3-fluorophenyl |
| 286. | —CH2cyp | 4-pyridyl |
| 287. | —CH2cyp | 4-(1-methyl)piperidyl |
| 288. | —CH2cyp | 3-(aminomethyl)phenyl |
| 289. | —CH2cyp | 2-methylthio pyrid-3-yl |
| 290. | —CH2cyp | 1-aminochxl |
| 291. | —CH2cyp | (1-phenyl)aminomethyl |
| 292. | —CH2cyp | 3-tetrahydrofuranyl |
| 293. | —CH2cyp | 2-thienyl |
| 294. | —CH2cyp | 2-indolyl |
| 295. | —CH2cyp | cyclohexyl |
| 296. | —CH2cyp | 2-aminoethyl |
| 297. | —CH2cyp | 3-piperidyl |
| 298. | —CH2cyp | phenyl |
| 299. | —CH2cyp | 4-chlorophenyl |
| 300. | —CH2cyp | 2-(4-pyridyl)oxazolyl |
| 301. | propyl | 3-fluorophenyl |
| 302. | propyl | 2-fluorophenyl |
| 303. | —CH2cyp | 2-naphthyl |
| 304. | —CH2cyp | 3-indolyl |
| 305. | —CH2cyp | 3-pyridyl |
| 306. | —CH2cyp | 3-isoquinolyl |
| 307. | —CH2cyp | 1-methylcyclopropyl |
| 308. | —CH2cyp | 2-chlorophenyl |
| 309. | —CH2cyp | phenyl(1-amino)ethyl |
| 310. | —CH2cyp | 2-(1,2,3,4-tetrahydronaphthyl) |
| 311. | —CH2cyp | phenyl-HC=C(CH3)— |
| 312. | —CH2cyp | isopropyl |
| 313. | —CH2cyp | phenyl-CH(CH3)CH2— |
| 314. | —CH2cyp | phenyl(1-hydroxy)ethyl |
| 315. | —CH2cyp | 3-indolylethyl |
| 316. | propyl | 2-fluorophenylethyl |
| 317. | —CH2cyp | 1-phenoxypropyl |
| 318. | —CH2cyp | —CH2C(CH3)3 |
| 319. | propyl | 1-(4-fluoronaphthyl) |
| 320. | H | 4-aminochxl |
| 321. | —CH2cyp | 2-benzothienyl |
| 322. | —CH2cyp | 2-(1-methylindolyl) |
| 323. | —CH2cyp | 5-(4-chloro-1,3-dimethyl)pyridylpyrazolyl |
| 324. | —CH2cyp | 2-indanylCH2— |
| 325. | H | 3-aminocyclopentyl- |
| 326. | H | 5-indolyl |
| 327. | —CH2cyp | phenyl(1-methylamino)ethyl |
| 328. | —CH2cyp | 3-indolylCH2— |
| 329. | —CH2cyp | 2-(7-pyridyl)oxazolyl |
| 330. | —CH2cyp | 2-benzoxazolyl |
| 331. | —CH2cyp | 2-methoxyphenyl |
| 332. | —CH2cyp | 3-(phenoxy)phenyl |
| 333. | —CH2cyp | 2-benzofuran |
| 334. | H | 3-pyridylethyl |
| 335. | H | 1-methyl-5-pyridyl-2-oxo-pyrrolidin-4-yl |
| 336. | —CH2cyp | 4-dimethylaminophenyl-CH2— |
| 337. | propyl | (2,5-di-trifluoromethylphenyl)ethyl |
| 338. | —CH2cyp | 2-methyl-3-indolyl |
| 339. | —CH2cyp | 1-(benzylamino)ethyl |
| 340. | H | 2-(4 pyridyloxazolyl) |
| 341. | H | 2-quinolyl |
| 342. | propyl | 4-piperidyl |
| 343. | CypCH2— | 4-ethoxycarbonylpiperid-1-yl |
| 344. | CypCH2— | 1-piperazinyl |
| 345. | CypCH2— | 4-Boc-piperid-1-yl |
| 346. | propyl | 3-CF3-phenyl |
| 347. | propyl | 4-CF3-phenyl |
| 348. | CypCH2— | 3-CF3-phenyl |
| 349. | CypCH2— | 4-CF3-phenyl |
| 350. | propyl | 4-fluorophenyl |
| 351. | propyl | 2-naphthyl |
| 352. | propyl | phenyl |
| 353. | propyl | 3-pyridyl |
| 354. | propyl | 4-pyridyl |
| 355. | CypCH2— | 4-pyridyl |
| 356. | CypCH2— | (phenyl-CH(CH3)-NH-CH3) |

TABLE 7

| # | R14 | R16 | R15 | R13a |
|---|---|---|---|---|
| 357. | 1-(N-(CypCH2)amino)ethyl | 6-quinolyl | H | Cl |
| 358. | 1-(N,N-(CypCH2)2-amino)ethyl | 6-quinolyl | H | Cl |
| 359. | 1-(N-(CypCH2)-N-propylamino)ethyl | 6-quinolyl | H | Cl |
| 360. | (N,N-(CypCH2)2amino)-CH2— | 6-quinolyl | H | Cl |
| 361. | N-(CypCH2)-N-propylaminomethyl | 6-quinolyl | H | Cl |

TABLE 7-continued

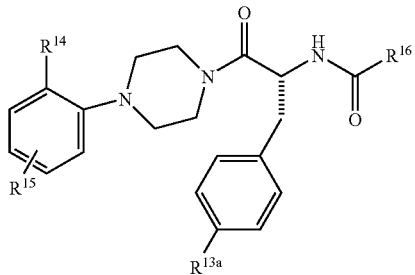

| # | R14 | R16 | R15 | R13a |
|---|---|---|---|---|
| 362. | N-(CypCH2)-N-ethylaminomethyl | 6-quinolyl | H | Cl |
| 363. | N,N-(propyl)2aminomethyl | 6-quinolyl | H | Cl |
| 364. | 1-(N-(CypCH2)-N-butylamino)ethyl | 6-quinolyl | H | Cl |
| 365. | 1-(N-CypCH2)-N-isopentylamino)ethyl | 6-quinolyl | H | Cl |
| 366. | 1-(N-(CypCH2)-N-(ChxlCH2)amino)ethyl | 6-quinolyl | H | Cl |
| 367. | 1-(N-(CypCH2)-N-(CH3S(CH2)3)amino)ethyl | 6-quinolyl | H | Cl |
| 368. | N-(CypCH2)-N-(MeSO2)-aminomethyl | 6-quinolyl | H | Cl |
| 369. | 1-(N-(CypCH2)-N-(3-thienylmethyl)amino)ethyl | H | 6-quinolyl | Cl |
| 370. | 1-(N-(CypCH2)-N-(CH3C=O)amino)ethyl | H | 6-quinolyl | Cl |
| 371. | 1-hydroxyethyl | H | 6-quinolyl | Cl |
| 372. | 1-(N-(CypCH2)-N-isobutylamino)ethyl | H | 6-quinolyl | Cl |
| 373. | 1-(N-(CypCH2)-N-(phenylethyl)amino)ethyl | H | 6-quinolyl | Cl |
| 374. | N-(CypCH2)-N-(MeSO2)aminomethyl | H | 6-quinolyl | Cl |
| 375. | 1-(N-(CypCH2)-N-(pentyl)amino)ethyl | H | 6-quinolyl | Cl |
| 376. | N,N-di(isobutyl)aminomethyl | H | 6-quinolyl | Cl |
| 377. | 1-(N-(CypCH2)-N-(2-ethylbutyl)amino)ethyl | H | 6-quinolyl | Cl |
| 378. | 1-(N-(CypCH2)-N-(3-methylphenyl)amino)ethyl | H | 6-quinolyl | Cl |
| 379. | N-(MeSO2)-N-(CypCH2)aminomethyl | H | 3-isoquinolyl | Cl |
| 380. | 1-(N-(CypCH2)amino)ethyl | H | 3-isoquinolyl | Cl |
| 381. | N-(MeSO2)-N-(CypCH2)aminomethyl | H | 4-piperidyl | Cl |
| 382. | N-propyl-N-(CypCH2)-aminomethyl | H | piperid-1-ylethyl | Cl |
| 383. | 1,2,3-triazol-1-ylmethyl | H | 1-ethylpiperid-4-yl | Cl |
| 384. | N-propyl-N-(CypCH2)aminomethyl | H | 1-isobutylpiperid-4-yl | Cl |
| 385. | N-isopropyl-N-(CypCH2)aminomethyl | H | 1-ethylpiperid-4-yl | Cl |
| 386. | N-ethyl-N-(CypCH2)aminomethyl | H | 1-ethylpiperid-4-yl | Cl |
| 387. | N-cyclopentyl-N-(CypCH2)aminomethyl | H | 1-ethylpiperid-4-yl | Cl |
| 388. | 1,2,3-triazol-1-ylmethyl | H | 1-isopropyl-piperid-4-yl | Cl |
| 389. | 1,2,3-triazol-1-ylmethyl | H | 1-(CypCH2)piperid-4-yl | Cl |
| 390. | 1,2,3-triazol-1-ylmethyl | H | 1-isobutyl-piperid-4-yl | Cl |
| 391. | 1,2,3-triazol-1-ylmethyl | H | 1-[(CH3)3CCH2]-piperid-4-yl | Cl |
| 392. | N-(CypCH2)-N-propylaminomethyl | H | 6-quinolyl | Br |
| 393. | N-(CypCH2)-N-propylaminomethyl | H | 3-quinolyl | Br |
| 394. | N-(CypCH2)-N-propylaminomethyl | H | 4-piperidyl | Br |
| 395. | N-(CypCH2)-N-propylaminomethyl | H | 1-ethylpiperid-4-yl | Br |
| 396. | N-propyl-N-(CypCH2)aminomethyl | H | 1-isobutyl-piperid-4-yl | Br |
| 397. | N-(CypCH2)-N-propylaminomethyl | H | 1-isopropyl-piperid-4-yl | Br |
| 398. | N-(CypCH2)-N-propylaminomethyl | H | 1-(CypCH2)piperid-4-yl | Br |
| 399. | N-(CypCH2)-N-propylaminomethyl | H | 1-isobutyl-piperid-4-yl | Br |
| 400. | N-(CypCH2)-N-propylaminomethyl | H | 1-[(CH3)3CCH2]-piperid-4-yl | Br |
| 401. | N-(CypCH2)-N-propylaminomethyl | H | piperid-1-ylethyl | Br |
| 402. | N-(CypCH2)-N-propylaminomethyl | H | ethyl-aminoethyl | Br |
| 403. | 1-(N-(CypCH2)-amino)ethyl | H | 2-quinolyl | Cl |
| 404. | 1-(N-(CypCH2)-amino)ethyl | H | 4-piperidyl | Cl |
| 405. | N-(CypCH2)-N-propylaminomethyl | F | piperid-1-ylethyl | Cl |
| 406. | N-(CypCH2)-N-propylaminomethyl | F | N-methyl-aminoethyl | Cl |
| 407. | N-(CypCH2)-N-propylaminomethyl | F | N,N-di(ethyl)-aminoethyl | Cl |
| 408. | N-(CypCH2)-N-propylaminomethyl | F | N-ethyl-aminoethyl | Cl |
| 409. | N-(CypCH2)-N-propylaminomethyl | F | 6-quinolyl | Cl |
| 410. | N-(CypCH2)-N-propylaminomethyl | F | 3-quinolyl | Cl |

TABLE 8

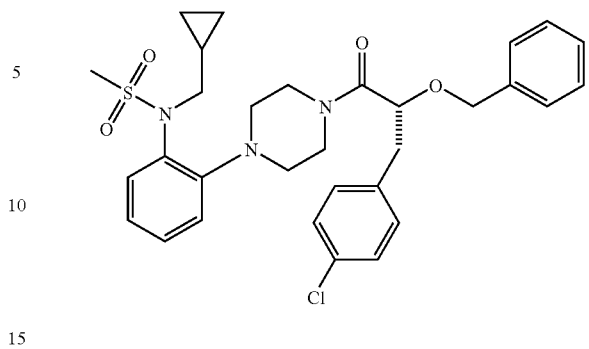

| # | R19 | R8a |
|---|---|---|
| 411. | —CH₂cyp | |

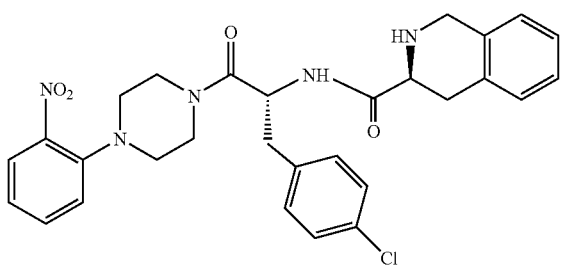

| | | |
|---|---|---|
| 412. | —CH₂cyp | phenyl |
| 413. | —CH₂cyp | benzyl |
| 414. | —CH₂cyp | 1-methylimidazol-4-yl |
| 415. | —CH₂cyp | 3,5-dimethylisoxazol-4-yl |
| 416. | —CH₂cyp | 2-methoxycarbonylthien-3-yl |
| 417. | —CH₂cyp | 4-fluorophenyl |
| 418. | —CH₂cyp | 4-methylcarbonylaminophenyl |
| 419. | —CH₂cyp | 2-(phenylcarbonylaminomethyl)thien-5-yl |
| 420. | —CH₂cyp | 1-naphthyl |
| 421. | —CH₂cyp | 6-quinolyl |
| 422. | —CH₂cyp | 2-(trifluoromethylcarbonyl)-1,2,3,4-tetrahydroisoquinol-7-yl |

EXAMPLE 423

N-{(1R)-1-[(4-Chlorophenyl)methyl]-2-[4-(2-nitrophenyl)piperazinyl]-2-oxoethyl}((3S)(3-1,2,3,4-tetrahydroisoquinolyl))carboxamide hydrochloride The titled compound was prepared from tert-butyl 3-(N-{(1R)-1-[(4-chlorophenyl)methyl]-2-[4-(2-nitrophenyl)piperazinyl]-2-oxoethyl}carbamoyl)(3S)-1,2,3,4-tetrahydroisoquinoline-2-carboxylate (120 mg, 0.18 mmol, Preparation VIII) by treatment with 5 mL of a satd soln of HCl in EtOAc. This was purified by preparative HPLC (TFA buffer) to give the title compound as white solid (65 mg). MS (ESI, pos. ion) m/z: 548 (M+H). Calc'd for C₂₉H₃₀ClN₅O₄: 547.20.

EXAMPLE 424

(2S)-3-(4-Chlorophenyl)-1-(4-{2-[(cyclopropylmethyl)(methylsulfonyl)amino]phenyl)-piperazinyl){2-(phenylmethoxy)propan-1-one Step 1

To a 250-mL round-bottomed flask equipped with a magnetic stir bar was added N-Boc-p-Cl-D-Phe-OH (PepTech Corp.) (5.0 g, 25 mmol) followed by 1M H₂SO₄ (50 mL). The heterogeneous solution was heated to dissolve the amino acid. Upon cooling the amino acid formed a white flocculent precipitate. The solution was cooled to 0° C. and water was added until efficient stirring was restored (ca. 25–50 mL). To the solution was added NaNO₂ (2.6 g in 10 mL H₂O, 38 mmol) over 2.5 h utilizing a syringe pump. Once the addition was complete the ice bath was allowed to melt on its own and warm to room temp. After stirring for 24 h the reaction mixture was diluted with H₂O (200 ml) and saturated with (NH₄)₂SO₄, extracted with Et₂O (3×200 mL), and the combined extracts were dried (Na₂SO₄) and concentrated onto silica gel. Purification by chromatography (0.5% to 5% MeOH/CH₂Cl₂) afforded (2S)-3-(4-chlorophenyl)-2-hydroxypropanoic acid as a white solid (1.8 g). MS (ESI, neg. ion) m/z 199 (M–1). Calc'd for C₉H₁₀ClNO₂: 199.04.

Step 2

To a 250-mL round-bottomed flask equipped with a magnetic stirring bar was added tert-butyl 4-{2-[(cyclopropylmethyl)(methylsulfonyl)aminophenyl}-piperazinecarboxylate (Example 58, Step 1) (7.8 g, 19 mmol) and CH₂Cl₂ (100 mL). To this solution at RT was added TFA (33 mL). This was stirred for 1 h and concentrated on a rotary evaporator. The residue was taken up in 10% Na₂CO₃ (aq.) and CH₂Cl₂ and stirred for 0.5 h. It was extracted with CH₂Cl₂ and the combined extracts were washed with brine, dried (MgSO₄) and concentrated to afford N-(cyclopropylmethyl)-(methylsulfonyl)(2-piperazinylphenyl)amine (5.9 g). This was used without further purification. MS (ESI, pos. ion) m/z 310 (M+1). Calc'd for C₁₅H₂₃N₃O₂S: 309.15.

Step 3

To a 250-mL round bottomed-flask equipped with a magnetic stir bar and containing a solution of N-(cyclopropylmethyl)(methylsulfonyl)(2-piperazinylphenyl)amine (Step 2) (1.8 g, 5.8 mmol) and (2S)-3-(4-chlorophenyl)-2-hydroxypropanoic acid (Step 1) (1.2 g, 5.8 mmol) in CH₂Cl₂ (30 mL) and DMF (30 mL) at RT was added HOAT (Aldrich ) (0.87 g, 6.4 mmol) followed by EDC (Aldrich) (1.3 g, 7.0 mmol). This was stirred for 18 h and diluted with CH₂Cl₂ (300 mL) The mixture was washed with H₂O (3×100 mL), aq. NaHCO₃ (1×100 mL) and brine (1×100 mL). It was dried (Na₂SO₄) and concentrated onto silica gel. Purification by chromatography (40 to 55%

EtOAc/hexanes) afforded (2S)-3-(4-chlorophenyl)-1-(4-{2-[(cyclopropylmethyl)-(methylsulfonyl)amino]-phenyl}-piperazinyl)-2-hydroxypropan-1-one as a slightly yellow oil (1.8 g). Analytically pure material was obtained by reverse phase preparative scale chromatography (Column: MetaChem Polaris $C_{18}$-A 5 micron, flow: 20 mL/min, gradient: 5 to 100% $CH_3CN$ (0.1% TFA)/$H_2O$ (0.1% TFA). MS (ESI, pos. ion) m/z 492 (M+1). Calc'd for $C_{24}H_{30}ClN_3O_4S$: 491.16.

Step 4

To a 15-mL round-bottomed flask equipped with a magnetic stir bar and containing (2S)-3-(4-chlorophenyl)-1-(4-{2-[(cyclopropylmethyl)-(methylsulfonyl)amino]phenyl}-piperazinyl)-2-hydroxy-propan-1-one (Step 3) (0.075 g, 0.15 mmol) in 2 mL THF at RT was added NaH (Aldrich) (0.007 g of 60% dispersion in oil, 0.17 mmol). Gas evolution was observed and after 5 min benzyl bromide (Aldrich) (20 ml, 0.17 mmol) was added. After stirring for 18 h, the mixture was quenched with aq. $NaHCO_3$ and extracted with $Et_2O$. The combined ether extracts were washed with $H_2O$ and brine, dried ($Na_2SO_4$) and concentrated onto silica gel. Purification by chromatography (30–55% EtOAc/hexanes) afforded (2S)-3-(4-chlorophenyl)-1-(4-{2-[(cyclopropylmethyl)-(methylsulfonyl)amino]-phenyl}piperazinyl)-2-(phenyl-methoxy)propan-1-one as a colorless oil (0.065 g). MS (ESI, pos. ion) m/z 582 (M+1). Calc'd for $C_{31}H_{36}ClN_3O_4S$: 581.21.

EXAMPLE 425

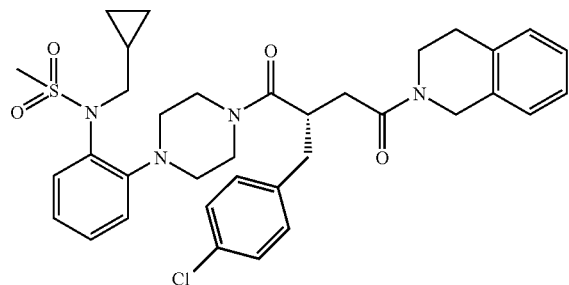

(2S)-2-[(4-Chlorophenyl)methyl]-1-(4-{2-[(cyclopropylmethyl)(methylsulfonyl)amino]phenyl}-piperazinyl)-4-(2-1,2,3,4-tetrahydroisoquinolyl)butane-1,4-dione Step 1

To a solution of 3-phenylpropanoic acid (5.5 g, 27 mmol) in anhydrous $CH_2Cl_2$ (50 mL, Aldrich) was added oxalyl chloride (5 mL, Aldrich), followed by 3 drops of DMF. The reaction mixture was stirred at RT for 2 h, then the solvent was removed in vacuo. The residue was re-dissolved in anhydrous $CH_2Cl_2$ (50 mL) and concentrated again. The product, 3-(4-chlorophenyl)propanoyl chloride, was dissolved in anhydrous THF (Aldrich) and cooled to −78° C. in a dry ice bath for the next step.

Step 2

To a solution of (4R)-(phenylmethyl)-2-oxazolidone (5.5 g, 30 mmol) and 5 mg of triphenylmethane (indicator) in 200 mL of anhydrous THF at −40° C. under $N_2$, was added n-butyllithium (2.5 M in hexane, 30 mmol, Aldrich) until an orange color persisted. The resulted solution was then cooled to −78° C., and the THF solution of 3-phenyl-propanoyl chloride (Step 1) was added. The reaction was stirred at −78° C. for 1 h. After warming to 0° C., the reaction mixture was poured onto 50 mL of satd. $NaHCO_3$ and extracted with 100 mL of $CH_2Cl_2$. The organic phase was washed with brine, dried over $Na_2SO_4$, and concentrated in vacuo. The product was purified by a silica gel column chromatography (EtOAc) to afford (4R)-3-[3-(4-chlorophenyl)propanoyl]-4-benzyl-1,3-oxazolidin-2-one as a white solid (7.5 g). MS (ESI, pos. ion) m/z: 344.0 (M+1). Calc'd for $C_{19}H_{19}ClNO_3$: 343.10.

Step 3

To a solution of (4R)-3-[3-(4-chlorophenyl)propanoyl]-4-benzyl-1,3-oxazolidin-2-one (Step 2) (3.0 g, 8.72 mmol) in anhydrous THF (100 mL, Aldrich) at −78° C. was added a THF solution of NaHMDS (13.1 mL, 1M, Aldrich). The solution was stirred at −78° C. for 30 min then at −20° C. for 30 min. The solution was cooled to −78° C. again and t-butyl bromoacetate (1.93 mL, 13.1 mol) was added to the reaction mixture via a syringe. The reaction was stirred at −78° C. for 2 h. After warming to RT, the reaction mixture was poured onto 1M $NaH_2PO_4$ (50 mL). The desired compound was extracted with 100 mL of EtOAc and the organic phase was washed with 50 mL of brine, dried over $Na_2SO_4$ and concentrated in vacuo. The compound was further purified with silica gel column chromatography (20% to 50% EtOAc in hexane) to provide tert-butyl 4-[(4R)-2-oxo-4-benzyl(1,3-oxazolidin-3-yl)](3S)-3-[(4-chlorophenyl)methyl]-4-oxobutanoate as a light yellow solid (3.5 g). MS (ESI, pos. ion) m/z: 458.0 (M+1). Calc'd for $C_{25}H_{28}ClNO_5$: 457.17.

Step 4

To a solution of tert-butyl 4-[(4R)-2-oxo-4-benzyl-(1,3-oxazolidin-3-yl)](3S)-3-[(4-chlorophenyl)methyl]-4-oxobutanoate (Step 3) (0.3 g, 0.656 mmol) in 10 mL of THF was added 0.1 mL of $H_2O_2$ (35%) and 33 mg of LiOH-$H_2O$ (0.787 mmol). The reaction was stirred at RT for 3 h and extracted with 30 mL of $Et_2O$. The aqueous solution was acidified with 2N HCl to pH~2 and extracted with 50 mL of EtOAc. These EtOAc extractions were combined, dried over $Na_2SO_4$ and concentrated in vacuo. (2S)-3-[(tert-Butyl)-oxycarbonyl]-2-[(4-chlorophenyl)methyl]-propanoic acid was obtained as light yellow oil (0.15 g) and was used in the next step without further purification. MS (ESI, pos. ion) m/z: 299.0 (M+1). Calc'd for $C_{15}H_{19}ClO_4$: 298.10.

Step 5

To a solution of (cyclopropylmethyl)(methylsulfonyl)-(2-piperazinyl-phenyl)amine (HCl salt, 2.3 g, 6.0 mmol), (2S)-3-[(tert-butyl)oxycarbonyl]-2-[(4-chlorophenyl)-methyl]propanoic acid (1.8 g, 6.02 mmol, Step 4), HOBt (0.81 g, 6.0 mmol, Novabiochem), and TEA (1.67 mL, 12.0 mmol) in 20 mL of $CH_2Cl_2$ at 0° C. was added EDC (1.73 g, 9.03 mmol, Advanced Chemtech). The reaction was warmed to RT and stirred for 12 h. The reaction was quenched with satd $NaHCO_3$, extracted with 80 mL of EtOAc and the organic solution was washed with brine, dried over $Na_2SO_4$ and concentrated in vacuo. The compound was further purified by silica gel column chromatography (50% EtOAc in hexane) to provide 2.3 g of tert-butyl (3S)-3-[(4-chlorophenyl)-methyl]-4-(4-{2-[(cyclopropylmethyl)(methylsulfonyl)-amino]phenyl}-piperazinyl)-4-oxobutanoate as a white foam. MS (ESI, pos. ion) m/z: 590.6 (M+1). Calc'd for $C_{30}H_{40}ClN_3O_5S$: 589.24. Anal. Calcd for $C_{30}H_{40}ClN_3O_5S$: C, 61.05; H, 6.83; N, 7.12; Cl, 6.01. Found: C, 60.91; H, 6.69; N, 7.09; Cl, 6.16.

Step 6

A solution of tert-butyl (3S)-3-[(4-chlorophenyl)-methyl]-4-(4-{2-[(cyclopropylmethyl)-(methylsulfonyl)-amino]phenyl}piperazinyl)-4-oxobutanoate (Step 5) (0.16 g, 0.27 mmol) in 10 mL of 50% TFA in $CH_2Cl_2$ mixture was stirred at RT for 2 h. The volatile solvent was removed in vacuo. The residue was dissolved in $CH_2Cl_2$ and concentrated in vacuo. (3S)-3-[(4-Chlorophenyl)-methyl]-4-(4-{2-[(cyclopropylmethyl)-(methylsulfonyl)-amino]phenyl}piperazinyl)-4-oxobutanoic acid was obtained as a light yellow solid (0.14 g) MS (ESI, pos. ion) m/z: 534.4 (M+1). Calc'd for $C_{26}H_{32}ClN_3O_5S$: 533.18. Anal. Calcd for $C_{26}H_{32}ClN_3O_5S$ $1.5H_2O$: C, 55.66; H, 6.29; N, 7.49; Cl, 6.32. Found: C, 55.51; H, 5.85; N, 7.35; Cl, 6.12.

Step 7

To a solution of (3S)-3-[(4-chlorophenyl)methyl]-4-(4-{2-[(cyclopropylmethyl)(methylsulfonyl)amino]phenyl}-piperazinyl)-4-oxobutanoic acid (Step 6) (0.63 g, 0.97 mmol), tert-butyl piperazinecarboxylate (0.272 g, 1.46 mmol), HOBt (0.131 g, 0.97 mmol) and TEA (0.135 mL, 0.97 mmol) in 10 mL of $CH_2Cl_2$ at 0° C. was added EDC (0.28 g, 1.46 mmol). The reaction was warmed to RT and stirred for 12 h. The reaction was quenched with satd. $NaHCO_3$, and extracted with 50 mL of EtOAc. The organic phase was washed with brine, dried over $Na_2SO_4$ and concentrated in vacuo. The crude compound was further purified by silica gel column chromatography (EtOAc) to afford tert-butyl 4-[(3S)-3-[(4-chlorophenyl)methyl]-4-(4-{2-[(cyclopropylmethyl)(methylsulfonyl)amino]-phenyl}piperazinyl)-4-oxobutanoyl]piperazinecarboxylate as a white foam (0.3 g). MS (ESI, pos. ion) m/z: 702.5 (M+1). Calc'd for $C_{35}H_{48}ClN_5O_6S$: 701.30. Anal. Calcd for $C_{35}H_{48}ClN_5O_6S$ $0.5H_2O$: C, 59.10; H, 6.94; N, 9.85; Cl, 4.98. Found: C, 59.32; H, 6.94; N, 9.81; Cl, 5.17.

Step 8

To a solution of (3S)-3-[(4-chlorophenyl)methyl]-4-(4-{2-[(cyclopropylmethyl)(methylsulfonyl)amino]-phenyl}-piperazinyl)-4-oxobutanoic acid (Step 7) (75 mg, 0.116 mmol), 1,2,3,4-tetrahydroisoquinoline (0.017 mL, 0.14 mmol), and TEA (0.064 mL, 0.46 mmol) in 5 mL of $CH_2Cl_2$ at 0° C. was added BOP-Cl (44 mg, 0.17 mmol). The reaction was warmed to RT and stirred for 12 h. The reaction was diluted with 20 mL of $CH_2Cl_2$ and washed with satd. $NaHCO_3$, followed by brine. The organic phase was dried over $Na_2SO_4$ and concentrated in vacuo. The crude product was purified by silica gel column chromatography (EtOAc) to afford a white foam (0.3 g, 44%). Final prep-HPLC purification was performed to provide 20 mg of (2S)-2-[(4-chlorophenyl)methyl]-1-(4-{2-[(cyclopropylmethyl)-(methylsulfonyl)amino]phenyl}-piperazinyl)-4-(2-1,2,3,4-tetrahydroisoquinolyl)butane-1,4-dione. MS (ESI, pos. ion) m/z: 649.4 (M+1). Calc'd for $C_{35}H_{48}ClN_5O_6S$: 648.25. Anal. Calcd for $C_{35}H_{48}ClN_5O_6S$ $0.5H_2O$: C, 59.10; H, 6.94; N, 9.85; Cl, 4.98. Found: C, 59.32; H, 6.94; N, 9.81; Cl, 5.17.

Other compounds included in this invention are set forth in Tables 9–13 below.

TABLE 9

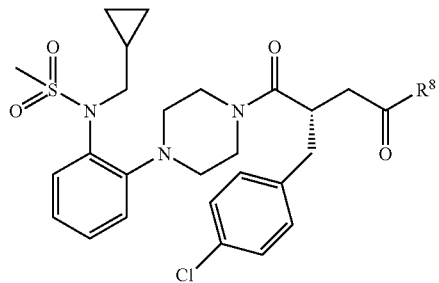

| # | $R^8$ | Formula | MW | $MH^+$ |
|---|---|---|---|---|
| 426. | tert-butoxy | $C_{30}H_{40}ClN_3O_5S$ | 589.24 | 590.6 |
| 427. | OH | $C_{26}H_{32}ClN_3O_5S$ | 533.18 | 534.4 |
| 428. | 1,2,3,4-tetrahydroisoquinolin-2-yl | $C_{35}H_{41}ClN_4O_4S$ | 648.25 | 649.4 |
| 429. | 2-furylmethyl-amino | $C_{31}H_{37}ClN_4O_5S$ | 612.22 | 613.5 |

TABLE 10

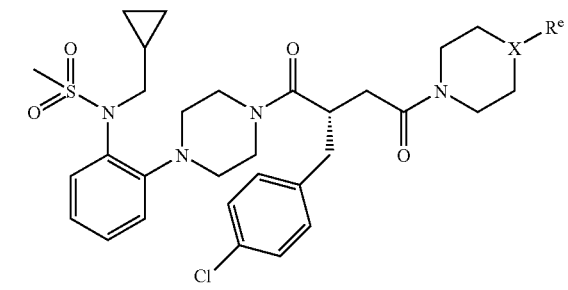

| # | $R^e$ | X | Formula | MW | $MH^+$ |
|---|---|---|---|---|---|
| 430. | H | N | $C_{30}H_{40}ClN_5O_4S$ | 601.25 | 602.6 |
| 431. | ethyl | N | $C_{32}H_{44}ClN_5O_4S$ | 629.28 | 630.3 |
| 432. | propyl | N | $C_{33}H_{46}ClN_5O_4S$ | 643.30 | 644.5 |
| 433. | 3-methylbutyl | N | $C_{35}H_{50}ClN_5O_4S$ | 671.33 | 673.4 |
| 434. | 2-methylpropyl | N | $C_{34}H_{48}ClN_5O_4S$ | 657.31 | 658.4 |
| 435. | cyclopropylmethyl | N | $C_{34}H_{46}ClN_5O_4S$ | 655.30 | 656.4 |
| 436. | H | CH | $C_{31}H_{41}ClN_4O_4S$ | 600.25 | 601.5 |
| 437. | pyrrolidinyl | CH | $C_{31}H_{41}ClN_4O_4S$ | 669.31 | 670.7 |

TABLE 11

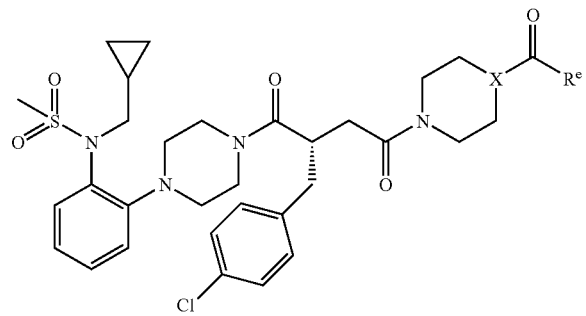

| # | $R^e$ | X | Formula | MW | $MH^+$ |
|---|---|---|---|---|---|
| 438. | methyl | N | $C_{32}H_{42}ClN_5O_5S$ | 643.26 | 644.6 |
| 439. | tert-butyloxy | N | $C_{35}H_{48}ClN_5O_6S$ | 701.30 | 702.5 |
| 440. | phenyl | N | $C_{37}H_{44}ClN_5O_5S$ | 705.28 | 706.3 |
| 441. | ethoxy | N | $C_{33}H_{44}ClN_5O_6S$ | 673.27 | 674.5 |

TABLE 11-continued

| # | R$^e$ | X | Formula | MW | MH$^+$ |
|---|---|---|---|---|---|
| 442. | 2,2-dimethyl-butyl | N | C$_{31}$H$_{40}$ClN$_7$O | 699.32 | 700.5 |
| 443. | ethyl | C | C$_{34}$H$_{45}$ClN$_4$O$_6$S | 672.27 | 673.6 |

TABLE 12

| # | R$^8$ | Formula | MW | MH$^+$ |
|---|---|---|---|---|
| 444. | 1,3-thiazolidinyl | C$_{30}$H$_{39}$ClN$_4$O$_3$S | 570.24 | 571.2 |
| 445. | morpholino | C$_{31}$H$_{41}$ClN$_4$O$_4$ | 568.28 | 569.2 |
| 446. | tert-butyl piperazinecarboxylate | C$_{36}$H$_{50}$ClN$_5$O$_5$ | 667.35 | 668.5 |
| 447. | cyclobutylamino | C$_{31}$H$_{41}$ClN$_4$O$_3$ | 552.29 | 553.3 |
| 448. | azetidinyl | C$_{30}$H$_{39}$ClN$_4$O$_3$ | 538.27 | 539.2 |
| 449. | (2-fluorophenyl)methylamino | C$_{34}$H$_{40}$ClFN$_4$O$_3$ | 606.28 | 607.2 |
| 450. | 2-pyridylmethylamino | C$_{33}$H$_{40}$ClN$_5$O$_3$ | 589.28 | 590.7 |
| 451. | (2-methoxyethyl)methylamino | C$_{31}$H$_{43}$ClN$_4$O$_4$ | 570.30 | 571.2 |

TABLE 13

| # | R$^2$ |
|---|---|
| 452. | 4-fluorobenzyl |
| 453. | 3-fluorobenzyl |
| 454. | 4-trifluoromethylbenzyl |
| 455. | 3-trifluoromethylbenzyl |
| 456. | 2-naphthyl |

Although the pharmacological properties of the compounds of Formula I vary with structural change, in general, activity possessed by compounds of Formula I may be demonstrated in vivo. The pharmacological properties of the compounds of this invention may be confirmed by a number of pharmacological in vitro assays. The exemplified pharmacological assays which follow have been carried out with the compounds according to the invention and their salts.

Biological Evaluation

A number of models exist for the study of obesity (see, e.g., Bray, G. A., 1992, Prog. Brain Res. 93: 333–341; and Bray, G. A., 1989, Amer. J. Clin. Nutr. 5: 891–902). Animals having mutations which lead to syndromes that include obesity symptoms have also been identified.

Attempts have been made to utilize such animals as models for the study of obesity, and the best studied animal models to date for genetic obesity are mice. For reviews, see, e.g., Friedman, J. M. et al., 1991, Mamm. Gen. 1: 130–144; Friedman, J. M. and Liebel, R. L., 1992, Cell 69: 217–220.

Assays which demonstrate MCR4/MCR3 agonistic activity of compounds are well known in the art. One particularly useful assay is the BioTrak TM cAMP direct enzyme immunoassay (EIA) system from Amersham Pharmacia Biotech, which quantitates the cAMP response of cells to MC ligands. This system allows the simple quantitation of total cellular cAMP measurement in cells exposed to selective ligands. Briefly summarized: HEK cells stably transfected with the MC-1, MC-3 or MC-4 receptors are plated into 96 well microtiter plates and grown overnight. Cells are dosed with the appropriate MC ligand for I hour and then lysed. A fraction of the lysed cell extract is transferred to the assay plate. The ELISA assay is performed according to kit instructions. Each plate contains a series of cAMP standards for calculating a standard curve, as well as a full MC agonist as a positive control for each MC receptor. cAMP activity is calculated as a % of the maximum cAMP activity of the full MC agonist control.

Penile Erection Test in the Rat

Method that can be used includes a modified version of that reported by Heaton et al. (J. Urol., 145, 1099–1102, 1991.) and Ghasi-Kanzari et al. (Pharmacol. Toxicol., 81, 81–84, 1997.). Rats are kept under a reversed 12-hr light/dark cycle for 5 days prior to testing. On the test day, animals are administered compound via intraperitoneal route of administration 1 hr after the lights go off and then immediately placed in individual Plexiglas cages (32×14×13 cm). Under red lighting, rats are observed for 1 hr. The number of penile erections and yawns are recorded. There are 10 animals per treatment group and bromocriptine (4 mg/kg) is used as the reference agent as well as a vehicle control. Data are analyzed by comparing treated groups with vehicle control using Mann Whitney U tests.

Fast-induced Food Intake in Mice

Male C57BL/6 mice (25–30 g) were used for studies. Food was removed from group-housed mice (5–8/ cage) overnight (16–18 hr). The next day, mice were dosed with compound (in 20% Captisol or HPMC/Tween or PBS, depending on the solubility) and then placed into individual cages. Fifteen min following systemic dosing or 30 min following intra-cerebroventricular (i.c.v) dosing (i.e., time to recover from anesthesia), a pre-weighed amount of food was placed in each cage. Food was then weighed 1, 2 and 4 hr after replacement. Cumulative food intake was determined as the difference between the initial weight of the food and the weight of the food at each time point. For statistical analysis, food intake values of compound treated animals were compared with that of vehicle treated animals using ANOVA followed by a post-hoc test (i.e., FLSD) when warranted. For these studies, group sizes for each treatment were 8–10 animals. For i.c.v. dosing, animals were anesthetized using isoflurane. Next, the i.c.v. injection was made using a free-hand technique. Mice were allowed 30 min to recover prior to the start of the test.

Examples 4, 67, 71, 270, 273 and 308 caused a reduction in feeding at concentrations of 30 mg/kg or below.

Formulations

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The compounds and compositions of the present invention may, for example, be administered orally, mucosally, topically, rectally, pulmonarily such as by inhalation spray, nasal or buccal or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For example, in the case of a 70 kg adult human, these may contain an amount of active ingredient from about 0.7 to 3500 mg, preferably from about 5 to 1500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.1 and about 50 mg/kg body weight and most preferably between about 0.5 to 20 mg/kg body weight, may be appropriate may be appropriate. The daily dose can be administered in one to four doses per day.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules.

Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose for the treatment of sexual dysfunction compounds of the present invention can be given orally or as a nasal spray.

In the case of skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula II

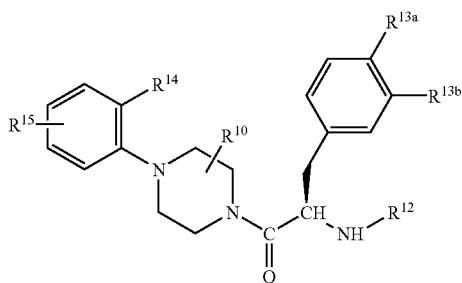

wherein $R^{10}$ is selected from H, chloro or fluoro;
wherein $R^{12}$ is

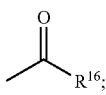

wherein $R^{13a}$ and $R^{13b}$ are independently selected from H, phenyl, fluoro, iodo, bromo, chloro, phenyl, $C_{1-2}$-alkyl, $C_{1-2}$-haloalkyl, and $C_{1-2}$-alkoxy; or wherein $R^{13a}$ and $R^{13b}$ together form an $C_{1-4}$-alkenylenyl bridge;
wherein $R^{14}$ is selected from $R^{19}R^{20}N-$, $R^{19}R^{20}N-C_{1-4}$-alkyl, $(R21R22N-)(O=)C-$, $C_{1-4}$-haloalkyl, $C_{2-4}$-hydroxyalkyl, heterocyclyloxy-$C_{1-4}$-alkyl, aryloxy-$C_{1-4}$-alkyl and $C_{1-4}$-alkoxycarbonyl;
wherein $R^{15}$ is selected from H, $C_{1-2}$-haloalkyl, $C_{1-4}$-alkyl, halo, $-OR^{17}$, and $-N(R^{17})_2$;
wherein $R^{16}$ is selected from 3-pyridyl, 4-pyridyl, 5-benzopyrrolyl, 2-benzofuran, 2-benzothienyl, 6-quinolyl, thienyl, 4-piperidyl, N-methyl-4-piperidyl, N-methyl-2-piperidyl, N-ethyl-4-piperidyl, N-isobutyl-4-piperidyl, 3-piperidyl and 3-azetidinyl optionally N-substituted with a substituent selected from methyl, ethyl, propyl, isopropyl, butyl, isobutyl, pentyl, cyclohexylmethyl and benzyl;
wherein $R^{17}$ is selected from H, $C_{1-4}$-alkyl, $C_{3-7}$-cyclhoalkyl-$(CH_2)_n-$, and aryl-$(CH_2)_n-$;
wherein $R^{19}$ is selected from H, $R^{23}SO_2-$, $C_{1-6}$-alkyl, $C_{3-7}$-cycloalkyl-$(CH_2)_n-$, amino-$C_{1-6}$-alkyl, $C_{1-6}$-alkylamino-$C_{1-6}$-alkyl, $C_{3-7}$-cycloalkylamino-$C_{1-6}$-alkyl, $C_{3-7}$-cycloalkyl-$C_{1-6}$-alkylamino-$C_{1-6}$-alkyl, heteroarylamino-$C_{1-6}$-alkyl, heteroaryl-$C_{1-6}$-alkylamino-$C_{1-6}$-alkyl, arylamino-$C_{1-6}$-alkyl, aryl-$C_{1-6}$-alkylamino-$C_{1-6}$-alkyl, heteroaryloxy-$C_{1-6}$-alkyl, heteroaryl-$C_{1-6}$-alkyloxy-$C_{1-6}$-alkyl, aryloxy-$C_{1-6}$-alkyl, aryl-$C_{1-6}$-alkyloxy-$C_{1-6}$-alkyl, hydroxy-$C_{1-6}$-alkyl, $C_{1-6}$-alkylthio-$C_{1-6}$-alkyl, $C_{1-6}$-alkoxy-$C_{1-6}$-alkyl, $C_{1-6}$-alkylcarbonyl, $C_{1-6}$-alkoxycarbonyl, $C_{1-6}$-alkoxy-$C_{1-6}$-alkylcarbonyl, $C_{1-6}$-alkylaminocarbonyl, arylcarbonyl, aralkylcarbonyl, $C_{3-7}$-cycloalkylcarbonyl, $C_{3-7}$-cycloalkyl-$C_{1-6}$-alkylcarbonyl, heteroaryl-$C_{1-6}$-alkylcarbonyl and heteroarylcarbonyl;
wherein $R^{20}$ is selected from H, $C_{1-8}$-alkyl, $C_{3-7}$-cycloalkyl-$(CH_2)_n-$, $C_{1-3}$-alkylsulfonyl, amino-$C_{1-3}$-alkylamino, heterocyclyl-$(CH_2)_n-$, and aryl-$(CH_2)_n-$;
alternatively $R^{19}$ and $R^{20}$ together with the nitrogen atom form a 4–8 membered heterocyclic ring;
wherein $R^{21}$ is selected from H, $C_{1-6}$-alkyl, $C_{2-6}$-alkenyl, $C_{1-6}$-alkylthio-$C_{1-6}$-alkyl, $C_{1-6}$-alkylcarbonylamino-$C_{1-6}$-alkyl, amino-$C_{1-6}$-alkyl, heterocyclyl-$(CH_2)_n-$, $C_{3-7}$-cycloalkyl-$(CH_2)_n-$, and aryl-$(CH_2)_n-$;
wherein $R^{22}$ is selected from H, $C_{1-6}$-alkyl, $C_{3-7}$-cycloalkyl-$(CH_2)_n-$, heterocyclyl-$(CH_2)_n-$ and aryl-$(CH_2)_n-$;
alternatively $R^{21}$ and $R^{22}$ together with the amide nitrogen atom form a 4–7 membered saturated heterocyclic ring;
wherein $R^{23}$ is selected from H, $C_{1-6}$-alkyl, $C_{3-7}$-cycloalkyl-$(CH_2)_n-$, heterocyclyl-$(CH_2)_n-$ and aryl-$(CH_2)_n-$;
wherein n is 0, 1, 2 or 3; and
wherein m is 0, 1 or 2;
wherein aryl, heterocyclyl are optionally substituted with one or more substituents selected from $C_{1-2}$-haloalkyl, $C_{1-3}$-alkyl, $C_{3-6}$-cycloalkyl-$(CH_2)_n-$, chloro, fluoro, $-OR^{17}$, $-NR^{17}CO_2R^{17}$, $-NR^{17}SO_2R^{17}$, $N(R^{17})_2$, cyano, $-COR^{17}$, $-C(R^{17})_2N(R^{17})_2$, nitro, $-SO_2N(R^{17})_2$, $-S(O)_mR^{17}$, and $C_{1-3}$-haloalkoxy;
and a pharmaceutically-acceptable salt thereof.

2. Compound of claim 1 wherein $R^{10}$ is H;
wherein $R^{13a}$ is selected from H, phenyl, bromo, chloro, trifluoromethyl and methoxy;
wherein $R^{13b}$ is H;
wherein $R^{15}$ is selected from H and $C_{1-2}$-haloalkyl;
wherein $R^{17}$ is selected from H, $C_{1-3}$-alkyl, $-(CH_2)_n-C_{3-6}$-cycloalkyl, and $-(CH_2)_n$-phenyl;
wherein $R^{19}$ is selected from H, $R^{23}SO_2-$, $C_{1-6}$-alkyl, amino-$C_{1-3}$-alkyl, $C_{1-6}$-alkylamino-$C_{1-3}$-alkyl, $C_{3-5}$-cycloalkylamino-$C_{1-3}$-alkyl, $C_{3-5}$-cycloalkyl-$C_{1-3}$-alkylamino-$C_{1-3}$-alkyl, $C_{1-3}$-alkylthio-$C_{1-3}$-alkyl, $C_{1-3}$-alkoxy-$C_{1-3}$-alkyl, heteroarylamino-$C_{1-3}$-alkyl, 5–6 membered heteroaryl-$C_{1-3}$-alkylamino-$C_{1-3}$-alkyl, phenylamino-$C_{1-3}$-alkyl, phenyl-$C_{1-3}$-alkylamino-$C_{1-3}$-alkyl, 5–6 membered heteroaryloxy-$C_{1-3}$-alkyl, phenyloxy-$C_{1-3}$-alkyl, hydroxy-$C_{1-3}$-alkyl, phenyl-$C_{1-3}$-alkoxy-$C_{1-3}$-alkyl, $C_{1-6}$-alkylcarbonyl, $C_{1-3}$-alkoxycarbonyl, $C_{1-3}$-alkoxy-$C_{1-3}$-alkylcarbonyl, $C_{1-3}$-alkylaminocarbonyl, $C_{3-6}$-cycloalkylcarbonyl, $C_{3-6}$-cycloalkyl-$C_{1-3}$-alkylcarbonyl, phenylcarbonyl, phenyl-$C_{1-3}$-alkylcarbonyl, 5- or 6-membered heteroaryl-$C_{1-3}$-alkylcarbonyl, 5- or 6-membered heteroarylcarbonyl and $-(CH_2)_n-C_{3-5}$-cycloalkyl optionally substituted with $C_{1-2}$-alkoxycarbonyl;
wherein $R^{20}$ is selected from H, $C_{1-7}$-alkyl, $-(CH_2)_n-C_{5-6}$-cycloalkyl, $-(CH_2)_n$-5–6-membered heterocyclyl, $C_{1-3}$-alkylsulfonyl, amino-$C_{1-3}$-alkyl and $-(CH_2)_n$-phenyl;
alternatively $R^{19}$ and $R^{20}$ together with the nitrogen atom form a 4–8 membered heterocyclic ring;
wherein $R^{21}$ is selected from H, $C_{1-3}$-alkyl, $C_{2-3}$-alkenyl, $C_{1-3}$-alkylthio-$C_{1-3}$-alkyl, $C_{1-3}$-alkylcarbonylamino-$C_{1-3}$-alkyl, amino-$C_{1-3}$-alkyl, $-(CH_2)_n$-[5- or 6-membered heterocyclyl], $-(CH_2)_n-C_{5-6}$-cycloalkyl, and $-(CH_2)_n$-phenyl;
wherein $R^{22}$ is selected from H, $C_{1-3}$-alkyl, $-(CH_2)_n-C_{4-6}$-cycloalkyl, $-(CH_2)_n$-[5- or 6-membered heterocyclyl] and $-(CH_2)_n$-phenyl;
alternatively $R^{21}$ and $R^{22}$ together with the amide nitrogen atom form a 5–6 membered heterocyclic ring; and
wherein $R^{23}$ is selected from H, $C_{1-3}$-alkyl, $-(CH_2)_n-C_{4-6}$-cycloalkyl, $-(CH_2)_n$-[5- or 6-membered heterocyclyl] and $-(CH_2)_n$-phenyl;
wherein phenyl and heterocyclyl are optionally substituted with one or more substituents selected from $C_{1-2}$-haloalkyl, $C_{1-2}$-alkyl, $-(CH_2)_n-C_{4-6}$-cycloalkyl, chloro, fluoro, $-OR^{17}$, $-NR^{17}CO_2R^{17}$, $-NR^{17}SO_2R^{17}$, $N(R^{17})_2$, cyano, $-COR^{17}$, $-C(R^{17})_2N(R^{17})_2$, nitro, $-SO_2N(R^{17})_2$, $-S(O)_mR^{17}$, and $C_{1-2}$-haloalkoxy;
and pharmaceutically-acceptable salts thereof.

3. Compound of claim 2 wherein $R^{13a}$ is selected from H, bromo and chloro;
wherein $R^{13b}$ is H;
wherein $R^{14}$ is selected from trifluoromethyl, 2-hydroxyethyl, 1-hydroxyethyl, $R^{19}R^{20}N-$, $R^{19}R^{20}N-C_{1-2}$-alkyl and $(R^{21}R^{22}N-)(O=)C-$;

wherein R¹⁵ is H or trifluoromethyl;
wherein R¹⁷ is selected from H, methyl, ethyl, propyl, isopropyl, cyclopropyl, cyclopropylmethyl, cyclopentyl, cyclopentylmethyl, cyclohexyl, cyclohexylmethyl, phenylpropyl, phenylethyl, benzyl and phenyl;
wherein R¹⁹ is selected from H, R²³SO₂—, methyl, ethyl, propyl, isopropyl, isopentyl, 3-ethylbutyl, hydroxymethyl, hydroxyethyl, cyclopropylmethyl, 1-(ethoxycarbonyl)cycloprop-2-ylmethyl, R²³ SO₂—, aminomethyl, aminoethyl, dimethylaminoethyl, diethylaminoethyl, dipropylaminoethyl, di-isobutylaminoethyl, di-tert-butylmethylaminoethyl, di(3-ethylbutyl)aminoethyl, furylmethylaminoethyl, thienylmethylaminoethyl, benzylaminoethyl, di(furylmethyl)aminoethyl, di(cyclohexylmethyl)aminoethyl, di(cyclopropylmethyl)aminoethyl, di(thienylmethyl)aminoethyl, di(benzyl)aminoethyl, phenylmethoxyethyl, pyridyloxymethyl, methylthiopropyl, methylcarbonyl, ethylcarbonyl, propylcarbonyl, isopropylcarbonyl, isobutylcarbonyl, tert-butylcarbonyl, pentylcarbonyl, butylcarbonyl, cyclopentylcarbonyl, cyclopropylcarbonyl, cyclobutylcarbonyl, cyclohexylcarbonyl, methoxycarbonyl, methoxymethylcarbonyl, ethoxycarbonyl, propoxycarbonyl, methylaminocarbonyl, ethylaminocarbonyl, propylaminocarbonyl, optionally substituted thienylmethylcarbonyl, optionally substituted benzylcarbonyl, optionally substituted phenylethylcarbonyl, optionally substituted phenylcarbonyl and optionally substituted pyridylcarbonyl;
wherein R²⁰ is selected from H, methyl, ethyl, propyl, isopropyl, butyl, isobutyl, pentyl, hexyl, heptyl, cyclopropylmethyl, cyclobutylmethyl, cyclopentylmethyl, cyclohexylmethyl, cyclopropyl, cyclohexyl, methylsulfonyl, aminoethyl, optionally substituted phenyl, optionally substituted imidazolyl, optionally substituted imidazolylmethyl, optionally substituted thienylmethyl, optionally substituted furylmethyl, optionally substituted pyrrolidinylmethyl, optionally substituted pyridylmethyl, optionally substituted thienylmethyl, optionally substituted benzyl, optionally substituted phenylethyl and optionally substituted phenylpropyl;
alternatively R¹⁹ and R²⁰ together with the nitrogen atom form a heterocyclic ring selected from triazolyl, tetrazolyl, 2-pyridone, oxo-pyrrolidinyl, 2-oxo-piperidinyl, 4,5-dihydro-2-oxo-oxazolyl, 1,1-dioxo-isothiazolidin-2-yl, 2-oxo-imidazolin-1-yl, 3-methyl-2-oxo-imidazolin-1-yl, piperidinyl optionally
  substituted with one or more substituents selected from methyl, ethyl, propyl, and isopropyl,
    piperazinyl optionally substituted with one or more substituents selected from methyl, ethyl, propyl, and isopropyl,
    imidazolyl optionally substituted with one or more substituents selected from methyl, ethyl, propyl, and isopropyl, and
    pyrrolidinyl optionally substituted with one or more substituents selected from methyl, ethyl, propyl, and isopropyl;
wherein R²¹ is selected from H, methyl, ethyl, propyl, isopropyl, allyl, methylthioethyl, methylthiomethyl, methylcarbonylaminoethyl, methylcarbonylaminomethyl, aminomethyl, aminoethyl, 1-methylpyrrolidinylethyl, piperidinylethyl, pyridyl, cyclopentylmethyl, cyclohexylmethyl, phenyl, 4-chlorophenylmethyl, 4-phenoxyphenylethyl, benzyl and phenylethyl;
wherein R²² is H or methyl;
alternatively R²¹ and R²² together form a ring selected from pyrrolidinyl, morpholino, piperidinyl, piperazinyl, 4-acetylpiperazinyl and 4-methylpiperazinyl; and
wherein R²³ is selected from H, methyl, ethyl, propyl, optionally substituted thienyl, optionally substituted phenyl, optionally substituted benzyl, optionally substituted phenylethyl and optionally substituted phenylpropyl;
wherein phenyl and heterocyclyl are optionally substituted with one or more substituents selected from trifluoromethyl, methyl, nitro, cyano, chloro, methoxy, phenyloxy, acetyl, amino, dimethylamino and aminomethyl;
and pharmaceutically-acceptable salts thereof.

4. Compound of claim 3 wherein R¹⁴ is selected from N-pyrrolidinylcarbonyl, N-morpholinocarbonyl, N-piperidinylethylaminocarbonyl, benzylaminocarbonyl, N-methyl-N-benzylaminocarbonyl, aminoethylaminocarbonyl, pyridylaminocarbonyl, methylthioethylaminocarbonyl, methylcarbonylaminoethylaminocarbonyl, 1-methylpyrrolidinylethylaminocarbonyl, phenethylaminocarbonyl, phenylaminocarbonyl, cyclohexylmethylaminocarbonyl, N-methyl-N-phenethylaminocarbonyl, N,N-dimethylaminocarbonyl, 4-chlorophenylmethylaminocarbonyl, phenoxyphenethylaminocarbonyl, allylaminocarbonyl, 4-methylpiperazinylcarbonyl, 4-acetylpiperazinylcarbonyl, isopropylaminocarbonyl,
  1-(N-cyclopropylmethylamino)ethyl, 1-(N-methyl-N-methylcarbonylamino)ethyl, 1-(N-isopropylamino)ethyl, 1-(N-isobutyl-N-methylamino)ethyl, N-cyclopropylmethyl-N-propylaminomethyl, N,N-dicyclopropylmethylaminomethyl, 1-(N-propyl-N-methylamino)ethyl, 1-(N-methyl-N-methylsulfonylamino)ethyl, triazolylmethyl, imidazol-1-ylmethyl, 2-isopropylimidazol-1-yl-methyl, 2-propylimidazol-1-yl-methyl, 2-oxo-pyrid-1-yl-methyl, 3-pyridyl-oxymethyl, 2-methylimidazol-1-yl-methyl, tetrazolylmethyl, 2,5-dimethylpyrrolidin-1-ylmethyl, 2-oxo-pyrrolidin-1-yl-methyl, 2-oxo-piperidin-1-yl-methyl, 4,5-dihydro-2-oxo-oxazol-3-yl-methyl, pyrrolidin-1-ylmethyl, 2,6-dimethylpiperidin-1-ylmethyl, piperazin-1-yl-methyl, 4-methylpiperazin-1-yl-methyl, piperidin-1-yl-methyl, 1-(N-ethyl-N-methylamino)ethyl, 1-(N,N-dipropylamino)ethyl, 1-(N,N-diisopropylamino)ethyl, 1-(N-(1-ethoxycarbonyl)cycloprop-2-ylmethyl-N-methylamino)ethyl, 1-(N-(2-methylbutyl)-N-methylamino)ethyl, 1-(N-(4-methylcarbonylaminophenyl)methyl-N-methylamino)ethyl, 1-(N-methylamino)ethyl, 1-(N,N-dimethylamino)ethyl, N,N-dimethylaminomethyl, N-cyclopropylmethyl-N-methylsulfonylaminomethyl, 1-(N-(3-thienyl)methyl-N-methylamino)ethyl, 1-(N-phenylmethoxyethyl-N-methylamino)ethyl, 1-(N-(2-methoxyphenyl)methyl-N-methylamino)ethyl, 1-(N-(4-pyridyl)methyl-N-methylamino)ethyl, 1-(N-(2-pyrrolidinyl)methyl-N-methylamino)ethyl, 1-(N-(3-methoxyphenyl)methyl-N-methylamino)ethyl, 1-(N-(4-methoxyphenyl)methyl-N-methylamino)ethyl, 1-(N-benzyl-N-methylamino)ethyl, 1-(N-methyl-N-aminoethylamino)ethyl, 1-(N-cyclohexylmethyl-N-methylamino)ethyl, N,N-dimethylaminomethyl, N-(1-hydroxyethyl)-N-methylaminomethyl, N-(1-hydroxyethyl)-N-methylaminomethyl,
  N-propyl-N-methylsulfonylamino, N-(methylsulfonyl)-N-propylamino, N-(methylsulfonyl)-N-cyclopropylmethylamino, N-(methylsulfonyl)-N-aminoethylamino, N-(methylsulfonyl)-N-(N',N'-dimethylaminoethyl)amino, N-(N',N'-diethylaminoethyl)-N-methylsulfonylamino, N-(N',N'- dipropylaminoethyl)-N-methylsulfonylamino, N-(N',N'-diisobutylaminoethyl)-N-methylsulfonylamino, N-(N',N'-di-tert-butylmethylaminoethyl)-N-methylsulfonylamino, N-(N',N'-di(cyclopropylmethyl)aminoethyl)-N-methylsulfonylamino, N-(N',N'-di(2-furylmethyl)aminoethyl)-N-methylsulfonylamino, N-(N',N'-di(3-thienylmethyl)aminoethyl)-N-methylsulfonylamino, N-(N',N'-di(benzyl)aminoethyl)-N-methylsulfonylamino, N-(methylsulfonyl)-N-isobutylamino, N-(methylsulfonyl)-N-methylamino, N-(methylsulfonyl)-N-phenethylamino, N-(methylsulfonyl)amino, N-(benzylsulfonyl)amino, N-(propylsulfonyl)amino, N-(phenylsulfonyl)amino, N-(methylsulfonyl)-N-phenylpropylamino, thienylsulfonylamino, (2-nitrophenyl)methylsulfonylamino, (2,4,6-trimethylphenyl)sulfonylamino, (2-cyanophenyl)sulfonylamino, N-methoxymethylcarbonyl-N-cyclopropylmethylamino, N-methylcarbonyl-N-cyclopropylmethylamino, N-phenylcarbonyl-N-cyclopropylmethylamino, N-(3-methoxyphenylcarbonyl-N-cyclopropylmethylamino, N-benzylcarbonyl-N-cyclopropylmethylamino, N-phenylethyl-N-cyclopropylmethylamino, N-(2-imidazolyl)-N-cyclopropylmethylamino, N-(4-methyl-5-imidazolyl)-N-cyclopropylmethylamino, N-(2-thienylmethyl)-N-cyclopropylmethylamino, N-(3-thienylmethyl)-N-cyclopropylmethylamino, N-(3-furylmethyl)-N-cyclopropylmethylamino, N-(4-imidazolyl)-N-cyclopropylmethylamino, N-cyclopentylcarbonyl-N-cyclopropylmethylamino, N-cyclohexylcarbonyl-N-cyclopropylmethylamino, N-methylthiopropyl-N-cyclopropylmethylamino, N-ethylcarbonyl-N-cyclopropylmethylamino, N-isopropylcarbonyl-N-cyclopropylmethylamino, N-isobutylcarbonyl-N-cyclopropylmethylamino, N-ethyl-N-cyclopropylmethylamino, N-isobutyl-N-cyclopropylmethylamino, N-cyclopropylcarbonyl-N-cyclopropylmethylamino, N,N-di(cyclopropylmethyl)amino, N-methoxymethylcarbonyl-N-aminoethylamino, N-ethylcarbonyl-N-aminoethylamino, N-isopropylcarbonyl-N-aminoethylamino, N-isobutylcarbonyl-N-aminoethylamino, N-tert-butylcarbonyl-N-aminoethylamino, N-propylcarbonyl-N-aminoethylamino, N-pentylcarbonyl-N-aminoethylamino, N-ethyl-N-aminoethylamino, N-propyl-N-aminoethylamino, N-cyclopropyl-N-aminoethylamino, N-cyclopropylmethyl-N-aminoethylamino, N-cyclobutylmethyl-N-aminoethylamino, N-butyl-N-aminoethylamino, N-pentyl-N-aminoethylamino, N-hexyl-N-aminoethylamino, N-heptyl-N-aminoethylamino, N-(3-ethylbutyl)-N-aminoethylamino, N-cyclohexylcarbonyl-N-aminoethylamino, N-phenylcarbonyl-N-aminoethylamino, N-(3-methoxyphenyl)carbonyl-N-aminoethylamino, N-benzylcarbonyl-N-aminoethylamino, N-phenylethylcarbonyl-N-aminoethylamino, N-pyridylcarbonyl-N-aminoethylamino, N-thienylmethyl-N-aminoethylamino, aminoethylamino, pyridylcarbonylamino, N-cyclopropylmethylamino, methylcarbonylamino, methoxycarbonylamino, trifluoromethyl, 2-hydroxyethyl, 1-hydroxyethyl, methylaminocarbonylamino, 1,1-dioxo-isothiazolidin-2-yl, 2-oxo-imidazolin-1-yl and 3-methyl-2-oxo-imidazolin-1-yl;

and pharmaceutically-acceptable salts thereof.

5. Compound of claim 1 wherein $R^{16}$ is selected from pyridyl, 4-pyridyl, 5-benzopyrrolyl, 2-benzofuran, 2-benzothienyl, 6-quinolyl, and thienyl, and pharmaceutically-acceptable salts thereof.

6. Compound of claim 1 wherein $R^{16}$ is selected from 3-azetidinyl optionally N-substituted with a substituent selected from methyl, ethyl, propyl, isopropyl, butyl, isobutyl, pentyl, cyclohexylmethyl and benzyl; and pharmaceutically-acceptable salts thereof.

7. Compound of claim 1 wherein $R^{16}$ is selected from 5-benzopyrrolyl, 2-benzofuran, 2-benzothienyl, and 4-quinolyl;

and pharmaceutically-acceptable salts thereof.

8. Compound of claim 1 wherein $R^{16}$ is selected from 4-pyridyl, 3-pyridyl and thienyl; and pharmaceutically-acceptable salts thereof.

9. Compound of claim 1 wherein $R^{16}$ is selected from 4-piperidyl, N-methyl-4-piperidyl, N-methyl-2-piperidyl, N-ethyl-4-piperidyl, N-isobutyl-4-piperidyl, and 3-piperidyl;

and pharmaceutically-acceptable salts thereof.

10. Compound of claim 1 and pharmaceutically acceptable salts thereof selected from N-[(1R)-1-[(3,4-dichlorophenyl)methyl]-2-(4-{2-[(methylsulfonyl)amino]phenyl}piperazinyl)-2-oxoethyl]azetidin-3-ylcarboxamide;

N-[(1R)-1-[(4-chlorophenyl)methyl]-2-(4-{2-[(methylsulfonyl)amino]phenyl}piperazinyl)-2-oxoethyl]((2S) (2-piperidyl))carboxamide;

N-[(1R)-1-[(4-chlorophenyl)methyl]-2-(4-{2-[(methylsulfonyl)amino]phenyl}piperazinyl)-2-oxoethyl]-4-piperidylcarboxamide;

((2R)azetidin-2-yl)-N-[(1R)-1-[(4-chlorophenyl)methyl]-2-(4-{2-[(methylsulfonyl)amino]phenyl}piperazinyl)-2-oxoethyl]carboxamide;

N-[(1R)-1-[(4-chlorophenyl)methyl]-2-(4-{2-[(methylsulfonyl)amino]phenyl}piperazinyl)-2-oxoethyl]-3-pyridylcarboxamide;

N-[(1R)-1-[(4-chlorophenyl)methyl]-2-(4-{2-[(methylsulfonyl)amino]phenyl}piperazinyl)-2-oxoethyl]-4-pyridylcarboxamide;

N-[(1R)-1-[(4-chlorophenyl)methyl]-2-(4-{2-[(methylsulfonyl)amino]phenyl}piperazinyl)-2-oxoethyl)-6-quinolylcarboxamide;

N-[(1R)-1-[(4-chlorophenyl)methyl]-2-(4-{2-[(methylsulfonyl)amino]phenyl}piperazinyl)-2-oxoethyl]azetidin-3-ylcarboxamide;

N-[(1R)-1-[(4-chlorophenyl)methyl]-2-(4-{2-[(methylsulfonyl)amino]phenyl}piperazinyl)-2-oxoethyl]-3-piperidylcarboxamide;

N-[(1R)-1-[(4-chlorophenyl)methyl]-2-(4-{2-[(methylsulfonyl)amino]phenyl}piperazinyl)-2-oxoethyl](1-methyl(2-piperidyl))carboxamide;

N-[(1R)-1-[(4-chlorophenyl)methyl]-2-(4-{2-[(methylsulfonyl)amino]phenyl}piperazinyl)-2-oxoethyl](1-methyl(4-piperidyl))carboxamide;

N-[(1S)-1-[(4-chlorophenyl)methyl]-2-(4-{2-[(cyclopropylmethyl)(methylsulfonyl)amino]phenyl}piperazinyl)-2-oxoethyl]azetidin-3-ylcarboxamide;

quinoline-6-carboxylic acid [1-(4-chloro-benzyl)-2-(4-{2-[1-(cyclopropylmethyl-amino)-ethyl]-phenyl}-piperazin-1-yl)-2-oxo-ethyl]-amide;

quinoline-6-carboxylic acid [2-(4-{2-(1-(bis-cyclopropylmethyl-amino)-ethyl]-phenyl}-piperazin-1-yl)-1-(4-chloro-benzyl)-2-oxo-ethyl]-amide;

quinoline-6-carboxylic acid [2-(4-{2-[(bis-cyclopropylmethyl-amino)methyl]phenyl}-piperazin-1-yl)-1-(4-chlorobenzyl)-2-oxo-ethyl]amide;

quinoline-6-carboxylic acid [1-(4-chlorobenzyl)-2-(4-{2-[(cyclopropylmethyl-propylamino)methyl]phenyl}-piperazin-1-yl)-2-oxo-ethyl]amide;
N-[1-(4-chlorobenzyl)-2-(4-{2-[(cyclopropylmethyl-propyl-amino)-methyl]-4-fluorophenyl}-piperazin-1-yl)-2-oxo-ethyl]-3-piperidin-1-yl-propionamide;
azetidine-3-carboxylic acid {1-(4-chlorobenzyl)-2-oxo-2-[4-(2-[1,2,3]triazol-2-ylmethylphenyl)piperazin-1-yl]ethyl}amide;
quinoline-6-carboxylic acid {1-(4-chlorobenzyl)-2-[4-(2-{1-[cyclopropylmethyl-(3-methylbutyl)amino]ethyl}-phenyl)-piperazin-1-yl]-2-oxo-ethyl}-amide;
quinoline-6-carboxylic acid [1-(4-chlorobenzyl)-2-(4-{2-[1-(cyclohexylmethyl-cyclopropylmethyl-amino)-ethyl]-phenyl}-piperazin-1-yl)-2-oxo-ethyl]-amide;
quinoline-6-carboxylic acid {1-(4-chlorobenzyl)-2-[4-(2-{1-[cyclopropylmethyl-(3-methylsulfanylpropyl)amino]-ethyl}phenyl)-piperazin-1-yl]-2-oxo-ethyl}-amide;
quinoline-6-carboxylic acid [1-(4-chlorobenzyl)-2-(4-{2-[1-(cyclopropylmethyl-thiophen-3-ylmethylamino)-ethyl]-phenyl}-piperazin-1-yl)-2-oxo-ethyl}-amide;
quinoline-6-carboxylic acid (1-(4-chlorobenzyl)-2-{4-[2-(cyclopropylmethyl-methylsulfonylamino)-phenyl]-piperazin-1-yl}-2-oxo-ethyl)-amide;
1-isobutyl-azetidine-3-carboxylic acid (1-(4-chloro-benzyl)-2-{4-[2-(cyclopropylmethyl-methylsulfonyl-amino)-phenyl]-piperazin-1-yl}-2-oxo-ethyl)-amide;
1-(2,2-dimethylpropyl)-azetidine-3-carboxylic acid (1-(4-chlorobenzyl)-2-{4-[2-(cyclopropylmethyl-methylsulfonylamino)phenyl]-piperazin-1-yl}-2-oxo-ethyl)-amide;
1-cyclopropylmethyl-azetidine-3-carboxylic acid (1-(4-chlorobenzyl)-2-{4-[2-(cyclopropylmethyl-methylsulfonylamino)phenyl]piperazin-1-yl}-2-oxo-ethyl)-amide; and
piperidine-4-carboxylic acid (1-(4-chlorobenzyl)-2-{4-[2-(cyclopropylmethyl-methanesulfonylamino)phenyl]-piperazin-1-yl}-2-oxo-ethyl)amide.

11. A compound and pharmaceutically acceptable salts thereof selected from
quinoline-6-carboxylic acid [1-(4-chloro-benzyl)-2-(4-{2-[1-(cyclopropylmethyl-amino)-ethyl]-phenyl)-piperazin-1-yl)-2-oxo-ethyl]-amide;
quinoline-6-carboxylic acid [2-(4-{2-[1-(bis-cyclopropylmethyl-amino)-ethyl]-phenyl}-piperazin-1-yl)-1-(4-chloro-benzyl)-2-oxo-ethyl]-amide;
quinoline-6-carboxylic acid [2-(4-{2-[(bis-cyclopropylmethyl-amino)methyl]phenyl}-piperazin-1-yl)-1-(4-chlorobenzyl)-2-oxo-ethyl]amide;
quinoline-6-carboxylic acid [1-(4-chlorobenzyl)-2-(4-{2-[(cyclopropylmethyl-propylamino)methyl]phenyl}-piperazin-1-yl)-2-oxo-ethyl]amide;
N-[1-(4-chlorobenzyl)-2-(4-{2-[(cyclopropylmethyl-propyl-amino)-methyl]-4-fluorophenyl}-piperazin-1-yl)-2-oxo-ethyl]-3-piperidin-1-yl-propionamide;
azetidine-3-carboxylic acid {1-(4-chlorobenzyl)-2-oxo-2-[4-(2-[1,2,3]triazol-2-ylmethylphenyl)piperazin-1-yl]ethyl}amide;
quinoline-6-carboxylic acid {1-(4-chlorobenzyl)-2-[4-(2-{1-[cyclopropylmethyl-(3-methylbutyl)amino]ethyl}-phenyl)-piperazin-1-yl]-2-oxo-ethyl}-amide;
quinoline-6-carboxylic acid [1-(4-chlorobenzyl)-2-(4-{2-[1-(cyclohexylmethyl-cyclopropylmethyl-amino)-ethyl]-phenyl}-piperazin-1-yl)-2-oxo-ethyl]-amide;
quinoline-6-carboxylic acid [1-(4-chlorobenzyl)-2-[4-(2-{1-[cyclopropylmethyl-(3-methylsulfanylpropyl)amino]-ethyl}phenyl)-piperazin-1-yl]-2-oxo-ethyl}-amide;
quinoline-6-carboxylic acid [1-(4-chlorobenzyl)-2-(4-(2-[1-(cyclopropylmethyl-thiophen-3-ylmethylamino)-ethyl]-phenyl)-piperazin-1-yl)-2-oxo-ethyl]-amide;
quinoline-6-carboxylic acid [1-(4-chlorobenzyl)-2-{4-[2-(cyclopropylmethyl-methylsulfonylamino)-phenyl]-piperazin-1-yl}-2-oxo-ethyl)-amide;
1-isobutyl-azetidine-3-carboxylic acid {1-(4-chloro-benzyl)-2-{4-[2-(cyclopropylmethyl-methylsulfonyl-amino)-phenyl]-piperazin-1-yl}-2-oxo-ethyl)-amide;
1-(2,2-dimethylpropyl)-azetidine-3-carboxylic acid (1-(4-chlorobenzyl)-2-}4-[2-(cyclopropylmethyl-methylsulfonylamino)phenyl]-piperazin-1-yl{-2-oxo-ethyl)-amide;
1-cyclopropylmethyl-azetidine-3-carboxylic acid (1-(4-chlorobenzyl)-2-[4-[2-(cyclopropylmethyl-methylsulfonylamino)phenyl]piperazin-1-yl}-2-oxo-ethyl)-amide; and
piperidine-4-carboxylic acid [1-(4-chlorobenzyl)-2-{4-[2-(cyclopropylmethyl-methylsulfonylamino)phenyl]-piperazin-1-yl}-2-oxo-ethyl)amide.

12. A pharmaceutical composition comprising a pharmaceutically-acceptable carrier and a compound as in claim 1.

13. A method of treating obesity in a subject, said method comprising administering an effective amount of a compound of claim 1.

14. A method of treating diabetes mellitus in a subject, said method comprising administering an effective amount of a compound of claim 1.

* * * * *

UNITED STATES PATENT AND TRADEMARK OFFICE
CERTIFICATE OF CORRECTION

PATENT NO. : 7,115,607 B2
APPLICATION NO. : 10/202823
DATED : October 3, 2006
INVENTOR(S) : Fotsch et al.

Page 1 of 1

It is certified that error appears in the above-identified patent and that said Letters Patent is hereby corrected as shown below:

Column 158, Line 2, --3- -- should be added in front of pyridyl.
Column 160, Line 29, the bracket is incorrect and should be changed to {.
Column 160, Line 30, the bracket is incorrect and should be changed to }.

Signed and Sealed this

Twenty-seventh Day of July, 2010

David J. Kappos
*Director of the United States Patent and Trademark Office*